(12) United States Patent
Garcia-Lopez et al.

(10) Patent No.: US 10,428,051 B2
(45) Date of Patent: Oct. 1, 2019

(54) SUBSTITUTED AMIDE DERIVATIVES HAVING MULTIMODAL ACTIVITY AGAINST PAIN

(71) Applicant: ESTEVE PHARMACEUTICALS, S.A., Barcelona (ES)

(72) Inventors: Monica Garcia-Lopez, Barcelona (ES); Carmen Almansa-Rosales, Barcelona (ES); Ana Virginia Llorente-Fernandez, Barcelona (ES); Lourdes Garriga-Sanahuja, Barcelona (ES); Ute Christmann, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 15/746,877

(22) PCT Filed: Jul. 28, 2016

(86) PCT No.: PCT/EP2016/001310
§ 371 (c)(1),
(2) Date: Jan. 23, 2018

(87) PCT Pub. No.: WO2017/016669
PCT Pub. Date: Feb. 2, 2017

(65) Prior Publication Data
US 2019/0002443 A1  Jan. 3, 2019

(30) Foreign Application Priority Data
Jul. 29, 2015 (EP) .................................. 15382390

(51) Int. Cl.
| | | |
|---|---|---|
| C07D 405/04 | (2006.01) |
| C07D 309/06 | (2006.01) |
| C07D 305/06 | (2006.01) |
| C07D 311/96 | (2006.01) |
| C07D 295/13 | (2006.01) |
| C07D 213/75 | (2006.01) |
| C07D 211/26 | (2006.01) |
| C07D 409/14 | (2006.01) |
| C07D 405/12 | (2006.01) |
| C07D 417/14 | (2006.01) |
| C07D 409/12 | (2006.01) |
| C07D 307/54 | (2006.01) |
| C07D 333/38 | (2006.01) |
| C07D 277/46 | (2006.01) |
| C07D 213/38 | (2006.01) |
| C07D 295/192 | (2006.01) |
| C07D 487/04 | (2006.01) |
| A61P 25/04 | (2006.01) |
| C07D 405/14 | (2006.01) |
| C07D 401/04 | (2006.01) |
| C07D 401/12 | (2006.01) |
| C07D 295/12 | (2006.01) |
| C07D 295/125 | (2006.01) |
| C07D 295/135 | (2006.01) |

(52) U.S. Cl.
CPC ............ C07D 405/04 (2013.01); A61P 25/04 (2018.01); C07D 211/26 (2013.01); C07D 213/38 (2013.01); C07D 213/75 (2013.01); C07D 277/46 (2013.01); C07D 295/12 (2013.01); C07D 295/125 (2013.01); C07D 295/13 (2013.01); C07D 295/135 (2013.01); C07D 295/192 (2013.01); C07D 305/06 (2013.01); C07D 307/54 (2013.01); C07D 309/06 (2013.01); C07D 311/96 (2013.01); C07D 333/38 (2013.01); C07D 401/04 (2013.01); C07D 401/12 (2013.01); C07D 405/12 (2013.01); C07D 405/14 (2013.01); C07D 409/12 (2013.01); C07D 409/14 (2013.01); C07D 417/14 (2013.01); C07D 487/04 (2013.01)

(58) Field of Classification Search
CPC .. C07D 405/04; C07D 211/26; C07D 213/38; C07D 213/75; C07D 277/46; C07D 295/12; C07D 295/125; C07D 295/13; C07D 295/135; C07D 295/192; C07D 305/06; C07D 307/54; C07D 309/06; C07D 311/96; C07D 333/38; C07D 401/04; C07D 401/12; C07D 405/12; C07D 405/14; C07D 409/12; C07D 409/14; C07D 417/14; C07D 487/04; A61P 25/04
USPC ....................................................... 514/235.8
See application file for complete search history.

(56) References Cited

FOREIGN PATENT DOCUMENTS

| WO | WO 2015/091939 A1 | 6/2015 |
| WO | WO 2015/091988 A1 | 6/2015 |
| WO | WO 2015/092009 A1 | 6/2015 |

OTHER PUBLICATIONS

International Search Reprot for PCT/EP2016/001310 dated Sep. 12, 2016.
Bornot et al., J. Med. Chem., 2013, 56, 1197-1210.
Chien, et al., Neuroscience Letters, 1995, 190, 137-139.
Dickenson, et al., Eur J Pain 9, 113-116 (2005).
Goldberg, et al., BMC Public Health, 11, 770 (2011).
Mao, et al., J. Pain, 12, 157-166 (2011).
Turk, et al., Lancet, 377, 2226-2235 (2011).
Zamanillo, et al., Eur. J. Pharmacol, 716, 78-93 (2013).

*Primary Examiner* — Kristin A Vajda
(74) *Attorney, Agent, or Firm* — Hueschen and Sage

(57) ABSTRACT

The present invention relates to substituted amide derivatives having dual pharmacological activity towards both the sigma (σ) receptor, and the μ-opioid receptor, to processes of preparation of such compounds, to pharmaceutical compositions comprising them, and to their use in therapy, in particular for the treatment of pain.

28 Claims, No Drawings

SUBSTITUTED AMIDE DERIVATIVES HAVING MULTIMODAL ACTIVITY AGAINST PAIN

FIELD OF THE INVENTION

The present invention relates to substituted amide derivatives having dual pharmacological activity towards both the sigma (σ) receptor, and the μ-opioid receptor (MOR or mu-opioid receptor), to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies*. Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opioid receptor and to the $\sigma_1$ receptor.

SUMMARY OF THE INVENTION

In this invention a family of structurally distinct substituted amide derivatives which have a dual pharmacological activity towards both the sigma (σ) receptor, and the μ-opioid receptor was identified thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a very preferred embodiment if the compound has a binding expressed as $K_i$ which is preferably <1000 nM for both receptors, more preferably <500 nM, even more preferably <100 nM.

The invention is directed in a main aspect to a compound of general Formula (I),

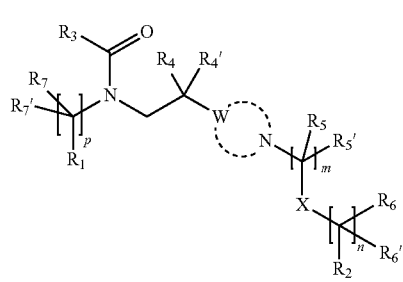

wherein $R_1$, $R_2$, $R_3$, $R_4$, $R_{4'}$, $R_5$, $R_{5'}$, $R_6$, $R_{6'}$, $R_7$, $R_{7'}$, X, W, m, n and p are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The invention is directed to a family of structurally distinct substituted amide derivatives which have a dual pharmacological activity towards both the sigma (σ) receptor and the μ-opioid receptor.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a preferred embodiment if the compound has a binding expressed as $K_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to μ-opioid receptor and to $\sigma_1$ receptor), thereby enhancing the opioid analgesia through the $\sigma_1$ activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ-opioid receptor agonists.

A dual compound that possess binding to both the μ-opioid receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: $\sigma_1$ receptor antagonism and μ-opioid receptor agonism. It has to be noted, though, that both functionalities "antagonism" and "agonism" are also subdivided in their effect into subfunctionalities like partial agonism or inverse agonism.

Accordingly, the functionalities of the dual compound should be considered within a relatively broad bandwidth.

An antagonist blocks or dampens agonist-mediated responses. Known subfunctionalities are neutral antagonists or inverse agonists.

An agonist increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients.

Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem*, 56, 1197-1210 (2013)].

In a particular aspect, the present invention is directed to compounds of general Formula (I):

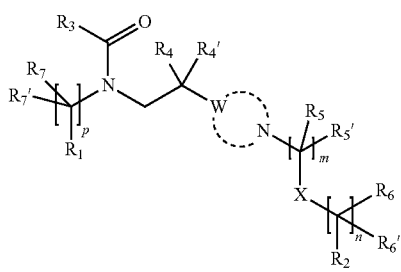
(I)

wherein
m is 1 or 2;
n is 0, 1 or 2;
p is 0, 1 or 2;
W is nitrogen or carbon;
X is a bond, —C($R_x R_{x'}$)—, C=O, —C(O)O— or —O—;
  wherein $R_x$ is selected from halogen, —$OR_{15}$, substituted or unsubstituted $C_{1-6}$ alkyl, substituted or unsubstituted $C_{2-6}$ alkenyl and substituted or unsubstituted $C_{2-6}$ alkynyl;
  $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
  $R_{15}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_9R_{9'}$ and —$CH_2OR_9$;
  wherein $R_9$ and $R_{9'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_4$ and $R_{4'}$ are independently selected from substituted or unsubstituted $C_{1-6}$ alkyl, substituted or unsubstituted $C_{2-6}$ alkenyl and substituted or unsubstituted $C_{2-6}$ alkynyl,
alternatively, $R_4$ and $R_{4'}$, may form together with the carbon atom to which they are attached a cycle of Formula (A)

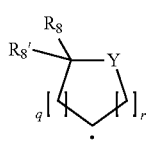
(A)

(with "●" marking the carbon atom to which $R_4$ and $R_{4'}$ are attached):
  wherein
  q is 0 or 1
  r is 0, 1 or 2
  Y is —$CH_2$—, —$N(R_y)$—, —S— or —O—;
  $R_8$ and $R_{8'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
  alternatively, $R_8$ and $R_{8'}$, taken together with the carbon atom to which they are attached, may form a $C_{3-6}$ cycloalkyl;
  Ry is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CH_2OR_{10}$ and —$C(O)OR_{10}$;
  wherein $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_7$ and $R_{7'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
and wherein

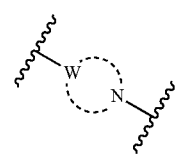

is selected from

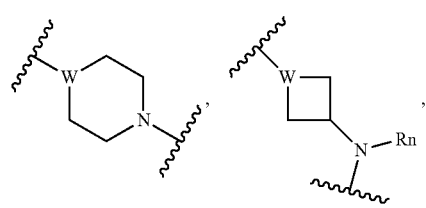

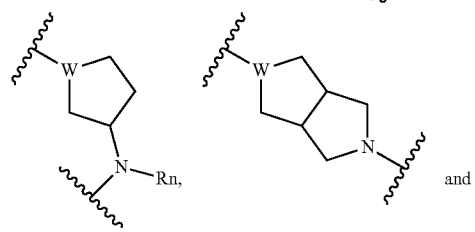
and

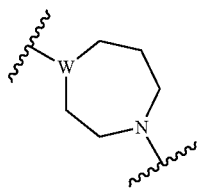

wherein $R_n$ is selected from unsubstituted $C_{1-6}$ alkyl, unsubstituted $C_{2-6}$ alkenyl and unsubstituted $C_{2-6}$ alkynyl.

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a particular embodiment the following proviso applies:
—[CR$_5$R$_{5'}$]$_m$—X—(CR$_6$R$_{6'}$)$_n$—R$_2$ is not unsubstituted methyl;

In another particular embodiment the following proviso applies:
$R_1$ is neither an unsubstituted nor a N-alkyl-substituted compound of the following formula:

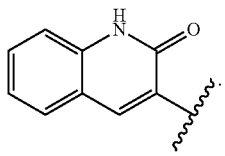 [SMILES: *c1cc2ccccc2[nH]c1=O]

In a further embodiment the compound according to the invention of general Formula (I) is a compound of general Formula (I')

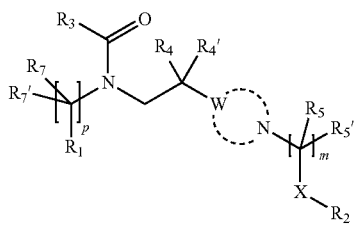

(I')

wherein

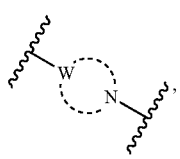

$R_1$, $R_2$, $R_3$, $R_4$, $R_{4'}$, $R_5$, $R_{5'}$, $R_7$, $R_{7'}$, m, p, X and W are as defined in the description.

In a further embodiment the compound according to the invention of general Formula (I) is a compound of general Formula (I$^{2'}$)

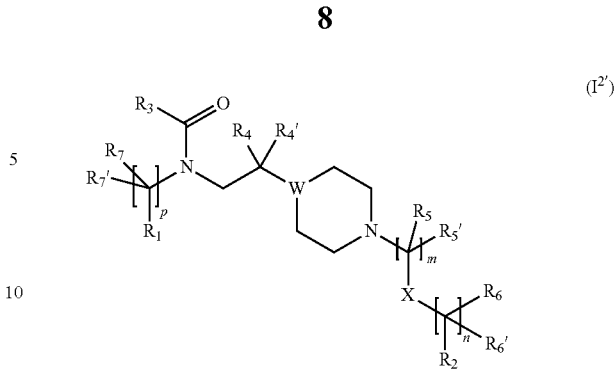

wherein $R_1$, $R_2$, $R_3$, $R_4$, $R_{4'}$, $R_5$, $R_{5'}$, $R_6$, $R_{6'}$, $R_7$, $R_{7'}$, X, W, m, n and p are as defined in the description.

In a further embodiment the compound according to the invention of general Formula (I) is a compound of general Formula (I$^{3'}$)

(I$^{3'}$)

wherein $R_1$, $R_2$, $R_3$, $R_4$, $R_{4'}$, $R_5$, $R_{5'}$, $R_7$, $R_{7'}$, m, p, X and W are as defined in the description.

In a further embodiment the compound according to the invention of general Formula (I) is a compound of general Formula (I$^{4'}$)

(I$^{4'}$)

wherein $R_1$, $R_2$, $R_3$, $R_4$, $R_{4'}$, $R_5$, $R_{5'}$, $R_7$, $R_{7'}$, p, X and W are as defined in the description. In addition, m', $R_{5''}$ and $R_{5'''}$ are added. These are reflecting the statements below in the definitions of substitutions on alkyl etc. or aryl etc. that "when different radicals $R_1$ to $R_{15}$ and $R_x$, $R_{x'}$, $R_y$ and $R_n$ are present simultaneously in Formula I they may be identical or different". Thus this is reflecting that $R_{5''}$ and $R_{5'''}$ are or could be different from $R_5$ and $R_{5'}$ or not and—accordingly—m' being 0 or 1 is naturally resulting from m being 1 or 2.

In a further embodiment the compound according to the invention of general Formula (I) is a compound of general Formula (I$^{5'}$)

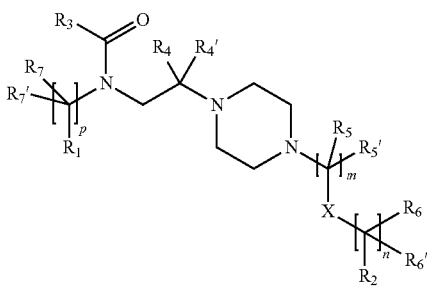

(I⁵')

wherein $R_1$, $R_2$, $R_3$, $R_4$, $R_{4'}$, $R_5$, $R_{5'}$, $R_6$, $R_{6'}$, $R_7$, $R_{7'}$, X, m, n and p are as defined in the description.

In a further embodiment the compound according to the invention of general Formula (I) is a compound of general Formula (I⁵')

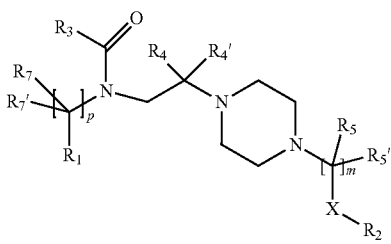

(I⁶')

wherein $R_1$, $R_2$, $R_3$, $R_4$, $R_{4'}$, $R_5$, $R_{5'}$, $R_7$, $R_{7'}$, X, m and p are as defined in the description.

In a further embodiment the compound according to the invention of general Formula (I) is a compound of general Formula (I⁷')

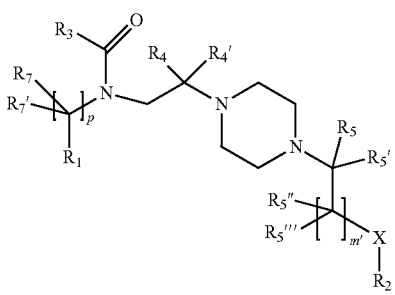

(I⁷')

wherein $R_1$, $R_2$, $R_3$, $R_4$, $R_{4'}$, $R_5$, $R_{5'}$, $R_7$, $R_{7'}$, X and p are as defined in the description. In addition, m', $R_{5''}$ and $R_{5'''}$ are added. These are reflecting the statements below in the definitions of substitutions on alkyl etc. or aryl etc. that "when different radicals $R_1$ to $R_{15}$ and $R_x$, $R_{x'}$, $R_y$ and $R_n$ are present simultaneously in Formula I they may be identical or different". Thus this is reflecting that $R_{5''}$ and $R_{5'''}$ are or could be different from $R_5$ and $R_{5'}$ or not and—accordingly—m' being 0 or 1 is naturally resulting from m being 1 or 2.

For clarity purposes, all groups and definitions described in the present description and referring to compounds of general Formula (I), also apply to compounds of general Formula (I'), (I²'), (I³'), (I⁴'), (I⁵'), (I⁶') or (I⁷') (where applicable), since compounds of general Formula (I'), (I²'), (I³'), (I⁴'), (I⁵'), (I⁶') or (I⁷') are included within the scope of the larger definition of general Formula (I).

For clarity purposes, the general Markush Formula (I)

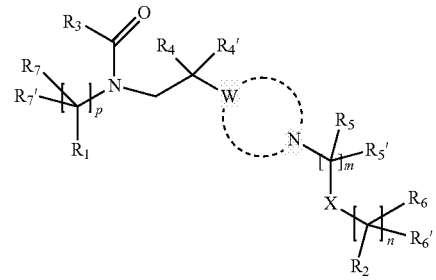

(I)

is equivalent to (I)

wherein only —C($R_7R_{7'}$)—, —C($R_5R_{5'}$)— and —C($R_6R_{6'}$)— are included into the brackets and p, m and n mean the number of times that —C($R_7R_{7'}$)—, —C($R_5R_{5'}$)— and —C($R_6R_{6'}$)— are repeated, respectively. The same would apply to general Markush Formulae (I'), (I²'), (I³'), (I⁴'), (I⁵'), (I⁶') or (I⁷').

In addition, and for clarity purposes, it should further be understood that naturally if p, m or n are 0, then X, $R_1$ or $R_2$ are still present in general Markush Formulae (I), (I'), (I²'), (I³'), (I⁴'), (I⁵'), (I⁶') or (I⁷').

In the context of this invention, alkyl is understood as meaning saturated, linear or branched hydrocarbons, which may be unsubstituted or substituted once or several times. It encompasses e.g. —CH₃ and —CH₂—CH₃. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C16-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF₂, CF₃ or CH₂OH etc. Preferably alkyl is understood in the context of this invention as $C_{1-8}$alkyl like methyl, ethyl, propyl, butyl, pentyl, hexyl, heptyl, or octyl;

preferably is $C_{1-6}$ alkyl like methyl, ethyl, propyl, butyl, pentyl, or hexyl; more preferably is $C_{1-4}$ alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—CH$_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—CH$_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —NR$_c$R$_{c'''}$, —SR$_c$, —S(O)R$_c$, —S(O)$_2$R$_c$, —OR$_c$, —C(O)OR$_c$, —CN, —C(O)NR$_c$R$_{c'}$, haloalkyl, haloalkoxy or —OC$_{1-6}$alkyl being unsubstituted or substituted by one or more of —OR$_c$ or halogen (F, Cl, I, Br), being R$_c$ represented by R$_{11}$, R$_{12}$, R$_{13}$, (being R$_{c'}$ represented by R$_{11'}$, R$_{12'}$, R$_{13'}$; being R$_{c''}$ represented by R$_{11''}$, R$_{12''}$, R$_{13''}$; being R$_{c'''}$ represented by R$_{11'''}$, R$_{12'''}$, R$_{13'''}$), being R$_{c''''}$ represented by R$_{11''''}$, R$_{12''''}$, R$_{13''''}$) wherein R$_1$ to R$_{15}$ and R$_x$, R$_y$ and R$_n$ are as defined in the description, and wherein when different radicals R$_1$ to R$_{15}$ and R$_x$, R$_{x'}$, R$_y$ and R$_n$ are present simultaneously in Formula I they may be identical or different.

Most preferably in connection with alkyl, alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted with one or more of halogen (F, Cl, Br, I), —OR$_c$, —CN, —SR$_c$, —S(O)R$_c$, and —S(O)$_2$R$_c$, haloalkyl, haloalkoxy or —OC$_{1-6}$alkyl being unsubstituted or substituted by one or more of —OR$_c$ or halogen (F, Cl, I, Br), being R$_c$ represented by R$_{11}$, R$_{12}$, R$_{13}$, (being R$_{c'}$ represented by R$_{11'}$, R$_{12'}$, R$_{13'}$; being R$_{c''}$ represented by R$_{11''}$, R$_{12''}$, R$_{13''}$; being R$_{c'''}$, represented by R$_{11'''}$, R$_{12'''}$, R$_{13'''}$, being R$_{c''''}$ represented by R$_{11''''}$, R$_{12''''}$, R$_{13''''}$), wherein R$_1$ to R$_{15}$ and R$_x$, R$_{x'}$, R$_y$, and R$_n$ are as defined in the description, and wherein when different radicals R$_1$ to R$_{15}$ and R$_x$, R$_{x'}$, R$_y$ and R$_n$ are present simultaneously in Formula I, they may be identical or different.

More than one replacement on the same molecule and also on the same carbon atom is possible with the same or different substituents. This includes for example 3 hydrogens being replaced on the same C atom, as in the case of CF$_3$, or at different places of the same molecule, as in the case of e.g. —CH(OH)—CH═CH—CHCl$_2$.

In the context of this invention haloalkyl is understood as meaning an alkyl being substituted once or several times by a halogen (selected from F, Cl, Br, I). It encompasses e.g. —CH$_2$Cl, —CH$_2$F, —CHCl$_2$, —CHF$_2$, —CCl$_3$, —CF$_3$ and —CH$_2$—CHCl$_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —CH$_2$Cl, —CH$_2$F, —CHCl$_2$, —CHF$_2$, and —CF$_3$.

In the context of this invention haloalkoxy is understood as meaning an —O-alkyl being substituted once or several times by a halogen (selected from F, Cl, Br, I). It encompasses e.g. —OCH$_2$Cl, —OCH$_2$F, —OCHCl$_2$, —OCHF$_2$, —OCCl$_3$, —OCF$_3$ and —OCH$_2$—CHCl$_2$. Preferably haloalkyl is understood in the context of this invention as halogen-substituted —OC$_{1-4}$-alkyl representing halogen substituted C1-, C2-, C3- or C4-alkoxy. The halogen-substituted alkyl radicals are thus preferably O-methyl, O-ethyl, O-propyl, and O-butyl.

Preferred examples include —OCH$_2$Cl, —OCH$_2$F, —OCHCl$_2$, —OCHF$_2$, and —OCF$_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$-cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphtyl or anthracenyl, preferably is phenyl.

A heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a 5 to 18 membered mono or polycyclic heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, oxetane, especially is benzodioxane, morpholine, tetrahydropyran, piperidine, oxopyrrolidine, oxetane and pyrrolidine.

Preferably in the context of this invention heterocyclyl is defined as a 5 to 18 membered mono or polycyclic heterocyclic ring system of one or more saturated or unsaturated rings of which at least one ring contains one or more heteroatoms from the group consisting of nitrogen, oxygen and/or sulfur in the ring. Preferably it is a 5 to 18 membered mono or polycyclic heterocyclic ring system of one or two saturated or unsaturated rings of which at least one ring contains one or more heteroatoms from the group consisting of nitrogen, oxygen and/or sulfur in the ring.

Preferred examples of heterocyclyls include oxetane, oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane, oxetane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —$C(O)OR_c$, $NR_cC(O)R_c$, —$C(O)NR_cR_{c'}$, —$NR_cS(O)_2R_c$, =O, —$OCH_2CH_2OH$, —$NR_cC(O)NR_cR_{c''}$, —$S(O)_2NR_cR_{c'}$, —$NR_cS(O)_2NR_cR_{c''}$, haloalkyl, haloalkoxy, —$SR_c$, —$S(O)R_c$, —$S(O)_2R_c$ or $C(CH_3)OR_c$; $NR_cR_{c'''}$, with $R_c$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$, $R_{12}$ or $R_{14}$, (being $R_{c'}$ one of $R_{11'}$, $R_{12'}$ or $R_{14'}$;

being $R_{c''}$ one of $R_{11'''}$, $R_{12'''}$ or $R_{14'''}$; being $R_{c'''}$ one of $R_{11''''}$, $R_{12''''}$, or $R_{14''''}$; being $R_{c''''}$ one of $R_{11'''''}$, $R_{12'''''}$ or $R_{14'''''}$), wherein $R_1$ to $R_{15}$ and $R_x$, $R_{x'}$, $R_y$ and $R_n$ are as defined in the description, and wherein when different radicals $R_1$ to $R_{15}$ and $R_x$, $R_{x'}$, $R_n$ and $R_y$ are present simultaneously in Formula I they may be identical or different.

Most preferably in connection with aryl (including alkylaryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alyklaryl, alkylcycloalkyl or alkylheterocyclyl) with one or more of halogen (F, Cl, Br, I), $-R_c$, $-OR_c$, $-CN$, $-NO_2$, $-NR_cR_{c'''}$, $NR_cC(O)R_{c'}$, $-NR_cS(O)_2R_{c'}$, $=O$, haloalkyl, haloalkoxy, or $C(CH_3)OR_c$; $-OC_{1-4}$alkyl being unsubstituted or substituted with one or more of $OR_c$ or halogen (F, Cl, I, Br), $-CN$, or $-C_{1-4}$alkyl being unsubstituted or substituted with one or more of $OR_c$ or halogen (F, Cl, I, Br), being $R_c$ one of $R_{11}$, $R_{12}$ or $R_{14}$, (being $R_{c'}$ one of $R_{11'}$, $R_{12'}$ or $R_{14'}$; being $R_{c''}$ one of $R_{11''}$, $R_{12''}$ or $R_{14''}$; being $R_{c'''}$ one of $R_{11'''}$, $R_{12'''}$ or $R_{14'''}$; being $R_{c''''}$ one of $R_{11''''}$, $R_{12''''}$ or $R_{14''''}$), wherein $R_1$ to $R_{15}$ and $R_x$, $R_{x'}$, $R_n$ and $R_y$ are as defined in the description, and wherein when different radicals $R_1$ to $R_{15}$ and $R_x$, $R_{x'}$, $R_y$ and $R_n$ are present simultaneously in Formula I they may be identical or different.

Additionally to the above-mentioned substitutions, in connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

or $=O$.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals.

Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I) is a compound wherein m is 1 or 2;
n is 0, 1 or 2;
p is 0, 1 or 2;
W is nitrogen or carbon;
X is a bond, —C($R_x R_{x'}$)—, C=O, —C(O)O— or —O—;
  wherein $R_x$ is selected from halogen, —$OR_{15}$, substituted or unsubstituted $C_{1-6}$ alkyl, substituted or unsubstituted $C_{2-6}$ alkenyl and substituted or unsubstituted $C_{2-6}$ alkynyl;
  $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
  $R_{15}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$NR_{11}S(O)_2NR_{11'}R_{11''}$ and $C(CH_3)_2OR_{11}$;
  additionally, the cycloalkyl or non-aromatic heterocyclyl in $R_1$, if substituted, may also be substituted with

or =O;
  wherein the alkyl, alkenyl or alkynyl in $R_1$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;
  wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$NR_{12}S(O)_2NR_{12'}R_{12''}$ and $C(CH_3)_2OR_{12}$;
  additionally, the cycloalkyl or non-aromatic heterocyclyl in $R_2$, if substituted, may also be substituted with

or =O;
  wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
  wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_9R_{9'}$ and —$CH_2OR_9$;
  wherein $R_9$ and $R_{9'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_4$ and $R_{4'}$ are independently selected from substituted or unsubstituted $C_{1-6}$ alkyl, substituted or unsubstituted $C_{2-6}$ alkenyl and substituted or unsubstituted $C_{2-6}$ alkynyl, alternatively, $R_4$ and $R_{4'}$, may form together with the carbon atom to which they are attached a cycle of Formula (A)

(A)

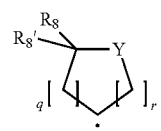

(with "●" marking the carbon atom to which $R_4$ and $R_{4'}$ are attached):
  wherein
  q is 0 or 1
  r is 0, 1 or 2
  Y is —$CH_2$—, —$N(R_y)$—, —S— or —O—;
  $R_8$ and $R_{8'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
  alternatively, $R_8$ and $R_{8'}$, taken together with the carbon atom to which they are attached, may form a $C_{3-6}$ cycloalkyl;
  $R_y$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CH_2OR_{10}$ and —$C(O)OR_{10}$;

wherein $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_7$ and $R_{7'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and wherein

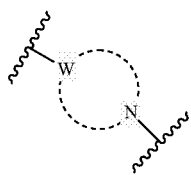

is selected from

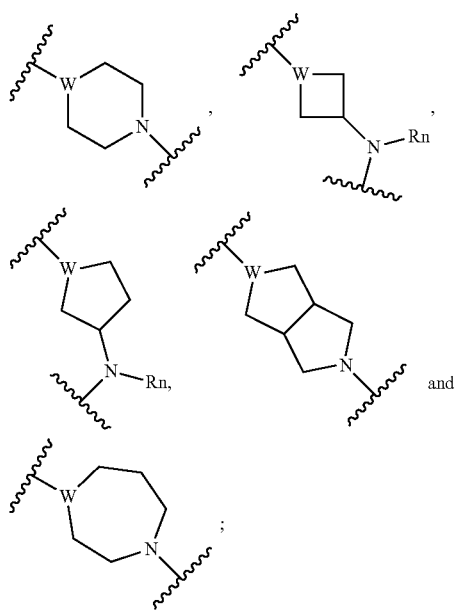

wherein $R_n$ is selected from unsubstituted $C_{1-6}$ alkyl, unsubstituted $C_{2-6}$ alkenyl and unsubstituted $C_{2-6}$ alkynyl;

the alkyl, alkenyl or alkynyl, other than those defined in $R_1$ or $R_2$, if substituted, is substituted with one or more substituent/s selected from —$OR_{13}$, halogen, —CN, haloalkyl, haloalkoxy, —$SR_{13}$, —$S(O)R_{13}$, and —$S(O)_2R_{13}$;

wherein $R_{13}$ is selected from hydrogen, unsubstituted $C_{1-6}$ alkyl, unsubstituted $C_{2-6}$ alkenyl, and unsubstituted $C_{2-6}$ alkynyl;

the aryl, heterocyclyl or cycloalkyl other than those defined in $R_1$ or $R_2$, if substituted, is substituted with one or more substituent/s selected from halogen, —$R_{14}$, —$OR_{14}$, —$NO_2$, —$NR_{14}R_{14'}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$NR_{14}S(O)_2NR_{14'}R_{14''}$ and $C(CH_3)_2OR_{14}$;

additionally, the cycloalkyl or non-aromatic heterocyclyl, other than those defined in $R_1$ or $R_2$, if substituted, may also be substituted with

or =O;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
m is 1, 2 or 3;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
m is 1 or 2;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
n is 0, 1 or 2;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein
p is 0, 1 or 2;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
p is 0 or 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein
W is nitrogen or carbon;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein
W is nitrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein
W is carbon;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is a bond, —C($R_xR_{x'}$)—, C=O, —C(O)O— or —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is a bond;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is —C($R_xR_{x'}$)—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is C=O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is —C(O)O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from substituted or unsubstituted $C_{1-6}$ alkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, substituted or unsubstituted $C_{1-6}$ alkyl, substituted or unsubstituted cycloalkyl, substituted or unsubstituted aryl and substituted or unsubstituted heterocyclyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from substituted or unsubstituted $C_{1-6}$ alkyl, substituted or unsubstituted cycloalkyl, substituted or unsubstituted aryl and substituted or unsubstituted heterocyclyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_9R_{9'}$ and —$CH_2OR_9$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted heterocyclyl, —$NR_9R_{9'}$ and —$CH_2OR_9$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_3$ is selected from substituted or unsubstituted $C_{1-6}$ alkyl, substituted or unsubstituted aryl, substituted or unsubstituted heterocyclyl, —$NR_9R_{9'}$ and —$CH_2OR_9$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_4$ and $R_{4'}$ are independently selected from substituted or unsubstituted $C_{1-6}$ alkyl, substituted or unsubstituted $C_{2-6}$ alkenyl and substituted or unsubstituted $C_{2-6}$ alkynyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_4$ and $R_{4'}$ are unsubstituted $C_{1-6}$ alkyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_4$ and $R_{4'}$, may form together with the carbon atom to which they are attached a cycle of Formula (A) (with "●" marking the carbon atom to which $R_4$ and $R_{4'}$ are attached):

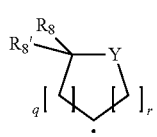

(A)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
q is 0 or 1
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein r is 0, 1 or 2 optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein Y is —$CH_2$—, —$N(R_y)$—, —S— or —O—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CH_2OR_{10}$ and —$C(O)OR_{10}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ are independently selected from hydrogen, substituted or unsubstituted $C_{1-6}$ alkyl, —$CH_2OR_{10}$ and —$C(O)OR_{10}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$ and $R_{7'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$ and $R_{7'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$ and $R_{8'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_8$ and $R_{8'}$, taken together with the carbon atom to which they are attached, may form a $C_{3-6}$ cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$ and $R_{8'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$ and $R_{8'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$ and $R_{8'}$, taken together with the carbon atom to which they are attached, may form a $C_{3-6}$ cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_9$ and $R_{9'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_9$ and $R_{9'}$ are independently selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{10}$ is selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{11}$, $R_{11'}$ and $R_{11''}$ are independently selected from hydrogen and unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{12}$, $R_{12'}$ and $R_{12'''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$ is selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{15}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, —$OR_{15}$, substituted or unsubstituted $C_{1-6}$ alkyl, substituted or unsubstituted $C_{2-6}$ alkenyl and substituted or unsubstituted $C_{2-6}$ alkynyl;

$R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, —$OR_{15}$, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_y$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_y$ is selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_n$ is selected from unsubstituted $C_{1-6}$ alkyl, unsubstituted $C_{2-6}$ alkenyl and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein

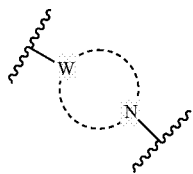

is selected from

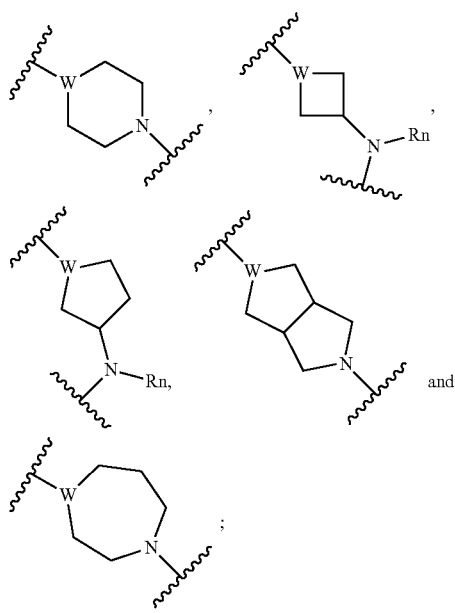

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein

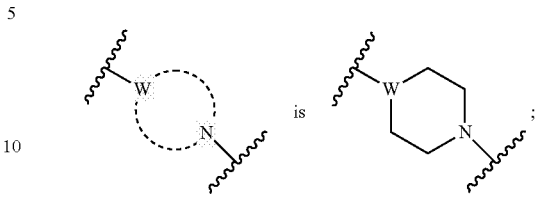

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I), is a compound wherein
m is 1 or 2; and/or
n is 0, 1 or 2; and/or
p is 0, 1 or 2; and/or
W is nitrogen or carbon; and/or
X is a bond, —C($R_x R_{x'}$)—, C=O, —C(O)O— or —O—; and/or
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
wherein
the $C_{1-6}$ alkyl is preferably selected from methyl, ethyl, propyl, butyl, pentyl, hexyl, isopropyl and 2-methylpropyl, more preferably the $C_{1-6}$ alkyl is ethyl or isobutyl; and/or
the $C_{2-6}$-alkenyl is preferably selected from ethylene, propylene, butylene, pentylene and hexylene;
the $C_{2-6}$-alkynyl is preferably selected from ethyne, propyne, butyne, pentyne and hexyne;
and/or
the aryl is selected from phenyl, naphtyl, or anthracene; preferably is napthyl and phenyl; more preferably is phenyl; and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine or thiazole:
and/or
the cycloalkyl is $C_{3-8}$ cycloalkyl like cyclopropyl, cyclobutyl, cyclopentyl, cyclohexyl, cycloheptyl, or cyclooctyl;

preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
wherein
the $C_{1-6}$ alkyl is preferably selected from methyl, ethyl, propyl, butyl, pentyl, hexyl, isopropyl and 2-methylpropyl, more preferably the $C_{1-6}$ alkyl is methyl, ethyl, propyl, isopropyl or isobutyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine, piperidine or morpholine:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl, more preferably the cycloalkyl is cyclopropyl;
and/or
$R_3$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, $-NR_9R_{9'}$ and $-CH_2OR_9$;
wherein
the $C_{1-6}$ alkyl is preferably selected from methyl, ethyl, propyl, butyl, pentyl, hexyl, isopropyl and 2-methylpropyl, more preferably the $C_{1-6}$ alkyl is methyl or ethyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is thiophen, thiazole or furane:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_4$ and $R_{4'}$ are independently selected from substituted or unsubstituted $C_{1-6}$ alkyl, substituted or unsubstituted $C_{2-6}$ alkenyl and substituted or unsubstituted $C_{2-6}$ alkynyl; or
$R_4$ and $R_{4'}$, may form together with the carbon atom to which they are attached a cycle of Formula (A);
wherein
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, $-CH_2OR_{10}$ and $-C(O)OR_{10}$;
wherein
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl, more preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_7$ and $R_{7'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl, more preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_8$ and $R_{8'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl; or $R_8$ and $R_{8'}$ taken together with the carbon atom to which they are attached, may form a $C_{3-6}$ cycloalkyl;

wherein the $C_{1-6}$ alkyl is preferably selected from methyl, ethyl, propyl, butyl, pentyl, hexyl, isopropyl and 2-methylpropyl, more preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the $C_{3-6}$ cycloalkyl is selected from cyclopropyl, cyclobutyl, cyclopentyl and cyclohexyl, more preferably the cycloalkyl is cyclopentyl;

and/or $R_9$ and $R_{9'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

wherein the $C_{1-6}$ alkyl is preferably selected from methyl, ethyl, propyl, butyl, pentyl, hexyl, isopropyl and 2-methylpropyl, more preferably the $C_{1-6}$ alkyl is methyl or ethyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{10}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl, more preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl, more preferably the $C_{1-6}$ alkyl is methyl or ethyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl, more preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{13}$ is selected from hydrogen, unsubstituted $C_{1-6}$ alkyl, unsubstituted $C_{2-6}$ alkenyl, and unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

$R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_{15}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_x$ is selected from halogen, —$OR_{15}$, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_y$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_n$ is selected from unsubstituted $C_{1-6}$ alkyl, unsubstituted $C_{2-6}$ alkenyl and unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is ethyl or isobutyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine or thiazole:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl, ethyl, propyl, isopropyl or isobutyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine, piperidine or morpholine:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl, more preferably the cycloalkyl is cyclopropyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl or ethyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphtyl and anthracene; preferably is napthyl or phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is thiophen, thiazole or furane:
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ and $R_{4'}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ and $R_{5'}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_{6'}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$ and $R_{7'}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$ and $R_{8'}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the $C_{3-6}$ cycloalkyl is selected from cyclopropyl, cyclobutyl, cyclopentyl and cyclohexyl, more preferably the cycloalkyl is cyclopentyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$ and $R_{9'}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl or ethyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl or ethyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11'''}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$ and $R_{12''}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12'''}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14'}$ and $R_{14''}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14'''}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{15}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_n$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{x'}$ as defined in any of the embodiments of the present invention,
the $C_{1-6}$ alkyl is preferably selected from methyl, ethyl, propyl, butyl, pentyl, hexyl, isopropyl and 2-methylpropyl; and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_y$ as defined in any of the embodiments of the present invention,
the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
n is 0, 1 or 2; more preferably n is 0 or 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
m is 1, 2 or 3;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
m is 1 or 2;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
p is 0, 1 or 2; preferably p is 0 or 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
X is a bond, —C(R$_x$R$_{x'}$)—, C=O, —C(O)O— or —O—; preferably, X is a bond, C=O, —C(O)O— or —O—; more preferably X is a bond;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

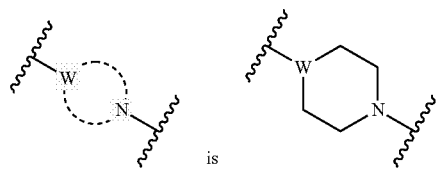

is and W is nitrogen or carbon; preferably W is nitrogen
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I') the compound is a compound, wherein

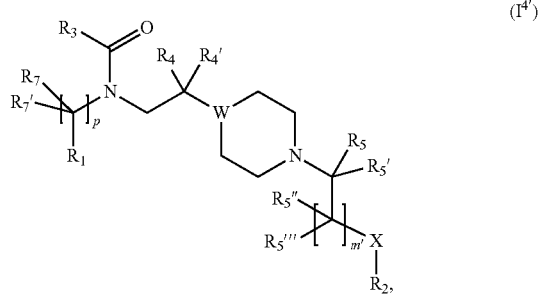

(I4')

wherein
m' is 0 or 1;
p is 0, 1 or 2;
W is nitrogen or carbon;
X is a bond, —C(R$_x$R$_{x'}$)—, C=O, —C(O)O— or —O—;
  wherein R$_x$ is selected from halogen, —OR$_{15}$, substituted or unsubstituted C$_{1-6}$ alkyl, substituted or unsubstituted C$_{2-6}$ alkenyl and substituted or unsubstituted C$_{2-6}$ alkynyl;
R$_{x'}$ is selected from hydrogen, halogen, substituted or unsubstituted C$_{1-6}$ alkyl, substituted or unsubstituted C$_{2-6}$ alkenyl and substituted or unsubstituted C$_{2-6}$ alkynyl;
R$_{15}$ is selected from hydrogen, substituted or unsubstituted C$_{1-6}$ alkyl, substituted or unsubstituted C$_{2-6}$ alkenyl and substituted or unsubstituted C$_{2-6}$ alkynyl;

R$_1$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted monocyclic heterocyclyl and unsubstituted polycyclic heterocyclyl;
  wherein said cycloalkyl, aryl or heterocyclyl in R$_1$ if substituted, is substituted with one or more substituent/s selected from halogen, —R$_{11}$, —OR$_{11}$, —NO$_2$, —NR$_{11}$R$_{11'''}$, NR$_{11}$C(O)R$_{11'}$, —NR$_{11}$S(O)$_2$R$_{11'}$, —S(O)$_2$NR$_{11}$R$_{11'}$, —NR$_{11}$C(O)NR$_{11'}$R$_{11'''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, —NR$_{11}$S(O)$_2$NR$_{11'}$R$_{11''}$ and C(CH$_3$)$_2$OR$_{11}$;
additionally, the cycloalkyl or non-aromatic heterocyclyl in R$_1$, if substituted, may also be substituted with

or =O;
  wherein the alkyl, alkenyl or alkynyl in R$_1$, if substituted, is substituted with one or more substituent/s selected from —OR$_{11}$, halogen, —CN, haloalkyl, haloalkoxy, —SR$_{11}$, —S(O)R$_{11}$, and —S(O)$_2$R$_{11}$;
  wherein R$_{11}$, R$_{11'}$ and R$_{11''}$ are independently selected from hydrogen, unsubstituted C$_{1-6}$ alkyl, unsubstituted C$_{2-6}$ alkenyl and unsubstituted C$_{2-6}$ alkynyl;
  and wherein R$_{11'''}$ is selected from hydrogen, unsubstituted C$_{1-6}$ alkyl, unsubstituted C$_{2-6}$ alkenyl, unsubstituted C$_{2-6}$ alkynyl and -Boc;

R$_2$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in R$_2$, if substituted, is substituted with one or more substituent/s selected from halogen, —R$_{12}$, —OR$_{12}$, —NO$_2$, —NR$_{12}$R$_{12'''}$, NR$_{12}$C(O)R$_{12'}$, —NR$_{12}$S(O)$_2$R$_{12'}$, —S(O)$_2$NR$_{12}$R$_{12'}$, —NR$_{12}$C(O)NR$_{12'}$R$_{12'''}$, —SR$_{12}$, —S(O)R$_{12}$, S(O)$_2$R$_{12}$, —CN, haloalkyl, haloalkoxy, —C(O)OR$_{12}$, —C(O)NR$_{12}$R$_{12'}$, —NR$_{12}$S(O)$_2$NR$_{12'}$R$_{12''}$ and C(CH$_3$)$_2$OR$_{12}$;
additionally, the cycloalkyl or non-aromatic heterocyclyl in R$_2$, if substituted, may also be substituted with

or =O;
  wherein the alkyl, alkenyl or alkynyl in R$_2$, if substituted, is substituted with one or more substituent/s selected from —OR$_{12}$, halogen, —CN, haloalkyl, haloalkoxy, —SR$_{12}$, —S(O)R$_{12}$, and —S(O)$_2$R$_{12}$;
  wherein R$_{12}$, R$_{12'}$ and R$_{12''}$ are independently selected from hydrogen, unsubstituted C$_{1-6}$ alkyl, unsubstituted C$_{2-6}$ alkenyl and unsubstituted C$_{2-6}$ alkynyl;
  and wherein R$_{12'''}$ is selected from hydrogen, unsubstituted C$_{1-6}$ alkyl, unsubstituted C$_{2-6}$ alkenyl, unsubstituted C$_{2-6}$ alkynyl and -Boc;

R$_3$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, —NR$_9$R$_9'$, and —CH$_2$OR$_9$;
  wherein R$_9$ and R$_9'$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;

R$_4$ and R$_4'$ are independently selected from substituted or unsubstituted C$_{1-6}$ alkyl, substituted or unsubstituted C$_{2-6}$ alkenyl and substituted or unsubstituted C$_{2-6}$ alkynyl, alternatively, R$_4$ and R$_4'$, may form together with the carbon atom to which they are attached a cycle of Formula (A) (with "●" marking the carbon atom to which R$_4$ and R$_4'$ are attached):

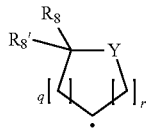

(A)

wherein
q is 0 or 1
r is 0, 1 or 2
Y is —CH$_2$—, —N(R$_y$)—, —S— or —O—;
R$_8$ and R$_8'$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
alternatively, R$_8$ and R$_8'$, taken together with the carbon atom to which they are attached, may form a C$_{3-6}$ cycloalkyl;
R$_y$ is selected from hydrogen, substituted or unsubstituted C$_{1-6}$ alkyl, substituted or unsubstituted C$_{2-6}$ alkenyl and substituted or unsubstituted C$_{2-6}$ alkynyl;

R$_5$ and R$_5'$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, —CH$_2$OR$_{10}$ and —C(O)OR$_{10}$;
  wherein R$_{10}$ is selected from hydrogen, substituted or unsubstituted C$_{1-6}$ alkyl, substituted or unsubstituted C$_{2-6}$ alkenyl and substituted or unsubstituted C$_{2-6}$ alkynyl;

R$_{5''}$ and R$_{5'''}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, —CH$_2$OR$_{10'}$ and —C(O)OR$_{10'}$;
  wherein R$_{10'}$ is selected from hydrogen, substituted or unsubstituted C$_{1-6}$ alkyl, substituted or unsubstituted C$_{2-6}$ alkenyl and substituted or unsubstituted C$_{2-6}$ alkynyl;

R$_7$ and R$_7'$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
the alkyl, alkenyl or alkynyl, other than those defined in R$_1$ or R$_2$, if substituted, is substituted with one or more substituent/s selected from —OR$_{13}$, halogen, —CN, haloalkyl, haloalkoxy, —SR$_{13}$, —S(O)R$_{13}$, and —S(O)$_2$R$_{13}$;
  wherein R$_{13}$ is selected from hydrogen, unsubstituted C$_{1-6}$ alkyl, unsubstituted C$_{2-6}$ alkenyl, and unsubstituted C$_{2-6}$ alkynyl;

the aryl, heterocyclyl or cycloalkyl other than those defined in R$_1$ or R$_2$, if substituted, is substituted with one or more substituent/s selected from halogen, —R$_{14}$, —OR$_{14}$, —NO$_2$, —NR$_{14}$R$_{14'''}$, NR$_{14}$C(O)R$_{14'}$, —NR$_{14}$S(O)$_2$R$_{14'}$, —S(O)$_2$NR$_{14}$R$_{14'}$, —NR$_{14}$C(O)NR$_{14'}$R$_{14''}$, —SR$_{14}$, —S(O)R$_{14}$, S(O)$_2$R$_{14}$, —CN, haloalkyl, haloalkoxy, —C(O)OR$_{14}$, —C(O)NR$_{14}$R$_{14'}$, —NR$_{14}$S(O)$_2$NR$_{14'}$R$_{14''}$ and C(CH$_3$)$_2$OR$_{14}$;

additionally, the cycloalkyl or non-aromatic heterocyclyl, other than those defined in R$_1$ or R$_2$, if substituted, may also be substituted with

or =O;
  wherein R$_{14}$, R$_{14'}$ and R$_{14''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted cycloalkyl and unsubstituted heterocyclyl;
  and wherein R$_{14'''}$ is selected from hydrogen, unsubstituted C$_{1-6}$ alkyl, unsubstituted C$_{2-6}$ alkenyl, unsubstituted C$_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein
X is a bond, C=O, —C(O)O— or —O—; preferably X is a bond or —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
R$_1$ is a substituted or unsubstituted group selected from ethyl, isobutyl, phenyl, pyridine and thiazole; preferably R$_1$ is unsubstituted ethyl, unsubstituted isobutyl, substituted or unsubstituted phenyl, substituted or unsubstituted pyridine and substituted or unsubstituted thiazole.

In another preferred embodiment
R$_1$ is a substituted or unsubstituted group selected from phenyl and pyridine.

In a preferred embodiment
R$_2$ is hydrogen or a substituted or unsubstituted group selected from methyl, ethyl, propyl, isopropyl, isobutyl, cyclopropyl, phenyl, pyridine, piperidine and morpholine.

In a preferred embodiment
R$_2$ is a substituted or unsubstituted group selected from methyl, ethyl, propyl, isopropyl, isobutyl, cyclopropyl, phenyl, pyridine, piperidine and morpholine.

In a preferred embodiment
R$_2$ is a substituted or unsubstituted group selected from ethyl, isopropyl, phenyl and pyridine.

In a preferred embodiment
R$_2$ is a substituted or unsubstituted group selected from isopropyl, phenyl and pyridine.

In a preferred embodiment
$R_3$ is —$CH_2O$—methyl, —NH-ethyl or a substituted or unsubstituted group selected from methyl, ethyl, thiophen, thizaole and furane.

In a preferred embodiment
$R_3$ is —$CH_2O$—methyl, —NH-ethyl or a substituted or unsubstituted ethyl.

In a preferred embodiment
$R_3$ is substituted or unsubstituted ethyl, preferably unsubstituted ethyl.

In a preferred embodiment
$R_4$ and $R_{4'}$ are both substituted or unsubstituted methyl.

In a preferred embodiment
$R_4$ and $R_{4'}$ are both substituted or unsubstituted methyl.

In a preferred embodiment
$R_4$ and $R_{4'}$ form together with the carbon to which they are attached a substituted or unsubstituted cycloalkyl or heterocyclyl selected from tetrahydropyrane, oxetane, piperidine, cyclopropyl and cyclohexyl.

In a preferred embodiment
$R_4$ and $R_{4'}$ form together with the carbon to which they are attached a substituted or unsubstituted cycloalkyl or heterocyclyl selected from tetrahydropyrane, tetrahydrothiopyrane, oxetane, piperidine, cyclobutyl, cyclopropyl and cyclohexyl.

In a preferred embodiment
$R_4$ and $R_{4'}$ form together with the carbon to which they are attached a substituted or unsubstituted cycloalkyl or heterocyclyl selected from tetrahydropyrane and cyclopropyl.

In a preferred embodiment
$R_4$ and $R_{4'}$ form together with the carbon to which they are attached a substituted or unsubstituted cycloalkyl or heterocyclyl selected from tetrahydrothiopyrane and cyclobutyl.

In a preferred embodiment
$R_5$ and $R_{5'}$ are independently selected from hydrogen and a substituted or unsubstituted group selected from methyl, —$CH_2OH$ or —$C(O)OCH_3$.

In a preferred embodiment
$R_5$ and $R_{5'}$ are independently selected from hydrogen and substituted or unsubstituted methyl.

In a preferred embodiment
$R_5$ is selected from hydrogen and a substituted or unsubstituted group selected from methyl, —$CH_2OH$ or —$C(O)OCH_3$, while $R_{5'}$ is hydrogen.

In a preferred embodiment
$R_5$ is selected from hydrogen and a unsubstituted group selected from methyl, —$CH_2OH$ or —$C(O)OCH_3$, while $R_{5'}$ is hydrogen.

In a preferred embodiment
$R_5$ and $R_{5'}$ are both hydrogen.

In a preferred embodiment
$R_6$ and $R_{6'}$ are independently selected from hydrogen, hydroxyl and substituted or unsubstituted methyl.

In a preferred embodiment
$R_6$ and $R_{6'}$ are independently selected from hydrogen, hydroxyl and unsubstituted methyl.

In a preferred embodiment
$R_6$ is hydrogen or substituted or unsubstituted methyl, while and $R_{6'}$ is hydrogen, hydroxyl or substituted or unsubstituted methyl In a preferred embodiment
$R_6$ is hydrogen or unsubstituted methyl, while and $R_{6'}$ is hydrogen, hydroxyl or unsubstituted methyl In a preferred embodiment
$R_6$ and $R_{6'}$ are both hydrogen.

In a preferred embodiment
$R_7$ is selected from hydrogen and substituted or unsubstituted methyl, while $R_{7'}$ is hydrogen.

In a preferred embodiment
$R_7$ is selected from hydrogen and unsubstituted methyl, while $R_{7'}$ is hydrogen.

In a preferred embodiment
$R_7$ and $R_{7'}$ are both hydrogen.

In a preferred embodiment
$R_8$ and $R_{8'}$ are independently selected from hydrogen or substituted or unsubstituted methyl.

In a preferred embodiment
$R_8$ and $R_{8'}$ are independently selected from hydrogen and unsubstituted methyl.

In a preferred embodiment
$R_8$ and $R_{8'}$ are both hydrogen.

In a preferred embodiment
$R_8$ and $R_{8'}$ are both substituted or unsubstituted methyl.

In a preferred embodiment
$R_8$ and $R_{8'}$ are both unsubstituted methyl.

In a preferred embodiment
$R_8$ and $R_{8'}$ form together with the carbon to which they are attached a substituted or unsubstituted cyclopentyl.

In a preferred embodiment
$R_8$ and $R_{8'}$ form together with the carbon to which they are attached a unsubstituted cyclopentyl.

In a preferred embodiment
$R_9$ is selected from hydrogen and substituted or unsubstituted methyl, while $R_{9'}$ is substituted or unsubstituted ethyl.

In a preferred embodiment
$R_9$ is selected from hydrogen and substituted or unsubstituted methyl.

In a preferred embodiment
$R_9$ is selected from hydrogen and unsubstituted methyl.

In a preferred embodiment
$R_9$ is hydrogen while $R_{9'}$ is substituted or unsubstituted ethyl.

In a preferred embodiment
$R_9$ is hydrogen while $R_{9'}$ is unsubstituted ethyl.

In a preferred embodiment
$R_{10}$ is selected from hydrogen and substituted or unsubstituted methyl.

In a preferred embodiment
$R_{10}$ is selected from hydrogen and unsubstituted methyl.

In a preferred embodiment
$R_{11}$ is selected from hydrogen, substituted or unsubstituted methyl and substituted or unsubstituted ethyl.

In a preferred embodiment
$R_{11}$ is selected from hydrogen, unsubstituted methyl and unsubstituted ethyl.

In a preferred embodiment
$R_{12}$ is selected from hydrogen and substituted or unsubstituted methyl.

In a preferred embodiment
$R_{12}$ is selected from hydrogen and unsubstituted methyl.

In a preferred embodiment
$R_{15}$ is hydrogen.

In a preferred embodiment
X is a bond, C=O, —C(O)O— or —O—;

In a preferred embodiment
X is a bond or —O—;

In a preferred embodiment
Y is —$CH_2$—, —N($R_y$)— or —O—;

In a preferred embodiment
Y is —$CH_2$— or —O—;

In a preferred embodiment
Y is —S—;

In a preferred embodiment
$R_y$ is selected from hydrogen and substituted or unsubstituted methyl.

In a preferred embodiment
R$_y$ is selected from hydrogen and unsubstituted methyl.
In another preferred embodiment
n is 0, 1 or 2;
In another preferred embodiment
m is 1 or 2;
In another preferred embodiment
m is 1, 2 or 3;
In another preferred embodiment
p is 0 or 1;
In another preferred embodiment
q is 0 or 1;
In another preferred embodiment
r is 0, 1 or 2;
In another preferred embodiment
Y is —O—, q is 1 and r is 2;
In another preferred embodiment
Y is —CH$_2$—, q is 1 and r is 2;
In another preferred embodiment
Y is —CH$_2$—, q is 0 and r is 0;
In another preferred embodiment
Y is —O—, q is 0 and r is 1;
In another preferred embodiment
Y is —NRy-, q is 1 and r is 2, while Ry is hydrogen or substituted or unsubstituted methyl.
In another preferred embodiment
Y is —NRy-, q is 1 and r is 2, while Ry is hydrogen or unsubstituted methyl.
In an particular embodiment
the halogen is fluorine or chlorine.
In a preferred further embodiment, the compounds of the general Formula (I) are selected from

| EX | Chemical name |
|---|---|
| 1 | N-((4-(4-benzylpiperazin-1-yl)tetrahydro-2H-pyran-4-yl)methyl)-N-phenylpropionamide |
| 2 | N-((4-(4-benzylpiperazin-1-yl)tetrahydro-2H-pyran-4-yl)methyl)-N-(2-chlorophenyl)propionamide |
| 3 | N-((4-(4-benzylpiperazin-1-yl)tetrahydro-2H-pyran-4-yl)methyl)-N-(2-methoxyphenyl)propionamide |
| 4 | N-((4-(4-benzylpiperazin-1-yl)tetrahydro-2H-pyran-4-yl)methyl)-N-(2-fluorophenyl)propionamide |
| 5 | N-((4-(4-benzylpiperazin-1-yl)tetrahydro-2H-pyran-4-yl)methyl)-N-(3-fluorophenyl)propionamide |
| 6 | N-((4-(4-benzylpiperazin-1-yl)tetrahydro-2H-pyran-4-yl)methyl)-N-(5-fluoropyridin-2-yl)propionamide |
| 7 | N-((4-(4-benzylpiperazin-1-yl)tetrahydro-2H-pyran-4-yl)methyl)-N-(5-(trifluoromethyl)pyridin-2-yl)propionamide |
| 8 | N-((4-(4-benzylpiperazin-1-yl)tetrahydro-2H-pyran-4-yl)methyl)-N-(4-(trifluoromethyl)pyridin-2-yl)propionamide |
| 9 | N-((4-(4-benzylpiperazin-1-yl)tetrahydro-2H-pyran-4-yl)methyl)-N-(5-(trifluoromethyl)pyridin-3-yl)propionamide |
| 10 | N-((4-(4-benzylpiperazin-1-yl)tetrahydro-2H-pyran-4-yl)methyl)-N-(5-fluoropyridin-3-yl)propionamide |
| 11 | N-((4-(4-benzylpiperazin-1-yl)tetrahydro-2H-pyran-4-yl)methyl)-N-(6-(trifluoromethyl)pyridin-3-yl)propionamide |
| 12 | N-((4-(4-benzylpiperazin-1-yl)tetrahydro-2H-pyran-4-yl)methyl)-N-(pyridin-4-yl)propionamide |
| 13 | N-((4-(4-benzylpiperazin-1-yl)tetrahydro-2H-pyran-4-yl)methyl)-N-(1-phenylethyl)propionamide |
| 14 | N-benzyl-N-((4-(4-benzylpiperazin-1-yl)tetrahydro-2H-pyran-4-yl)methyl)propionamide |
| 15 | N-((4-(4-benzylpiperazin-1-yl)tetrahydro-2H-pyran-4-yl)methyl)-N-isobutylpropionamide |
| 16 | N-((4-(4-benzylpiperazin-1-yl)-2,2-dimethyltetrahydro-2H-pyran-4-yl)methyl)-N-(pyridin-2-yl)propionamide |
| 17 | N-((9-(4-benzylpiperazin-1-yl)-6-oxaspiro[4.5]decan-9-yl)methyl)-N-(pyridin-2-yl)propionamide |
| 18 | N-((3-(4-benzylpiperazin-1-yl)oxetan-3-yl)methyl)-N-phenylpropionamide |
| 19 | N-((1-(4-benzylpiperazin-1-yl)cyclohexyl)methyl)-N-phenylpropionamide |
| 20 | N-((1-(4-phenethylpiperazin-1-yl)cyclohexyl)methyl)-N-phenylpropionamide |
| 21 | N-((1-(4-phenethylpiperazin-1-yl)cyclohexyl)methyl)-N-(pyridin-2-yl)propionamide |
| 22 | N-((4-(4-benzylpiperazin-1-yl)-1-methylpiperidin-4-yl)methyl)-N-phenylpropionamide |
| 23 | N-((1-methyl-4-(4-phenethylpiperazin-1-yl)piperidin-4-yl)methyl)-N-phenylpropionamide |
| 24 | N-((4-(4-benzylpiperazin-1-yl)-1-methylpiperidin-4-yl)methyl)-N-(4-ethoxyphenyl)propionamide |
| 25 | N-(2-(4-benzylpiperazin-1-yl)-2-methylpropyl)-N-phenylpropionamide |
| 26 | N-(2-methyl-2-(4-phenethylpiperazin-1-yl)propyl)-N-phenylpropionamide |
| 27 | N-(2-methyl-2-(4-phenethylpiperazin-1-yl)propyl)-N-(pyridin-2-yl)propionamide |
| 28 | N-((1-(4-benzylpiperazin-1-yl)cyclopropyl)methyl)-N-phenylpropionamide |
| 29 | N-((1-(4-phenethylpiperazin-1-yl)cyclopropyl)methyl)-N-phenylpropionamide |
| 30 | N-((1-(4-benzylpiperazin-1-yl)cyclopropyl)methyl)-N-(pyridin-2-yl)propionamide |
| 31 | N-((1-(4-benzylpiperazin-1-yl)cyclopropyl)methyl)-N-(pyridin-4-yl)propionamide |
| 32 | N-((1-(4-benzylpiperazin-1-yl)cyclopropyl)methyl)-N-(2-methoxyphenyl)propionamide |
| 33 | N-((1-(4-benzylpiperazin-1-yl)cyclopropyl)methyl)-N-(5-fluoropyridin-2-yl)propionamide |
| 34 | N-((1-(4-benzylpiperazin-1-yl)cyclopropyl)methyl)-N-(2-chlorophenyl)propionamide |
| 35 | N-((1-(4-benzylpiperazin-1-yl)cyclopropyl)methyl)-N-(2-fluorophenyl)propionamide |
| 36 | N-((1-(4-benzylpiperazin-1-yl)cyclopropyl)methyl)-N-(pyridin-3-yl)propionamide |
| 37 | N-((4-(4-benzylpiperazin-1-yl)tetrahydro-2H-pyran-4-yl)methyl)-2-methoxy-N-phenylacetamide |
| 38 | N-((4-(4-benzylpiperazin-1-yl)tetrahydro-2H-pyran-4-yl)methyl)-N-(pyridin-2-yl)thiophene-2-carboxamide |
| 39 | N-((4-(4-isobutylpiperazin-1-yl)tetrahydro-2H-pyran-4-yl)methyl)-2-methoxy-N-(6-(trifluoromethyl)pyridin-2-yl)acetamide |

-continued

| EX | Chemical name |
|---|---|
| 40 | N-((4-(4-isobutylpiperazin-1-yl)tetrahydro-2H-pyran-4-yl)methyl)-N-(6-(trifluoromethyl)pyridin-2-yl)acetamide |
| 41 | N-((4-(4-benzylpiperazin-1-yl)-1-methylpiperidin-4-yl)methyl)-N-phenylthiazole-2-carboxamide |
| 42 | N-((4-(4-benzylpiperazin-1-yl)-1-methylpiperidin-4-yl)methyl)-N-phenylthiophene-2-carboxamide |
| 43 | N-(2-(4-benzylpiperazin-1-yl)-2-methylpropyl)-2-methoxy-N-phenylacetamide |
| 44 | N-(2-methyl-2-(4-phenethylpiperazin-1-yl)propyl)-N-phenylfuran-2-carboxamide |
| 45 | 3-ethyl-1-(2-methyl-2-(4-phenethylpiperazin-1-yl)propyl)-1-phenylurea |
| 46 | N-((1-(4-benzylpiperazin-1-yl)cyclopropyl)methyl)-2-methoxy-N-phenylacetamide |
| 47 | N-((1-(4-benzylpiperazin-1-yl)cyclopropyl)methyl)-N-(pyridin-2-yl)thiophene-2-carboxamide |
| 48 | 1-(2-(4-benzylpiperazin-1-yl)-2-methylpropyl)-3-ethyl-1-phenylurea |
| 49 | 1-((4-(4-benzylpiperazin-1-yl)tetrahydro-2H-pyran-4-yl)methyl)-3-ethyl-1-(pyridin-2-yl)urea |
| 50 | 3-ethyl-1-((1-(4-phenethylpiperazin-1-yl)cyclohexyl)methyl)-1-phenylurea |
| 51 | 2-methoxy-N-(2-methyl-2-(4-phenethylpiperazin-1-yl)propyl)-N-phenylacetamide |
| 52 | 1-((1-(4-benzylpiperazin-1-yl)cyclopropyl)methyl)-3-ethyl-1-phenylurea |
| 53 | 3-ethyl-1-((1-(4-phenethylpiperazin-1-yl)cyclopropyl)methyl)-1-phenylurea |
| 54 | N-((4-(4-benzylpiperazin-1-yl)tetrahydro-2H-pyran-4-yl)methyl)-N-(2-hydroxyphenyl)propionamide |
| 55 | N-((1-(4-benzylpiperazin-1-yl)cyclopropyl)methyl)-N-(2-hydroxyphenyl)propionamide |
| 56 | N-((4-(4-benzylpiperazin-1-yl)tetrahydro-2H-pyran-4-yl)methyl)-N-(pyridin-2-yl)propionamide |
| 57 | N-((4-(4-benzylpiperazin-1-yl)tetrahydro-2H-pyran-4-yl)methyl)-N-(3-cyanophenyl)propionamide |
| 58 | N-((4-(4-benzylpiperazin-1-yl)tetrahydro-2H-pyran-4-yl)methyl)-N-(3-cyanopyridin-2-yl)propionamide |
| 59 | N-((4-(4-benzylpiperazin-1-yl)tetrahydro-2H-pyran-4-yl)methyl)-N-(3-(trifluoromethyl)pyridin-2-yl)propionamide |
| 60 | N-((4-(4-benzylpiperazin-1-yl)tetrahydro-2H-pyran-4-yl)methyl)-N-(3-cyano-6-(trifluoromethyl)pyridin-2-yl)propionamide |
| 61 | N-((4-(4-benzylpiperazin-1-yl)tetrahydro-2H-pyran-4-yl)methyl)-N-(6-cyano-5-fluoropyridin-2-yl)propionamide |
| 62 | N-(3-cyanopyridin-2-yl)-N-((4-(4-isobutylpiperazin-1-yl)tetrahydro-2H-pyran-4-yl)methyl)propionamide |
| 63 | N-((4-(4-isobutylpiperazin-1-yl)tetrahydro-2H-pyran-4-yl)methyl)-N-(3-(trifluoromethyl)pyridin-2-yl)propionamide |
| 64 | N-((4-(4-benzylpiperazin-1-yl)-2,2-dimethyltetrahydro-2H-pyran-4-yl)methyl)-N-(3-fluoropyridin-2-yl)propionamide |
| 65 | N-((4-(4-benzylpiperazin-1-yl)-2,2-dimethyltetrahydro-2H-pyran-4-yl)methyl)-N-(6-cyanopyridin-2-yl)propionamide |
| 66 | N-((4-(4-benzylpiperazin-1-yl)-2,2-dimethyltetrahydro-2H-pyran-4-yl)methyl)-N-(6-(trifluoromethyl)pyridin-2-yl)propionamide |
| 67 | N-((4-(4-benzylpiperazin-1-yl)-2,2-dimethyltetrahydro-2H-pyran-4-yl)methyl)-N-(3-(trifluoromethyl)pyridin-2-yl)propionamide |
| 68 | N-((4-(4-benzylpiperazin-1-yl)-2,2-dimethyltetrahydro-2H-pyran-4-yl)methyl)-N-(3-cyanopyridin-2-yl)propionamide |
| 69 | N-(2-(4-(2-fluorophenethyl)piperazin-1-yl)-2-methylpropyl)-N-(3-fluoropyridin-2-yl)propionamide |
| 70 | N-(2-(4-(2-(3-fluoropyridin-2-yl)ethyl)piperazin-1-yl)-2-methylpropyl)-N-(pyridin-2-yl)propionamide |
| 71 | N-(2-fluorophenyl)-N-(2-(4-(2-(3-fluoropyridin-2-yl)ethyl)piperazin-1-yl)-2-methylpropyl)propionamide |
| 72 | N-(2-(4-(2-(3-fluoropyridin-2-yl)ethyl)piperazin-1-yl)-2-methylpropyl)-N-phenylpropionamide |
| 73 | N-(3-fluoropyridin-2-yl)-N-(2-(4-(2-isopropoxyethyl)piperazin-1-yl)-2-methylpropyl)propionamide |
| 74 | N-(3-fluoropyridin-2-yl)-N-(2-(4-isobutylpiperazin-1-yl)-2-methylpropyl)propionamide |
| 75 | N-(3-fluoropyridin-2-yl)-N-(2-(4-isopentylpiperazin-1-yl)-2-methylpropyl)propionamide |
| 76 | N-((1-(4-benzylpiperazin-1-yl)cyclopropyl)methyl)-N-(2-(trifluoromethyl)pyridin-3-yl)propionamide |
| 77 | N-((1-(4-benzylpiperazin-1-yl)cyclopropyl)methyl)-N-(3-fluoropyridin-2-yl)propionamide |
| 78 | N-((1-(4-benzylpiperazin-1-yl)cyclopropyl)methyl)-N-(4-(trifluoromethyl)pyridin-3-yl)propionamide |
| 79 | N-((1-(4-benzylpiperazin-1-yl)cyclopropyl)methyl)-N-(3-(trifluoromethyl)pyridin-2-yl)propionamide |
| 80 | N-((1-(4-benzylpiperazin-1-yl)cyclopropyl)methyl)-N-(3-cyanopyridin-2-yl)propionamide |
| 81 | N-((4-(4-benzylpiperazin-1-yl)tetrahydro-2H-pyran-4-yl)methyl)-N-(4-fluorophenyl)propionamide |
| 82 | N-((4-(4-benzylpiperazin-1-yl)tetrahydro-2H-pyran-4-yl)methyl)-N-(3-fluoropyridin-2-yl)propionamide |
| 83 | N-((4-(4-benzylpiperazin-1-yl)tetrahydro-2H-pyran-4-yl)methyl)-N-(6-(trifluoromethyl)pyridin-2-yl)propionamide |
| 84 | N-((4-(4-benzylpiperazin-1-yl)tetrahydro-2H-pyran-4-yl)methyl)-N-(6-cyanopyridin-2-yl)propionamide |

-continued

| EX | Chemical name |
|---|---|
| 85 | N-(6-cyanopyridin-2-yl)-N-((4-(4-isobutylpiperazin-1-yl)tetrahydro-2H-pyran-4-yl)methyl)propionamide |
| 86 | N-(6-cyanopyridin-2-yl)-N-((4-(4-isopentylpiperazin-1-yl)tetrahydro-2H-pyran-4-yl)methyl)propionamide |
| 87 | N-(6-cyanopyridin-2-yl)-N-((4-(4-isobutylpiperazin-1-yl)-2,2-dimethyltetrahydro-2H-pyran-4-yl)methyl)propionamide |
| 88 | N-(6-cyanopyridin-2-yl)-N-((4-(4-isopentylpiperazin-1-yl)-2,2-dimethyltetrahydro-2H-pyran-4-yl)methyl)propionamide |
| 89 | N-((9-(4-benzylpiperazin-1-yl)-6-oxaspiro[4.5]decan-9-yl)methyl)-N-(6-(trifluoromethyl)pyridin-2-yl)propionamide |
| 90 | N-((4-(1-benzylpiperidin-4-yl)tetrahydro-2H-pyran-4-yl)methyl)-N-(6-(trifluoromethyl)pyridin-2-yl)propionamide |
| 91 | N-((1-(4-benzylpiperazin-1-yl)cyclopropyl)methyl)-N-(6-(trifluoromethyl)pyridin-2-yl)propionamide |
| 92 | N-((1-(4-benzylpiperazin-1-yl)cyclopropyl)methyl)-N-(thiazol-2-yl)propionamide |
| 93 | N-((1-(4-benzylpiperazin-1-yl)cyclopropyl)methyl)-N-(5-fluoropyridin-3-yl)propionamide |
| 94 | N-((1-(4-benzylpiperazin-1-yl)cyclopropyl)methyl)-N-(5-(trifluoromethyl)pyridin-2-yl)propionamide |
| 95 | N-((1-(4-benzylpiperazin-1-yl)cyclopropyl)methyl)-N-(3-fluorophenyl)propionamide |
| 96 | N-((1-(4-benzylpiperazin-1-yl)cyclopropyl)methyl)-N-(3-cyanophenyl)propionamide |
| 97 | N-((1-(4-benzylpiperazin-1-yl)cyclopropyl)methyl)-N-(6-cyanopyridin-2-yl)propionamide |
| 98 | N-benzyl-N-((1-(4-benzylpiperazin-1-yl)cyclopropyl)methyl)propionamide |
| 99 | N-((4-4-benzylpiperazin-1-yl)tetrahydro-2H-pyran-4-yl)methyl)-N-ethylpropionamide |
| 100 | N-((4-(4-(3-fluorobenzyl)piperazin-1-yl)tetrahydro-2H-pyran-4-yl)methyl)-N-phenylpropionamide |
| 101 | N-phenyl-N-((4-(4-(pyridin-3-ylmethyl)piperazin-1-yl)tetrahydro-2H-pyran-4-yl)methyl)propionamide |
| 102 | N-phenyl-N-((4-(4-(pyridin-2-ylmethyl)piperazin-1-yl)tetrahydro-2H-pyran-4-yl)methyl)propionamide |
| 103 | N-phenyl-N-((4-(4-((6-(trifluoromethyl)pyridin-3-yl)methyl)piperazin-1-yl)tetrahydro-2H-pyran-4-yl)methyl)propionamide |
| 104 | N-((4-(4-(2-fluorobenzyl)piperazin-1-yl)tetrahydro-2H-pyran-4-yl)methyl)-N-phenylpropionamide |
| 105 | N-((4-(4-(4-fluorobenzyl)piperazin-1-yl)tetrahydro-2H-pyran-4-yl)methyl)-N-phenylpropionamide |
| 106 | N-phenyl-N-((4-(4-(pyridin-4-ylmethyl)piperazin-1-yl)tetrahydro-2H-pyran-4-yl)methyl)propionamide |
| 107 | N-((4-(4-((5-fluoropyridin-3-yl)methyl)piperazin-1-yl)tetrahydro-2H-pyran-4-yl)methyl)-N-phenylpropionamide |
| 108 | N-((4-(4-(3,4-difluorobenzyl)piperazin-1-yl)tetrahydro-2H-pyran-4-yl)methyl)-N-phenylpropionamide |
| 109 | N-((4-(4-((6-methoxypyridin-3-yl)methyl)piperazin-1-yl)tetrahydro-2H-pyran-4-yl)methyl)-N-phenylpropionamide |
| 110 | N-((4-(4-(3-fluorobenzyl)piperazin-1-yl)tetrahydro-2H-pyran-4-yl)methyl)-N-(pyridin-2-yl)propionamide |
| 111 | N-((4-(4-(4-fluorobenzyl)piperazin-1-yl)tetrahydro-2H-pyran-4-yl)methyl)-N-(pyridin-2-yl)propionamide |
| 112 | N-((4-(4-(1-methoxypropan-2-yl)piperazin-1-yl)tetrahydro-2H-pyran-4-yl)methyl)-N-(6-(trifluoromethyl)pyridin-2-yl)propionamide |
| 113 | N-phenyl-N-((1-(4-((6-(trifluoromethyl)pyridin-3-yl)methyl)piperazin-1-yl)cyclopropyl)methyl)propionamide |
| 114 | N-phenyl-N-((1-(4-(pyridin-2-ylmethyl)piperazin-1-yl)cyclopropyl)methyl)propionamide |
| 115 | N-((1-(4-(4-acetamidobenzyl)piperazin-1-yl)cyclopropyl)methyl)-N-phenylpropionamide |
| 116 | N-((1-(4-(3-fluorobenzyl)piperazin-1-yl)cyclopropyl)methyl)-N-phenylpropionamide |
| 117 | N-((1-(4-(3,4-difluorobenzyl)piperazin-1-yl)cyclopropyl)methyl)-N-phenylpropionamide |
| 118 | N-((1-(4-(2-fluorobenzyl)piperazin-1-yl)cyclopropyl)methyl)-N-phenylpropionamide |
| 119 | N-phenyl-N-((1-(4-(pyridin-3-ylmethyl)piperazin-1-yl)cyclopropyl)methyl)propionamide |
| 120 | N-((1-(4-((3-fluoropyridin-2-yl)methyl)piperazin-1-yl)cyclopropyl)methyl)-N-phenylpropionamide |
| 121 | N-((1-(4-((5-fluoropyridin-2-yl)methyl)piperazin-1-yl)cyclopropyl)methyl)-N-phenylpropionamide |
| 122 | N-((1-(4-((5-fluoropyridin-3-yl)methyl)piperazin-1-yl)cyclopropyl)methyl)-N-phenylpropionamide |
| 123 | N-((1-(4-isobutylpiperazin-1-yl)cyclopropyl)methyl)-N-(6-(trifluoromethyl)pyridin-2-yl)propionamide |
| 124 | N-((1-(4-isopentylpiperazin-1-yl)cyclopropyl)methyl)-N-(6-(trifluoromethyl)pyridin-2-yl)propionamide |
| 125 | N-methyl-4-((4-(4-((N-phenylpropionamido)methyl)tetrahydro-2H-pyran-4-yl)piperazin-1-yl)methyl)benzamide |
| 126 | N-((4-(4-phenethylpiperazin-1-yl)tetrahydro-2H-pyran-4-yl)methyl)-N-phenylpropionamide |
| 127 | N-((4-(4-(2-oxo-2-(piperidin-1-yl)ethyl)piperazin-1-yl)tetrahydro-2H-pyran-4-yl)methyl)-N-phenylpropionamide |
| 128 | N-((4-(4-phenethylpiperazin-1-yl)tetrahydro-2H-pyran-4-yl)methyl)-N-(6-(trifluoromethyl)pyridin-2-yl)propionamide |
| 129 | N-((3-(4-phenethylpiperazin-1-yl)oxetan-3-yl)methyl)-N-phenylpropionamide |
| 130 | N-((1-(4-(4-fluorobenzyl)piperazin-1-yl)cyclopropyl)methyl)-N-phenylpropionamide |
| 131 | N-methyl-4-((4-(1-((N-phenylpropionamido)methyl)cyclopropyl)piperazin-1-yl)methyl)benzamide |

| EX | Chemical name |
|---|---|
| 132 | N-((1-(4-(2-oxo-2-(piperidin-1-yl)ethyl)piperazin-1-yl)cyclopropyl)methyl)-N-phenylpropionamide |
| 133 | N-((4-(4-(1-phenylethyl)piperazin-1-yl)tetrahydro-2H-pyran-4-yl)methyl)-N-(6-(trifluoromethyl)pyridin-2-yl)propionamide |
| 134 | N-((4-(4-(1-phenylethyl)piperazin-1-yl)tetrahydro-2H-pyran-4-yl)methyl)-N-(pyridin-2-yl)propionamide |
| 135 | N-((4-(4-isobutylpiperazin-1-yl)tetrahydro-2H-pyran-4-yl)methyl)-N-phenylpropionamide |
| 136 | N-((4-(4-isobutylpiperazin-1-yl)tetrahydro-2H-pyran-4-yl)methyl)-N-(6-(trifluoromethyl)pyridin-2-yl)propionamide |
| 137 | N-((4-(4-isopentylpiperazin-1-yl)tetrahydro-2H-pyran-4-yl)methyl)-N-(6-(trifluoromethyl)pyridin-2-yl)propionamide |
| 138 | N-((4-(4-(2-isopropoxyethyl)piperazin-1-yl)tetrahydro-2H-pyran-4-yl)methyl)-N-(6-(trifluoromethyl)pyridin-2-yl)propionamide |
| 139 | N-((4-(4-sec-butylpiperazin-1-yl)tetrahydro-2H-pyran-4-yl)methyl)-N-(6-(trifluoromethyl)pyridin-2-yl)propionamide |
| 140 | N-((4-(4-(2-ethoxyethyl)piperazin-1-yl)tetrahydro-2H-pyran-4-yl)methyl)-N-(6-(trifluoromethyl)pyridin-2-yl)propionamide |
| 141 | N-((4-(4-(2-(trifluoromethoxy)ethyl)piperazin-1-yl)tetrahydro-2H-pyran-4-yl)methyl)-N-(6-(trifluoromethyl)pyridin-2-yl)propionamide |
| 142 | N-((4-(4-(2-isobutoxyethyl)piperazin-1-yl)tetrahydro-2H-pyran-4-yl)methyl)-N-(6-(trifluoromethyl)pyridin-2-yl)propionamide |
| 143 | N-((4-(4-(2-(2,2,2-trifluoroethoxy)ethyl)piperazin-1-yl)tetrahydro-2H-pyran-4-yl)methyl)-N-(6-(trifluoromethyl)pyridin-2-yl)propionamide |
| 144 | ethyl 3-(4-(4-((N-(6-(trifluoromethyl)pyridin-2-yl)propionamido)methyl)tetrahydro-2H-pyran-4-yl)piperazin-1-yl)propanoate |
| 145 | N-((4-(4-(3-methoxypropyl)piperazin-1-yl)tetrahydro-2H-pyran-4-yl)methyl)-N-(6-(trifluoromethyl)pyridin-2-yl)propionamide |
| 146 | N-((4-(4-propylpiperazin-1-yl)tetrahydro-2H-pyran-4-yl)methyl)-N-(6-(trifluoromethyl)pyridin-2-yl)propionamide |
| 147 | N-((4-(4-butylpiperazin-1-yl)tetrahydro-2H-pyran-4-yl)methyl)-N-(6-(trifluoromethyl)pyridin-2-yl)propionamide |
| 148 | N-((4-(4-(2-hydroxyethyl)piperazin-1-yl)tetrahydro-2H-pyran-4-yl)methyl)-N-(6-(trifluoromethyl)pyridin-2-yl)propionamide |
| 149 | N-((4-(4-(2-phenoxyethyl)piperazin-1-yl)tetrahydro-2H-pyran-4-yl)methyl)-N-(6-(trifluoromethyl)pyridin-2-yl)propionamide |
| 150 | N-((4-(4-(3-ethoxypropyl)piperazin-1-yl)tetrahydro-2H-pyran-4-yl)methyl)-N-(6-(trifluoromethyl)pyridin-2-yl)propionamide |
| 151 | N-((4-(4-isobutylpiperazin-1-yl)tetrahydro-2H-pyran-4-yl)methyl)-N-(pyridin-2-yl)propionamide |
| 152 | N-((4-(4-(2-isopropoxyethyl)piperazin-1-yl)tetrahydro-2H-pyran-4-yl)methyl)-N-(pyridin-2-yl)propionamide |
| 153 | N-((4-(4-isopentylpiperazin-1-yl)tetrahydro-2H-pyran-4-yl)methyl)-N-(pyridin-2-yl)propionamide |
| 154 | N-((4-(4-sec-butylpiperazin-1-yl)tetrahydro-2H-pyran-4-yl)methyl)-N-(pyridin-2-yl)propionamide |
| 155 | N-(3-fluoropyridin-2-yl)-N-((4-(4-isopentylpiperazin-1-yl)tetrahydro-2H-pyran-4-yl)methyl)propionamide |
| 156 | N-((4-(4-(2-ethoxyethyl)piperazin-1-yl)tetrahydro-2H-pyran-4-yl)methyl)-N-(3-fluoropyridin-2-yl)propionamide |
| 157 | N-(3-fluoropyridin-2-yl)-N-((4-(4-(2-isopropoxyethyl)piperazin-1-yl)tetrahydro-2H-pyran-4-yl)methyl)propionamide |
| 158 | N-(3-fluoropyridin-2-yl)-N-((4-(4-isobutylpiperazin-1-yl)tetrahydro-2H-pyran-4-yl)methyl)propionamide |
| 159 | N-((4-(4-isopentylpiperazin-1-yl)-2,2-dimethyltetrahydro-2H-pyran-4-yl)methyl)-N-(6-(trifluoromethyl)pyridin-2-yl)propionamide |
| 160 | N-((4-(4-isobutylpiperazin-1-yl)-2,2-dimethyltetrahydro-2H-pyran-4-yl)methyl)-N-(6-(trifluoromethyl)pyridin-2-yl)propionamide |
| 161 | N-((4-(4-(2-isopropoxyethyl)piperazin-1-yl)-2,2-dimethyltetrahydro-2H-pyran-4-yl)methyl)-N-(6-(trifluoromethyl)pyridin-2-yl)propionamide |
| 162 | N-((4-(4-sec-butylpiperazin-1-yl)-2,2-dimethyltetrahydro-2H-pyran-4-yl)methyl)-N-(6-(trifluoromethyl)pyridin-2-yl)propionamide |
| 163 | N-((4-(4-(2-isopropoxyethyl)piperazin-1-yl)-2,2-dimethyltetrahydro-2H-pyran-4-yl)methyl)-N-(pyridin-2-yl)propionamide |
| 164 | N-((4-(4-isopentylpiperazin-1-yl)-2,2-dimethyltetrahydro-2H-pyran-4-yl)methyl)-N-(pyridin-2-yl)propionamide |
| 165 | N-((4-(4-(2-ethoxyethyl)piperazin-1-yl)-2,2-dimethyltetrahydro-2H-pyran-4-yl)methyl)-N-(pyridin-2-yl)propionamide |
| 166 | N-((4-(4-isobutylpiperazin-1-yl)-2,2-dimethyltetrahydro-2H-pyran-4-yl)methyl)-N-(pyridin-2-yl)propionamide |
| 167 | N-(3-fluoropyridin-2-yl)-N-((4-(4-(2-isopropoxyethyl)piperazin-1-yl)-2,2-dimethyltetrahydro-2H-pyran-4-yl)methyl)propionamide |
| 168 | N-(3-fluoropyridin-2-yl)-N-((4-(4-isopentylpiperazin-1-yl)-2,2-dimethyltetrahydro-2H-pyran-4-yl)methyl)propionamide |
| 169 | N-((4-(4-(2-ethoxyethyl)piperazin-1-yl)-2,2-dimethyltetrahydro-2H-pyran-4-yl)methyl)-N-(3-fluoropyridin-2-yl)propionamide |
| 170 | N-(3-fluoropyridin-2-yl)-N-((4-(4-isobutylpiperazin-1-yl)-2,2-dimethyltetrahydro-2H-pyran-4-yl)methyl)propionamide |

| EX | Chemical name |
|---|---|
| 171 | N-(6-cyanopyridin-2-yl)-N-((4-(4-(2-ethoxyethyl)piperazin-1-yl)-2,2-dimethyltetrahydro-2H-pyran-4-yl)methyl)propionamide |
| 172 | N-(6-cyanopyridin-2-yl)-N-((4-(4-(2-isopropoxyethyl)piperazin-1-yl)-2,2-dimethyltetrahydro-2H-pyran-4-yl)methyl)propionamide |
| 173 | N-((9-(4-isopentylpiperazin-1-yl)-6-oxaspiro[4.5]decan-9-yl)methyl)-N-(6-(trifluoromethyl)pyridin-2-yl)propionamide |
| 174 | N-((9-(4-(2-isopropoxyethyl)piperazin-1-yl)-6-oxaspiro[4.5]decan-9-yl)methyl)-N-(6-(trifluoromethyl)pyridin-2-yl)propionamide |
| 175 | N-((9-(4-isobutylpiperazin-1-yl)-6-oxaspiro[4.5]decan-9-yl)methyl)-N-(6-(trifluoromethyl)pyridin-2-yl)propionamide |
| 176 | N-((9-(4-(2-ethoxyethyl)piperazin-1-yl)-6-oxaspiro[4.5]decan-9-yl)methyl)-N-(6-(trifluoromethyl)pyridin-2-yl)propionamide |
| 177 | N-((4-(1-(2-ethoxyethyl)piperidin-4-yl)tetrahydro-2H-pyran-4-yl)methyl)-N-(6-(trifluoromethyl)pyridin-2-yl)propionamide |
| 178 | N-((4-(1-isobutylpiperidin-4-yl)tetrahydro-2H-pyran-4-yl)methyl)-N-(6-(trifluoromethyl)pyridin-2-yl)propionamide |
| 179 | N-((1-(4-(2-isopropoxyethyl)piperazin-1-yl)cyclopropyl)methyl)-N-(6-(trifluoromethyl)pyridin-2-yl)propionamide |
| 180 | methyl 2-phenyl-2-(4-(4-((N-(pyridin-2-yl)propionamido)methyl)tetrahydro-2H-pyran-4-yl)piperazin-1-yl)acetate |
| 181 | N-((4-(4-(2-hydroxy-1-phenylethyl)piperazin-1-yl)tetrahydro-2H-pyran-4-yl)methyl)-N-(pyridin-2-yl)propionamide |
| 182 | N-((4-(4-(1-(4-fluorophenyl)ethyl)piperazin-1-yl)tetrahydro-2H-pyran-4-yl)methyl)-N-(6-(trifluoromethyl)pyridin-2-yl)propionamide |
| 183 | N-((4-(4-(2-cyclopropoxyethyl)piperazin-1-yl)tetrahydro-2H-pyran-4-yl)methyl)-N-(6-(trifluoromethyl)pyridin-2-yl)propionamide |
| 184 | N-((4-(4-(2-morpholinoethyl)piperazin-1-yl)tetrahydro-2H-pyran-4-yl)methyl)-N-(6-(trifluoromethyl)pyridin-2-yl)propionamide |
| 185 | N-((4-(4-(2-methoxyethyl)piperazin-1-yl)tetrahydro-2H-pyran-4-yl)methyl)-N-(6-(trifluoromethyl)pyridin-2-yl)propionamide |
| 186 | N-((4-(4-(2-(2-hydroxy-2-methylpropoxy)ethyl)piperazin-1-yl)tetrahydro-2H-pyran-4-yl)methyl)-N-(6-(trifluoromethyl)pyridin-2-yl)propionamide |
| 187 | N-((4-(4-(2-propoxyethyl)piperazin-1-yl)tetrahydro-2H-pyran-4-yl)methyl)-N-(6-(trifluoromethyl)pyridin-2-yl)propionamide |
| 188 | N-((4-(4-(2-hydroxy-2-methylpropyl)piperazin-1-yl)tetrahydro-2H-pyran-4-yl)methyl)-N-(6-(trifluoromethyl)pyridin-2-yl)propionamide |
| 189 | N-((4-(4-(2-(2-fluoro-2-methylpropoxy)ethyl)piperazin-1-yl)tetrahydro-2H-pyran-4-yl)methyl)-N-(6-(trifluoromethyl)pyridin-2-yl)propionamide |
| 190 | N-((4-(4-(2-fluoro-2-methylpropyl)piperazin-1-yl)tetrahydro-2H-pyran-4-yl)methyl)-N-(6-(trifluoromethyl)pyridin-2-yl)propionamide |
| 191 | N-((4-(4-(2-Methoxy-2-methylpropyl)piperazin-1-yl)tetrahydro-2H-pyran-4-yl)methyl)-N-(6-(trifluoromethyl)pyridin-2-yl)propionamide |
| 192 | N-((4-(4-(2-(3-Fluoropyridin-2-yl)ethyl)piperazin-1-yl)tetrahydro-2H-pyran-4-yl)methyl)-N-(6-(trifluoromethyl)pyridin-2-yl)propionamide |
| 193 | N-((4-(4-(2-hydroxy-2-phenylethyl)piperazin-1-yl)tetrahydro-2H-pyran-4-yl)methyl)-N-(6-(trifluoromethyl)pyridin-2-yl)propionamide |
| 194 | N-((4-(4-(2-hydroxy-1-phenylethyl)piperazin-1-yl)tetrahydro-2H-pyran-4-yl)methyl)-N-(6-(trifluoromethyl)pyridin-2-yl)propionamide |
| 195 | N-((4-(4-benzylpiperazin-1-yl)piperidin-4-yl)methyl)-N-phenylpropionamide | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compounds of the general Formula (I) are selected from

| EX | Chemical name |
|---|---|
| 196 | N-((4-(5-benzylhexahydropyrrolo[3,4-c]pyrrol-2(1H)-yl)tetrahydro-2H-pyran-4-yl)methyl)-N-(6-(trifluoromethyl)pyridin-2-yl)propionamide |
| 197 | N-((1-(4-benzylpiperazin-1-yl)cyclobutyl)methyl)-N-(6-(trifluoromethyl)pyridin-2-yl)propionamide |
| 198 | N-((4-(4-benzylpiperazin-1-yl)tetrahydro-2H-thiopyran-4-yl)methyl)-N-(6-(trifluoromethyl)pyridin-2-yl)propionamide |
| 199 | N-((4-(5-isobutylhexahydropyrrolo[3,4-c]pyrrol-2(1H)-yl)tetrahydro-2H-pyran-4-yl)methyl)-N-(6-(trifluoromethyl)pyridin-2-yl)propionamide |
| 200 | N-((4-(5-(2-ethoxyethyl)hexahydropyrrolo[3,4-c]pyrrol-2(1H)-yl)tetrahydro-2H-pyran-4-yl)methyl)-N-(6-(trifluoromethyl)pyridin-2-yl)propionamide |
| 201 | N-((4-(4-(2-(pyridin-3-yl)ethyl)piperazin-1-yl)tetrahydro-2H-pyran-4-yl)methyl)-N-(6-(trifluoromethyl)pyridin-2-yl)propionamide |

| EX | Chemical name |
|---|---|
| 202 | N-((1-(4-(2-ethoxyethyl)piperazin-1-yl)cyclobutyl)methyl)-N-(6-(trifluoromethyl)pyridin-2-yl)propionamide |
| 203 | N-((1-(4-isobutylpiperazin-1-yl)cyclobutyl)methyl)-N-(6-(trifluoromethyl)pyridin-2-yl)propionamide |
| 204 | N-((4-(4-isobutylpiperazin-1-yl)tetrahydro-2H-thiopyran-4-yl)methyl)-N-(6-(trifluoromethyl)pyridin-2-yl)propionamide |
| 205 | N-((4-(4-(2-ethoxyethyl)piperazin-1-yl)tetrahydro-2H-thiopyran-4-yl)methyl)-N-(6-(trifluoromethyl)pyridin-2-yl)propionamide |
| 206 | N-((4-(4-(2-(pyridin-4-yl)ethyl)piperazin-1-yl)tetrahydro-2H-pyran-4-yl)methyl)-N-(6-(trifluoromethyl)pyridin-2-yl)propionamide | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein
m is 1 or 2, n is 0 or 1, p is 0 or 1, X is a bond or —O—, $R_1$ is substituted or unsubstituted phenyl or substituted or unsubstituted pyridine, $R_2$ is substituted or unsubstituted phenyl, substituted or unsubstituted pyridine or substituted or unsubstituted isopropyl and $R_3$ is substituted or unsubstituted ethyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein
m is 1, n is 0, p is 0, X is a bond or —O—, $R_1$ is substituted or unsubstituted phenyl or substituted or unsubstituted pyridine, $R_2$ is substituted or unsubstituted phenyl, substituted or unsubstituted pyridine or substituted or unsubstituted isopropyl and $R_3$ is substituted or unsubstituted ethyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein
m is 1, n is 0, p is 0, X is a bond $R_1$ is substituted or unsubstituted phenyl or substituted or unsubstituted pyridine, $R_2$ is substituted or unsubstituted phenyl, substituted or unsubstituted pyridine or substituted or unsubstituted isopropyl and $R_3$ is substituted or unsubstituted ethyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
$R_1$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$NR_{11}S(O)_2NR_{11'}R_{11''}$ and $C(CH_3)_2OR_{11}$;
  additionally, the cycloalkyl or non-aromatic heterocyclyl in $R_1$, if substituted, may also be substituted

or =O;
  wherein the alkyl, alkenyl or alkynyl in $R_1$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;
  wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$NR_{12}S(O)_2NR_{12'}R_{12''}$ and $C(CH_3)_2OR_{12}$;
  additionally, the cycloalkyl or non-aromatic heterocyclyl in $R_2$, if substituted, may also be substituted with

or =O;
wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
the alkyl, alkenyl or alkynyl, other than those defined in $R_1$ or $R_2$, if substituted, is substituted with one or more substituent/s selected from —$OR_{13}$, halogen, —CN, haloalkyl, haloalkoxy, —$SR_{13}$, —$S(O)R_{13}$, and —$S(O)_2R_{13}$;
wherein $R_{13}$ is selected from hydrogen, unsubstituted $C_{1-6}$ alkyl, unsubstituted $C_{2-6}$ alkenyl, and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the aryl, heterocyclyl or cycloalkyl other than those defined in $R_1$ or $R_2$, if substituted, is substituted with one or more substituent/s selected from halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14'''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$NR_{14}S(O)_2NR_{14'}R_{14''}$ and $C(CH_3)_2OR_{14}$;
additionally, the cycloalkyl or non-aromatic heterocyclyl, other than those defined in $R_1$ or $R_2$, if substituted, may also be substituted with

or =O;
wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;
and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention,
the cycloalkyl, aryl or heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$NR_{11}S(O)_2NR_{11'}R_{11''}$ and $C(CH_3)_2OR_{11}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention,
the cycloalkyl or non-aromatic heterocyclyl in $R_1$, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention,
the alkyl, alkenyl or alkynyl in $R_1$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12'''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$NR_{12}S(O)_2NR_{12'}R_{12''}$ and $C(CH_3)_2OR_{12}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the cycloalkyl or non-aromatic heterocyclyl in $R_2$, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in $R_1$ or $R_2$ of any of the embodiments of the present invention,
the alkyl, alkenyl or alkynyl, other than those defined in $R_1$ or $R_2$, if substituted, is substituted with one or more substituent/s selected from —$OR_{13}$, halogen, —CN, haloalkyl, haloalkoxy, —$SR_{13}$, —$S(O)R_{13}$, and —$S(O)_2R_{13}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_1$ or $R_2$ of any of the embodiments of the present invention,
the aryl, heterocyclyl or cycloalkyl other than those defined in $R_1$ or $R_2$, if substituted, is substituted with one or more substituent/s selected from halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$NR_{14}S(O)_2NR_{14'}R_{14''}$, and $C(CH_3)_2OR_{14}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to to the cycloalkyl, aryl or heterocyclyl other than those defined in $R_1$ or $R_2$ of any of the embodiments of the present invention, the cycloalkyl or non-aromatic heterocyclyl, other than those defined in $R_1$ or $R_2$, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I),
the halogen is fluorine, chlorine, iodine or bromine;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general Formula (I)
the halogen is fluorine or chlorine
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I),
the haloalkyl is —$CF_3$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I),
the haloalkoxy is —$OCF_3$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the σ1 receptor and the μ-opioid receptor it is a very preferred embodiment in which the compounds are selected which act as dual ligands of the $σ_1$ receptor and the μ-opioid receptor and especially compounds which have a binding expressed as $K_i$ which is preferably <1000 nM for both receptors, more preferably <500 nM, even more preferably <100 nM.

In the following the phrase "compound of the invention" is used. This is to be understood as any compound according to the invention as described above according to general Formula (I), (I'), (I²'), (I³'), (I⁴'), (I⁵'), (I⁶') or (I).

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to Formula (I), following scheme 1.

A preferred embodiment of the invention is a process for the production of a compound according to Formula (I), wherein $R_1$, $R_2$, $R_3$, $R_4$, $R_{4'}$, $R_5$, $R_{5'}$, $R_6$, $R_{6'}$, $R_7$, $R_{7'}$, X, W, m, n and p are as defined in the description, following scheme 1.

In all processes and uses described underneath and in scheme 1, the values of $R_1$, $R_2$, $R_3$, $R_4$, $R_{4'}$, $R_5$, $R_{5'}$, $R_6$, $R_{6'}$, $R_7$, $R_{7'}$, X, W, m, n and p are as defined in the description, L is a leaving group such as halogen, mesylate, tosylate or triflate Z is chloro, bromo, hydroxy, methoxy or ethoxy, Y is

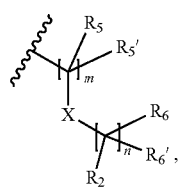

and PG is a protecting group, such as benzyl and tert-butoxycarbonyl.

In a particular embodiment there is a process for the production of a compound of Formula (I),

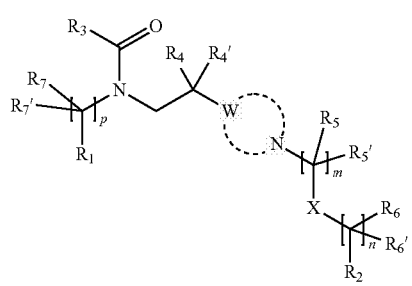

said process comprises reacting a compound of Formula (VIII)

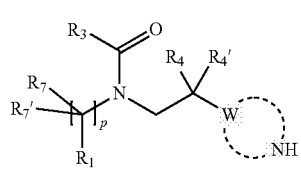

with a compound of formula (IXa) through an alkylation reaction or (IXb) through a reductive amination reaction

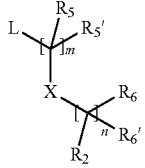

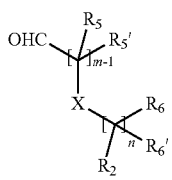

In a particular embodiment there is a process for the production of a compound of Formula (I),

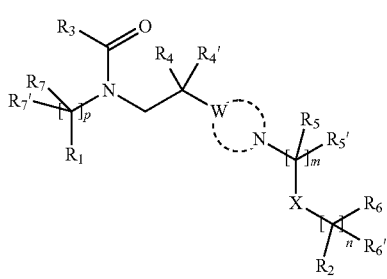

said process comprises an acylation reaction of a compound of formula Vb

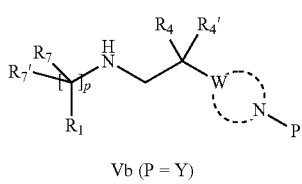

Vb (P = Y)

with an acyl halide of formula VIa or with an anhydride of formula VIb,

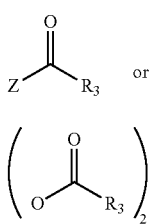

In a particular embodiment there is a process for the production of a compound of Formula (I),

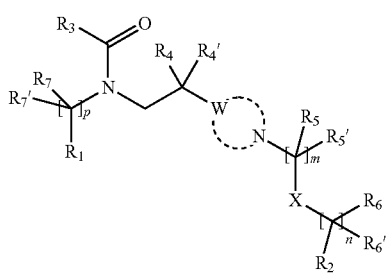

(I)

said process comprises treating compounds of formula Xb

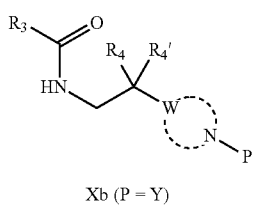

Xb (P = Y)

with a reagent of formula Xb with a reagent of formula IVa

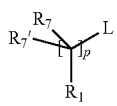

IVa

In a particular embodiment there is a process for the production of a compound of Formula VIII,

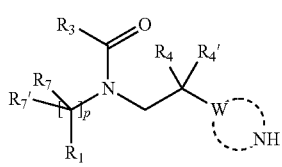

VIII said process comprises deprotecting a compound of Formula VII

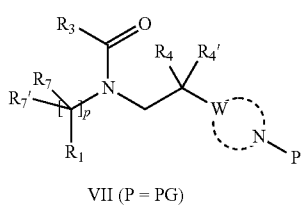

VII (P = PG)

In a particular embodiment there is a process for the production of a compound of Formula VII or I

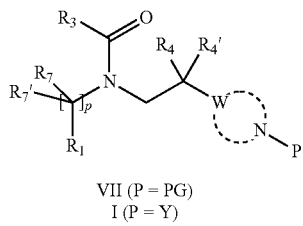

VII (P = PG)
I (P = Y)

said process comprises an acylation reaction of a compound of formula Va or Vb, respectively

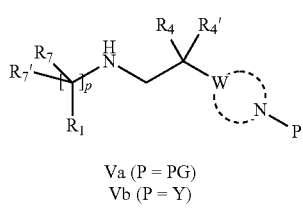

Va (P = PG)
Vb (P = Y)

with an acyl halide of formula VIa or with an anhydride of formula VIb,

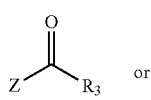

VIa or

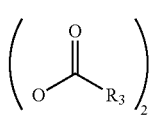

VIb

In a particular embodiment there is a process for the production of a compound of Formula VII or I

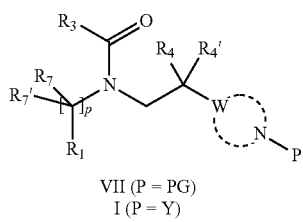

VII (P = PG)
I (P = Y)

said process comprises treating compounds of formula Xa or Xb, respectively

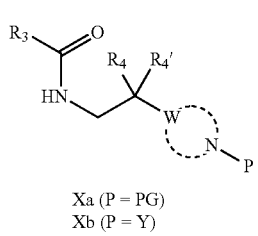

Xa (P = PG)
Xb (P = Y)

with reagent of formula IVa

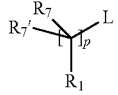

IVa

In a particular embodiment there is a process for the production of a compound of Formula Xa or Xb

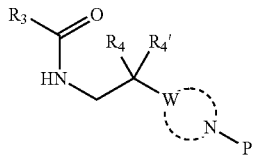

Xa (P = PG)
Xb (P = Y)

said process comprises an acylation or urea formation of compound of formula IIIa or IIIb, respectively

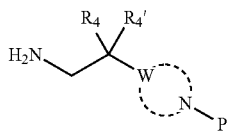

IIIa (P = PG)
IIIb (P = Y)

with a compound VIa, VIb or VIc

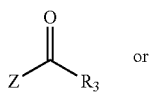

VIa

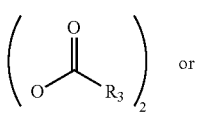

VIb

R₃NCO

VIc

In a particular embodiment there is a process for the production of a compound of Formula Va or Vb,

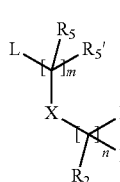

Va (P = PG)
Vb (P = Y)

said process comprises reduction of compounds of formula XIVa or XIVb, respectively

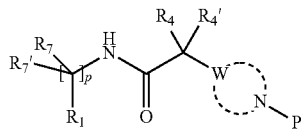

XIVa (P = PG)
XIVb (P = Y)

In a particular embodiment there is a process for the production of a compounds of formula XIVb,

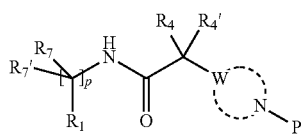

XIVb (P = Y)

said process comprises reacting a compound of formula XV

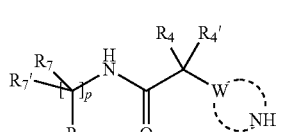

XV with a compound of Formula IXa through a reductive amination reaction or IXb through an alkylation reaction

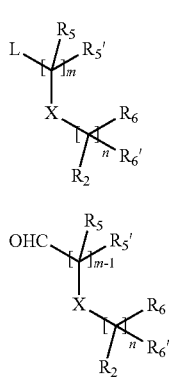

IXa

IXb

In a particular embodiment there is a process for the production of compounds of formula XIVa or XIVb,

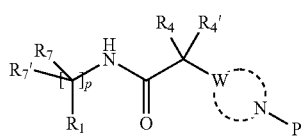

XIVa (P = PG)
XIVb (P = Y)

said process comprises reacting a compound of formula XVIa or XVIb, respectively

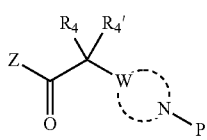

XVIa (P = PG)
XVIb (P = Y)

with amines of formula IVb

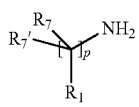

IVb

In a particular embodiment there is a process for the production of a compound of formula XVIa or XVIb

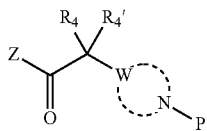

XVIa (P = PG)
XVIb (P = Y)

said process comprises an alkylation of a compound of formula XI

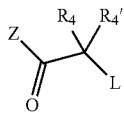

XI with derivatives of formula XIIIa and XIIIb, respectively

XIIIa (P = PG)
XIIIb (P = Y)
W = ——NH——

In a particular embodiment there is a process for the production of a compound of formula XIVa or XIVb,

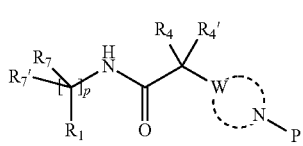

XIVa (P = PG)
XIVb (P = Y)

said process comprises an alkylation reaction of compound of formula XII

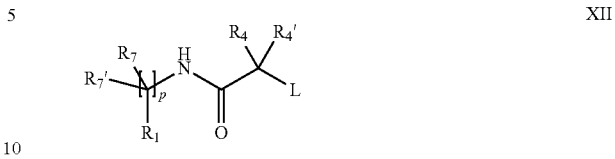

XII with the corresponding derivatives of formula XIIIa or XIIIb,

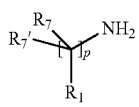

XIIIa (P = PG)
XIIIb (P = Y)
W = ——NH——

In a particular embodiment there is a process for the production of a compound of formula XII

XII said process comprises an acylation reaction between a compound of formula

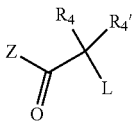

XI and an amine of formula IVb

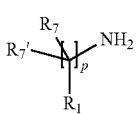

IVb

In a particular embodiment there is a process for the production of a compound of Formula Va or Vb,

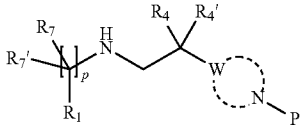

Va (P = PG)
Vb (P = Y)

said process comprises reacting a compound of general formula IIIa or IIIb, respectively,

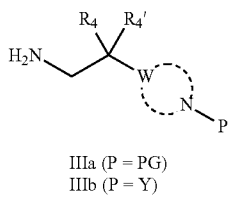

IIIa (P = PG)
IIIb (P = Y)

with a compound of formula IVa

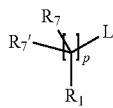

IVa

In a particular embodiment there is a process for the production of a compound of Formula IIIa or IIIb,

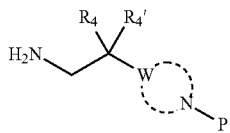

IIIa (P = PG)
IIIb (P = Y)

said process comprises the reduction of a nitrile in a compound of formula IIa or IIb, respectively

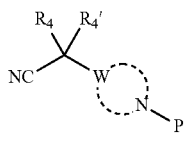

IIa (P = PG)
IIb (P = Y)

In another particular embodiment a compound of Formula (XI),

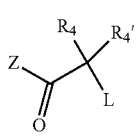

XI is used for the preparation of a compound of Formula (I).

In another particular embodiment a compound of Formula (IVb)

IVb is used for the preparation of a compound of Formula (I).

In another particular embodiment a compound of Formula (XII),

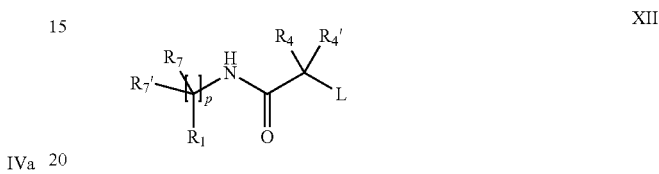

XII is used for the preparation of a compound of Formula (I).

In another particular embodiment a compound of Formula (XIIIa) or (XIIIb),

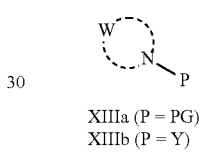

XIIIa (P = PG)
XIIIb (P = Y)

is used for the preparation of a compound of Formula (I).

In another particular embodiment a compound of Formula (XVIa) or (XVIb),

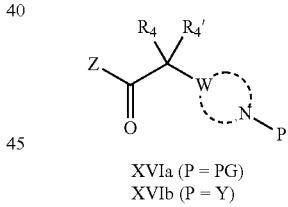

XVIa (P = PG)
XVIb (P = Y)

is used for the preparation of a compound of Formula (I).

In another particular embodiment a compound of Formula (XIVa) or (XIVb),

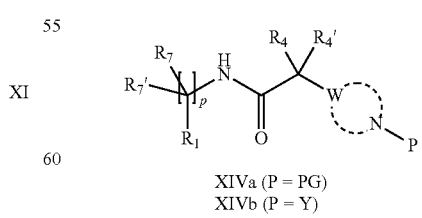

XIVa (P = PG)
XIVb (P = Y)

is used for the preparation of a compound of Formula (I).

In another particular embodiment a compound of Formula (XV),

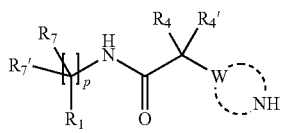

XV is used for the preparation of a compound of Formula (I).

In another particular embodiment a compound of Formula (IIa) or (IIb),

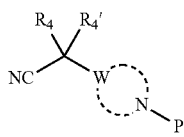

IIa (P = PG)
IIb (P = Y)

is used for the preparation of a compound of Formula (I).

In another particular embodiment a compound of Formula (IIIa) or (IIIb),

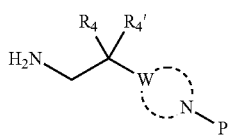

IIIa (P = PG)
IIIb (P = Y)

is used for the preparation of a compound of Formula (I).

In another particular embodiment a compound of Formula (IVa),

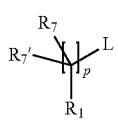

IVa is used for the preparation of a compound of Formula (I).

In another particular embodiment a compound of Formula (Va) or (Vb)

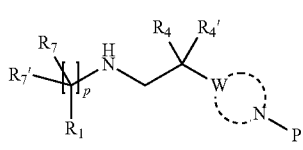

Va (P = PG)
Vb (P = Y)

is used for the preparation of a compound of Formula (I).

In another particular embodiment a compound of Formula (VIa), (VIb) or (VIc),

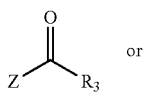

VIa

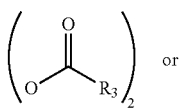

VIb

R$_3$NCO

VIc is used for the preparation of a compound of Formula (I).

In another particular embodiment a compound of Formula (Xa) or (Xb)

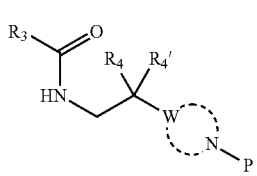

Xa (P = PG)
Xb (P = Y)

is used for the preparation of a compound of Formula (I).

In another particular embodiment a compound of Formula (VII),

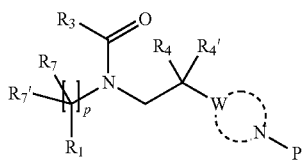

VII (P = PG)

is used for the preparation of a compound of Formula (I).

In another particular embodiment a compound of Formula (IXa),

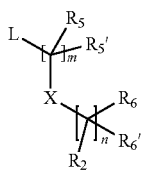

IXa is used for the preparation of a compound of Formula (I).

In another particular embodiment a compound of Formula (IXb),

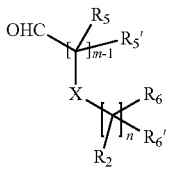

IXb is used for the preparation of a compound of Formula (I).

In another particular embodiment a compound of Formula (VIII)

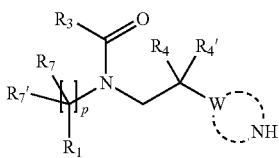

VIII is used for the preparation of a compound of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

A process is described in Scheme 1 for the preparation of compounds of general formula I, wherein $R_1$, $R_2$, $R_3$, $R_4$, $R_{4'}$, $R_5$, $R_{5'}$, $R_6$, $R_{6'}$, $R_7$, $R_{7'}$, m, n, p, W and X have the meanings defined above.

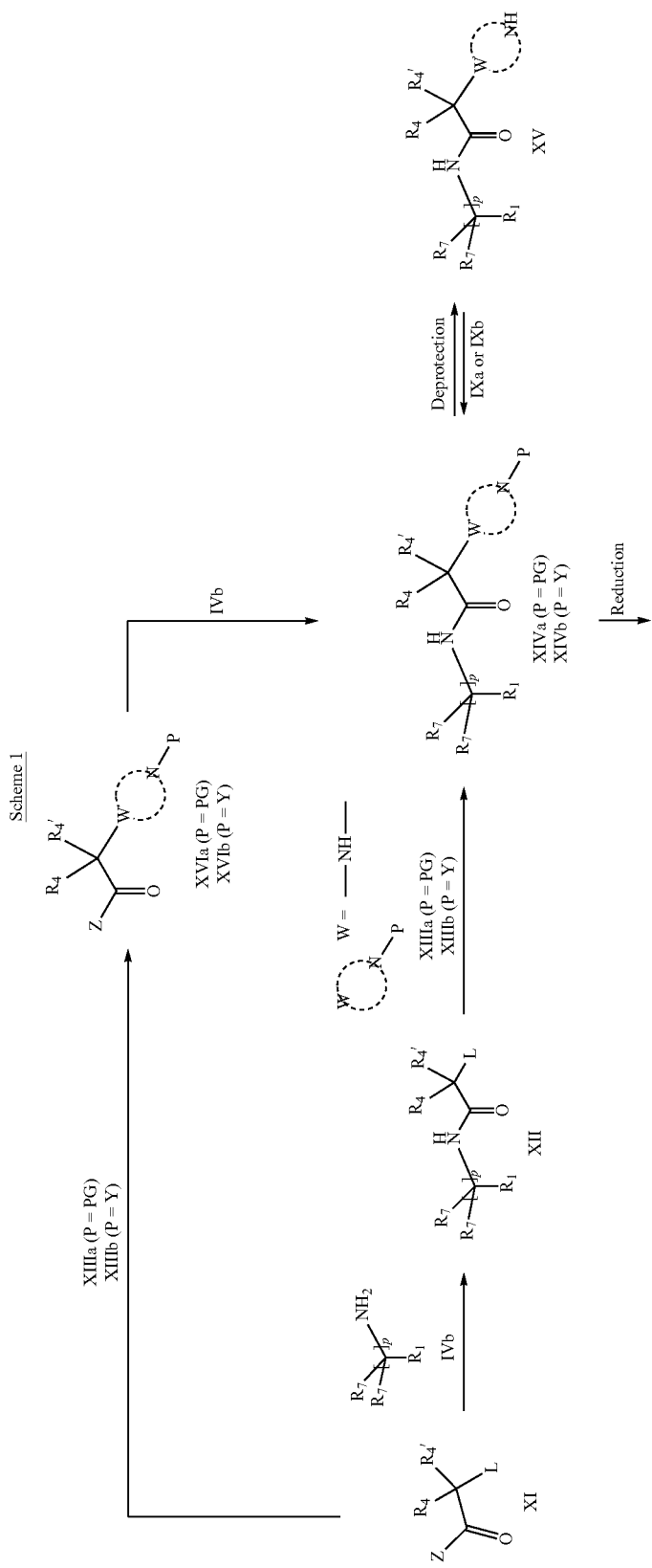

-continued
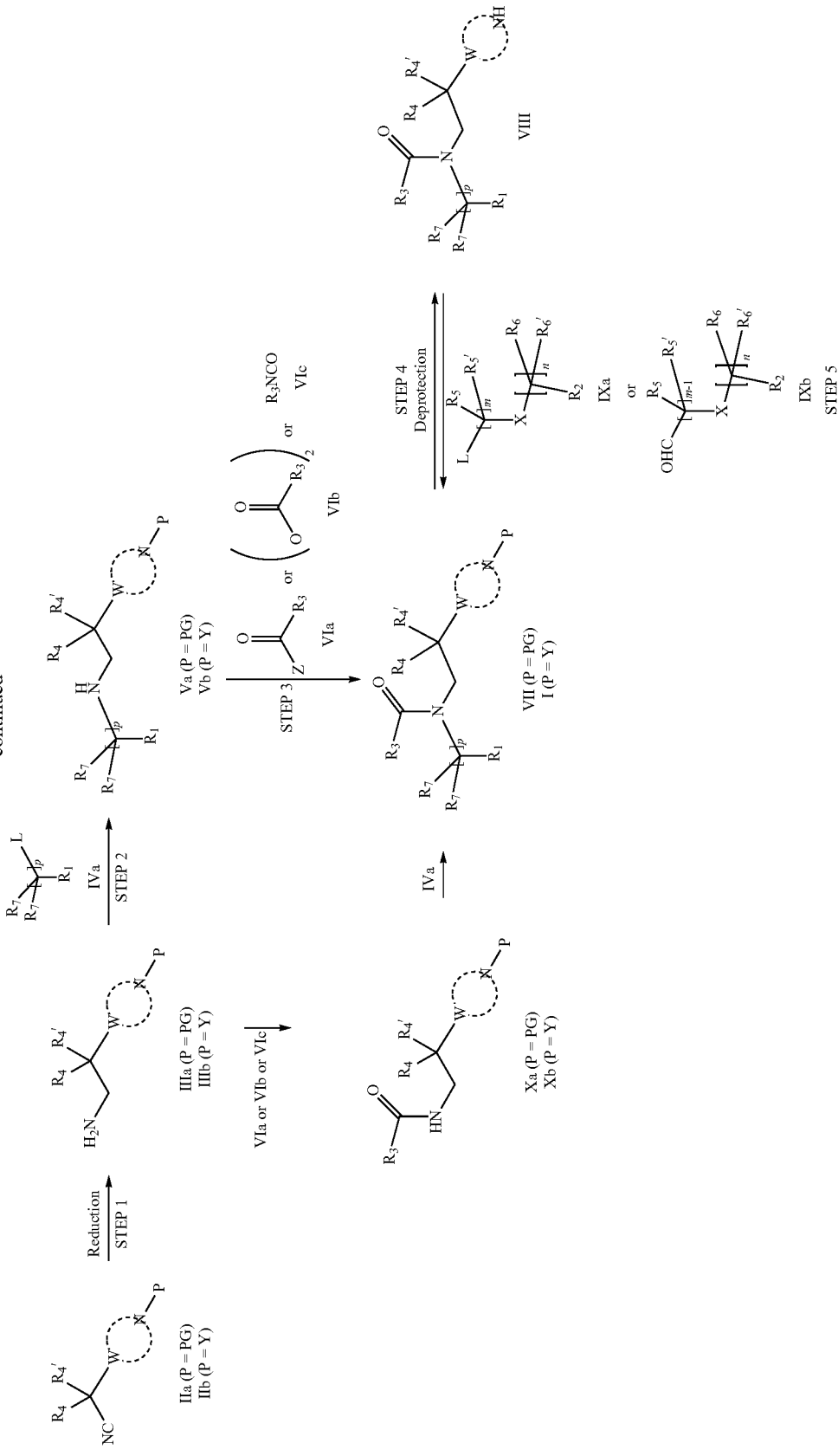

-continued
PG = Protecting Group
Y = 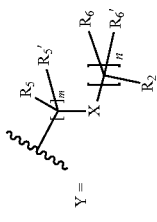

wherein, L is a leaving group such as halogen, mesylate, tosylate or triflate and Z is chloro, bromo, hydroxy, methoxy or ethoxy, V is the group indicated in a square in Scheme 1 and PG is a protecting group.

This process is carried out as described below:

Step 1: The reduction of nitrile in a compound of formula IIa or IIb renders a compound of general formula IIIa or IIIb. The reduction can be carried out in the presence of a suitable reducing agent such as lithium aluminium hydride, in a suitable solvent such as THF or diethylether, at a suitable temperature comprised between 0° C. and room temperature, preferably at room temperature. This reaction can be also effected with hydrogen at a pressure comprised between 1 and 10 bar, in a suitable solvent such as methanol or ethanol, in the presence of Raney nickel, at a suitable temperature comprised between room temperature and the reflux temperature.

Step 2: The compounds of general formula Va or Vb are prepared by reacting a compound of general formula IIIa or IIIb, respectively, with a compound of formula IVa. Depending on the meaning of p and $R_1$, different reaction conditions will apply:
  a) When p is 0 and $R_1$ is aryl or heterocyclyl, compound IVa is an arylating agent and L represents halogen (preferably bromo or iodo) or triflate. This arylation reaction is carried out under catalytic conditions using a palladium or copper catalyst, in the presence of a suitable ligand and a suitable base, in a suitable solvent, and at a suitable temperature, preferably heating at the reflux temperature or in a microwave reactor. When using copper catalysts such as copper iodide, L-proline is the preferred ligand, potassium phosphate is used preferably as the base and dimethylsulfoxide is the solvent of choice. When using palladium catalysts, such as tris(dibenzylideneacetone)dipalladium or palladium diacetate, 4, 5-bis(diphenylphosphino)-9,9-dimethyxanthene (XAMPHOS) or 2,2'-is(diphenylphosphino)-1,1'-binaphthyl (BINAP) are the preferred ligands, cesium carbonate or sodium tert-butoxide are used preferably as the base and 1,4-dioxane or toluene are the solvents of choice.
  b) When p is 1 or 2, compound IVa is an alkylating agent and L represents a leaving group such as halogen, mesylate, tosylate or triflate. The alkylation reaction is carried out in a suitable solvent, such as acetonitrile, dichloromethane, 1,4-dioxane or dimethylformamide, preferably in acetonitrile, in the presence of an inorganic base such as $K_2CO_3$ or $Cs_2CO_3$, or an organic base such as triethylamine or diisopropylethylamine, preferably $K_2CO_3$, at a suitable temperature comprised between room temperature and the reflux temperature, preferably heating, or alternatively, the reactions can be carried out in a microwave reactor. Additionally, an activating agent, such as NaI, can be used.

Step 3: Compounds of general formula VII or I are prepared by substitution of the NH group of compounds Va or Vb, respectively, with appropriate methods. Thus the acylation reaction of a compound of formula Va or Vb with an acyl halide of formula VIa or with an anhydride of formula VIb, is carried out in the presence of a suitable solvent, such as acetonitrile, dichloromethane, 1,4-dioxane, 1,2-dichloroethane, toluene or dimethylformamide, in the presence of an organic base such as triethylamine, pyridine or diisopropylethylamine, at a suitable temperature comprised between room temperature and the reflux temperature, or alternatively, the reactions can be carried out in a microwave reactor.

The formation of a urea derivative of general formula VII or I is performed by reaction of compound of formula Va or Vb with an isocyanate compound of formula VIc, in a suitable solvent, such as dichloromethane, in the presence of an organic base such as triethylamine, at a suitable temperature comprised between room temperature and the reflux temperature, preferably at room temperature.

For compounds of general formula VII, wherein P is a protecting group, two additional steps are necessary to obtain compounds of formula I:

Step 4: A compound of formula VIII is prepared by deprotection of a compound of formula VII. If the protecting group is benzyl the deprotection is carried out under hydrogenation conditions, preferably by treatment with ammonium formate as hydrogen source, in the presence of Pd, in a suitable solvent such as methanol or ethanol, at a suitable temperature comprised between room temperature and the reflux temperature, preferably at the reflux temperature. If the protecting group is Boc, the deprotection is carried out in the presence of an inorganic acid such as HCl or trifluoroacetic acid, preferably trifluoroacetic acid, in a suitable solvent such as dichloromethane, at a suitable temperature comprised between room temperature and the reflux temperature, preferably at room temperature.

Step 5: From deprotected compounds of general formula VIII, compounds of general formula I can be prepared by reaction with suitable reagents, such as those of formula IXa-b, using different conditions depending on the reagent nature. Thus: The alkylation reaction with a compound of formula IXa is carried out in a suitable solvent, such as acetonitrile, dichloromethane, 1,4-dioxane, ethanol or dimethylformamide, preferably in acetonitrile or ethanol, in the presence of an inorganic base such as $K_2CO_3$ or $Cs_2CO_3$, or an organic base such as triethylamine or diisopropylethylamine, preferably $K_2CO_3$, at a suitable temperature comprised between room temperature and the reflux temperature, preferably heating, or alternatively, this reaction can be carried out in a microwave reactor. Additionally, an activating agent such as NaI or KI can be used.

The reductive amination with a compound of formula IXb, is carried out in the presence of a reductive reagent, preferably sodium triacetoxyborohydride, in a suitable solvent, preferably methanol, at a suitable temperature comprised between room temperature and the reflux temperature, preferably in a microwave reactor.

Alternatively, the transformation of amine compounds of formula IIIa or IIIb to compounds of formula VII or I can be effected in a different two step procedure. The first step of this alternative process involves acylation or urea formation with compounds VIa-c to give compounds of formula Xa or Xb, respectively. These reactions can be carried out under the conditions described in Step 3. In the second step of this alternative process, compounds of general formula VII or I are prepared by treating compounds of formula Xa or Xb with reagent of formula IVa. When p=1 or 2 the alkylation reaction may be carried out in a suitable solvent, such as tetrahydrofuran, in the presence of an inorganic base such as sodium hydride, at a suitable temperature comprised between room temperature and the reflux temperature, preferably at the reflux temperature.

Additionally, intermediate compounds of formula Va or Vb wherein W is nitrogen can be obtained in an alternative three step procedure from compounds of general formula XI. This process involves the acylation reaction between a compound of formula XI and an amine of formula IVb to give amide derivatives of formula XII. This reaction can be effected in different conditions depending on the nature of Z.

When Z is hydroxy, the reaction is carried out using a suitable coupling reagent such as N-(3-dimethylaminopropyl)-N'-ethylcarbodiimide (EDC), dicyclohexylcarbodiimide (DCC), N-[(dimethylamino)-1H-1,2,3-triazolo-[4,5-b]pyridin-1-ylmethylene]-N-methylmethanaminium hexafluorophosphate N-oxide (HATU) or N,N,N',N'-tetramethyl-O-(1H-benzotriazol-1-yl)uronium hexafluorophosphate (HBTU), optionally in the presence of 1-hydroxybenzotriazole and an organic base such as triethylamine, in a suitable solvent such as dichloromethane or dimethylformamide, and at a suitable temperature, preferably at room temperature. When Z is chloro of bromo, the acylation reaction is carried out in the conditions previously described in Step 3.

Compounds of formula XIVa or XIVb wherein W is nitrogen are obtained by alkylation reaction with the corresponding derivatives of formula XIIIa or XIIIb, in a suitable solvent such as acetonitrile, in the presence of an inorganic base such as $K_2CO_3$ and at a suitable temperature comprised between room temperature and the reflux temperature, preferably heating.

For compounds of general formula XIVa, wherein P is a protecting group, two additional steps can be effected to obtain compounds of formula XIVb. Deprotection of compounds of formula XIVa in the conditions described in Step 4, afford compounds of formula XV. Compounds of formula XIVb are obtained by alkylation or reductive amination reaction of compounds of formula XV with reagents IXa-b under the conditions described in Step 5.

The final step of this alternative method for the preparation of intermediate compounds of formula Va or Vb involves the reduction of compounds of formula XIVa or XIVb, respectively, with a reducing agent such as aluminium hydride, in a suitable solvent such as tetrahydrofurane, at a suitable temperature comprised between 0° C. and room temperature, preferably at 0° C.

As described in the Scheme 1, the order of the above described steps for preparation of compounds of formula XIVa or XIVb can be interchanged. Compounds of formula XVIa and XVIb in the case where Z=hydroxyl, can be obtained by alkylation of compound of formula XI with derivatives of formula XIIIa and XIIIb under the previously described conditions. Reaction of compounds of formula XVIa or XVIb with amines of formula IVb, under the coupling reaction conditions previously described, afford the intermediate amides XIVa or XIVb.

The process described by Steps 1 to 5 and the corresponding alternative methods, represent the general route for the preparation of compounds of formula I. Additionally, the functional groups present in any of the positions can be interconverted using reactions known to those skilled in the art.

Compounds of formula II, IV, IX, XI and XIII where $R_1$, $R_2$, $R_3$, $R_4$, $R_{4'}$, $R_5$, $R_{5'}$, $R_6$, $R_{6'}$, $R_7$, $R_{7'}$, W and X have the meanings as defined above, are commercially available or can be prepared by conventional methods described in the bibliography. Compounds II, wherein W is nitrogen, are prepared by Strecker reaction of conveniently substituted ketones with amino compounds of formula XIIIa or XIIIb. The preparation of compounds II wherein W is carbon, involves the treatment of a conveniently substituted nitrile compound with adequate ketones in the presence of a strong base such as LDA, dehydration of the resulting tertiary alcohol and final reduction of the generated alkene.

EXAMPLES

Intermediates and Examples

The following abbreviations are used in the examples:

ACN: Acetonitrile
AcOH: Acetic acid
AcOEt: Ethyl acetate
BINAP: 2,2'-Bis(diphenylphosphino)-1,1'-binaphthyl
Conc: Concentrated
CH: Cyclohexane
DCM: Dichloromethane
DCE: 1,2-Dicloroethane
DIPEA: N,N-Diisopropylethylamine
DMF: Dimethylformamide
DMSO: Dimethyl sulfoxide
EDC: 1-Ethyl-3-(3-dimethylaminopropyl)carbodiimide
EtOH: Ethanol
$Et_2O$: Diethyl ether
Ex: Example
h: Hour/s
HOBt: Hydroxybenzotriazole
HPLC: High-performance liquid chromatography
INT: Intermediate
LDA: Lithium diisopropilamide
LiHMDS: Lithium bis(trimethylsilyl)amide
MeOH: Methanol
MS: Mass spectrometry
Min: Minutes
Quant: Quantitative
Ret: Retention
rt: Room temperature
Sat: Saturated
TEA: $Et_3N$, Triethylamine
TFA: Trifluoroacetic acid
THF: Tetrahydrofuran
Wt: Weight
Xamphos: 4,5-Bis(diphenylphosphino)-9,9-dimethylxanthene The following methods were used to obtain the HPLC-MS data:

A: Column Acquity UPLC BEH C18 2.1×50 mm, 1.7 µm; flow rate 0.61 mL/min; A: $NH_4HCO_3$ 10 mM; B: ACN; Gradient: 0.3 min in 98% A, 98% A to 5% A in 2.7 min, 2 min in 5% A, 5% A to 98% A in 0.2 min, 0.55 min in 98% A B: Column: Aqcuity BEH C18 2.1×50 mm 1.7 µm; flow rate 600 µl/min; A: $NH_4HCO_3$ 10 mM; B: ACN; Gradient: 0.3 min in 90% A, 90% A to 5% A in 2.7 min, 0.7 min in 5% A, 5% A to 90% A in 0.1 min, 1.2 min in 90% A C: Column: Gemini-NX 30×4.6 mm, 3 um; flow rate: 2.0 mL/min; A: $NH_4HCO_3$ pH 8; B: ACN; Gradient: 0.5 min in 95% A, 95% A to 0% A in 6.5 min, 1 min in 0% A; 40° C.; sample dissolved aprox. 1 mg/mL in $NH_4HCO_3$ pH 8/ACN Intermediate 1A. 4-(4-Benzylpiperazin-1-yl)tetrahydro-2H-pyran-4-carbonitrile

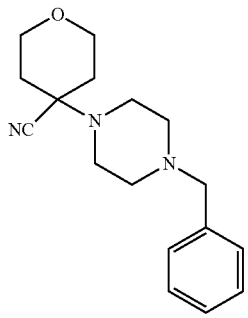 [SMILES: N#CC1(N2CCN(Cc3ccccc3)CC2)CCOCC1]

In a 2 L round bottomed flask, dihydro-2H-pyran-4(3H)-one (10.8 g, 107.8 mmol) was dissolved in water (500 mL) along with sodium metabisulfite (10.2 g, 54 mmol). The mixture was allowed to stir at rt for 1.5 h, then benzylpiperazine (19 g, 108 mmol) was added. The mixture was stirred for 2 h and potassium cyanide (11.2 g, 173 mmol) was added to the reaction mixture. After stirring at rt for 2 days the solid formed was filtered and dried, to give the title compound as a white solid (27.8 g, yield 90%).

HPLC-MS (Method A): Ret, 1.72 min; ESI$^+$-MS m/z, 286 (M+1).

This method was used for the preparation of intermediates 1B-L using suitable starting materials:

| INT | Structure | Chemical name | Method | Ret (min) | MS (M + H) |
|---|---|---|---|---|---|
| 1B | 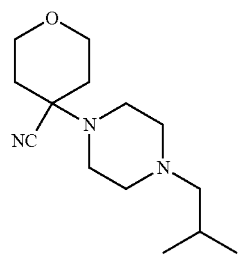 [SMILES: CC(C)CN1CCN(C2(C#N)CCOCC2)CC1] | 4-(4-isobutylpiperazin-1-yl)tetrahydro-2H-pyran-4-carbonitrile | A | 1.68 | 252 |
| 1C | 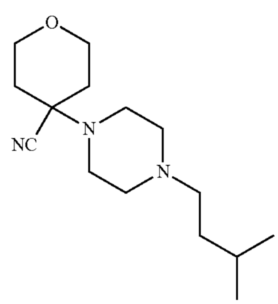 [SMILES: CC(C)CCN1CCN(C2(C#N)CCOCC2)CC1] | 4-(4-isopentylpiperazin-1-yl)tetrahydro-2H-pyran-4-carbonitrile | A | 1.70 | 266 |
| 1D | 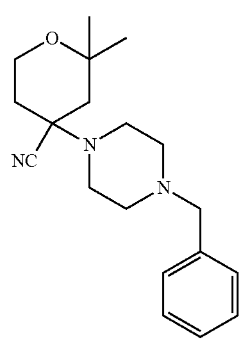 [SMILES: CC1(C)CC(C#N)(N2CCN(Cc3ccccc3)CC2)CCO1] | 4-(4-benzylpiperazin-1-yl)-2,2-dimethyltetrahydro-2H-pyran-4-carbonitrile | A | 1.98 | 314 |

| INT | Structure | Chemical name | Method | Ret (min) | MS (M + H) |
|---|---|---|---|---|---|
| 1E | 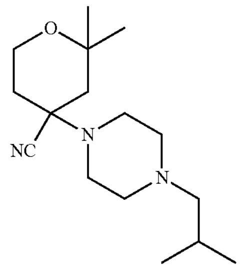 [SMILES: CC(C)CN1CCN(C2(C#N)CCOC(C)(C)C2)CC1] | 4-(4-isobutylpiperazin-1-yl)-2,2-dimethyltetrahydro-2H-pyran-4-carbonitrile | A | 2.03 | 280 |
| 1F | 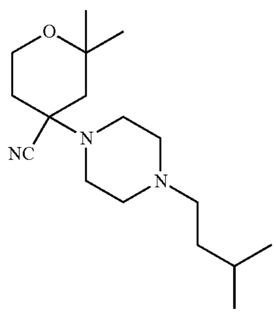 [SMILES: CC(C)CCN1CCN(C2(C#N)CCOC(C)(C)C2)CC1] | 4-(4-isopentylpiperazin-1-yl)-2,2-dimethyltetrahydro-2H-pyran-4-carbonitrile | A | 1.98 | 294 |
| 1G | 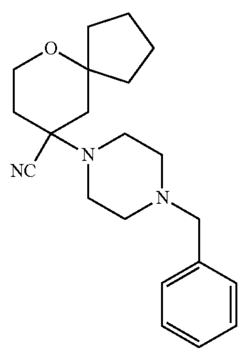 [SMILES: N#CC1(N2CCN(Cc3ccccc3)CC2)CCOC2(CCCC2)C1] | 9-(4-benzylpiperazin-1-yl)-6-oxaspiro[4.5]decane-9-carbonitrile | A | 2.21 | 340 |
| 1H | 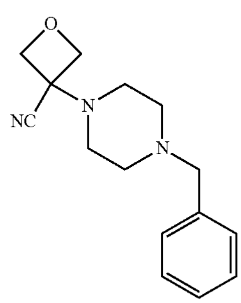 [SMILES: N#CC1(N2CCN(Cc3ccccc3)CC2)COC1] | 3-(4-benzylpiperazin-1-yl)oxetane-3-carbonitrile | A | 1.66 | 258 |
| 1I | 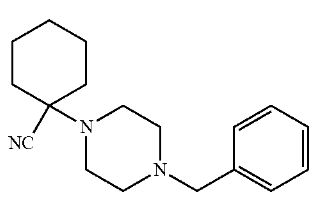 [SMILES: N#CC1(N2CCN(Cc3ccccc3)CC2)CCCCC1] | 1-(piperazin-1-yl)cyclohexanecarbonitrile | A | 2.26 | 284 |

| INT | Structure | Chemical name | Method | Ret (min) | MS (M + H) |
|---|---|---|---|---|---|
| 1J | 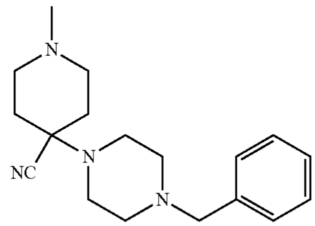 [SMILES: CN1CCC(C#N)(N2CCN(Cc3ccccc3)CC2)CC1] | 4-(4-benzylpiperazin-1-yl)-1-methylpiperidine-4-carbonitrile | A | 1.69 | 286 |
| 1K | 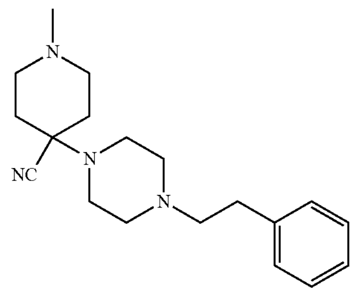 [SMILES: CN1CCC(C#N)(N2CCN(CCc3ccccc3)CC2)CC1] | 1-methyl-4-(4-phenethylpiperazin-1-yl)piperidine-4-carbonitrile | A | 1.60 | 313 |
| 1L | 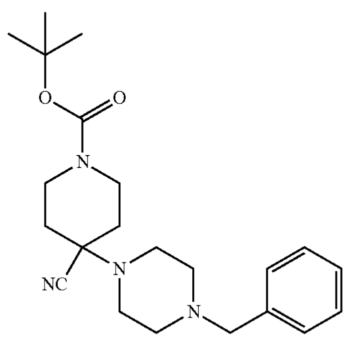 [SMILES: CC(C)(C)OC(=O)N1CCC(C#N)(N2CCN(Cc3ccccc3)CC2)CC1] | tert-butyl 4-(4-benzylpiperazin-1-yl)-4-cyanopiperidine-1-carboxylate | A | 2.28 | 384 |

Intermediate 1 N. 4-(1-Benzylpiperidin-4-yl)tetrahydro-2H-pyran-4-carbonitrile

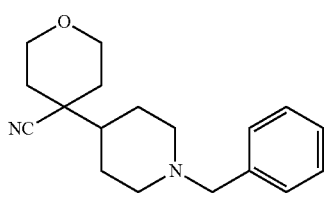 [SMILES: N#CC1(C2CCN(Cc3ccccc3)CC2)CCOCC1]

a) tert-Butyl-4-(4-cyanotetrahydro-2H-pyran-4-yl)-4-hydroxypiperidine 1 carboxylate To a solution of tetrahydro-2H-pyran-4-carbonitrile (4.85 g, 43.6 mmol) in dry THF (41 mL), cooled at −78° C., an LDA solution (30.5 mL, 1.5 M in a mixture of THF/ethylbenzene/heptane, 45.8 mmol) was added dropwise under a nitrogen atmosphere. The mixture was stirred at −50° C. for 45 min and then it was cooled at −78° C. A solution of tert-butyl 4-oxopiperidine-1-carboxylate (8.69 g, 43.6 mmol) in dry THF (5.2 mL) was added and the reaction mixture was stirred at −78° C. for 2 h. Then, NH$_4$Cl sat aqueous solution was added and the mixture was extracted with ethyl acetate. The organic phases were combined, dried over MgSO$_4$, filtered and concentrated to dryness. The residue was purified by flash chromatography, silica gel, gradient DCM to MeOH:DCM (1:9) to give the title compound (7.11 g, 53% yield).

HPLC-MS (Method C): Ret, 3.18 min; ESI$^+$-MS m/z, 255 (M+H-56).

b) tert-Butyl 4-(4-cyanotetrahydro-2H-pyran-4-yl)-5,6-dihydropyridine-1 (2H)-carboxylate To a solution of the product obtained in step 1 (6.10 g, 19.7 mmol) in toluene (71 mL), (methoxycarbonylsulfamoyl)triethylammonium hydroxide inner salt ("Burgess reagent", 7.03 g, 29.5 mmol) was added and the mixture was heated at 90° C. overnight under a nitrogen atmosphere. It was then cooled to rt and water and DCM were added. The aqueous phase was back extracted with DCM. The organic phases were combined, washed with sat NaHCO$_3$ solution, dried over Na$_2$SO$_4$, filtered and concentrated to dryness to give the title compound (6.14 g crude product, 5.75 g theoretical weight; quant yield).

HPLC-MS (Method C): Ret, 3.91 min; ESI$^+$-MS m/z, 237.1 (M+H-56).

c) tert-Butyl 4-(4-cyanotetrahydro-2H-pyran-4-yl)piperidine-1-carboxylate

A mixture of the crude product obtained in step 2 (6.14 g crude, 19.7 mmol) and palladium (1.23 g, 5% wt on charcoal, wet) in EtOH (115 mL) was stirred at rt. under 1 bar of H$_2$ overnight. Then, the solids were filtered off over a pad of celite and the solvent was evaporated to dryness. The residue was purified by flash chromatography, silica gel, gradient DCM to MeOH:DCM (1:9) to give the title compound (4.04 g, 70% yield).

HPLC-MS (Method C): Ret, 3.79 min; ESI$^+$-MS m/z, 239.1 (M+H-56).

d) 4-(Piperidin-4-yl)tetrahydro-2H-pyran-4-carbonitrile trifluoroacetate

To a solution of the product obtained in step 3 (4.0 g, 13.6 mmol) in DCM (40 mL), TFA (10.4 mL, 136 mmol) was added, and the reaction mixture was stirred at rt. for 1 h. The solvent was evaporated to dryness to give the title compound as a crude product (7.18 g, 4.19 g theoretical weight, quant yield), that was used in the following step without further purification.

HPLC-MS (Method C): Ret, 0.98 min (peak corresponds to TIC spectrum, no peak detected in UV detector at 210 nm) ESI$^+$-MS m/z, 195.1 (M+H).

e): Title Compound

To a solution of the crude product obtained in step d (7.18 g crude, 13.6 mmol) and benzaldehyde (1.3 mL, 17.7 mmol) in dry THF (92 mL), AcOH (1.73 mL, 30.2 mmol) was added. The mixture was stirred at rt. for 15 min and then sodium triacetoxyborohydride (7.99 g, 40.8 mmol) was added in portions. The resulting mixture was stirred at rt overnight. Then, conc. NH$_4$OH (50 mL) was carefully added and it was extracted with ethyl acetate. The organic phases were combined, washed with brine, dried over MgSO$_4$, filtered and concentrated to dryness. The residue was purified by flash chromatography, silica gel, gradient DCM to MeOH:DCM (1:4) to give the title compound (1.75 g, 45% yield).

HPLC-MS (Method C): Ret, 3.83 min; ESI$^+$-MS m/z, 252.2 (M+H).

Intermediates 1O-1Q were prepared according to the procedure described in intermediate 1A using suitable starting materials

| INT | Structure | Chemical name | Method | Ret (min) | MS (M + H) |
|---|---|---|---|---|---|
| 1O | 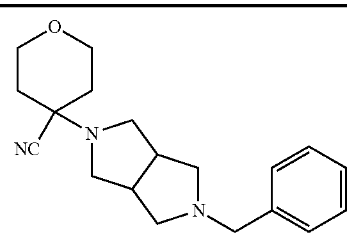 | 4-(5-benzylhexahydropyrrolo[3,4-c]pyrrol-2(1H)-yl)tetrahydro-2H-pyran-4-carbonitrile | RMN* | | |
| 1P | 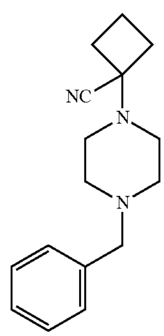 [SMILES: N#CC1(N2CCN(Cc3ccccc3)CC2)CCC1] | 1-(4-benzylpiperazin-1-yl)cyclobutanecarbonitrile | A | 2.01 | 256 |
| 1Q | 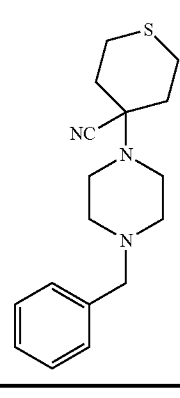 | 4-(4-benzylpiperazin-1-yl)tetrahydro-2H-thiopyran-4-carbonitrile | A | 2.13 | 302 |

*$^1$H NMR (400 MHz, Chloroform-d) δ 7.36-7.28 (m, 4H), 7.25-7.20 (m, 1H), 3.96 (dt, J = 12.3, 4.0 Hz, 2H), 3.68 (ddd, J = 12.1, 10.6, 2.4 Hz, 2H), 3.58 (s, 2H), 2.81-2.70 (m, 6H), 2.57 (d, J = 5.8 Hz, 2H), 2.27-2.20 (m, 2H), 2.00 (ddt, J = 13.5, 4.0, 2.1 Hz, 2H), 1.84 (ddd, J = 13.4, 10.6, 4.2 Hz, 2H).

Intermediate 2A. (4-(4-Benzylpiperazin-1-yl)tetrahydro-2H-pyran-4-yl)methanamine

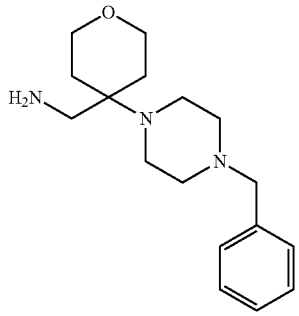 [SMILES: NCC1(N2CCN(Cc3ccccc3)CC2)CCOCC1]

4-(4-Benzylpiperazin-1-yl)tetrahydro-2H-pyran-4-carbonitrile (INT 1A, 2 g, 7 mmol) in THF/Et$_2$O (40/20 mL) was added at 0° C. to a stirred solution of fresh lithium aluminium hydride in Et$_2$O (1M, 14 mL, 14 mmol). The reaction was stirred at rt for 1 h, a few drops of an aqueous sat solution of potassium sodium tartrate were added and the mixture was stirred overnight at rt. Then, water and AcOEt were added and the aqueous layer was separated and extracted several times with AcOEt. The organic layers were combined, dried over Na$_2$SO$_4$, filtered and concentrated to give the title compound as a solid (1.8 g, 88% yield).

HPLC-MS (Method B): Ret, 1.42 min; ESI$^+$-MS m/z, 290 (M+1).

This method was used for the preparation of intermediates 2B-2P using the corresponding intermediates 1 as starting materials:

| INT | Structure | Chemical name | Method | Ret (min) | MS (M + H) |
|---|---|---|---|---|---|
| 2B | 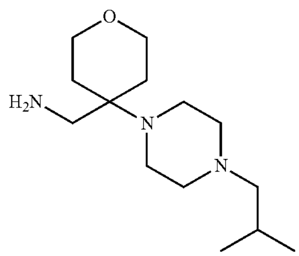 [SMILES: CC(C)CN1CCN(C2(CN)CCOCC2)CC1] | (4-(4-isobutylpiperazin-1-yl)tetrahydro-2H-pyran-4-yl)methanamine | A | 1.05 | 256 |
| 2C | 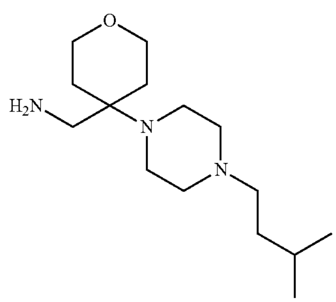 [SMILES: CC(C)CCN1CCN(C2(CN)CCOCC2)CC1] | (4-(4-isopentylpiperazin-1-yl)tetrahydro-2H-pyran-4-yl)methanamine | A | 1.11 | 270 |
| 2D | 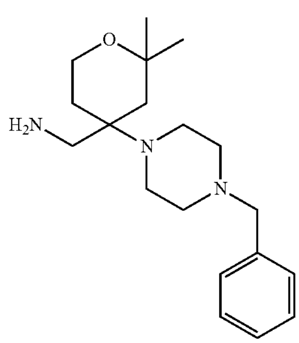 [SMILES: CC1(C)CC(CN)(N2CCN(Cc3ccccc3)CC2)CCO1] | (4-(4-benzylpiperazin-1-yl)-2,2-dimethyltetrahydro-2H-pyran-4-yl)methanamine | A | 1.47 | 318 |

-continued

| INT | Structure | Chemical name | Method | Ret (min) | MS (M + H) |
|---|---|---|---|---|---|
| 2E | 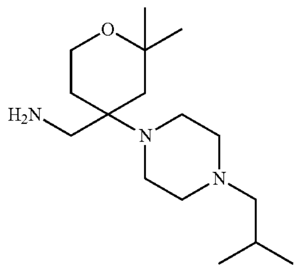 [SMILES: CC(C)CN1CCN(C2(CN)CCOC(C)(C)C2)CC1] | (4-(4-isobutylpiperazin-1-yl)-2,2-dimethyltetrahydro-2H-pyran-4-yl)methanamine | A | 1.24 | 284 |
| 2F | 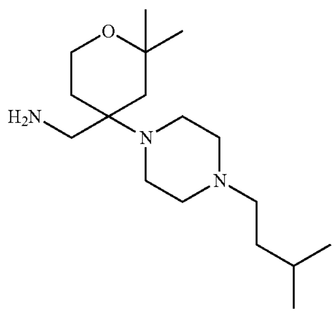 [SMILES: CC(C)CCN1CCN(C2(CN)CCOC(C)(C)C2)CC1] | (4-(4-isopentylpiperazin-1-yl)-2,2-dimethyltetrahydro-2H-pyran-4-yl)methanamine | A | 1.35 | 298 |
| 2G | 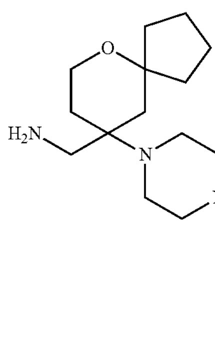 | (9-(4-benzylpiperazin-1-yl)-6-oxaspiro[4.5]decan-9-yl)methanamine | A | 1.46 | 344 |
| 2H | 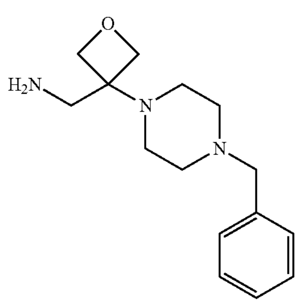 [SMILES: NCC1(N2CCN(Cc3ccccc3)CC2)COC1] | (3-(4-benzylpiperazin-1-yl)oxetan-3-yl)methanamine | A | 1.12 | 262 |
| 2I | 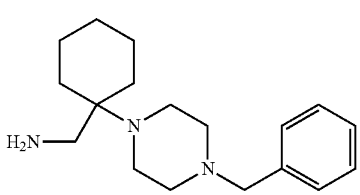 [SMILES: NCC1(N2CCN(Cc3ccccc3)CC2)CCCCC1] | (1-(4-benzylpiperazin-1-yl)cyclohexyl)methanamine | C | — | 288 |

-continued

| INT | Structure | Chemical name | Method | Ret (min) | MS (M + H) |
|---|---|---|---|---|---|
| 2J | 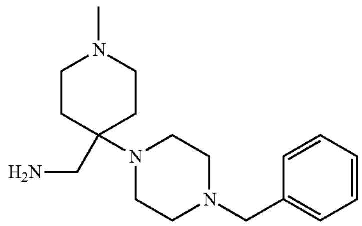 [SMILES: CN1CCC(CN)(N2CCN(Cc3ccccc3)CC2)CC1] | (4-(4-benzylpiperazin-1-yl)-1-methylpiperidin-4-yl)methanamine | A | 1.13 | 303 |
| 2K | 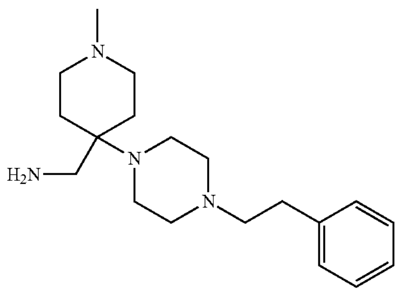 [SMILES: CN1CCC(CN)(N2CCN(CCc3ccccc3)CC2)CC1] | (1-methyl-4-(4-phenethylpiperazin-1-yl)piperidin-4-yl)methanamine | A | 1.41 | 317 |
| 2L | 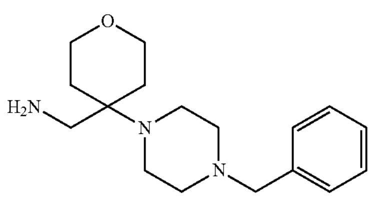 [SMILES: NCC1(N2CCN(Cc3ccccc3)CC2)CCOCC1] | (4-(1-benzylpiperidin-4-yl)tetrahydro-2H-pyran-4-yl)methanamine | C | 3.4 | 289.2 |
| 2M | 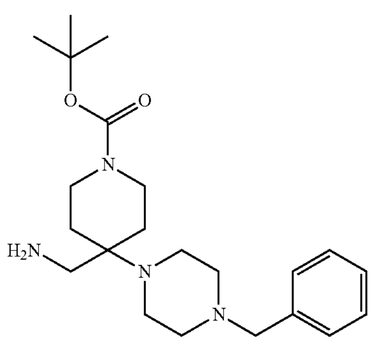 [SMILES: CC(C)(C)OC(=O)N1CCC(CN)(N2CCN(Cc3ccccc3)CC2)CC1] | tert-butyl 4-(aminomethyl)-4-(4-benzylpiperazin-1-yl)piperidine-1-carboxylate | A | 1.82 | 389 |
| 2N | 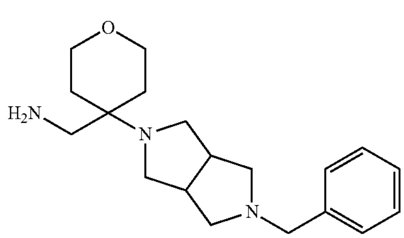 [SMILES: NCC1(N2CC3CN(Cc4ccccc4)CC3C2)CCOCC1] | (4-(5-benzylhexahydropyrrolo[3,4-c]pyrrol-2(1H)-yl)tetrahydro-2H-pyran-4-yl)methanamine | A | 1.24 | 316.2 |

| INT | Structure | Chemical name | Method | Ret (min) | MS (M + H) |
|---|---|---|---|---|---|
| 2O | 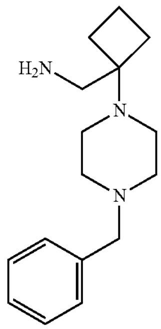 [SMILES: NCC1(N2CCN(Cc3ccccc3)CC2)CCC1] | (1-(4-benzylpiperazin-1-yl)cyclobutyl)methanamine | A | 1.29 | 260 |
| 2P | 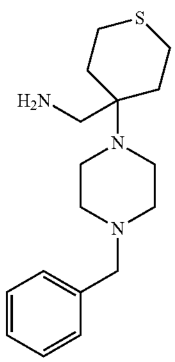 [SMILES: NCC1(N2CCN(Cc3ccccc3)CC2)CCSCC1] | (4-(4-benzylpiperazin-1-yl)tetrahydro-2H-thiopyran-4-yl)methanamine | A | 1.49 | 306 |

Intermediate 3A. N-((4-(4-Benzylpiperazin-1-yl)tetrahydro-2H-pyran-4-yl)methyl)aniline

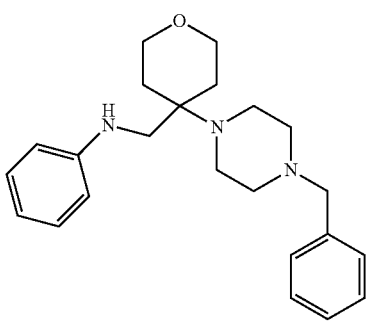 [SMILES: c1ccc(CN2CCN(C3(CNc4ccccc4)CCOCC3)CC2)cc1]

(4-(4-Benzylpiperazin-1-yl)tetrahydro-2H-pyran-4-yl)methanamine (INT 2A, 0.5 g, 1.73 mmol), Pd$_2$(dba)$_3$ (0.16 g, 0.17 mmol), 2,2'-bis(diphenylphosphino)-1,1'-binaphthyl (BINAP, 0.13 g, 0.21 mmol) and $^t$BuOK (581 g, 5.18 mmol) were added to a Raddley tube, under nitrogen, and dissolved in anhydrous THF (10 mL). Bromobenzene (0.41 g, 2.59 mmol) was added and the reaction mixture was stirred at 50° C. overnight. The solvents were evaporated and the residue was dissolved in EtOAc and an aqueous sat NaHCO$_3$ solution. The aqueous layer was extracted with EtOAc and the combined organic layers were dried over Na$_2$SO$_4$, filtered and concentrated. The crude product thus obtained was purified by flash chromatography on silica gel, gradient CH:AcOEt from (100:0) to (0:100) to give the title compound as a solid (0.47 g, 74% yield).

HPLC-MS (Method A): Ret, 2.32 min; ESI$^+$-MS m/z, 366 (M+1).

This method was used for the preparation of intermediates 3B-3AG using the corresponding intermediates 2 as starting materials and the required halides:

| EX | Structure | Chemical name | Method | Ret (min) | MS (M + H) |
|---|---|---|---|---|---|
| 3B | 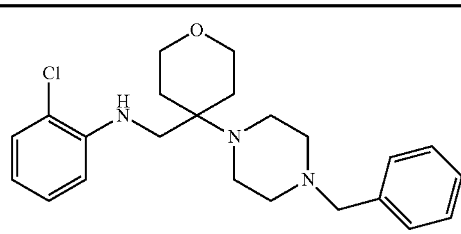 | N-((4-(4-benzylpiperazin-1-yl)tetrahydro-2H-pyran-4-yl)methyl)-2-chloroaniline | A | 2.6 | 400 |

| EX | Structure | Chemical name | Method | Ret (min) | MS (M + H) |
|---|---|---|---|---|---|
| 3C | 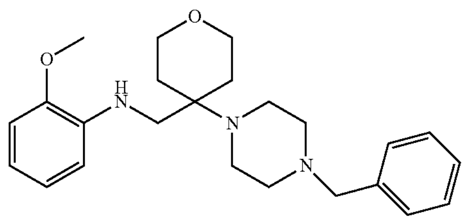 [SMILES: COc1ccccc1NCC1(N2CCN(Cc3ccccc3)CC2)CCOCC1] | N-((4-(4-benzylpiperazin-1-yl)tetrahydro-2H-pyran-4-yl)methyl)-2-methoxyaniline | A | 2.36 | 396 |
| 3D | 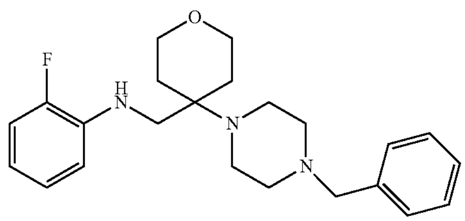 [SMILES: Fc1ccccc1NCC1(N2CCN(Cc3ccccc3)CC2)CCOCC1] | N-((4-(4-benzylpiperazin-1-yl)tetrahydro-2H-pyran-4-yl)methyl)-2-fluoroaniline | A | 2.43 | 384 |
| 3E | 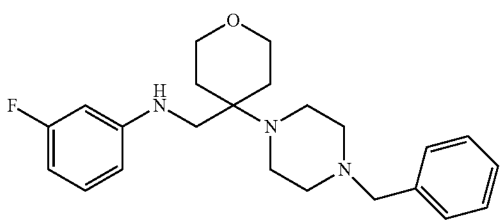 [SMILES: Fc1cccc(NCC2(N3CCN(Cc4ccccc4)CC3)CCOCC2)c1] | N-((4-(4-benzylpiperazin-1-yl)tetrahydro-2H-pyran-4-yl)methyl)-3-fluoroaniline | A | 2.36 | 384 |
| 3F | 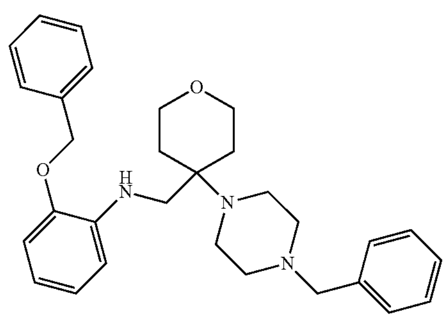 [SMILES: c1ccc(COc2ccccc2NCC2(N3CCN(Cc4ccccc4)CC3)CCOCC2)cc1] | 2-(benzyloxy)-N-((4-(4-benzylpiperazin-1-yl)tetrahydro-2H-pyran-4-yl)methyl)aniline | B | 3.30 | 472 |
| 3G | 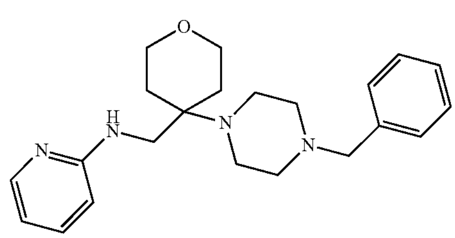 [SMILES: c1ccc(CN2CCN(C3(CNc4ccccn4)CCOCC3)CC2)cc1] | N-((4-(4-benzylpiperazin-1-yl)tetrahydro-2H-pyran-4-yl)methyl)pyridin-2-amine | A | 1.83 | 367 |
| 3H | 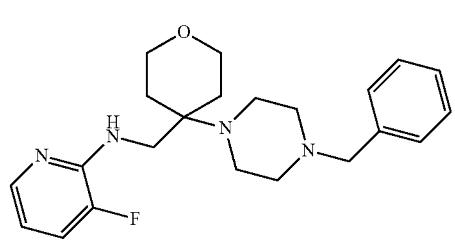 [SMILES: Fc1cccnc1NCC1(N2CCN(Cc3ccccc3)CC2)CCOCC1] | N-((4-(4-benzylpiperazin-1-yl)tetrahydro-2H-pyran-4-yl)methyl)-3-fluoropyridin-2-amine | A | 2.11 | 385 |

-continued

| EX | Structure | Chemical name | Method | Ret (min) | MS (M + H) |
|---|---|---|---|---|---|
| 3I | 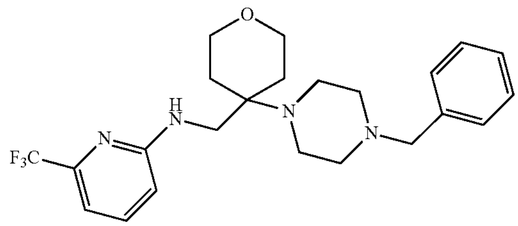 [SMILES: FC(F)(F)c1cccc(NCC2(N3CCN(Cc4ccccc4)CC3)CCOCC2)n1] | N-((4-(4-benzylpiperazin-1-yl)tetrahydro-2H-pyran-4-yl)methyl)-6-(trifluoromethyl)pyridin-2-amine | A | 2.37 | 435 |
| 3J | 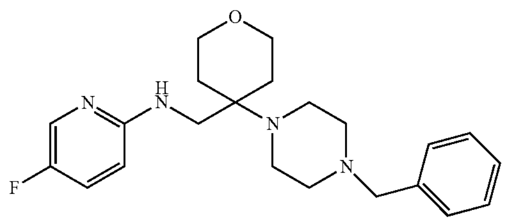 [SMILES: Fc1ccc(NCC2(N3CCN(Cc4ccccc4)CC3)CCOCC2)nc1] | N-((4-(4-benzylpiperazin-1-yl)tetrahydro-2H-pyran-4-yl)methyl)-5-fluoropyridin-2-amine | A | 2.00 | 385 |
| 3K | 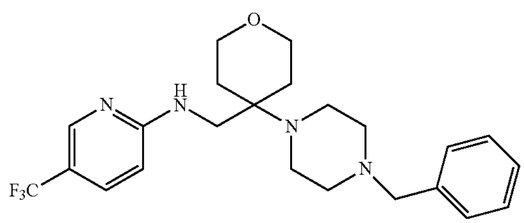 [SMILES: FC(F)(F)c1ccc(NCC2(N3CCN(Cc4ccccc4)CC3)CCOCC2)nc1] | N-((4-(4-benzylpiperazin-1-yl)tetrahydro-2H-pyran-4-yl)methyl)-5-(trifluoromethyl)pyridin-2-amine | A | 2.28 | 435 |
| 3L | 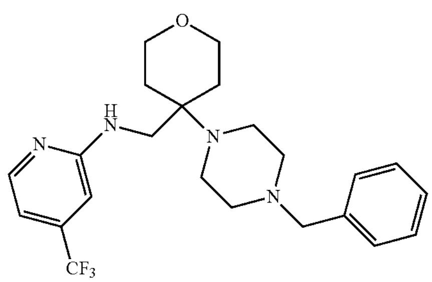 [SMILES: FC(F)(F)c1ccnc(NCC2(N3CCN(Cc4ccccc4)CC3)CCOCC2)c1] | N-((4-(4-benzylpiperazin-1-yl)tetrahydro-2H-pyran-4-yl)methyl)-4-(trifluoromethyl)pyridin-2-amine | A | 2.29 | 435 |
| 3M | 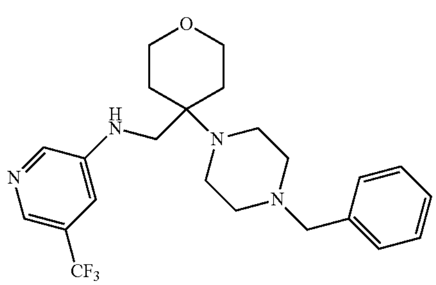 [SMILES: FC(F)(F)c1cncc(NCC2(N3CCN(Cc4ccccc4)CC3)CCOCC2)c1] | N-((4-(4-benzylpiperazin-1-yl)tetrahydro-2H-pyran-4-yl)methyl)-5-(trifluoromethyl)pyridin-3-amine | A | 2.14 | 435 |
| 3N | 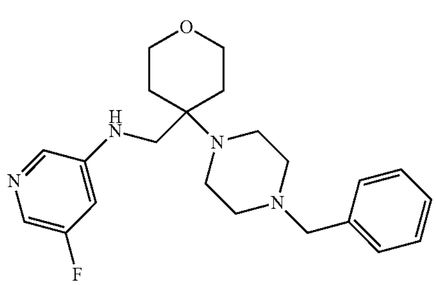 [SMILES: Fc1cncc(NCC2(N3CCN(Cc4ccccc4)CC3)CCOCC2)c1] | N-((4-(4-benzylpiperazin-1-yl)tetrahydro-2H-pyran-4-yl)methyl)-5-fluoropyridin-3-amine | A | 1.91 | 385 |

| EX | Structure | Chemical name | Method | Ret (min) | MS (M + H) |
|---|---|---|---|---|---|
| 3O | 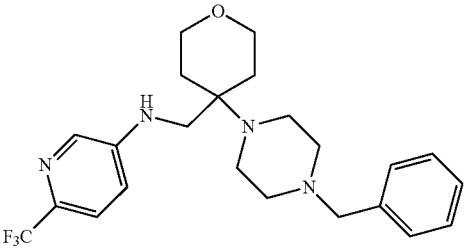 [SMILES: FC(F)(F)c1ccc(NCC2(N3CCN(Cc4ccccc4)CC3)CCOCC2)cn1] | N-((4-(4-benzylpiperazin-1-yl)tetrahydro-2H-pyran-4-yl)methyl)-6-(trifluoromethyl)pyridin-3-amine | A | 2.18 | 435 |
| 3P | 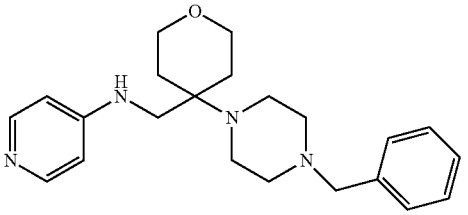 [SMILES: c1ccc(CN2CCN(C3(CNc4ccncc4)CCOCC3)CC2)cc1] | N-((4-(4-benzylpiperazin-1-yl)tetrahydro-2H-pyran-4-yl)methyl)pyridin-4-amine | A | 1.51 | 367 |
| 3Q | 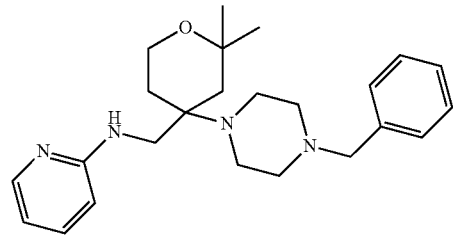 [SMILES: CC1(C)CC(CNc2ccccn2)(N2CCN(Cc3ccccc3)CC2)CCO1] | N-((4-(4-benzylpiperazin-1-yl)-2,2-dimethyltetrahydro-2H-pyran-4-yl)methyl)pyridin-2-amine | A | 2.11 | 395 |
| 3R | 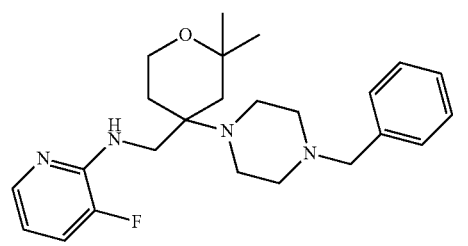 [SMILES: CC1(C)CC(CNc2ncccc2F)(N2CCN(Cc3ccccc3)CC2)CCO1] | N-((4-(4-benzylpiperazin-1-yl)-2,2-dimethyltetrahydro)-2H-pyran-4-yl)methyl)-3-fluoropyridin-2-amine | A | 2.33 | 413 |
| 3S | 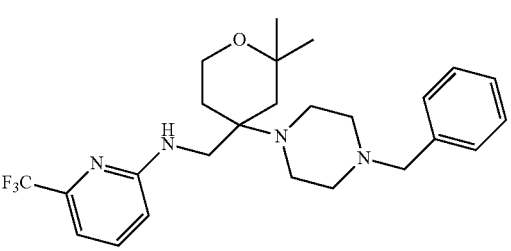 [SMILES: CC1(C)CC(CNc2cccc(C(F)(F)F)n2)(N2CCN(Cc3ccccc3)CC2)CCO1] | N-((4-(4-benzylpiperazin-1-yl)-2,2-dimethyltetrahydro-2H-pyran-4-yl)methyl)-6-(trifluoromethyl)pyridin-2-amine | A | 2.54 | 463 |
| 3T | 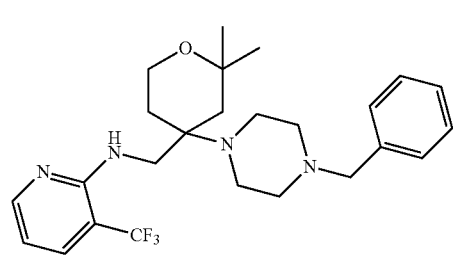 [SMILES: CC1(C)CC(CNc2ncccc2C(F)(F)F)(N2CCN(Cc3ccccc3)CC2)CCO1] | N-((4-(4-benzylpiperazin-1-yl)-2,2-dimethyltetrahydro-2H-pyran-4-yl)methyl)-3-(trifluoromethyl)pyridin-2-amine | A | 2.61 | 463 |

| EX | Structure | Chemical name | Method | Ret (min) | MS (M + H) |
|---|---|---|---|---|---|
| 3U | 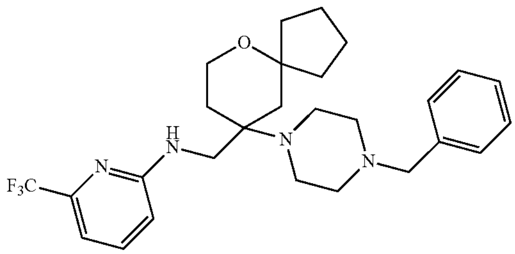 [SMILES: FC(F)(F)c1cccc(NCC2(N3CCN(Cc4ccccc4)CC3)CCOC3(CCCC3)C2)n1] | N-((9-(4-benzylpiperazin-1-yl)-6-oxaspiro[4.5]decan-9-yl)methyl)-6-(trifluoromethyl)pyridin-2-amine | B | 3.27 | 489 |
| 3V | 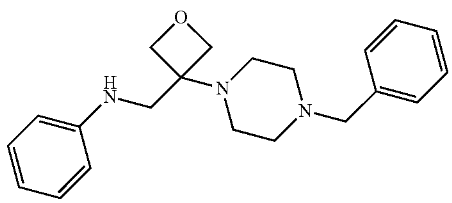 [SMILES: c1ccc(CN2CCN(C3(CNc4ccccc4)COC3)CC2)cc1] | N-((3-(4-benzylpiperazin-1-yl)oxetan-3-yl)methyl)aniline | A | 2.06 | 338 |
| 3W | 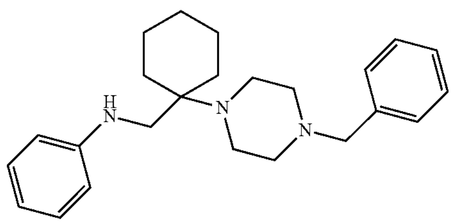 [SMILES: c1ccc(CN2CCN(C3(CNc4ccccc4)CCCCC3)CC2)cc1] | N-((1-(4-benzylpiperazin-1-yl)cyclohexyl)methyl)aniline | C | | 364 |
| 3X | 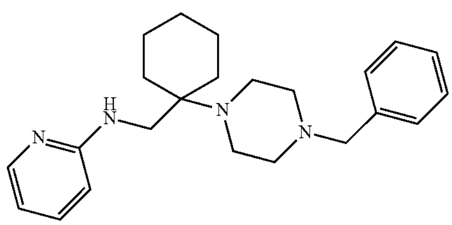 [SMILES: c1ccc(CN2CCN(C3(CNc4ccccn4)CCCCC3)CC2)cc1] | N-((1-(4-benzylpiperazin-1-yl)cyclohexyl)methyl)pyridin-2-amine | C | | 365 |
| 3Y | 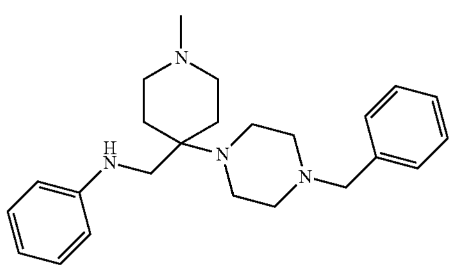 [SMILES: CN1CCC(CNc2ccccc2)(N2CCN(Cc3ccccc3)CC2)CC1] | N-((4-(4-benzylpiperazin-1-yl)-1-methylpiperidin-4-yl)methyl)aniline | A | 2.01 | 379 |
| 3Z | 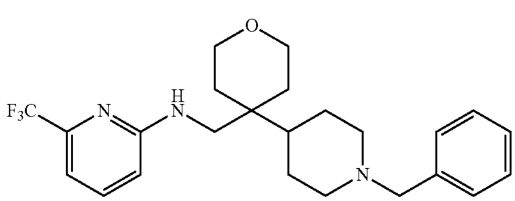 [SMILES: FC(F)(F)c1cccc(NCC2(C3CCN(Cc4ccccc4)CC3)CCOCC2)n1] | N-((4-(1-benzylpiperidin-4-yl)tetrahydro-2H-pyran-4-yl)methyl)-6-(trifluoromethyl)pyridin-2-amine | C | 5.16 | 434 |
| 3AA | 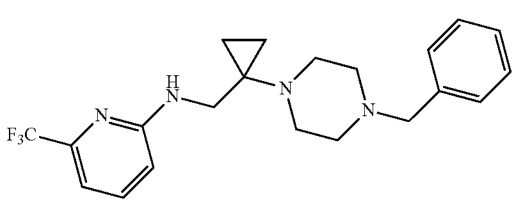 [SMILES: FC(F)(F)c1cccc(NCC2(N3CCN(Cc4ccccc4)CC3)CC2)n1] | N-((1-(4-benzylpiperazin-1-yl)cyclopropyl)methyl)-6-(trifluoromethyl)pyridin-2-amine | A | 2.48 | 391 |

-continued

| EX | Structure | Chemical name | Method | Ret (min) | MS (M + H) |
|---|---|---|---|---|---|
| 3AB | 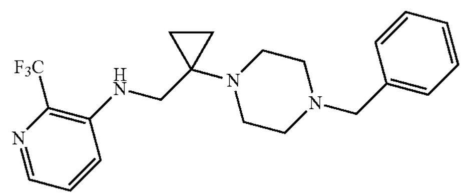 [SMILES: FC(F)(F)c1ncccc1NCC1(N2CCN(Cc3ccccc3)CC2)CC1] | N-((1-(4-benzylpiperazin-1-yl)cyclopropyl)methyl)-2-(trifluoromethyl)pyridin-3-amine | A | 2.37 | 391 |
| 3AC | 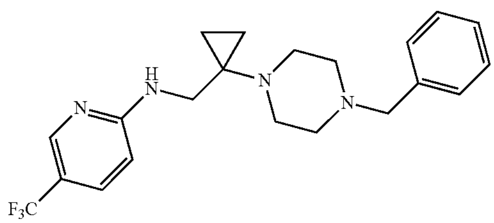 [SMILES: FC(F)(F)c1ccc(NCC2(N3CCN(Cc4ccccc4)CC3)CC2)nc1] | N-((1-(4-benzylpiperazin-1-yl)cyclopropyl)methyl)-5-(trifluoromethyl)pyridin-2-amine | A | 2.38 | 391 |
| 3AD | 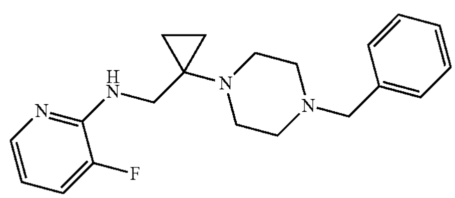 [SMILES: Fc1cccnc1NCC1(N2CCN(Cc3ccccc3)CC2)CC1] | N-((1-(4-benzylpiperazin-1-yl)cyclopropyl)methyl)-3-fluoropyridin-2-amine | A | 2.19 | 341 |
| 3AE | 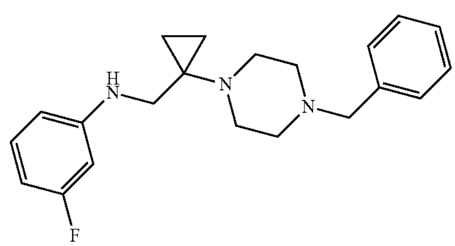 [SMILES: Fc1cccc(NCC2(N3CCN(Cc4ccccc4)CC3)CC2)c1] | N-((1-(4-benzylpiperazin-1-yl)cyclopropyl)methyl)-3-fluoroaniline | B | 3.10 | 340 |
| 3AF | 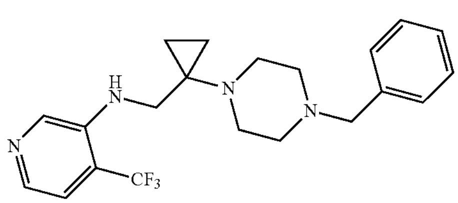 [SMILES: FC(F)(F)c1ccncc1NCC1(N2CCN(Cc3ccccc3)CC2)CC1] | N-((1-(4-benzylpiperazin-1-yl)cyclopropyl)methyl)-4-(trifluoromethyl)pyridin-3-amine | A | 2.35 | 391 |
| 3AG | 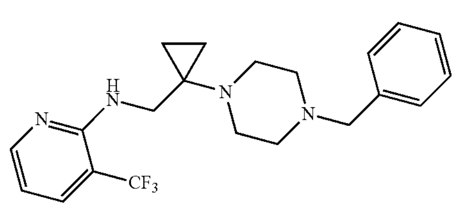 | N-((1-(4-benzylpiperazin-1-yl)cyclopropyl)methyl)-3-(trifluoromethyl)pyridin-2-amine | A | 2.58 | 391 |

Intermediate 3AH. 3-((4-(4-Benzylpiperazin-1-yl)tetrahydro-2H-pyran-4-yl)methylamino)benzonitrile

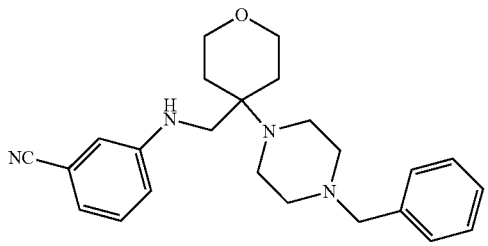 [SMILES: N#Cc1cccc(NCC2(N3CCN(Cc4ccccc4)CC3)CCOCC2)c1]

(4-(4-Benzylpiperazin-1-yl)tetrahydro-2H-pyran-4-yl)methanamine (INT 2A, 0.15 g, 0.518 mmol), Pd$_2$(dba)$_3$ (0.047 g, 0.052 mmol), (9,9-dimethyl-9H-xanthene-4,5-diyl)bis(diphenylphosphine) (XAMPHOS) (0.036, 0.062 mmol) and $^t$BuOK (0.149 g, 1.55 mmol) were added to a Raddley tube, under nitrogen, and dissolved in anhydrous toluene (5 mL). 3-Bromobenzonitrile (0.141 g, 0.777 mmol) was added and the reaction mixture was stirred at 110° C. overnight. The solvent was evaporated and the residue was dissolved in EtOAc and NaHCO$_3$ sat solution. The aqueous layer was extracted twice and the combined organic layers were dried over Na$_2$SO$_4$ filtered and concentrated. The crude product thus obtained was purified by flash chromatography on silica gel, DCM to MeOH:DCM (0.5.9.5) to give the title compound as a solid (0.179 g, 80% yield).

HPLC-MS (Method A): Ret, 2.24 min; ESI+-MS m/z, 391 (M+1).

This method was used for the preparation of intermediates 3AI-3AL using intermediate 2A as starting material and the corresponding halides:

| EX | Structure | Chemical name | Method | Ret (min) | MS (M + H) |
|---|---|---|---|---|---|
| 3AI | 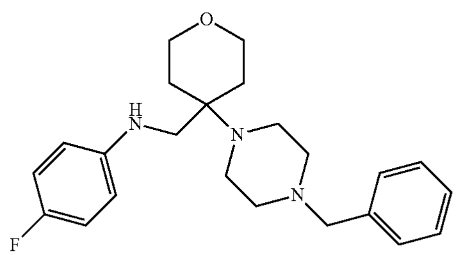 [SMILES: Fc1ccc(NCC2(N3CCN(Cc4ccccc4)CC3)CCOCC2)cc1] | N-((4-(4-benzylpiperazin-1-yl)tetrahydro-2H-pyran-4-yl)methyl)-4-fluoroaniline | A | 2.31 | 384 |
| 3AJ | 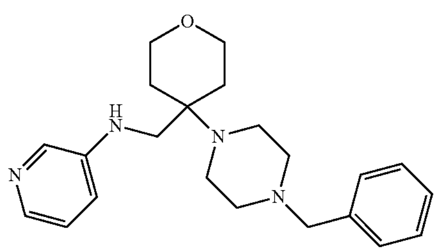 [SMILES: c1ccc(CN2CCN(C3(CNc4cccnc4)CCOCC3)CC2)cc1] | N-((4-(4-benzylpiperazin-1-yl)tetrahydro-2H-pyran-4-yl)methyl)pyridin-3-amine | A | 1.74 | 367 |
| 3AK | 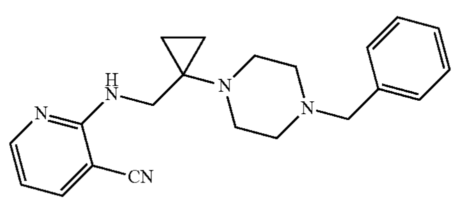 [SMILES: N#Cc1cccnc1NCC1(N2CCN(Cc3ccccc3)CC2)CC1] | 2-((1-(4-benzylpiperazin-1-yl)cyclopropyl)methylamino)nicotinonitrile | A | 2.18 | 248 |
| 3AL | 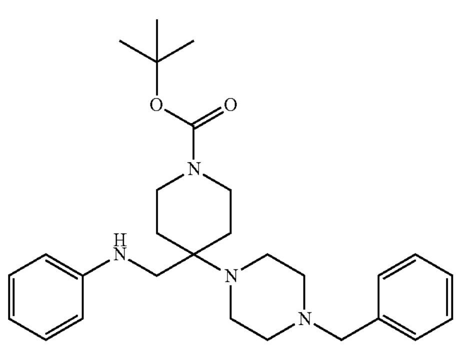 [SMILES: CC(C)(C)OC(=O)N1CCC(CNc2ccccc2)(N2CCN(Cc3ccccc3)CC2)CC1] | tert-butyl 4-(4-benzylpiperazin-1-yl)-4-((phenylamino)methyl)piperidine-1-carboxylate | A | 2.74 | 465 |

Intermediate 3AM. N-((4-(4-Benzylpiperazin-1-yl)tetrahydro-2H-pyran-4-yl)methyl)-3-(trifluoromethyl)pyridin-2-amine

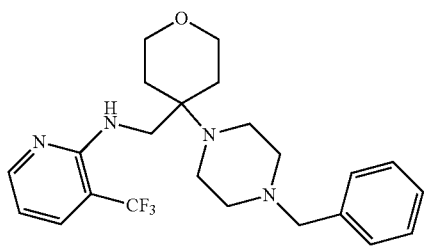 [SMILES: FC(F)(F)c1cccnc1NCC1(N2CCN(Cc3ccccc3)CC2)CCOCC1]

(4-(4-Benzylpiperazin-1-yl)tetrahydro-2H-pyran-4-yl)methanamine (INT 2A, 0.15 g, 0.518 mmol), palladium(II) acetate (0.023 g, 0.104 mmol), 2,2'-bis(diphenylphosphino)-1,1'-binaphthyl (BINAP, 0.097 g, 0.155 mmol) and $Cs_2CO_3$ (0.253 g, 0.777 mmol) were added to a Raddley tube, under nitrogen, and dissolved in anhydrous toluene (8 mL). 2-Bromo-3-(trifluoromethyl)pyridine (0.140 g, 0.622 mmol) was added and the reaction mixture was stirred at 90° C. overnight. The solvent was evaporated and the crude product thus obtained was purified by flash chromatography on neutral alumina, gradient CH:AcOEt from (100:0) to (92:8) to give the title compound as an oil (0.069 g, 31% yield).

HPLC-MS (Method A): Ret, 2.41 min; ESI+-MS m/z, 435 (M+1).

This method was used for the preparation of the following intermediates using intermediate 2A as starting material and the corresponding halides:

| EX | Structure | Chemical name | Method | Ret (min) | MS (M + H) |
|---|---|---|---|---|---|
| 3AN | 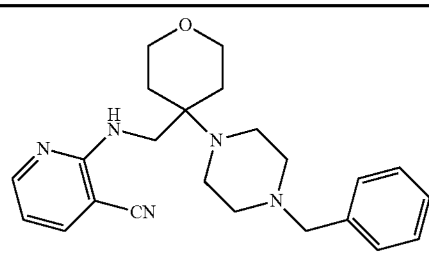 | 2-((4-(4-benzylpiperazin-1-yl)tetrahydro-2H-pyran-4-yl)methylamino)nicotinonitrile | A | 2.06 | 392 |
| 3AO | 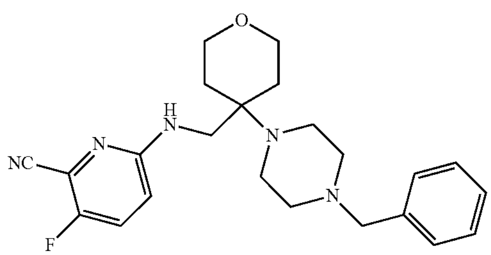 [SMILES: N#Cc1nc(NCC2(N3CCN(Cc4ccccc4)CC3)CCOCC2)ccc1F] | 6-((4-(4-benzylpiperazin-1-yl)tetrahydro-2H-pyran-4-yl)methylamino)-3-fluoropicolinonitrile | A | 2.10 | 410 |
| 3AP | 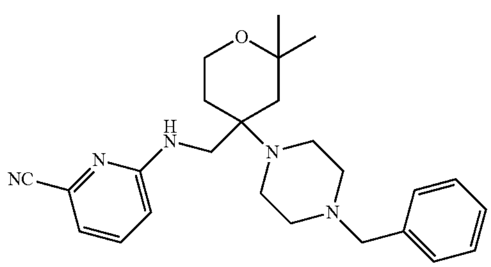 [SMILES: CC1(C)CC(CNc2cccc(C#N)n2)(N2CCN(Cc3ccccc3)CC2)CCO1] | 6-((4-(4-benzylpiperazin-1-yl)-2,2-dimethyltetrahydro-2H-pyran-4-yl)methylamino)picolinonitrile | A | 2.24 | 420 |
| 3AQ | 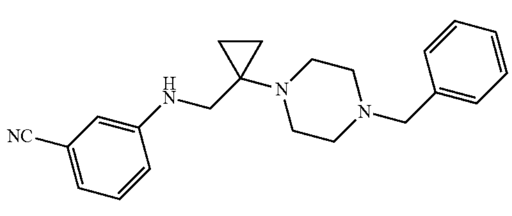 [SMILES: N#Cc1cccc(NCC2(N3CCN(Cc4ccccc4)CC3)CC2)c1] | 3-((1-(4-benzylpiperazin-1-yl)cyclopropyl)methylamino)benzonitrile | A | 2.34 | 347 |
| 3AR | 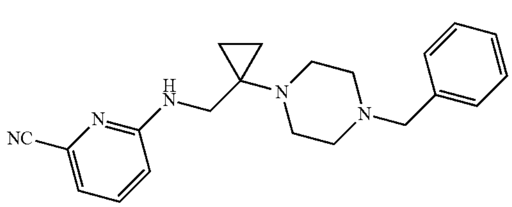 [SMILES: N#Cc1cccc(NCC2(N3CCN(Cc4ccccc4)CC3)CC2)n1] | 6-((1-(4-benzylpiperazin-1-yl)cyclopropyl)methylamino)picolinonitrile | A | 2.71 | 348 |

Intermediate 3AS. 6-((4-(4-Benzylpiperazin-1-yl)tetrahydro-2H-pyran-4-yl)methylamino)picolinonitrile

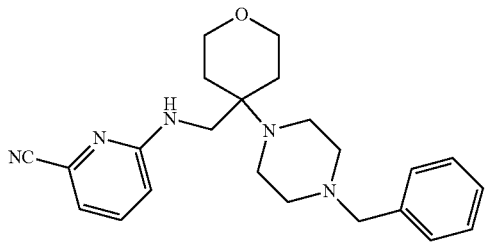 [SMILES: N#Cc1cccc(NCC2(N3CCN(Cc4ccccc4)CC3)CCOCC2)n1]

(4-(4-Benzylpiperazin-1-yl)tetrahydro-2H-pyran-4-yl)methanamine (INT 2A, 1 g, 3.45 mmol), palladium(II) acetate (0.077 g, 0.35 mmol), (9,9-dimethyl-9H-xanthene-4,5-diyl)bis(diphenylphosphine) (XAMPHOS, 0.30 g, 0.52 mmol) and $Cs_2CO_3$ (1.69 g, 5.18 mmol) were added to a flask, under nitrogen, and dissolved in anhydrous toluene (100 mL). 6-Bromopicolinonitrile (0.984 g, 5.18 mmol) was added and the reaction mixture was stirred at 100° C. overnight. The solvent was evaporated and the crude product thus obtained was diluted with DCM (100 mL) and water (100 mL). The aqueous phase was acidified with 10% HCl and stirred for 10 min. The layers were separated and the organic phase was extracted 10% HCl. The aqueous phase was washed with DCM and treated with 20% NaOH up to pH 12. The aqueous phase was extracted with AcOEt and the organic layers were dried over $Na_2SO_4$, filtered and concentrated to give the title compound (1.2 g, yield 40%).

HPLC-MS (Method A): Ret, 2.05 min; ESI+-MS m/z, 392 (M+1).

This method was used for the preparation of intermediates 3AT-3AY using the corresponding intermediates 2 as starting material and the required halides:

| EX | Structure | Chemical name | Method | Ret (min) | MS (M + H) |
|---|---|---|---|---|---|
| 3AT | 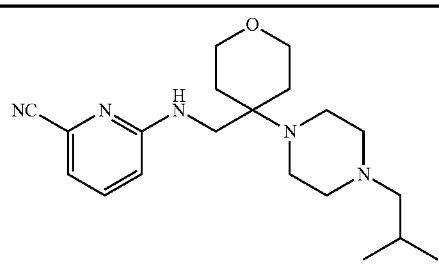 | 6-((4-(4-isobutylpiperazin-1-yl)tetrahydro-2H-pyran-4-yl)methylamino)picolinonitrile | A | 1.88 | 358 |
| 3AU | 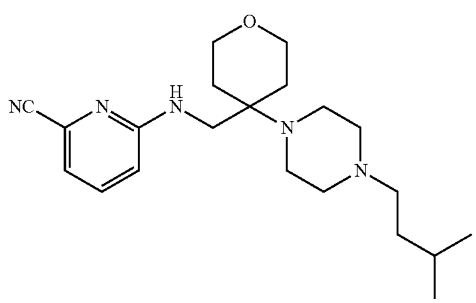 [SMILES: CC(C)CCN1CCN(C2(CNc3cccc(C#N)n3)CCOCC2)CC1] | 6-((4-(4-isopentylpiperazin-1-yl)tetrahydro-2H-pyran-4-yl)methylamino)picolinonitrile | A | 1.88 | 372 |
| 3AV | 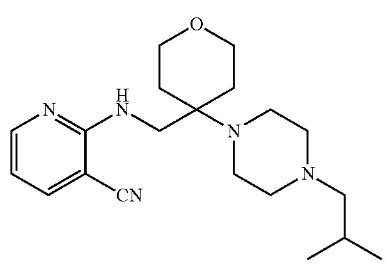 [SMILES: CC(C)CN1CCN(C2(CNc3ncccc3C#N)CCOCC2)CC1] | 2-((4-(4-isobutylpiperazin-1-yl)tetrahydro-2H-pyran-4-yl)methylamino)nicotinonitrile | A | 1.98 | 358 |
| 3AW | 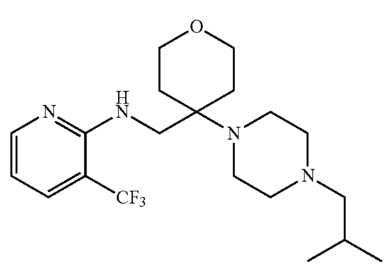 | N-((4-(4-isobutylpiperazin-1-yl)tetrahydro-2H-pyran-4-yl)methyl)-3-(trifluoromethyl)pyridin-2-amine | A | 2.53 | 401 |

| EX | Structure | Chemical name | Method | Ret (min) | MS (M + H) |
|---|---|---|---|---|---|
| 3AX | 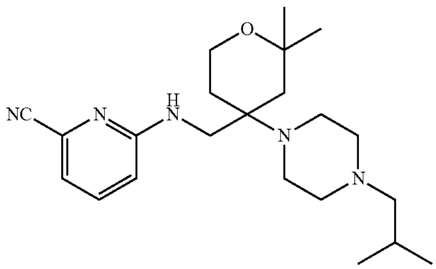 [SMILES: CC(C)CN1CCN(C2(CNc3cccc(C#N)n3)CCOC(C)(C)C2)CC1] | 6-((4-(4-isobutylpiperazin-1-yl)-2,2-dimethyltetrahydro-2H-pyran-4-yl)methylamino)picolinonitrile | A | 2.17 | 386 |
| 3AY | 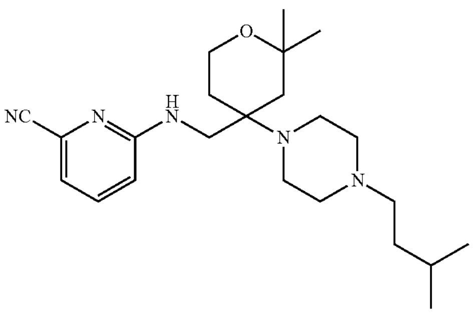 [SMILES: CC(C)CCN1CCN(C2(CNc3cccc(C#N)n3)CCOC(C)(C)C2)CC1] | 6-((4-(4-isopentylpiperazin-1-yl)-2,2-dimethyltetrahydro-2H-pyran-4-yl)methylamino)picolinonitrile | A | 2.56 | 400 |

Intermediate 3AZ. N-((4-(4-Benzylpiperazin-1-yl)tetrahydro-2H-pyran-4-yl)methyl)-1-phenylethanamine

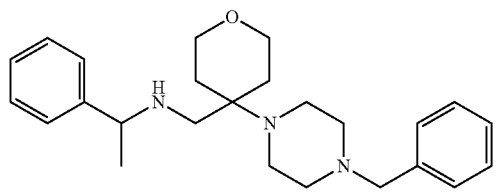 [SMILES: CC(NCC1(N2CCN(Cc3ccccc3)CC2)CCOCC1)c1ccccc1]

(1-Bromoethyl)benzene (57 mg, 0.31 mmol) was added to a solution of (4-(4-benzylpiperazin-1-yl)tetrahydro-2H-pyran-4-yl)methanamine (INT 2A, 50 mg, 0.17 mmol) and $K_2CO_3$ (71 mg, 0.52 mmol) in ACN (4 mL). The reaction mixture was stirred at 80° C. overnight and then cooled down to rt. AcOEt (10 mL) and aqueous $NaHCO_3$ sat solution (10 mL) was added and the phases were separated. The organic layer was dried over $Na_2SO_4$, filtered and concentrated to give the title compound as an oil (68 mg, yield 99%).

HPLC-MS (Method A): Ret, 3.23 min; $ESI^+$-MS m/z, 394 (M+1).

This method was used for the preparation of intermediates 3BA-3BC using intermediate 2A as starting material and the corresponding alkylating agents:

| EX | Structure | Chemical name | Method | Ret (min) | MS (M + H) |
|---|---|---|---|---|---|
| 3BA | 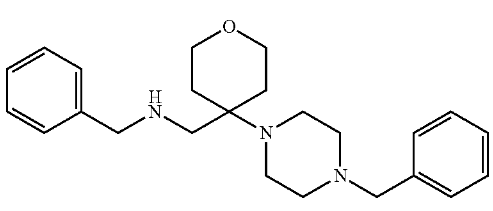 [SMILES: c1ccc(CNCC2(N3CCN(Cc4ccccc4)CC3)CCOCC2)cc1] | N-benzyl-1-(4-(4-benzylpiperazin-1-yl)tetrahydro-2H-pyran-4-yl)methanamine | A | 1.97 | 380 |
| 3BB | 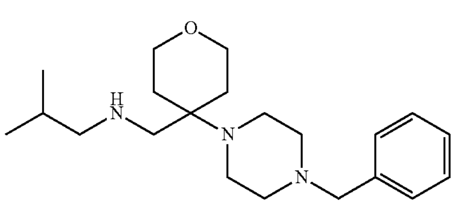 [SMILES: CC(C)CNCC1(N2CCN(Cc3ccccc3)CC2)CCOCC1] | N-((4-(4-benzylpiperazin-1-yl)tetrahydro-2H-pyran-4-yl)methyl)-2-methylpropan-1-amine | A | 1.72 | 346 |

| EX | Structure | Chemical name | Method | Ret (min) | MS (M + H) |
|---|---|---|---|---|---|
| 3BC | 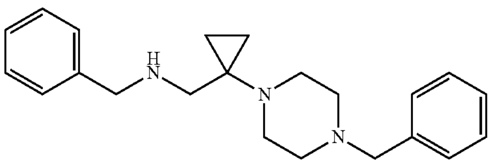 [SMILES: c1ccc(CNCC2(N3CCN(Cc4ccccc4)CC3)CC2)cc1] | N-benzyl-1-(1-(4-benzylpiperazin-1-yl)cyclopropyl)methanamine | A | 2.07 | 335 |

Intermediate 3BD. 2-((4-(4-Benzylpiperazin-1-yl)-2,2-dimethyltetrahydro-2H-pyran-4-yl)methylamino)nicotinonitrile

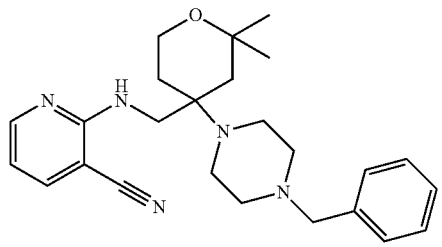 [SMILES: CC1(C)CC(CNc2ncccc2C#N)(N2CCN(Cc3ccccc3)CC2)CCO1]

A mixture of (4-(4-benzylpiperazin-1-yl)-2,2-dimethyltetrahydro-2H-pyran-4-yl)methanamine (INT 2D, 272 mg, 0.86 mmol), $K_3PO_4$ (364 mg, 1.72 mmol), CuI (32.7 mg, 0.17 mmol), L-proline (29.6 mg, 0.26 mmol) and 2-bromonicotinonitrile (172.8 mg, 0.94 mmol) in DMSO (10 mL), under nitrogen atmosphere was heated under microwave irradiation for 80 min at 90° C. The reaction mixture was diluted with AcOEt, dried and concentrated to dryness. The crude residue was purified by flash chromatography on neutral alumina, gradient CH:AcOEt 5% to give the title compound (120 mg, yield 33%).

HPLC-MS (Method F): Ret, 2.27 min; $ESI^+$-MS m/z, 420 (M+1).

This method was used for the preparation of intermediates 3BE-3BG using the corresponding intermediates 2 and the required halides:

| EX | Structure | Chemical name | Method | Ret (min) | MS (M + H) |
|---|---|---|---|---|---|
| 3BE | 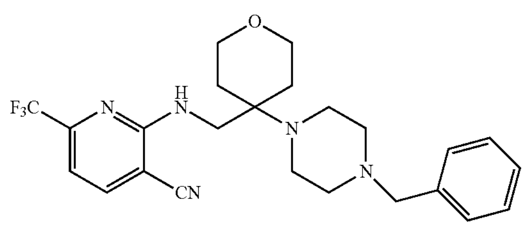 [SMILES: N#Cc1ccc(C(F)(F)F)nc1NCC1(N2CCN(Cc3ccccc3)CC2)CCOCC1] | 2-((4-(4-benzylpiperazin-1-yl)tetrahydro-2H-pyran-4-yl)methylamino)-6-(trifluoromethyl)nicotinonitrile | A | 2.54 | 460 |
| 3BF | 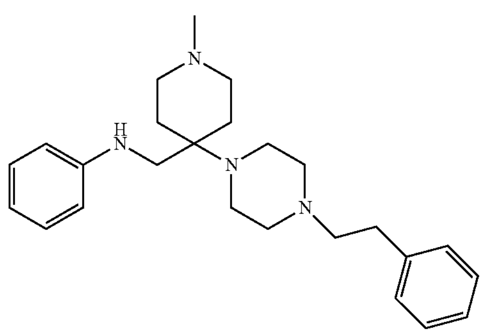 [SMILES: CN1CCC(CNc2ccccc2)(N2CCN(CCc3ccccc3)CC2)CC1] | N-((1-methyl-4-(4-phenethylpiperazin-1-yl)piperidin-4-yl)methyl)aniline | A | 2.06 | 393 |
| 3BG | 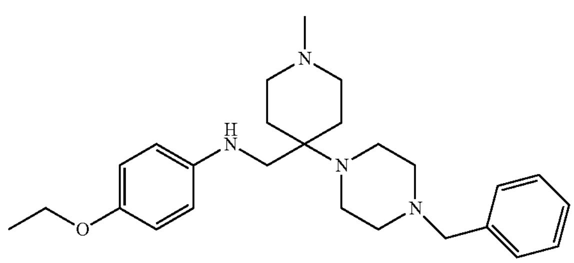 [SMILES: CCOc1ccc(NCC2(N3CCN(Cc4ccccc4)CC3)CCN(C)CC2)cc1] | N-((4-(4-benzylpiperazin-1-yl)-1-methylpiperidin-4-yl)methyl)-4-ethoxyaniline | A | 2.03 | 423 |

Intermediates 3BH-3BJ were prepared according to the procedure described in intermediate 3A using suitable starting materials

| EX | Structure | Chemical name | Method | Ret (min) | MS (M + H) |
|---|---|---|---|---|---|
| 3BH | 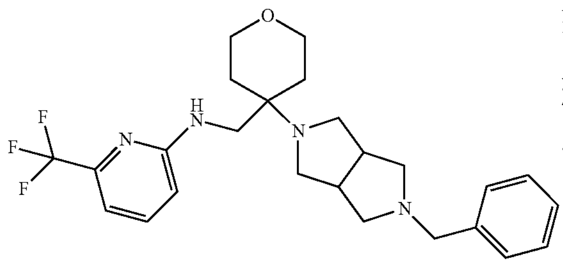 [SMILES: FC(F)(F)c1cccc(NCC2(N3CC4CN(Cc5ccccc5)CC4C3)CCOCC2)n1] | N-((4-(5-benzylhexahydropyrrolo[3,4-c]pyrrol-2(1H)-yl)tetrahydro-2H-pyran-4-yl)methyl)-6-(trifluoromethyl)pyridin-2-amine | A | 2.38 | 462 |
| 3BI | 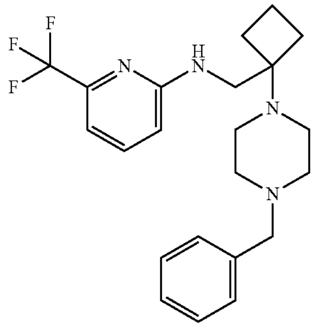 [SMILES: FC(F)(F)c1cccc(NCC2(N3CCN(Cc4ccccc4)CC3)CCC2)n1] | N-((1-(4-benzylpiperazin-1-yl)cyclobutyl)methyl)-6-(trifluoromethyl)pyridin-2-amine | A | 2.59 | 405 |
| 3BJ | 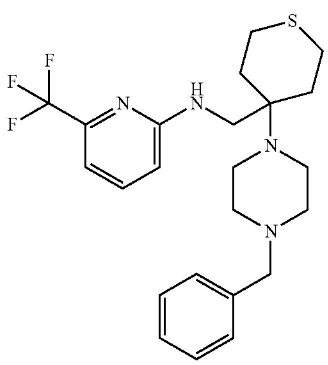 [SMILES: FC(F)(F)c1cccc(NCC2(N3CCN(Cc4ccccc4)CC3)CCSCC2)n1] | N-((4-(4-benzylpiperazin-1-yl)tetrahydro-2H-thiopyran-4-yl)methyl)-6-(trifluoromethyl)pyridin-2-amine | A | 2.70 | 451 |

Intermediate 4A. N-((4-(4-Benzylpiperazin-1-yl)tetrahydro-2H-pyran-4-yl)methyl)proplonamide

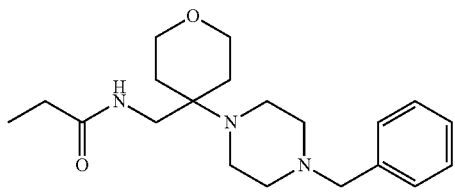 [SMILES: CCC(=O)NCC1(N2CCN(Cc3ccccc3)CC2)CCOCC1]

Propionyl chloride (358 µl, 4.33 mmol) was added to a solution of (4-(4-benzylpiperazin-1-yl)tetrahydro-2H-pyran-4-yl)methanamine (INT 1A, 1.2 g, 3.94 mmol) and dry TEA (714 µL, 5.12 mmol) in DCM (60 mL) at 0° C., under nitrogen atmosphere. The reaction mixture was allowed to reach rt and stirred for 5 h. Then, the mixture was washed twice with water and the organic layer was dried with Na$_2$SO$_4$, filtered and concentrated to dryness to give the title compound as a white solid (1.37 g, yield 96%).

HPLC-MS (Method A): Ret, 1.5 min; ESI$^+$-MS m/z, 346 (M+1).

Intermediate 5A. 2-Bromo-2-methyl-N-phenylpropanamide

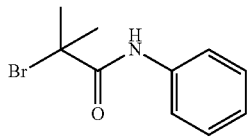

Aniline (200 µL, 2.19 mmol) was dissolved in DCM (20 mL) and TEA (917 µL, 6.58 mmol) was added. The solution was stirred at 0° C. for 15 min, after which 2-bromo-2-methylpropanoyl bromide (271 µL, 2.19 mmol) was added and the mixture was stirred at rt overnight. The volatile components were removed in vacuum and the residue was partitioned between AcOEt and H$_2$O. The organic phase was dried with Na$_2$SO$_4$, filtered and concentrated to give the title compound as a light brown solid (530 mg, 100% yield).

HPLC-MS (Method A): Ret, 1.77 min; ESI+-MS m/z, 244 (M+2).

This method was used for the preparation of the following intermediates using the corresponding starting products:

| EX | EST | Structure | Chemical name | Method | Ret (min) | MS (M + H) |
|---|---|---|---|---|---|---|
| 5B | | 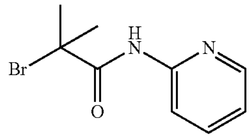 | 2-bromo-2-methyl-N-(pyridin-2-yl)propanamide | A | 1.60 | 245 |
| 5C | | 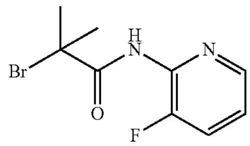 | 2-bromo-N-(3-fluoropyridin-2-yl)-2-methylpropanamide | A | 1.36 | 263 |
| 5D | | 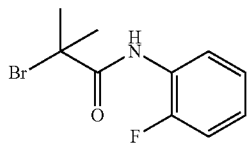 | 2-bromo-N-(2-fluorophenyl)-2-methylpropanamide | A | 1.85 | No ionization |

Intermediate 6A. 2-(4-(2-(3-Fluoropyridin-2-yl)ethyl)piperazin-1-yl)-2-methyl-N-phenylpropanamide

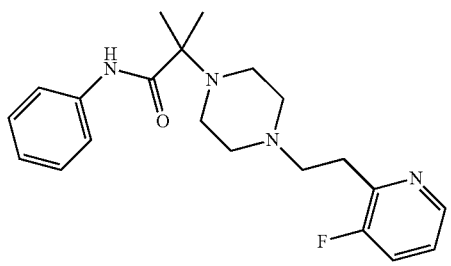 [SMILES: CC(C)(C(=O)Nc1ccccc1)N1CCN(CCc2ncccc2F)CC1]

2-Bromo-2-methyl-N-phenylpropanamide (INT 5A, 250 mg, 1.03 mmol) was added to a solution of 1-(2-(3-fluoropyridin-2-yl)ethyl)piperazine (259 mg, 1.24 mmol) and K$_2$CO$_3$ (428 mg, 3.1 mmol) in ACN (15 mL). The reaction mixture was stirred at 75° C. overnight and then it was cooled down to rt. The solvent was concentrated in vacuo and the residue was partitioned between AcOEt and 5% aqueous NaOH. The organic layer was separated, dried over Na$_2$SO$_4$, filtered and concentrated to give the title compound (268 mg, yield 50%).

HPLC-MS (Method A): Ret, 1.84 min; ESI+-MS m/z, 371 (M+1).

This method was used for the preparation of intermediates 6B-6F using the corresponding bromopropanamides and piperazine derivates as starting materials:

| EX | Structure | Chemical name | Method | Ret (min) | MS (M + H) |
|---|---|---|---|---|---|
| 6B | 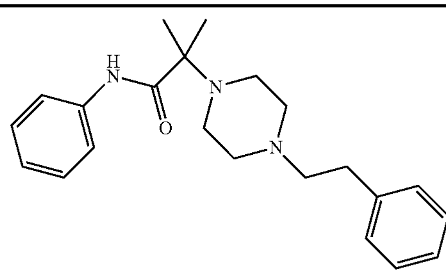 | 2-methyl-2-(4-phenethylpiperazin-1-yl)-N-phenylpropanamide | A | 2.00 | 352 |
| 6C | 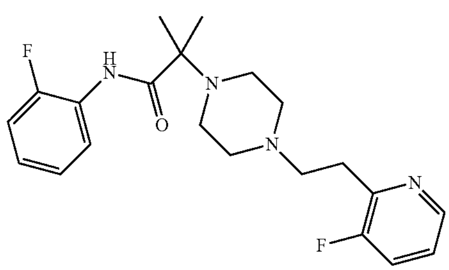 [SMILES: CC(C)(C(=O)Nc1ccccc1F)N1CCN(CCc2ncccc2F)CC1] | N-(2-fluorophenyl)-2-(4-(2-(3-fluoropyridin-2-yl)ethyl)piperazin-1-yl)-2-methylpropanamide | A | 1.96 | 389 |

| EX | Structure | Chemical name | Method | Ret (min) | MS (M + H) |
|---|---|---|---|---|---|
| 6D | 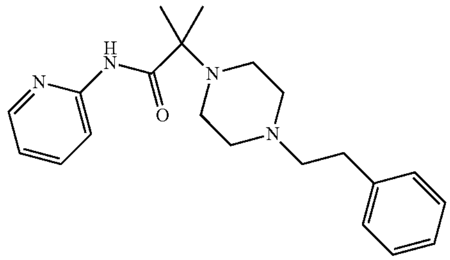 [SMILES: CC(C)(C(=O)Nc1ccccn1)N1CCN(CCc2ccccc2)CC1] | 2-methyl-2-(4-phenethylpiperazin-1-yl)-N-(pyridin-2-yl)propanamide | A | 2.06 | 353 |
| 6E | 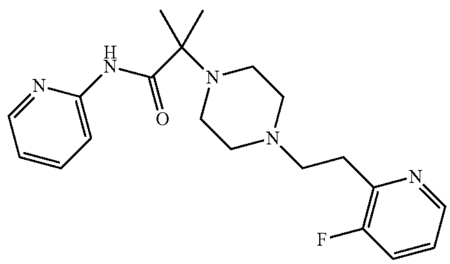 [SMILES: CC(C)(C(=O)Nc1ccccn1)N1CCN(CCc2ncccc2F)CC1] | 2-(4-(2-(3-fluoropyridin-2-yl)ethyl)piperazin-1-yl)-2-methyl-N-(pyridin-2-yl)propanamide | A | 1.66 | 372 |
| 6F | 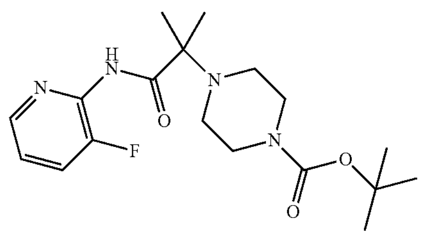 [SMILES: CC(C)(C)OC(=O)N1CCN(C(C)(C)C(=O)Nc2ncccc2F)CC1] | tert-butyl 4-(1-(3-fluoropyridin-2-ylamino)-2-methyl-1-oxopropan-2-yl)piperazine-1-carboxylate | A | 1.81 | 367 |

Intermediate 7. N-(3-Fluoropyridin-2-yl)-2-methyl-2-(piperazin-1-yl)propanamide

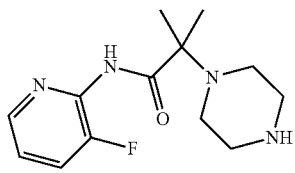 [SMILES: CC(C)(C(=O)Nc1ncccc1F)N1CCNCC1]

Over a suspension of tert-butyl 4-(1-(3-fluoropyridin-2-ylamino)-2-methyl-1-oxopropan-2-yl)piperazine-1-carboxylate (INT 6F, 540 mg, 1.47 mmol) in DCM (15 mL), TFA (1.1 mL, 14.7 mmol) was added and the mixture was stirred at rt for 2 h. The solvent was concentrated off. The crude residue was diluted with H₂O (30 mL), taken up to pH 12 with 10% aqueous NaOH solution and extracted with DCM (30 mL). The combined organic layers were dried over Na₂SO₄, filtered and concentrated to give the title compound as an off-white solid (335 mg, yield 86%).

HPLC-MS (Method A): Ret, 0.82 min; ESI+-MS m/z, 267 (M+1).

Intermediate 8A. 2-(4-(2-Fluorophenethyl)piperazin-1-yl)-N-(3-fluoropyridin-2-yl)-2-methylpropanamide

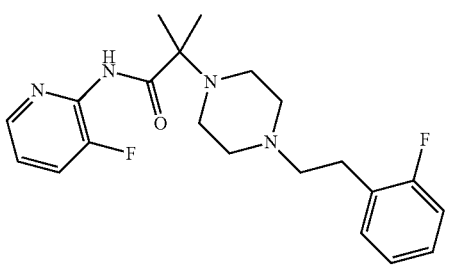 [SMILES: CC(C)(C(=O)Nc1ncccc1F)N1CCN(CCc2ccccc2F)CC1]

1-(2-Bromoethyl)-2-fluorobenzene (44 µL, 0.31 mmol) was added to a solution of N-(3-fluoropyridin-2-yl)-2-methyl-2-(piperazin-1-yl)propanamide (INT 7, 46 mg, 0.17 mmol) and K₂CO₃ (71.6 mg, 0.52 mmol) in ACN (5 mL). The reaction mixture was stirred at 50° C. overnight and then was cooled down to rt. AcOEt (10 mL) and sat aqueous NaHCO₃ solution (10 mL) were added and the phases were separated. The organic layer was dried over Na₂SO₄, filtered and concentrated to give the title compound as a oil (67 mg, quant yield).

HPLC-MS (Method A): Ret, 1.91 min; ESI+-MS m/z, 389 (M+1).

This method was used for the preparation of intermediates 8B-D using the corresponding piperazine derivates as starting materials:

| EX | Structure | Chemical name | Method | Ret (min) | MS (M + H) |
|---|---|---|---|---|---|
| 8B | 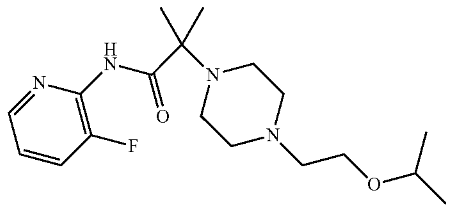 [SMILES: CC(C)OCCN1CCN(C(C)(C)C(=O)Nc2ncccc2F)CC1] | N-(3-fluoropyridin-2-yl)-2-(4-(2-isopropoxyethyl)piperazin-1-yl)-2-methylpropanamide | A | 1.52 | 353 |
| 8C | 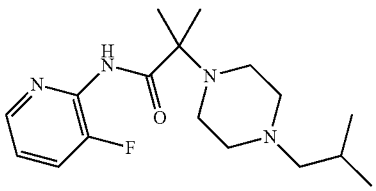 [SMILES: CC(C)CN1CCN(C(C)(C)C(=O)Nc2ncccc2F)CC1] | N-(3-fluoropyridin-2-yl)-2-(4-isobutylpiperazin-1-yl)-2-methylpropanamide | A | 1.84 | 323 |
| 8D | 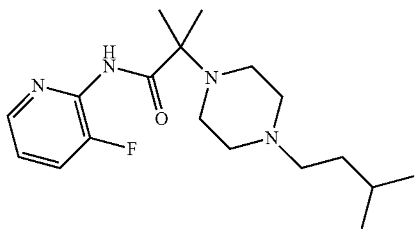 [SMILES: CC(C)CCN1CCN(C(C)(C)C(=O)Nc2ncccc2F)CC1] | N-(3-fluoropyridin-2-yl)-2-(4-isopentylpiperazin-1-yl)-2-methylpropanamide | A | 1.77 | 337 |

Intermediate 9A. Ethyl 1-(4-benzylpiperazin-1-yl)cyclopropanecarboxylate

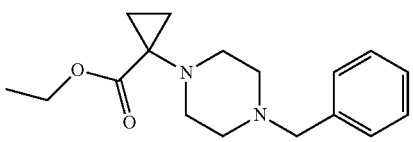 [SMILES: CCOC(=O)C1(N2CCN(Cc3ccccc3)CC2)CC1]

a) 2,2'-(Benzylazanediyl)diethanol $K_2CO_3$ (8.65 g, 62.58 mmol), and (bromomethyl)benzene (2.96 g, 25 mmol) were added to a solution of 2,2'-azanediyldiethanol (2.63 g, 53.08 mmol) in dry acetone (65 mL). The reaction mixture was heated to reflux overnight. The white suspension thus obtained was filtered and the solvent was evaporated to afford 5.6 g as a yellow liquid, which was dissolved in DCM and washed with water. The organic layer was dried over sodium sulphate and concentrated under vacuum to afford the title compound (4.88, 100% yield).

HPLC-MS (Method A): Ret, 1.14 min; ESI$^+$-MS m/z, 196 (M+1).

b) N-Benzyl-2-chloro-N-(2-chloroethyl)ethanamine hydrochloride

Sulfurous dichloride (35.8 mL, 482 mmol) in anhydride DCM (60 mL), was added to a cold solution of 2,2'-(Benzylazanediyl)diethanol (obtained in step a, 31.4 g, 160 mmol) in DCM (200 mL) and the reaction mixture was stirred at rt. overnight. The solvent was removed to dryness to give the title compound (47.2 g, 100% yield), that was used in the next step without further purification.

HPLC-MS (Method A): Ret, 2.34 min; ESI$^+$-MS m/z, 262 (M+1).

c) Title Compound

N-Benzyl-2-chloro-N-(2-chloroethyl)ethanamine hydrochloride (obtained in the previous step, 10.37 g, 38.61 mmol) was added to a solution of ethyl 1-aminocyclopropanecarboxylate hydrochloride (6.4 g, 38.6 mmol) and $NaHCO_3$ (17.5 g, 208.5 mmol) in EtOH (200 mL). The reaction mixture was stirred at 80° C. for 4 h and overnight at rt. The solvent was concentrated and the crude product was diluted with AcOEt and water. The layers were separated and the organic layer was dried over $Na_2SO_4$, filtered and concentrated. The crude residue was purified by flash chromatography on silica gel, eluents CH/AcOEt (100:0 to 0:100) to give the title compound (2.86 g, 24% yield).

HPLC-MS (Method A): Ret, 2.26 min; ESI$^+$-MS m/z, 289 (M+1).

This method was used for the preparation of intermediates 9B-9C using the corresponding starting products:

| EX | Structure | Chemical name | Method | Ret (min) | MS (M + H) |
|---|---|---|---|---|---|
| 9B | 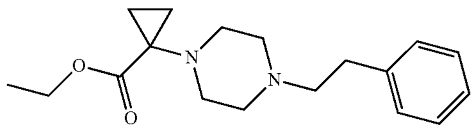 [SMILES: CCOC(=O)C1(N2CCN(CCc3ccccc3)CC2)CC1] | ethyl 1-(4-phenethylpiperazin-1-yl)cyclopropanecarboxylate | A | 2.19 | 303 |
| 9C | 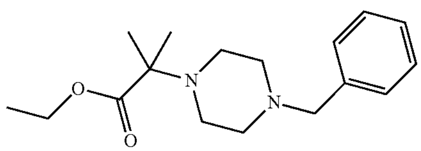 [SMILES: CCOC(=O)C(C)(C)N1CCN(Cc2ccccc2)CC1] | ethyl 2-(4-benzylpiperazin-1-yl)-2-methylpropanoate | A | 1.98 | 291 |

Intermediate 10A.
1-(4-Benzylpiperazin-1-yl)cyclopropanecarboxylic acid

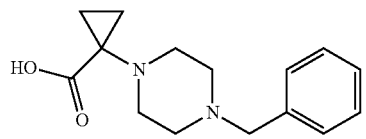 [SMILES: O=C(O)C1(N2CCN(Cc3ccccc3)CC2)CC1]

To a solution of ethyl 1-(4-benzylpiperazin-1-yl)cyclopropanecarboxylate (INT 9A, 2.36 g, 8.21 mmol) in EtOH (100 mL), KOH (5.4 g, 82.07 mmol) in EtOH (50 mL) was added and the solution was heated at 120° C. for 5 h. The reaction mixture was cooled at 0° C. and acetic acid (4.7 mL, 82.07 mmol) was added. After stirring the solution for 10 min, it was concentrated under vacuum. The residue was stirred with ethyl acetate at rt and the solid thus obtained was filtered and washed several times with water. Then, it was dried to afford the title compound as a beige solid (1.76 g, 82% yield)

HPLC-MS (Method A): Ret, 0.98 min; ESI+-MS m/z, 261 (M+1).

This method was used for the preparation of intermediates 10B-10C using the corresponding starting products:

Intermediate 11A. 1-(4-Benzylpiperazin-1-yl)-N-phenylcyclopropanecarboxamlide

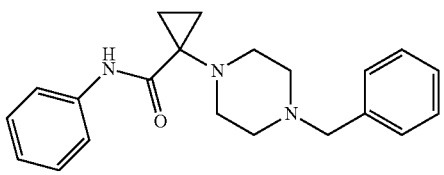

A mixture of 1-(4-benzylpiperazin-1-yl)cyclopropanecarboxylic acid (obtained in the previous step, 0.18 g, 0.71 mmol), and HOBt (0.22 g, 1.42 mmol) was added to a solution of EDC (0.27 g, 1.42 mmol) in DCM (4 mL). Then aniline (97 μL, 1.07 mmol) and TEA (495 μL, 3.55 mmol) were added and the reaction mixture was stirred at rt overnight. The mixture was diluted with DCM and washed with water, dried over $Na_2SO_4$, filtered and concentrated to obtain a crude compound that was purified by flash chromatography on silica gel, gradient CH: AcOEt from (100:0) to (90:10) to afford the title compound (0.15 g, yield 62%).

HPLC-MS (Method A): Ret, 2.25 min; ESI+-MS m/z, 336 (M+1).

This method was used for the preparation of the following intermediates using the corresponding starting products:

| EX | Structure | Chemical name | Method | Ret (min) | MS (M + H) |
|---|---|---|---|---|---|
| 10B | 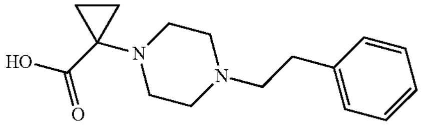 [SMILES: O=C(O)C1(N2CCN(CCc3ccccc3)CC2)CC1] | 1-(4-phenethylpiperazin-1-yl)cyclopropanecarboxylic acid | A | 1.06 | 275 |
| 10C | 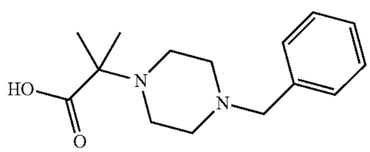 [SMILES: CC(C)(C(=O)O)N1CCN(Cc2ccccc2)CC1] | 2-(4-benzylpiperazin-1-yl)-2-methylpropanoic acid | A | 0.96 | 263 |

| EX | Structure | Chemical name | Method | Ret (min) | MS (M + H) |
|---|---|---|---|---|---|
| 11B | 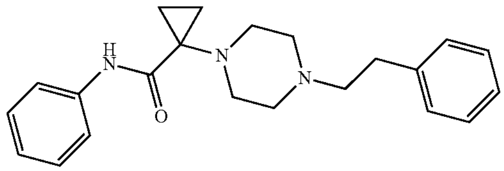 [SMILES: O=C(Nc1ccccc1)C1(N2CCN(CCc3ccccc3)CC2)CC1] | 1-(4-phenethylpiperazin-1-yl)-N-phenylcyclopropane-carboxamide | A | 2.23 | 350 |
| 11C | 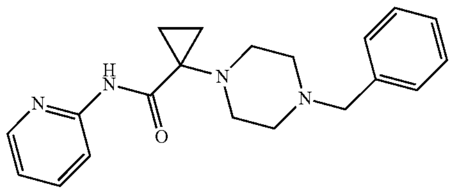 [SMILES: O=C(Nc1ccccn1)C1(N2CCN(Cc3ccccc3)CC2)CC1] | 1-(4-benzylpiperazin-1-yl)-N-(pyridin-2-yl)cyclopropanecarbox-amide | A | 2.04 | 337 |
| 11D | 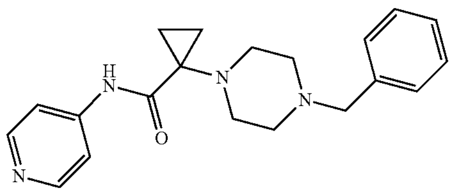 [SMILES: O=C(Nc1ccncc1)C1(N2CCN(Cc3ccccc3)CC2)CC1] | 1-(4-benzylpiperazin-1-yl)-N-(pyridin-4-yl)cyclopropanecarbox-amide | A | 1.79 | 337 |
| 11E | 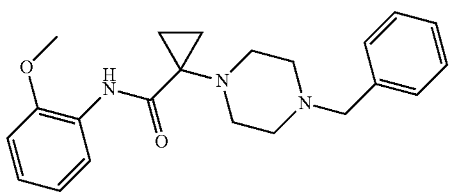 [SMILES: COc1ccccc1NC(=O)C1(N2CCN(Cc3ccccc3)CC2)CC1] | 1-(4-benzylpiperazin-1-yl)-N-(2-methoxyphenyl)cyclo-propanecarboxamide | A | 2.31 | 366 |
| 11F | 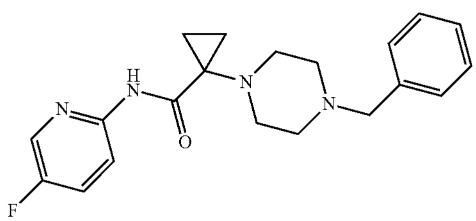 [SMILES: O=C(Nc1ccc(F)cn1)C1(N2CCN(Cc3ccccc3)CC2)CC1] | 1-(4-benzylpiperazin-1-yl)-N-(5-fluoropyridin-2-yl)cyclopropanecarbox-amide | A | 2.20 | 355 |
| 11G | 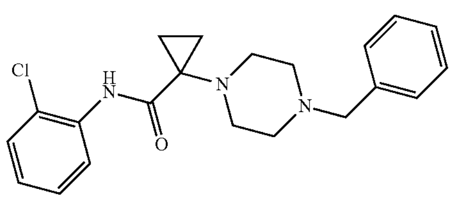 [SMILES: O=C(Nc1ccccc1Cl)C1(N2CCN(Cc3ccccc3)CC2)CC1] | 1-(4-benzylpiperazin-1-yl)-N-(2-chlorophenyl)cyclopro-panecarboxamide | A | 2.52 | 370 |
| 11H | 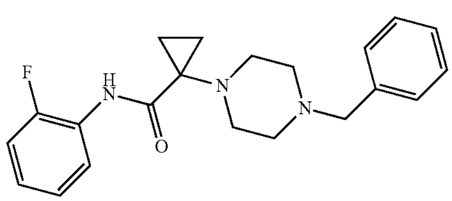 [SMILES: O=C(Nc1ccccc1F)C1(N2CCN(Cc3ccccc3)CC2)CC1] | 1-(4-benzylpiperazin-1-yl)-N-(2-fluorophenyl)cyclopro-panecarboxamide | A | 2.39 | 354 |
| 11I | 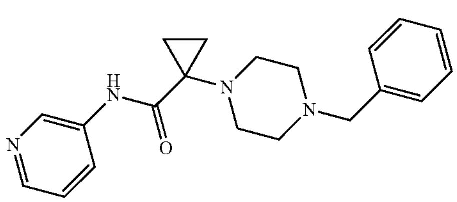 [SMILES: O=C(Nc1cccnc1)C1(N2CCN(Cc3ccccc3)CC2)CC1] | 1-(4-benzylpiperazin-1-yl)-N-(pyridin-3-yl)cyclopropanecarbox-amide | A | 1.77 | 337 |

| EX | Structure | Chemical name | Method | Ret (min) | MS (M + H) |
|---|---|---|---|---|---|
| 11J | 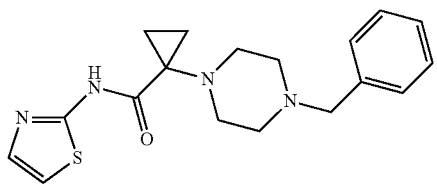 [SMILES: O=C(Nc1nccs1)C1(N2CCN(Cc3ccccc3)CC2)CC1] | 1-(4-benzylpiperazin-1-yl)-N-(thiazol-2-yl)cyclopropanecarboxamide | A | 1.95 | 343 |
| 11K | 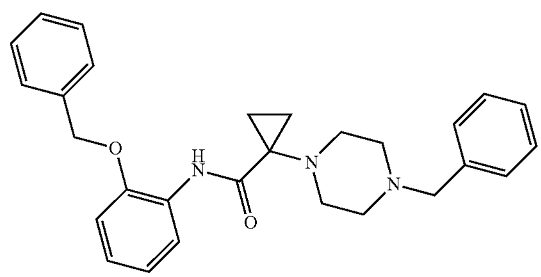 [SMILES: O=C(Nc1ccccc1OCc1ccccc1)C1(N2CCN(Cc3ccccc3)CC2)CC1] | N-(2-(benzyloxy)phenyl)-1-(4-benzylpiperazin-1-yl)cyclopropanecarboxamide | A | 2.59 | 442 |
| 11L | 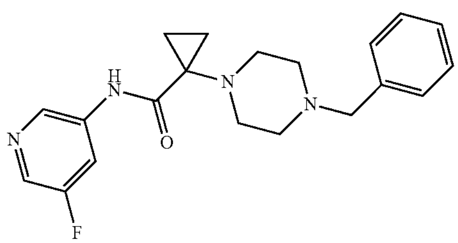 [SMILES: O=C(Nc1cncc(F)c1)C1(N2CCN(Cc3ccccc3)CC2)CC1] | 1-(4-benzylpiperazin-1-yl)-N-(5-fluoropyridin-3-yl)cyclopropanecarboxamide | A | 1.98 | 355 |
| 11M | 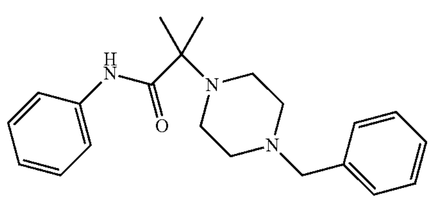 [SMILES: CC(C)(C(=O)Nc1ccccc1)N1CCN(Cc2ccccc2)CC1] | 2-(4-benzylpiperazin-1-yl)-2-methyl-N-phenylpropanamide | A | 2.26 | 338 |

Intermediate 12A. N-(2-(4-(2-(3-Fluoropyridin-2-yl)ethyl)piperazin-1-yl)-2-methylpropyl)aniline

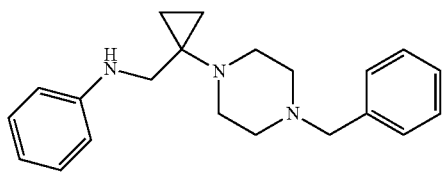 [SMILES: c1ccc(CN2CCN(C3(CNc4ccccc4)CC3)CC2)cc1]

To a vigorously stirred solution of LiAlH$_4$ (1M in THF, 10 mL; 15 mmol) at −70° C. sulfuric acid (0.3 mL) was added dropwise. The reaction was stirred at −70° C. to −50° C. for 2 h and left at rt for 2 h without stirring (white solid appeared).

In a round bottomed flask the previously prepared fresh alane solution (0.82 mL, 5 eq) decanted via syringe, was cooled to 0° C. in argon atmosphere. 1-(4-Benzylpiperazin-1-yl)-N-phenylcyclopropanecarboxamide (INT 11A, 155 mg, 0.44 mmol) dissolved in THF (6 mL), was added dropwise and the mixture was stirred at 0° C. for 2.5 h and then allowed to stir at rt overnight. The reaction was quenched carefully with EtOAc and ice water. The aqueous layer was extracted twice with EtOAc. The combined organic layers were washed with water, dried over sodium sulphate and concentrated to afford the title compound (0.13 g, 84% yield).

HPLC-MS (Method A): Ret, 2.42 min; ESI+-MS m/z, 322 (M+1).

This method was used for the preparation of the following intermediates using the corresponding starting products:

| EX | Chemical name | Method | Ret (min) | MS (M + H) |
|---|---|---|---|---|
| 12B | N-((1-(4-phenethylpiperazin-1-yl)cyclopropyl)methyl)aniline | A | 2.37 | 336 |
| 12C | N-((1-(4-benzylpiperazin-1-yl)cyclopropyl)methyl)pyridin-2-amine | A | 1.93 | 323 |
| 12D | N-((1-(4-benzylpiperazin-1-yl)cyclopropyl)methyl)pyridin-4-amine | A | 1.59 | 323 |
| 12E | N-((1-(4-benzylpiperazin-1-yl)cyclopropyl)methyl)-2-methoxyaniline | A | 2.54 | 352 |
| 12F | N-((1-(4-benzylpiperazin-1-yl)cyclopropyl)methyl)-5-fluoropyridin-2-amine | A | 2.10 | 341 |
| 12G | N-((1-(4-benzylpiperazin-1-yl)cyclopropyl)methyl)-2-chloroaniline | A | 2.73 | 356 |
| 12H | N-((1-(4-benzylpiperazin-1-yl)cyclopropyl)methyl)-2-fluoroaniline | A | 2.55 | 340 |
| 12I | N-((1-(4-benzylpiperazin-1-yl)cyclopropyl)methyl)pyridin-3-amine | A | 1.84 | 323 |

-continued

| EX | Structure | Chemical name | Method | Ret (min) | MS (M + H) |
|---|---|---|---|---|---|
| 12J | 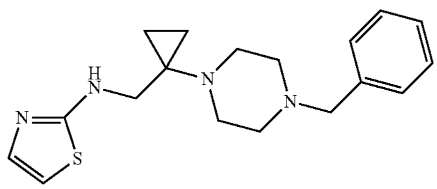 [SMILES: c1ccc(CN2CCN(C3(CNc4nccs4)CC3)CC2)cc1] | N-((1-(4-benzylpiperazin-1-yl)cyclopropyl)methyl)thiazol-2-amine | A | 1.85 | 329 |
| 12K | 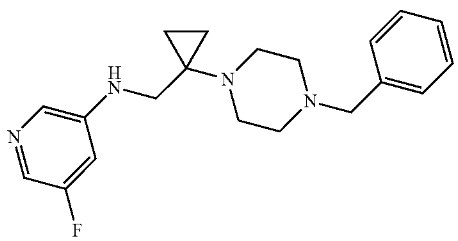 [SMILES: Fc1cncc(NCC2(N3CCN(Cc4ccccc4)CC3)CC2)c1] | N-((1-(4-benzylpiperazin-1-yl)cyclopropyl)methyl)-5-fluoropyridin-3-amine | A | 1.99 | 341 |
| 12L | 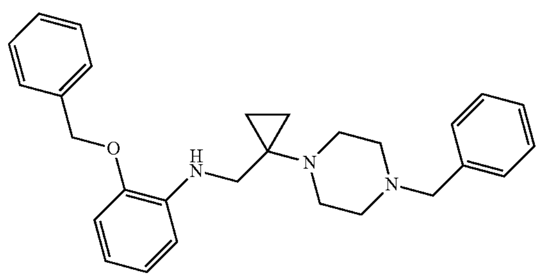 [SMILES: c1ccc(COc2ccccc2NCC2(N3CCN(Cc4ccccc4)CC3)CC2)cc1] | 2-(benzyloxy)-N-((1-(4-benzylpiperazin-1-yl)cyclopropyl)methyl)aniline | A | 2.81 | 428 |
| 12M | 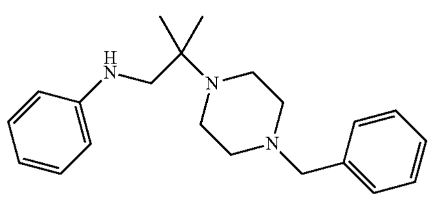 [SMILES: CC(C)(CNc1ccccc1)N1CCN(Cc2ccccc2)CC1] | N-(2-(4-benzylpiperazin-1-yl)-2-methylpropyl)aniline | A | 2.55 | 324 |
| 12N | 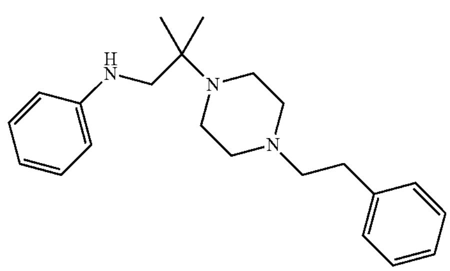 [SMILES: CC(C)(CNc1ccccc1)N1CCN(CCc2ccccc2)CC1] | N-(2-methyl-2-(4-phenethylpiperazin-1-yl)propyl)aniline | A | 2.48 | 338 |
| 12O | 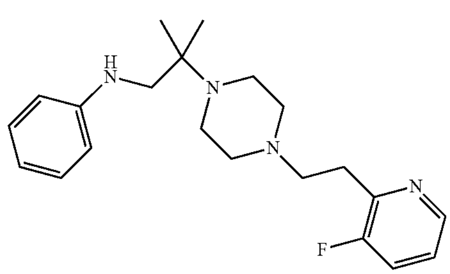 [SMILES: CC(C)(CNc1ccccc1)N1CCN(CCc2ncccc2F)CC1] | N-(2-(4-(2-(3-fluoropyridin-2-yl)ethyl)piperazin-1-yl)-2-methylpropyl)aniline | A | 2.07 | 357 |

-continued

| EX | Structure | Chemical name | Method | Ret (min) | MS (M + H) |
|---|---|---|---|---|---|
| 12P | 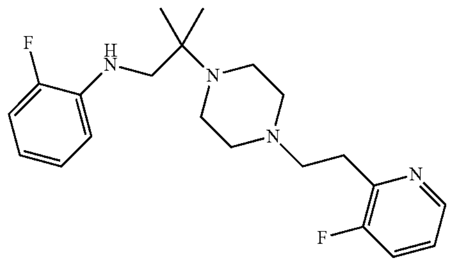 [SMILES: CC(C)(CNc1ccccc1F)N1CCN(CCc2ncccc2F)CC1] | 2-fluoro-N-(2-(4-(2-(3-fluoropyridin-2-yl)ethyl)piperazin-1-yl)-2-methylpropyl)aniline | A | 2.25 | 375 |
| 12Q | 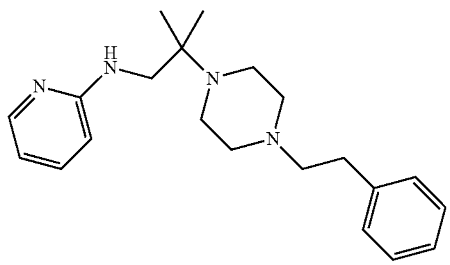 [SMILES: CC(C)(CNc1ccccn1)N1CCN(CCc2ccccc2)CC1] | N-(2-methyl-2-(4-phenethylpiperazin-1-yl)propyl)pyridin-2-amine | A | 1.91 | 339 |
| 12R | 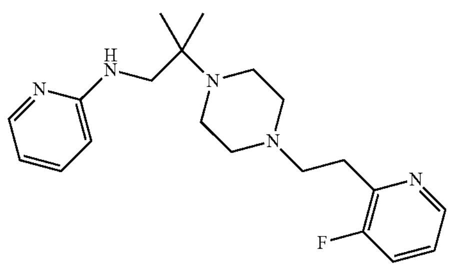 [SMILES: CC(C)(CNc1ccccn1)N1CCN(CCc2ncccc2F)CC1] | N-(2-(4-(2-(3-fluoropyridin-2-yl)ethyl)piperazin-1-yl)-2-methylpropyl)pyridin-2-amine | A | 1.51 | 358 |
| 12S | 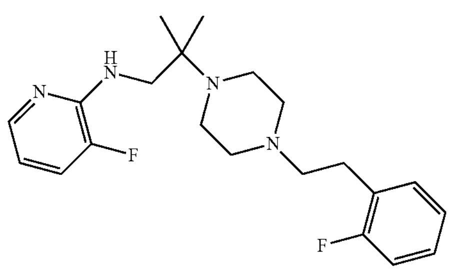 [SMILES: CC(C)(CNc1ncccc1F)N1CCN(CCc2ccccc2F)CC1] | 3-fluoro-N-(2-(4-(2-fluorophenethyl)piperazin-1-yl)-2-methylpropyl)pyridin-2-amine | A | 2.27 | 375 |
| 12T | 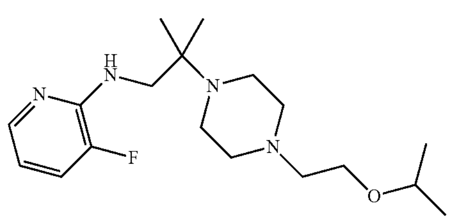 [SMILES: CC(C)OCCN1CCN(C(C)(C)CNc2ncccc2F)CC1] | 3-fluoro-N-(2-(4-(2-isopropoxyethyl)piperazin-1-yl)-2-methylpropyl)pyridin-2-amine | A | 1.81 | 339 |
| 12U | 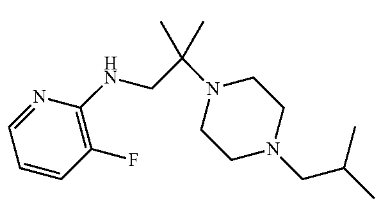 [SMILES: CC(C)CN1CCN(C(C)(C)CNc2ncccc2F)CC1] | 3-fluoro-N-(2-(4-isobutylpiperazin-1-yl)-2-methylpropyl)pyridin-2-amine | A | 2.21 | 309 |

| EX | Structure | Chemical name | Method | Ret (min) | MS (M + H) |
|---|---|---|---|---|---|
| 12V | 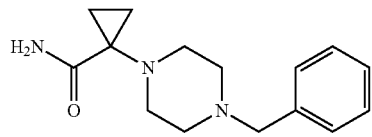 [SMILES: NC(=O)C1(N2CCN(Cc3ccccc3)CC2)CC1] | 3-fluoro-N-(2-(4-isopentylpiperazin-1-yl)-2-methylpropyl)pyridin-2-amine | A | 2.15 | 323 |

Intermediate 13. 1-(4-Benzylpiperazin-1-yl)cyclopropanecarboxamide

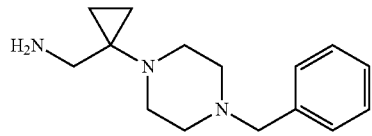 [SMILES: NCC1(N2CCN(Cc3ccccc3)CC2)CC1]

HATU (O-(7-Azabenzotriazol-1-yl)-N,N,N',N'-tetramethyluronium PF6, 6.3 g, 17 mmol), TEA (4.2 mL, 30 mmol) and ammonium bicarbonate (1.19 g, 15 mmol) were added to a solution of 1-(4-benzylpiperazin-1-yl)cyclopropanecarboxylic acid (INT 10A, 12.7 g, 15.07 mmol) in DMF (100 mL) at 0° C. and the mixture was stirred at rt for 2 days. The reaction mixture was partitioned between water and EtOAc/Et₂O 1:1 and the combined organic layers were washed twice with water, dried over MgSO₄, filtered and concentrated to afford the title compound (1.75 g, 45% yield).

HPLC-MS (Method A): Ret, 1.45 min ESI+-MS; m/z, 260 (M+1)

Intermediate 14. (1-(4-Benzylpiperazin-1-yl)cyclopropyl)methanamine

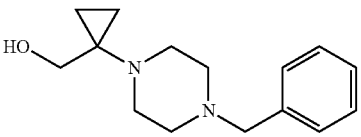 [SMILES: OCC1(N2CCN(Cc3ccccc3)CC2)CC1]

LiAlH₄ solution (1 M in THF, 13.5 mL, 13.5 mmol) was added to a −10° C. cooled solution of 1-(4-benzylpiperazin-1-yl)cyclopropanecarboxamide (INT 9A, 1.75 g, 6.76 mmol) in dry THF (20 mL). The reaction mixture was stirred at this temperature for 5 h, allowed to reach rt and stirred at this temperature overnight. The reaction mixture was cooled down to 0° C., and H₂O/NaOH (5% aqueous solution (4:1) was added. The mixture was filtered and rinsed with EtOAc. The filtrate was washed with H₂O and the organic layer was dried over Na₂SO₄, filtered and concentrated to give the title compound as an oil (0.9 g, yield 54%).

HPLC-MS (Method A): Ret, 1.25 min; ESI⁺-MS m/z, 246 (M+1).

Intermediate 15. (1-(4-Benzylpiperazin-1-yl)cyclopropyl)methanol

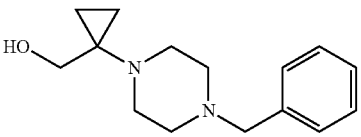 [SMILES: OCC1(N2CCN(Cc3ccccc3)CC2)CC1]

LiAlH₄ solution (1M in THF, 50.2 mL, 50.2 mmol) was added at 0° C. to a solution of ethyl 1-(4-benzylpiperazin-1-yl)cyclopropanecarboxylate (INT 9A, 3.86 g, 13.39 mmol) in THF (100 mL). The reaction mixture was allowed to reach rt and stirred at this temperature for 7 h. The mixture was cooled down to 0° C., and H₂O (30 mL), NaOH (40% aqueous solution, 25 mL) and AcOEt (40 mL) were added. The suspension thus obtained was stirred at 0° C. for 10 min and then filtered and rinsed with AcOEt and water. The filtrate was concentrated off to give the title compound as a white solid (3.11 g, yield 95%).

HPLC-MS (Method A): Ret, 1.40 min; ESI+-MS m/z, 247 (M+1).

Intermediate 16. 2-((1-(4-Benzylpiperazin-1-yl)cyclopropyl)methyl)isoindoline-1,3-dione

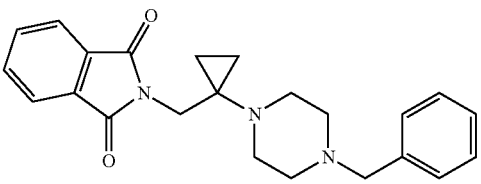 [SMILES: O=C1c2ccccc2C(=O)N1CC1(N2CCN(Cc3ccccc3)CC2)CC1]

(1-(4-Benzylpiperazin-1-yl)cyclopropyl)methanol (INT 15, 2.47 g, 10.02 mmol) in dry THF (60 mL) was cooled at 0° C. under argon atmosphere and isoindoline-1,3-dione (3.24 g, 22 mmol) and triphenylphosphine (5.78 g, 22.06 mmol) were added. After that DEAD ((E)-diethyl diazene-1,2-dicarboxylate, 3.84 g, 22.06 mmol) in dry THF (20 mL) was slowly added and the reaction mixture was stirred at rt overnight. The mixture was concentrated to dryness and the residue was stirred with water and 1N HCl and then extracted twice with EtOAc. The combined organic layers were made alkaline with 20% aqueous NH₄OH and then extracted twice with EtOAc. The combined organic layers were washed with water, dried over sodium sulphate and

Intermediate 17. (1-(4-Benzylpiperazin-1-yl)cyclopropyl)methanamine

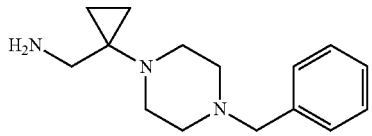 [SMILES: NCC1(N2CCN(Cc3ccccc3)CC2)CC1]

Hydrazine hydrate (2.5 g, 50.6 mmol) was added to a solution of 2-((1-(4-benzylpiperazin-1-yl)cyclopropyl)methyl)isoindoline-1,3-dione (INT 16, 1.9 g, 5.06 mmol) in EtOH (200 mL), and the reaction mixture was heated under reflux for 5 h.

Then, it was cooled down to rt and the white suspension thus obtained was filtered. The filtrate was concentrated under vacuum to afford a white solid. The residue was stirred in Et₂O and decanted twice. The decanted solution was concentrated under vacuum to afford the title compound as colorless oil (1.2 g, 100% yield)

HPLC-MS (Method H): Ret, 1.26 min; ESI+-MS m/z, 246 (M+1).

Intermediate 18A. N-(2-(benzyloxy)phenyl)-N-((4-(4-benzylpiperazin-1-yl)tetrahydro-2H-pyran-4-yl)methyl)propionamide

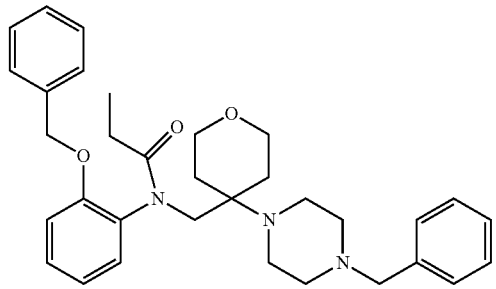 [SMILES: CCC(=O)N(CC1(N2CCN(Cc3ccccc3)CC2)CCOCC1)c1ccccc1OCc1ccccc1]

Propionyl chloride (23 µL, 0.269 mmol) was added to a solution of 2-(benzyloxy)-N-((4-(4-benzylpiperazin-1-yl)tetrahydro-2H-pyran-4-yl)methyl)aniline (INT 3F, 0.15 g, 0.22 mmol) and dry TEA (72 µL, 0.515 mmol) in DCM (5 mL) under nitrogen atmosphere. The reaction mixture was stirred at rt. After that, the mixture was washed twice with water and the organic layer was dried with Na₂SO₄, filtered and concentrated to dryness. The crude residue was purified by flash chromatography on silica gel, eluents CH:AcoEt (0:30) to give the title compound as a colourless oil (0.065 g, yield 55%).

HPLC-MS (Method B): Ret, 3.01 min; ESI+-MS m/z, 528 (M+1).

This method was used for the preparation of the intermediates 18B-C using the corresponding starting products:

| EX | Structure | Chemical name | Method | Ret (min) | MS (M + H) |
|---|---|---|---|---|---|
| 18B | 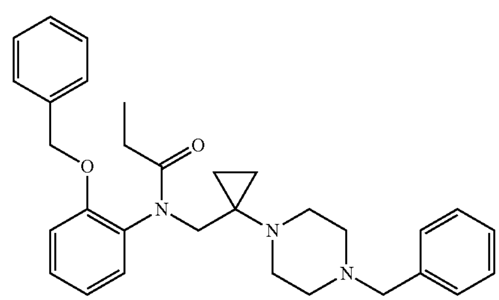 [SMILES: CCC(=O)N(CC1(N2CCN(Cc3ccccc3)CC2)CC1)c1ccccc1OCc1ccccc1] | N-(2-(benzyloxy)phenyl)-N-((1-(4-benzylpiperazin-1-yl)cyclopropyl)methyl)propionamide | A | 2.58 | 484 |
| 18C | 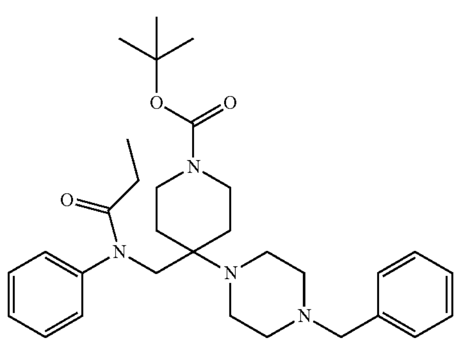 [SMILES: CCC(=O)N(CC1(N2CCN(Cc3ccccc3)CC2)CCN(C(=O)OC(C)(C)C)CC1)c1ccccc1] | tert-butyl 4-(4-benzylpiperazin-1-yl)-4-((N-phenylpropionamido)methyl)piperidine-1-carboxylate | A | 2.60 | 521 |

Intermediate 19A. N-phenyl-N-((4-(piperazin-1-yl)tetrahydro-2H-pyran-4-yl)methyl)proplonamide

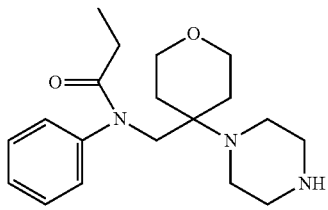

N-((4-(4-Benzylpiperazin-1-yl)tetrahydro-2H-pyran-4-yl)methyl)-N-phenylpropionamide (Example 1, 0.6 g, 1.42 mmol) was dissolved in MeOH (20 mL) and ammonium formate (0.269 g, 4.27 mmol) and Pd (0.12 g, 20% Wt) was added. The suspension was stirred under $N_2$ atmosphere for 2 h at 65° C. The reaction mixture was filtered through celite, washed with MeOH and concentrated, to give the title compound (0.471 g, yield 98%).

HPLC-MS (Method A): Ret, 1.17 min; ESI$^+$-MS m/z, 332 (M+1).

This method was used for the preparation of the following intermediates using the corresponding starting products:

| EX | Structure | Chemical name | Method | Ret (min) | MS (M + H) |
|---|---|---|---|---|---|
| 19B | 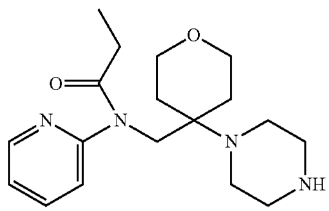 [SMILES: CCC(=O)N(CC1(N2CCNCC2)CCOCC1)c1ccccn1] | N-((4-(piperazin-1-yl)tetrahydro-2H-pyran-4-yl)methyl)-N-(pyridin-2-yl)propionamide | A | 0.93 | 333 |
| 19C | 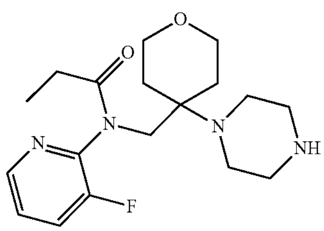 [SMILES: CCC(=O)N(CC1(N2CCNCC2)CCOCC1)c1ncccc1F] | N-(3-fluoropyridin-2-yl)-N-((4-(piperazin-1-yl)tetrahydro-2H-pyran-4-yl)methyl)propionamide | A | 1.06 | 351 |
| 19D | 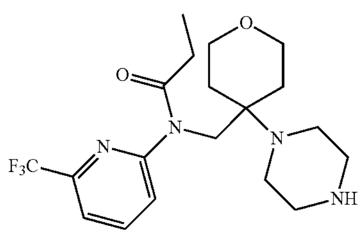 | N-((4-(piperazin-1-yl)tetrahydro-2H-pyran-4-yl)methyl)-N-(6-(trifluoromethyl)pyridin-2-yl)propionamide | A | 1.28 | 401 |
| 19E | 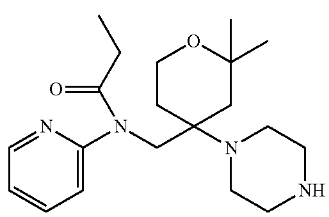 [SMILES: CCC(=O)N(CC1(N2CCNCC2)CCOC(C)(C)C1)c1ccccn1] | N-((2,2-dimethyl-4-(piperazin-1-yl)tetrahydro-2H-pyran-4-yl)methyl)-N-(pyridin-2-yl)propionamide | A | 1.11 | 361 |
| 19F | 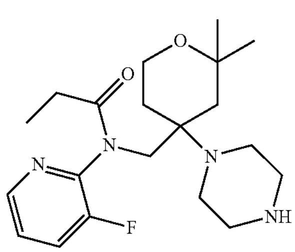 [SMILES: CCC(=O)N(CC1(N2CCNCC2)CCOC(C)(C)C1)c1ncccc1F] | N-(3-fluoropyridin-2-yl)-N-((4-(piperazin-1-yl)tetrahydro-2H-pyran-4-yl)methyl)propionamide | A | 1.12 | 379 |

-continued

| EX | Structure | Chemical name | Method | Ret (min) | MS (M + H) |
|---|---|---|---|---|---|
| 19G | 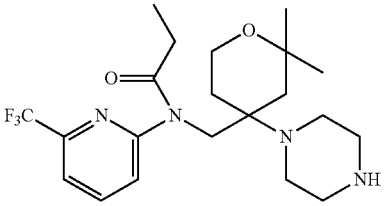 [SMILES: CCC(=O)N(CC1(N2CCNCC2)CCOC(C)(C)C1)c1cccc(C(F)(F)F)n1] | N-((2,2-dimethyl-4-(piperazin-1-yl)tetrahydro-2H-pyran-4-yl)methyl)-N-(6-(trifluoromethyl)pyridin-2-yl)propionamide | A | 1.46 | 429 |
| 19H | 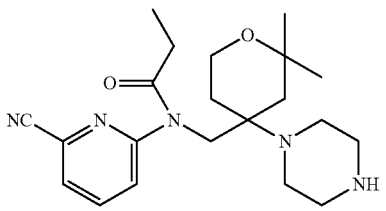 [SMILES: CCC(=O)N(CC1(N2CCNCC2)CCOC(C)(C)C1)c1cccc(C#N)n1] | N-(6-cyanopyridin-2-yl)-N-((2,2-dimethyl-4-(piperazin-1-yl)tetrahydro-2H-pyran-4-yl)methyl)propionamide | A | 1.17 | 386 |
| 19I | 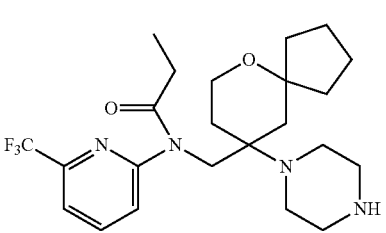 [SMILES: CCC(=O)N(CC1(N2CCNCC2)CCOC2(CCCC2)C1)c1cccc(C(F)(F)F)n1] | N-((9-(piperazin-1-yl)-6-oxaspiro[4.5]decan-9-yl)methyl)-N-(6-(trifluoromethyl)pyridin-2-yl)propionamide | A | 1.61 | 455 |
| 19J | 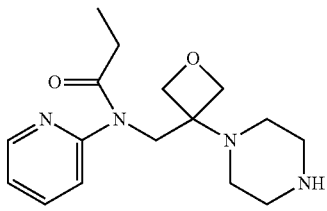 [SMILES: CCC(=O)N(CC1(N2CCNCC2)COC1)c1ccccn1] | N-phenyl-N-((3-(piperazin-1-yl)oxetan-3-yl)methyl)propionamide | A | 1.17 | 304 |
| 19K | 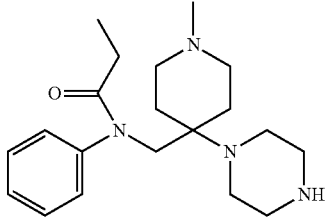 [SMILES: CCC(=O)N(CC1(N2CCNCC2)CCN(C)CC1)c1ccccc1] | N-((1-methyl-4-(piperazin-1-yl)piperidin-4-yl)methyl)-N-phenylpropionamide | A | | |
| 19L | 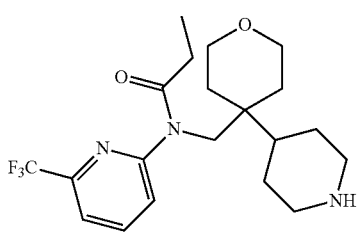 | N-((4-(piperidin-4-yl)tetrahydro-2H-pyran-4-yl)methyl)-N-(6-(trifluoromethyl)pyridin-2-yl)propionamide | A | — | 400 |
| 19M | 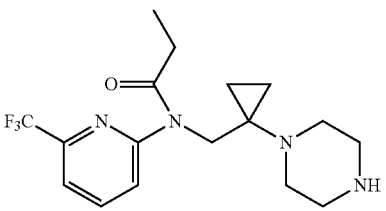 [SMILES: CCC(=O)N(CC1(N2CCNCC2)CC1)c1cccc(C(F)(F)F)n1] | N-((1-(piperazin-1-yl)cyclopropyl)methyl)-N-(6-(trifluoromethyl)pyridin-2-yl)propionamide | A | 1.46 | 357 |

| EX | Structure | Chemical name | Method | Ret (min) | MS (M + H) |
|---|---|---|---|---|---|
| 19N | 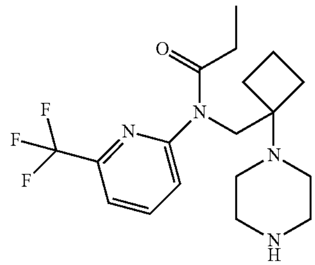 [SMILES: CCC(=O)N(CC1(N2CCNCC2)CCC1)c1cccc(C(F)(F)F)n1] | N-((1-(piperazin-1-yl)cyclobutyl)methyl)-N-(6-(trifluoromethyl)pyridin-2-yl)propionamide | A | 1.49 | 371 |

Intermediate 190. N-((4-(hexahydropyrrolo[3,4-c]pyrrol-2(1H)-yl)tetrahydro-2H-pyran-4-yl)methyl)-N-(6-(trifluoromethyl)pyridin-2-yl)proplonamide

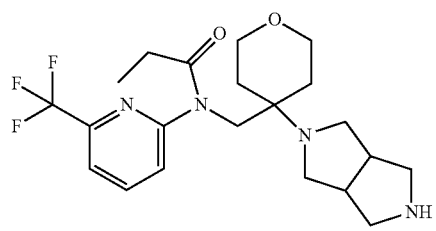 [SMILES: CCC(=O)N(CC1(N2CC3CNCC3C2)CCOCC1)c1cccc(C(F)(F)F)n1]

N-((4-(5-benzylhexahydropyrrolo[3,4-c]pyrrol-2(1H)-yl)tetrahydro-2H-pyran-4-yl)methyl)-N-(6-(trifluoromethyl)pyridin-2-yl)propionamide (Example 196, 380 mg, 0.74 mmol) was disolved in DCE (15 mL) and chloroethyl chloroformate (210 mg, 1.47 mmol) was added. The mixture was stirred for 16 h at 85° C. Then, volatiles were removed under vacuum and MeOH (15 mL) was added and stirred at the reflux temperature for 2 h. The crude was concentrated to give the title compound (174 mg, yield 51%), that was used in the next step without further purification.

HPLC-MS (Method A): Ret, 1.43 min; ESI⁺-MS m/z, 427 (M+1).

This method was used for the preparation of intermediate 19P using example 197 as starting product:

Example 1. N-(((4-(4-Benzylpiperazin-1-yl)tetrahydro-2H-pyran-4-yl)methyl)-N-phenylpropionamide

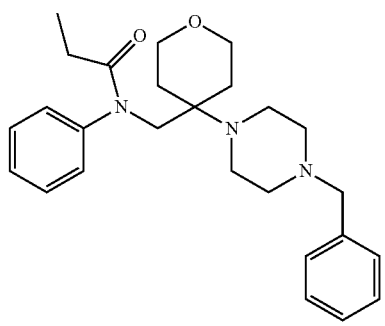 [SMILES: CCC(=O)N(CC1(N2CCN(Cc3ccccc3)CC2)CCOCC1)c1ccccc1]

Propionyl chloride (2.8 g, 10.63 mmol) was added to a solution of N-((4-(4-benzylpiperazin-1-yl)tetrahydro-2H-pyran-4-yl)methyl)aniline (INT 3A, 1.1 g, 3 mmol) and dry TEA (964 μL, 6.92 mmol) in DCM (20 mL) under nitrogen atmosphere. The reaction mixture was stirred at rt. After that, the mixture was washed twice with water and the organic layer was dried with Na₂SO₄, filtered and concentrated to dryness.

The crude residue was purified by flash chromatography on silica gel, eluents DCM:MeOH, gradient from (100:0) to (95:5) to give the title compound as a colourless oil (1.02 g, yield 81%).

HPLC-MS (Method A): Ret, 2.12 min; ESI⁺-MS m/z, 422 (M+1).

This method was used for the preparation of examples 2-48 using intermediates 3 and 12 as starting materials and suitable acyl chlorides:

| EX | Structure | Chemical name | Method | Ret (min) | MS (M + H) |
|---|---|---|---|---|---|
| 19P | 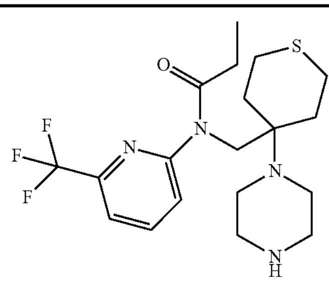 | N-((4-(piperazin-1-yl)tetrahydro-2H-thiopyran-4-yl)methyl)-N-(6-(trifluoromethyl)pyridin-2-yl)propionamide | A | 1.56 | 417 |

| EX | Structure | Chemical name | Method | Ret (min) | MS (M + H) |
|---|---|---|---|---|---|
| 2 | 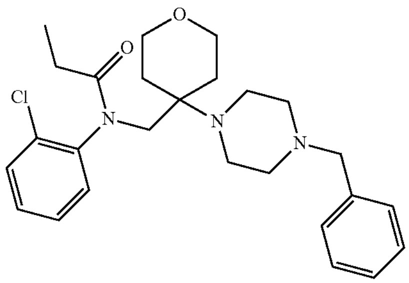 [SMILES: CCC(=O)N(CC1(N2CCN(Cc3ccccc3)CC2)CCOCC1)c1ccccc1Cl] | N-((4-(4-benzylpiperazin-1-yl)tetrahydro-2H-pyran-4-yl)methyl)-N-(2-chlorophenyl)propionamide | A | 2.26 | 456 |
| 3 | 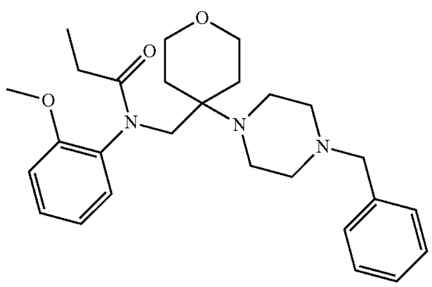 [SMILES: CCC(=O)N(CC1(N2CCN(Cc3ccccc3)CC2)CCOCC1)c1ccccc1OC] | N-((4-(4-benzylpiperazin-1-yl)tetrahydro-2H-pyran-4-yl)methyl)-N-(2-methoxyphenyl)propionamide | A | 2.13 | 452 |
| 4 | 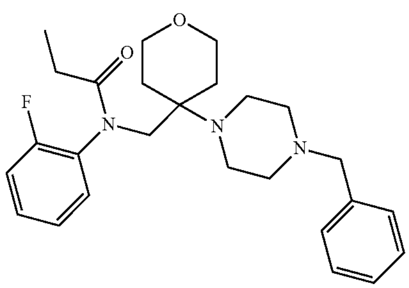 [SMILES: CCC(=O)N(CC1(N2CCN(Cc3ccccc3)CC2)CCOCC1)c1ccccc1F] | N-((4-(4-benzylpiperazin-1-yl)tetrahydro-2H-pyran-4-yl)methyl)-N-(2-fluorophenyl)propionamide | A | 2.13 | 440 |
| 5 | 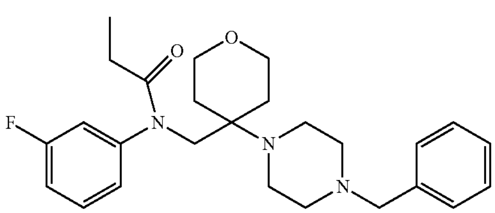 [SMILES: CCC(=O)N(CC1(N2CCN(Cc3ccccc3)CC2)CCOCC1)c1cccc(F)c1] | N-((4-(4-benzylpiperazin-1-yl)tetrahydro-2H-pyran-4-yl)methyl)-N-(3-fluorophenyl)propionamide | A | 2.14 | 440 |
| 6 | 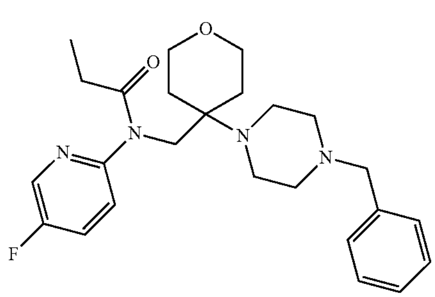 [SMILES: CCC(=O)N(CC1(N2CCN(Cc3ccccc3)CC2)CCOCC1)c1ccc(F)cn1] | N-((4-(4-benzylpiperazin-1-yl)tetrahydro-2H-pyran-4-yl)methyl)-N-(5-fluoropyridin-2-yl)propionamide | A | 1.94 | 441 |

-continued

| EX | Structure | Chemical name | Method | Ret (min) | MS (M + H) |
|---|---|---|---|---|---|
| 7 | 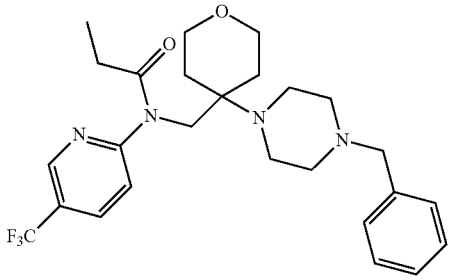 [SMILES: CCC(=O)N(CC1(N2CCN(Cc3ccccc3)CC2)CCOCC1)c1ccc(C(F)(F)F)cn1] | N-((4-(4-benzylpiperazin-1-yl)tetrahydro-2H-pyran-4-yl)methyl)-N-(5-(trifluoromethyl)pyridin-2-yl)propionamide | B | 2.21 | 491 |
| 8 | 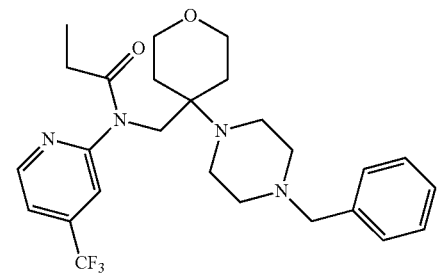 [SMILES: CCC(=O)N(CC1(N2CCN(Cc3ccccc3)CC2)CCOCC1)c1cc(C(F)(F)F)ccn1] | N-((4-(4-benzylpiperazin-1-yl)tetrahydro-2H-pyran-4-yl)methyl)-N-(4-(trifluoromethyl)pyridin-2-yl)propionamide | A | 2.15 | 491 |
| 9 | 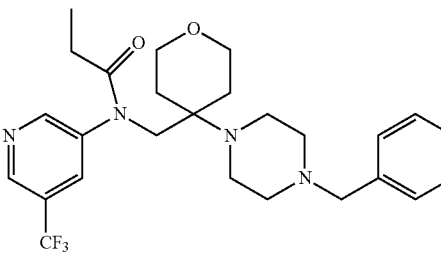 | N-((4-(4-benzylpiperazin-1-yl)tetrahydro-2H-pyran-4-yl)methyl)-N-(5-(trifluoromethyl)pyridin-3-yl)propionamide | A | 2.01 | 491 |
| 10 | 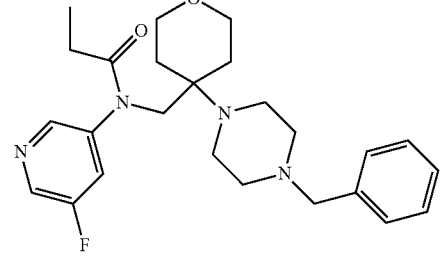 | N-((4-(4-benzylpiperazin-1-yl)tetrahydro-2H-pyran-4-yl)methyl)-N-(5-fluoropyridin-3-yl)propionamide | A | 1.8 | 441 |
| 11 | 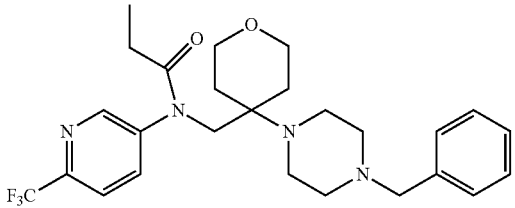 [SMILES: CCC(=O)N(CC1(N2CCN(Cc3ccccc3)CC2)CCOCC1)c1ccc(C(F)(F)F)nc1] | N-((4-(4-benzylpiperazin-1-yl)tetrahydro-2H-pyran-4-yl)methyl)-N-(6-(trifluoromethyl)pyridin-3-yl)propionamide | A | 2.10 | 491 |
| 12 | 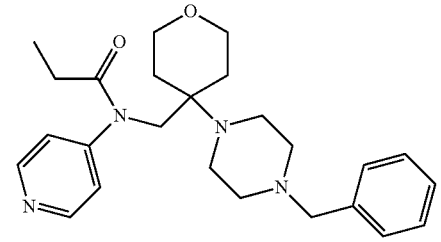 [SMILES: CCC(=O)N(CC1(N2CCN(Cc3ccccc3)CC2)CCOCC1)c1ccncc1] | N-((4-(4-benzylpiperazin-1-yl)tetrahydro-2H-pyran-4-yl)methyl)-N-(pyridin-4-yl)propionamide | A | 1.64 | 423 |

-continued

| EX | Structure | Chemical name | Method | Ret (min) | MS (M + H) |
|---|---|---|---|---|---|
| 13 | 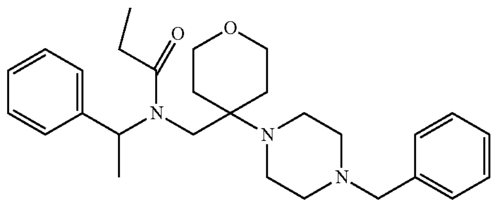 | N-((4-(4-benzylpiperazin-1-yl)tetrahydro-2H-pyran-4-yl)methyl)-N-(1-phenylethyl)propionamide | B | 2.82 | 450 |
| 14 | 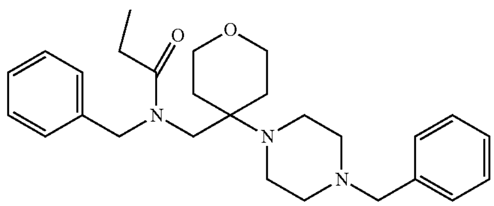 [SMILES: CCC(=O)N(Cc1ccccc1)CC1(N2CCN(Cc3ccccc3)CC2)CCOCC1] | N-benzyl-N-((4-(4-benzylpiperazin-1-yl)tetrahydro-2H-pyran-4-yl)methyl)propionamide | A | 2.15 | 436 |
| 15 | 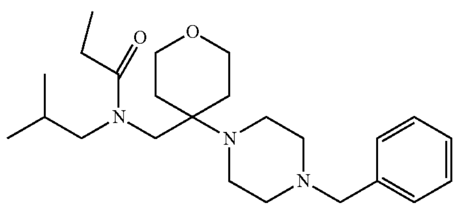 [SMILES: CCC(=O)N(CC(C)C)CC1(N2CCN(Cc3ccccc3)CC2)CCOCC1] | N-((4-(4-benzylpiperazin-1-yl)tetrahydro-2H-pyran-4-yl)methyl)-N-isobutylpropionamide | A | 2.15 | 402 |
| 16 | 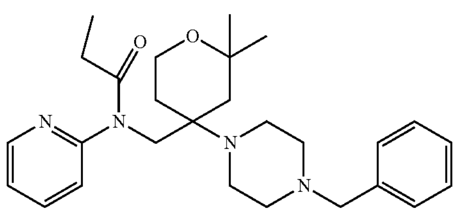 [SMILES: CCC(=O)N(CC1(N2CCN(Cc3ccccc3)CC2)CCOC(C)(C)C1)c1ccccn1] | N-((4-(4-benzylpiperazin-1-yl)-2,2-dimethyltetrahydro-2H-pyran-4-yl)methyl)-N-(pyridin-2-yl)propionamide | A | 2.02 | 451 |
| 17 | 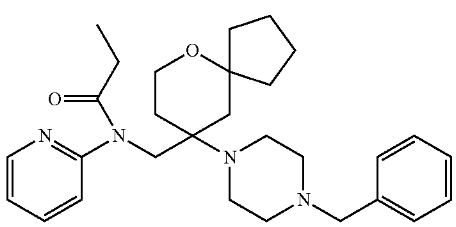 [SMILES: CCC(=O)N(CC1(N2CCN(Cc3ccccc3)CC2)CCOC2(CCCC2)C1)c1ccccn1] | N-((9-(4-benzylpiperazin-1-yl)-6-oxaspiro[4.5]decan-9-yl)methyl)-N-(pyridin-2-yl)propionamide | A | 2.25 | 477 |
| 18 | 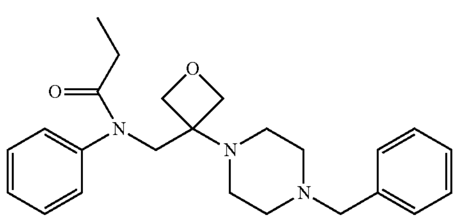 [SMILES: CCC(=O)N(CC1(N2CCN(Cc3ccccc3)CC2)COC1)c1ccccc1] | N-((3-(4-benzylpiperazin-1-yl)oxetan-3-yl)methyl)-N-phenylpropionamide | A | 1.95 | 394 |

| EX | Structure | Chemical name | Method | Ret (min) | MS (M + H) |
|---|---|---|---|---|---|
| 19 | 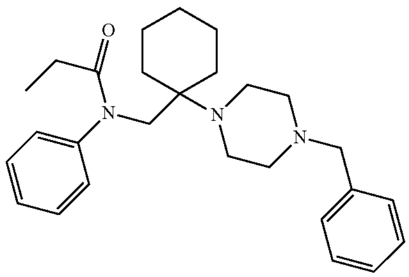 [SMILES: CCC(=O)N(CC1(N2CCN(Cc3ccccc3)CC2)CCCCC1)c1ccccc1] | N-((1-(4-benzylpiperazin-1-yl)cyclohexyl)methyl)-N-phenylpropionamide | C | 2.73 | 420 |
| 20 | 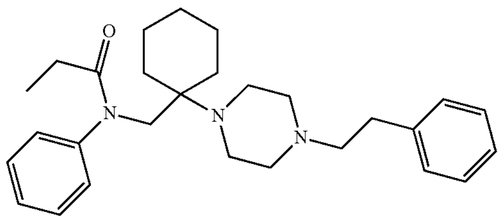 [SMILES: CCC(=O)N(CC1(N2CCN(CCc3ccccc3)CC2)CCCCC1)c1ccccc1] | N-((1-(4-phenethylpiperazin-1-yl)cyclohexyl)methyl)-N-phenylpropionamide | C | 6.27 | 434 |
| 21 | 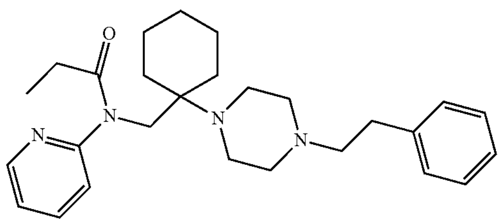 [SMILES: CCC(=O)N(CC1(N2CCN(CCc3ccccc3)CC2)CCCCC1)c1ccccn1] | N-((1-(4-phenethylpiperazin-1-yl)cyclohexyl)methyl)-N-(pyridin-2-yl)propionamide | C | 5.07 | 435 |
| 22 | 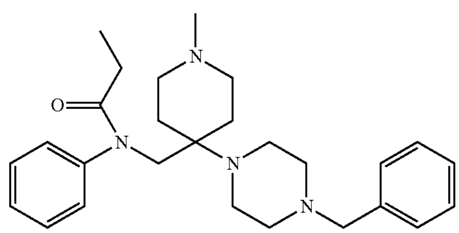 [SMILES: CCC(=O)N(CC1(N2CCN(Cc3ccccc3)CC2)CCN(C)CC1)c1ccccc1] | N-((4-(4-benzylpiperazin-1-yl)-1-methylpiperidin-4-yl)methyl)-N-phenylpropionamide | A | 1.79 | 435 |
| 23 | 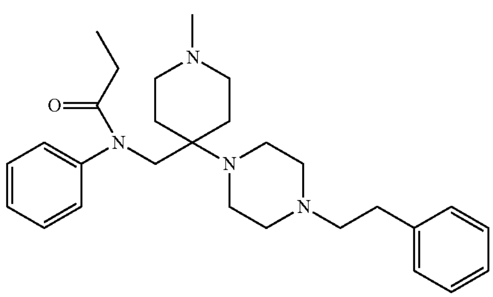 [SMILES: CCC(=O)N(CC1(N2CCN(CCc3ccccc3)CC2)CCN(C)CC1)c1ccccc1] | N-((1-methyl-4-(4-phenethylpiperazin-1-yl)piperidin-4-yl)methyl)-N-phenylpropionamide | A | 1.88 | 449 |
| 24 | 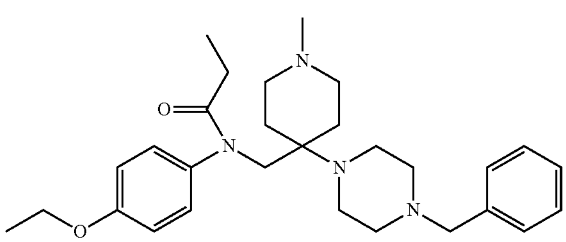 [SMILES: CCOc1ccc(N(CC2(N3CCN(Cc4ccccc4)CC3)CCN(C)CC2)C(=O)CC)cc1] | N-((4-(4-benzylpiperazin-1-yl)-1-methylpiperidin-4-yl)methyl)-N-(4-ethoxyphenyl)propionamide | A | 2.02 | 479 |

-continued

| EX | Structure | Chemical name | Method | Ret (min) | MS (M + H) |
|---|---|---|---|---|---|
| 25 | 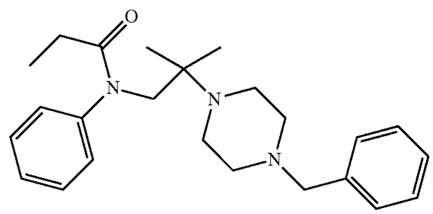 [SMILES: CCC(=O)N(CC(C)(C)N1CCN(Cc2ccccc2)CC1)c1ccccc1] | N-(2-(4-benzylpiperazin-1-yl)-2-methylpropyl)-N-phenylpropionamide | A | 2.22 | 380 |
| 26 | 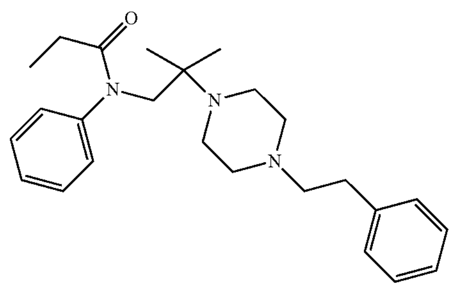 [SMILES: CCC(=O)N(CC(C)(C)N1CCN(CCc2ccccc2)CC1)c1ccccc1] | N-(2-methyl-2-(4-phenethylpiperazin-1-yl)propyl)-N-phenylpropionamide | A | 2.19 | 394 |
| 27 | 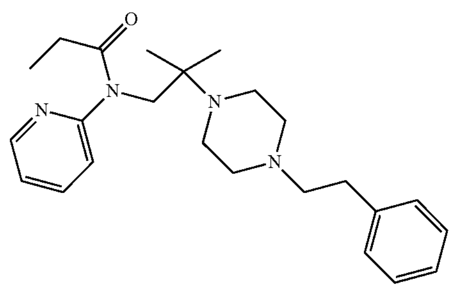 [SMILES: CCC(=O)N(CC(C)(C)N1CCN(CCc2ccccc2)CC1)c1ccccn1] | N-(2-methyl-2-(4-phenethylpiperazin-1-yl)propyl)-N-(pyridin-2-yl)propionamide | A | 1.82 | 395 |
| 28 | 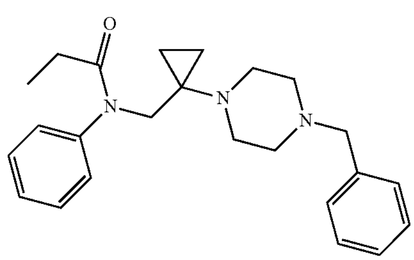 [SMILES: CCC(=O)N(CC1(N2CCN(Cc3ccccc3)CC2)CC1)c1ccccc1] | N-((1-(4-benzylpiperazin-1-yl)cyclopropyl)methyl)-N-phenylpropionamide | A | 2.28 | 378 |
| 29 | 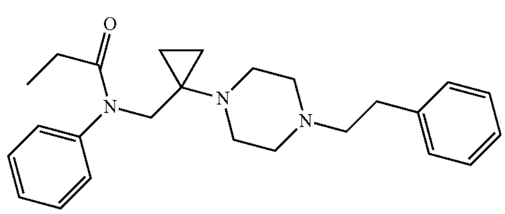 [SMILES: CCC(=O)N(CC1(N2CCN(CCc3ccccc3)CC2)CC1)c1ccccc1] | N-((1-(4-phenethylpiperazin-1-yl)cyclopropyl)methyl)-N-phenylpropionamide | A | 2.29 | 392 |
| 30 | 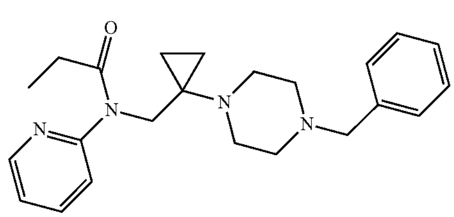 [SMILES: CCC(=O)N(CC1(N2CCN(Cc3ccccc3)CC2)CC1)c1ccccn1] | N-((1-(4-benzylpiperazin-1-yl)cyclopropyl)methyl)-N-(pyridin-2-yl)propionamide | A | 1.91 | 379 |

| EX | Structure | Chemical name | Method | Ret (min) | MS (M + H) |
|---|---|---|---|---|---|
| 31 | 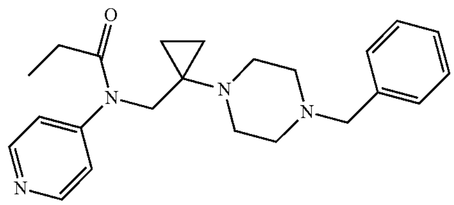 | N-((1-(4-benzylpiperazin-1-yl)cyclopropyl)methyl)-N-(pyridin-4-yl)propionamide | A | 1.75 | 379 |
| 32 | 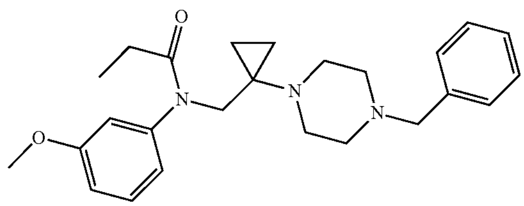 [SMILES: CCC(=O)N(CC1(N2CCN(Cc3ccccc3)CC2)CC1)c1cccc(OC)c1] | N-((1-(4-benzylpiperazin-1-yl)cyclopropyl)methyl)-N-(3-methoxyphenyl)propionamide | A | 2.30 | 408 |
| 33 | 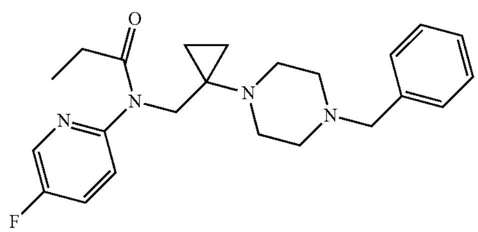 [SMILES: CCC(=O)N(CC1(N2CCN(Cc3ccccc3)CC2)CC1)c1ccc(F)cn1] | N-((1-(4-benzylpiperazin-1-yl)cyclopropyl)methyl)-N-(5-fluoropyridin-2-yl)propionamide | A | 2.06 | 397 |
| 34 | 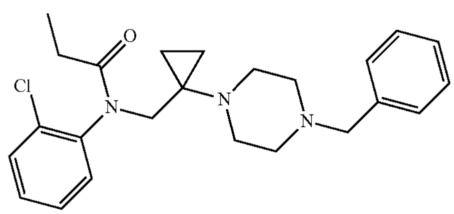 [SMILES: CCC(=O)N(CC1(N2CCN(Cc3ccccc3)CC2)CC1)c1ccccc1Cl] | N-((1-(4-benzylpiperazin-1-yl)cyclopropyl)methyl)-N-(2-chlorophenyl)propionamide | A | 2.42 | 412 |
| 35 | 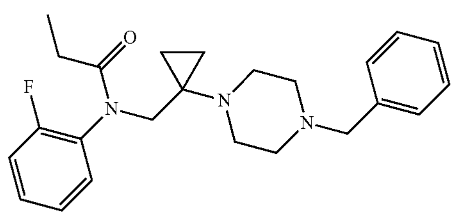 | N-((1-(4-benzylpiperazin-1-yl)cyclopropyl)methyl)-N-(2-fluorophenyl)propionamide | A | 2.31 | 396 |
| 36 | 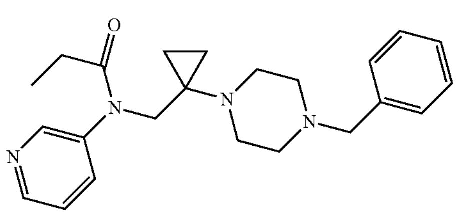 [SMILES: CCC(=O)N(CC1(N2CCN(Cc3ccccc3)CC2)CC1)c1cccnc1] | N-((1-(4-benzylpiperazin-1-yl)cyclopropyl)methyl)-N-(pyridin-3-yl)propionamide | A | 1.77 | 379 |
| 37 | 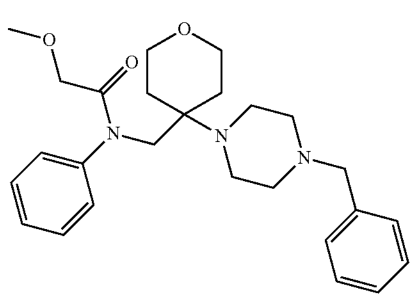 [SMILES: COCC(=O)N(CC1(N2CCN(Cc3ccccc3)CC2)CCOCC1)c1ccccc1] | N-((4-(4-benzylpiperazin-1-yl)tetrahydro-2H-pyran-4-yl)methyl)-2-methoxy-N-phenylacetamide | A | 1.87 | 438 |

| EX | Structure | Chemical name | Method | Ret (min) | MS (M + H) |
|---|---|---|---|---|---|
| 38 | 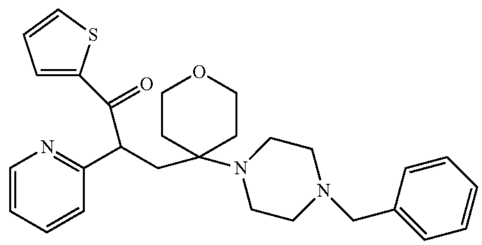 [SMILES: O=C(c1cccs1)C(CC1(N2CCN(Cc3ccccc3)CC2)CCOCC1)c1ccccn1] | N-((4-(4-benzylpiperazin-1-yl)tetrahydro-2H-pyran-4-yl)methyl)-N-(pyridin-2-yl)thiophene-2-carboxamide | A | 1.97 | 477 |
| 39 | 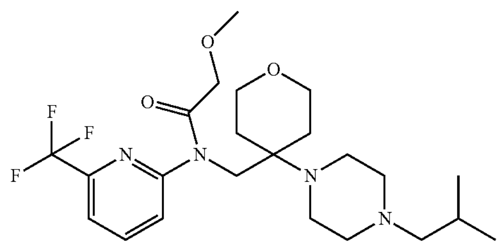 [SMILES: COCC(=O)N(CC1(N2CCN(CC(C)C)CC2)CCOCC1)c1cccc(C(F)(F)F)n1] | N-((4-(4-isobutylpiperazin-1-yl)tetrahydro-2H-pyran-4-yl)methyl)-2-methoxy-N-(6-(trifluoromethyl)pyridin-2-yl)acetamide | A | 2.01 | 473 |
| 40 | 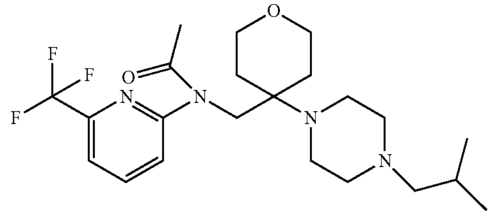 [SMILES: CC(=O)N(CC1(N2CCN(CC(C)C)CC2)CCOCC1)c1cccc(C(F)(F)F)n1] | N-((4-(4-isobutylpiperazin-1-yl)tetrahydro-2H-pyran-4-yl)methyl)-N-(6-(trifluoromethyl)pyridin-2-yl)acetamide | A | 2.07 | 443 |
| 41 | 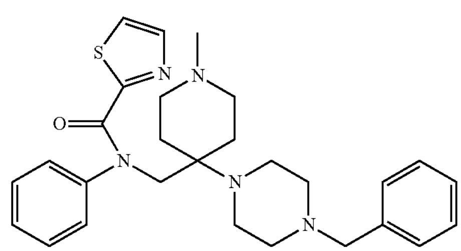 [SMILES: CN1CCC(CN(C(=O)c2nccs2)c2ccccc2)(N2CCN(Cc3ccccc3)CC2)CC1] | N-((4-(4-benzylpiperazin-1-yl)-1-methylpiperidin-4-yl)methyl)-N-phenylthiazole-2-carboxamide | A | 1.79 | 490 |
| 42 | 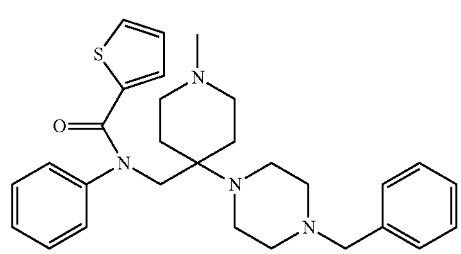 [SMILES: CN1CCC(CN(C(=O)c2cccs2)c2ccccc2)(N2CCN(Cc3ccccc3)CC2)CC1] | N-((4-(4-benzylpiperazin-1-yl)-1-methylpiperidin-4-yl)methyl)-N-phenylthiophene-2-carboxamide | A | 2.00 | 489 |
| 43 | 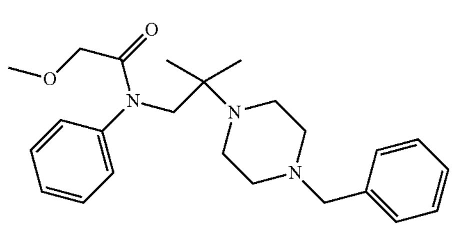 [SMILES: COCC(=O)N(CC(C)(C)N1CCN(Cc2ccccc2)CC1)c1ccccc1] | N-(2-(4-benzylpiperazin-1-yl)-2-methylpropyl)-2-methoxy-N-phenylacetamide | A | 1.95 | 396 |

| EX | Structure | Chemical name | Method | Ret (min) | MS (M + H) |
|---|---|---|---|---|---|
| 44 | 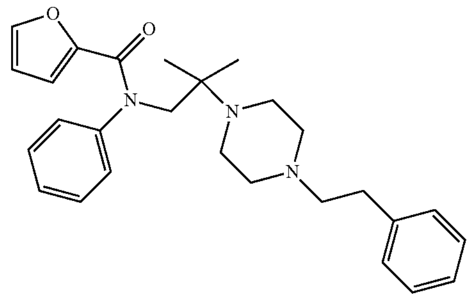 [SMILES: CC(C)(CN(C(=O)c1ccco1)c1ccccc1)N1CCN(CCc2ccccc2)CC1] | N-(2-methyl-2-(4-phenethylpiperazin-1-yl)propyl)-N-phenylfuran-2-carboxamide | A | 2.18 | 432 |
| 45 | 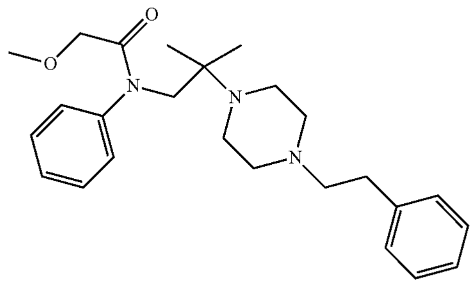 [SMILES: COCC(=O)N(CC(C)(C)N1CCN(CCc2ccccc2)CC1)c1ccccc1] | 2-methoxy-N-(2-methyl-2-(4-phenethylpiperazin-1-yl)propyl)-N-phenylacetamide | A | 2.01 | 409 |
| 46 | 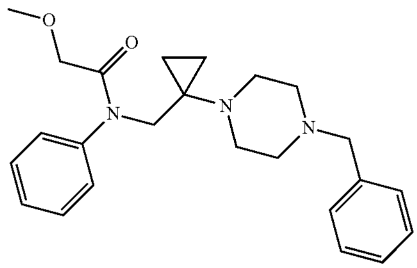 [SMILES: COCC(=O)N(CC1(N2CCN(Cc3ccccc3)CC2)CC1)c1ccccc1] | N-((1-(4-benzylpiperazin-1-yl)cyclopropyl)methyl)-2-methoxy-N-phenylacetamide | B | 2.67 | 394 |
| 47 | 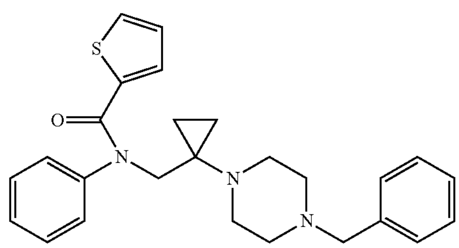 [SMILES: O=C(c1cccs1)N(CC1(N2CCN(Cc3ccccc3)CC2)CC1)c1ccccc1] | N-((1-(4-benzylpiperazin-1-yl)cyclopropyl)methyl)-N-(pyridin-2-yl)thiophene-2-carboxamide | A | 2.12 | 433 |

Example 48. 1-(2-(4-Benzylpiperazin-1-yl)-2-methylpropyl)-3-ethyl-1-phenylurea

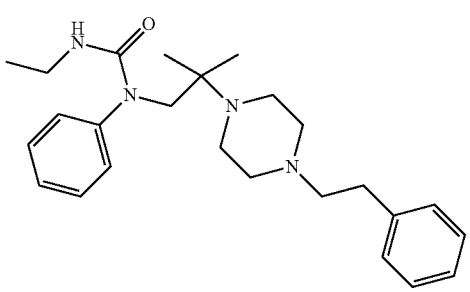 [SMILES: CCNC(=O)N(CC(C)(C)N1CCN(CCc2ccccc2)CC1)c1ccccc1]

Ethylisocyanate (6 mg, 0.085 mmol) was added to a solution of N-(2-(4-benzylpiperazin-1-yl)-2-methylpropyl) aniline (INT 12N, 27.4 mg, 0.085 mmol) and dry TEA (24 µL, 0.17 mmol) in DCM (5 mL) under nitrogen atmosphere. The reaction mixture was stirred at rt. Additional ethylisocyanate and TEA (the same amount as before) was added and the reaction mixture was stirred until full conversion was achieved (3 days, checked by HPLC analysis). The solvent was removed to dryness and crude residue was purified by flash chromatography on neutral alumina, gradient CH:AcOEt to give the title compound (19 mg, yield 57%).

HPLC-MS (Method A): Ret, 1.99 min; ESI$^+$-MS m/z, 395 (M+1).

This method was used for the preparation of the following examples using the corresponding starting products:

| EX | Structure | Chemical name | Method | Ret (min) | MS (M + H) |
|---|---|---|---|---|---|
| 49 | 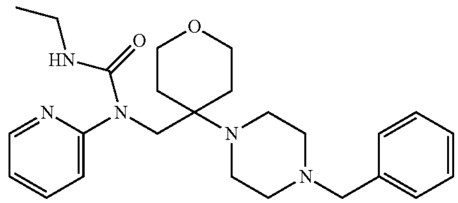 [SMILES: CCNC(=O)N(CC1(N2CCN(Cc3ccccc3)CC2)CCOCC1)c1ccccn1] | 1-((4-(4-benzylpiperazin-1-yl)tetrahydro-2H-pyran-4-yl)methyl)-3-ethyl-1-(pyridin-2-yl)urea | A | 1.76 | 438 |
| 50 | 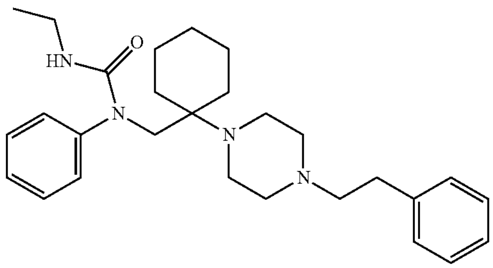 [SMILES: CCNC(=O)N(CC1(N2CCN(CCc3ccccc3)CC2)CCCCC1)c1ccccc1] | 3-ethyl-1-((1-(4-phenethylpiperazin-1-yl)cyclohexyl)methyl)-1-phenylurea | C | 5.67 | 449 |
| 51 | 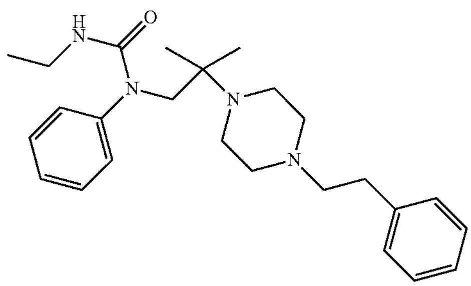 [SMILES: CCNC(=O)N(CC(C)(C)N1CCN(CCc2ccccc2)CC1)c1ccccc1] | 3-ethyl-1-(2-methyl-2-(4-phenethylpiperazin-1-yl)propyl)-1-phenylurea | A | 1.94 | 410 |
| 52 | 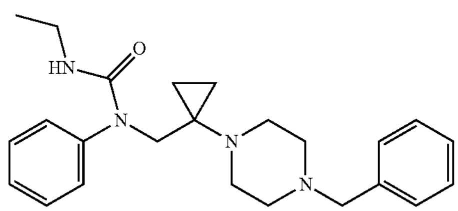 [SMILES: CCNC(=O)N(CC1(N2CCN(Cc3ccccc3)CC2)CC1)c1ccccc1] | 1-((1-(4-benzylpiperazin-1-yl)cyclopropyl)methyl)-3-ethyl-1-phenylurea | A | 2.12 | 393 |
| 53 | 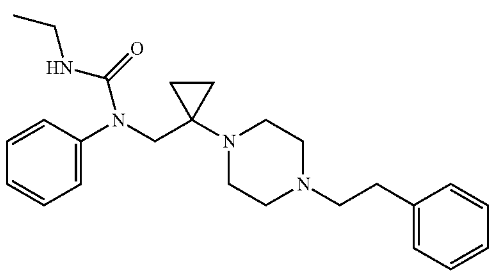 [SMILES: CCNC(=O)N(CC1(N2CCN(CCc3ccccc3)CC2)CC1)c1ccccc1] | 3-ethyl-1-((1-(4-phenethylpiperazin-1-yl)cyclopropyl)methyl)-1-phenylurea | A | 2.13 | 407 |

Example 54. N-((4-(4-Benzylpiperazin-1-yl)tetrahydro-2H-pyran-4-yl)methyl)-N-(2-hydroxyphenyl)proplonamide

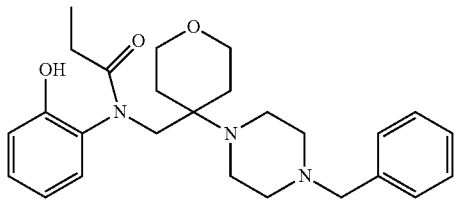 [SMILES: CCC(=O)N(CC1(N2CCN(Cc3ccccc3)CC2)CCOCC1)c1ccccc1O]

N-(2-(Benzyloxy)phenyl)-N-((4-(4-benzylpiperazin-1-yl)tetrahydro-2H-pyran-4-yl)methyl) propionamide (INT 18A, 65 mg, 0.123 mmol) was dissolved in 1 mL of TFA. The reaction mixture was stirred at 80° C. for several days, until full conversion was achieved (HPLC analysis). The solvent was concentrated off and the residue was diluted with sat. solution of NH$_4$OH and extracted several times with AcOEt. The combined organic fractions were dried over sodium sulphate, filtered and the solvent removed to give a crude product which was purified under preparative HPLC (Column X-Bridge C18, ACN: NH$_4$HCO$_3$ 10 mM from (2:98 to 95-5), flow 20 ml/min, rt) to afford the title compound as an oil (6 mg, 11% yield).

HPLC-MS (Method A): Ret, 2.01 min; ESI$^+$-MS m/z, 438 (M+1).

This method was used for the preparation of the example 55 using INT 18B:

atmosphere. The reaction mixture was heated under microwave irradiating conditions for 60 min at 80° C. after which it was allowed to reach rt. The reaction mixture was diluted with DCM (30 mL) and water (45 mL) was added. The aqueous phase was acidified with 10% HCl and the phases were separated. The organic phase was extracted with 10% HCl and the aqueous phase was made alkaline with 20% NaOH while cooling. AcOEt (10 mL) was added, the phases were separated and the aqueous phase was extracted with AcOEt. The combined organic phases were dried over Na$_2$SO$_4$, filtered and concentrated to give the title compound (0.96 g, yield 90%).

HPLC-MS (Method A): Ret, 1.78 min; ESI+-MS m/z, 423 (M+1).

This method was used for the preparation of examples 57-98 using INT 3 and 12 as starting materials. In some cases DCE was substituted by THF or toluene.

| EX | Structure | Chemical name | Method | Ret (min) | MS (M + H) |
|---|---|---|---|---|---|
| 55 | 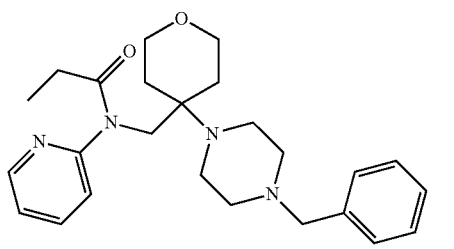 [SMILES: CCC(=O)N(CC1(N2CCN(Cc3ccccc3)CC2)CCOCC1)c1ccccn1] | N-((1-(4-benzylpiperazin-1-yl)cyclopropyl)methyl)-N-(2-hydroxyphenyl) propionamide | A | 2.20 | 394 |

Example 56. N-((4-(4-Benzylpiperazin-1-yl)tetrahydro-2H-pyran-4-yl)methyl)-N-(3-cyanophenyl)proplonamide Propionyl chloride (143 µL, 1.637 mmol) was added to a solution of N-((4-(4-benzylpiperazin-1-yl)tetrahydro-2H-pyran-4-yl)methyl)pyridin-2-amine (INT 3G, 0.3 g, 0.819 mmol) and N-ethyl-N-isopropylpropan-2-amine (427 µL, 2.45 mmol) in DCE (14 mL) in a process vial under nitrogen

| EX | Structure | Chemical name | Method | Ret (min) | MS (M + H) |
|---|---|---|---|---|---|
| 57 | 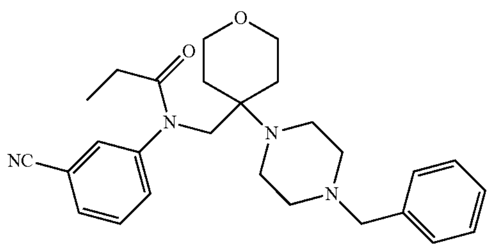 [SMILES: CCC(=O)N(CC1(N2CCN(Cc3ccccc3)CC2)CCOCC1)c1cccc(C#N)c1] | N-((4-(4-benzylpiperazin-1-yl)tetrahydro-2H-pyran-4-yl)methyl)-N-(3-cyanophenyl)propionamide | A | 1.97 | 447 |
| 58 | 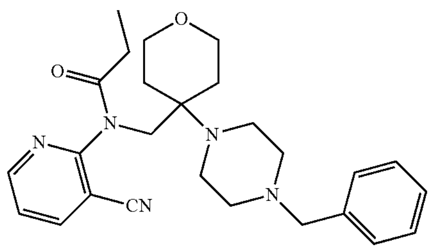 [SMILES: CCC(=O)N(CC1(N2CCN(Cc3ccccc3)CC2)CCOCC1)c1ncccc1C#N] | N-((4-(4-benzylpiperazin-1-yl)tetrahydro-2H-pyran-4-yl)methyl)-N-(3-cyanopyridin-2-yl)propionamide | A | 1.77 | 448 |
| 59 | 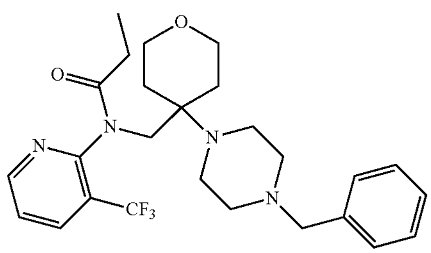 | N-((4-(4-benzylpiperazin-1-yl)tetrahydro-2H-pyran-4-yl)methyl)-N-(3-(trifluoromethyl)pyridin-2-yl)propionamide | A | 2.11 | 491 |
| 60 | 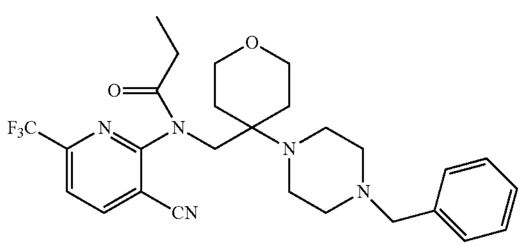 [SMILES: CCC(=O)N(CC1(N2CCN(Cc3ccccc3)CC2)CCOCC1)c1nc(C(F)(F)F)ccc1C#N] | N-((4-(4-benzylpiperazin-1-yl)tetrahydro-2H-pyran-4-yl)methyl)-N-(3-cyano-6-(trifluoromethyl)pyridin-2-yl)propionamide | A | 2.19 | 516 |
| 61 | 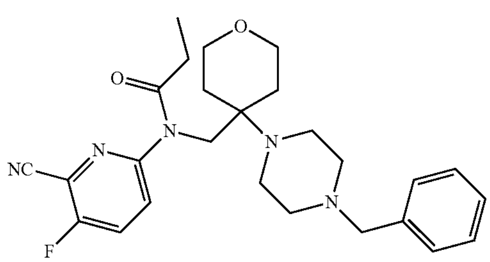 [SMILES: CCC(=O)N(CC1(N2CCN(Cc3ccccc3)CC2)CCOCC1)c1ccc(F)c(C#N)n1] | N-((4-(4-benzylpiperazin-1-yl)tetrahydro-2H-pyran-4-yl)methyl)-N-(6-cyano-5-fluoropyridin-2-yl)propionamide | A | 2.02 | 466 |
| 62 | 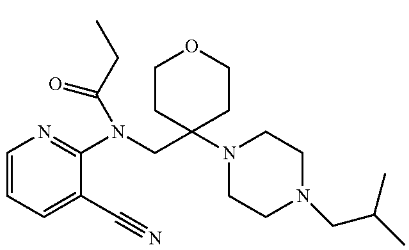 [SMILES: CCC(=O)N(CC1(N2CCN(CC(C)C)CC2)CCOCC1)c1ncccc1C#N] | N-(3-cyanopyridin-2-yl)-N-((4-(4-isobutylpiperazin-1-yl)tetrahydro-2H-pyran-4-yl)methyl)propionamide | B | 2.13 | 414 |

-continued

| EX | Structure | Chemical name | Method | Ret (min) | MS (M + H) |
|---|---|---|---|---|---|
| 63 | 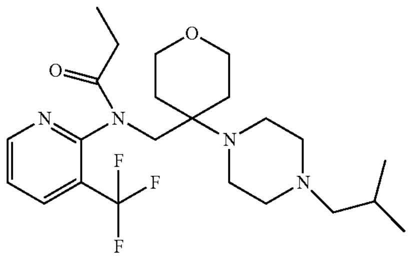 [SMILES: CCC(=O)N(CC1(N2CCN(CC(C)C)CC2)CCOCC1)c1ncccc1C(F)(F)F] | N-((4-(4-isobutylpiperazin-1-yl)tetrahydro-2H-pyran-4-yl)methyl)-N-(3-(trifluoromethyl)pyridin-2-yl)propionamide | B | 2.48 | 457 |
| 64 | 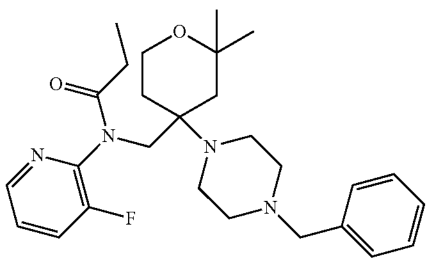 [SMILES: CCC(=O)N(CC1(N2CCN(Cc3ccccc3)CC2)CCOC(C)(C)C1)c1ncccc1F] | N-((4-(4-benzylpiperazin-1-yl)-2,2-dimethyltetrahydro-2H-pyran-4-yl)methyl)-N-(3-fluoropyridin-2-yl)propionamide | A | 2.16 | 469 |
| 65 | 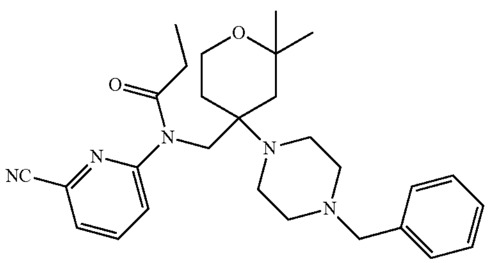 [SMILES: CCC(=O)N(CC1(N2CCN(Cc3ccccc3)CC2)CCOC(C)(C)C1)c1cccc(C#N)n1] | N-((4-(4-benzylpiperazin-1-yl)-2,2-dimethyltetrahydro-2H-pyran-4-yl)methyl)-N-(6-cyanopyridin-2-yl)propionamide | A | 2.11 | 476 |
| 66 | 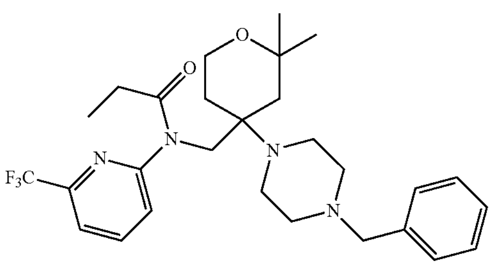 [SMILES: CCC(=O)N(CC1(N2CCN(Cc3ccccc3)CC2)CCOC(C)(C)C1)c1cccc(C(F)(F)F)n1] | N-((4-(4-benzylpiperazin-1-yl)-2,2-dimethyltetrahydro-2H-pyran-4-yl)methyl)-N-(6-(trifluoromethyl)pyridin-2-yl)propionamide | A | 2.41 | 519 |
| 67 | 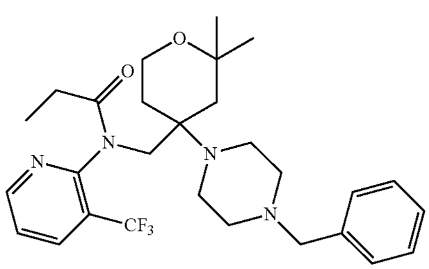 [SMILES: CCC(=O)N(CC1(N2CCN(Cc3ccccc3)CC2)CCOC(C)(C)C1)c1ncccc1C(F)(F)F] | N-((4-(4-benzylpiperazin-1-yl)-2,2-dimethyltetrahydro-2H-pyran-4-yl)methyl)-N-(3-(trifluoromethyl)pyridin-2-yl)propionamide | A | 2.35 | 519 |
| 68 | 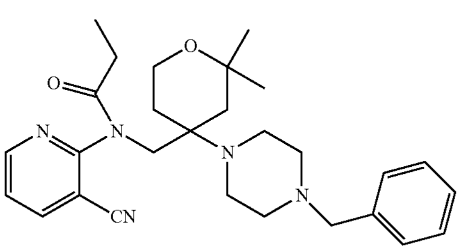 [SMILES: CCC(=O)N(CC1(N2CCN(Cc3ccccc3)CC2)CCOC(C)(C)C1)c1ncccc1C#N] | N-((4-(4-benzylpiperazin-1-yl)-2,2-dimethyltetrahydro-2H-pyran-4-yl)methyl)-N-(3-cyanopyridin-2-yl)propionamide | A | 2.04 | 476 |

-continued

| EX | Structure | Chemical name | Method | Ret (min) | MS (M + H) |
|---|---|---|---|---|---|
| 69 | 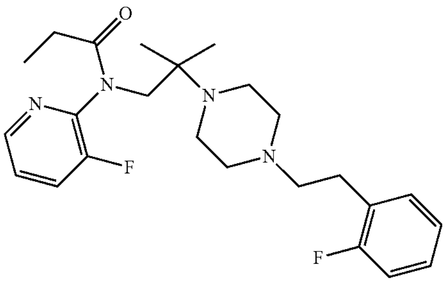 [SMILES: CCC(=O)N(CC(C)(C)N1CCN(CCc2ccccc2F)CC1)c1ncccc1F] | N-(2-(4-(2-fluorophenethyl)piperazin-1-yl)-2-methylpropyl)-N-(3-fluoropyridin-2-yl)propionamide | B | 2.68 | 431 |
| 70 | 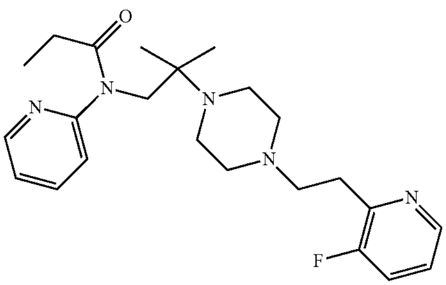 [SMILES: CCC(=O)N(CC(C)(C)N1CCN(CCc2ncccc2F)CC1)c1ccccn1] | N-(2-(4-(2-(3-fluoropyridin-2-yl)ethyl)piperazin-1-yl)-2-methylpropyl)-N-(pyridin-2-yl)propionamide | A | 1.49 | 414 |
| 71 | 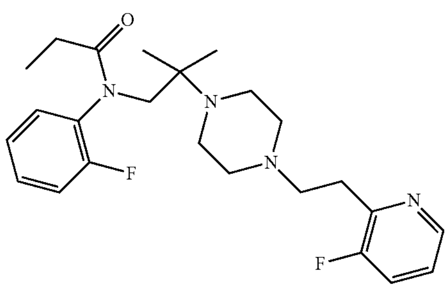 [SMILES: CCC(=O)N(CC(C)(C)N1CCN(CCc2ncccc2F)CC1)c1ccccc1F] | N-(2-fluorophenyl)-N-(2-(4-(2-(3-fluoropyridin-2-yl)ethyl)piperazin-1-yl)-2-methylpropyl) propionamide | A | 1.88 | 431 |
| 72 | 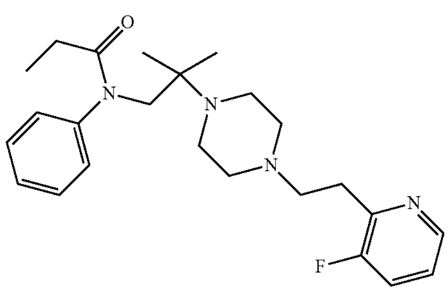 [SMILES: CCC(=O)N(CC(C)(C)N1CCN(CCc2ncccc2F)CC1)c1ccccc1] | N-(2-(4-(2-(3-fluoropyridin-2-yl)ethyl)piperazin-1-yl)-2-methylpropyl)-N-phenylpropionamide | A | 1.79 | 413 |
| 73 | 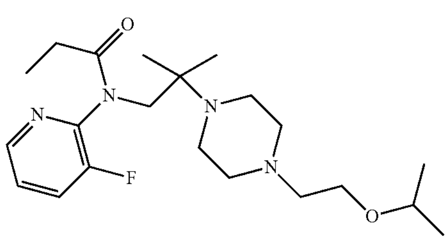 [SMILES: CCC(=O)N(CC(C)(C)N1CCN(CCOC(C)C)CC1)c1ncccc1F] | N-(3-fluoropyridin-2-yl)-N-(2-(4-(2-isopropoxyethyl)piperazin-1-yl)-2-methylpropyl) propionamide | A | 1.71 | 395 |

-continued

| EX | Structure | Chemical name | Method | Ret (min) | MS (M + H) |
|---|---|---|---|---|---|
| 74 | 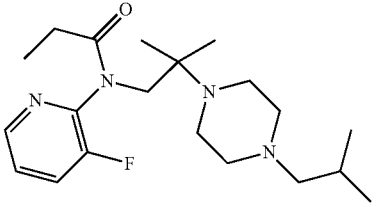 [SMILES: CCC(=O)N(CC(C)(C)N1CCN(CC(C)C)CC1)c1ncccc1F] | N-(3-fluoropyridin-2-yl)-N-(2-(4-isobutylpiperazin-1-yl)-2-methylpropyl) propionamide | A | 2.02 | 365 |
| 75 | 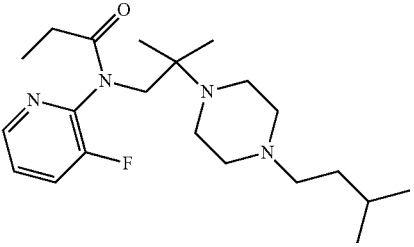 [SMILES: CCC(=O)N(CC(C)(C)N1CCN(CCC(C)C)CC1)c1ncccc1F] | N-(3-fluoropyridin-2-yl)-N-(2-(4-isopentylpiperazin-1-yl)-2-methylpropyl) propionamide | A | 1.95 | 379 |
| 76 | 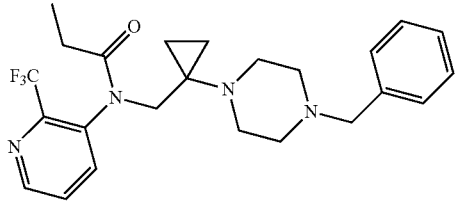 [SMILES: CCC(=O)N(CC1(N2CCN(Cc3ccccc3)CC2)CC1)c1cccnc1C(F)(F)F] | N-((1-(4-benzylpiperazin-1-yl)cyclopropyl)methyl)-N-(2-(trifluoromethyl)pyridin-3-yl)propionamide | A | 2.78 | 447 |
| 77 | 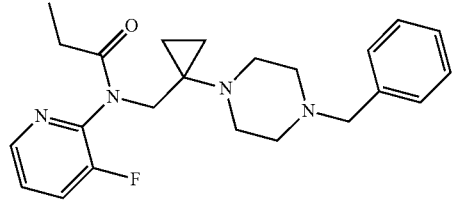 [SMILES: CCC(=O)N(CC1(N2CCN(Cc3ccccc3)CC2)CC1)c1ncccc1F] | N-((1-(4-benzylpiperazin-1-yl)cyclopropyl)methyl)-N-(3-fluoropyridin-2-yl)propionamide | A | 2.06 | 397 |
| 78 | 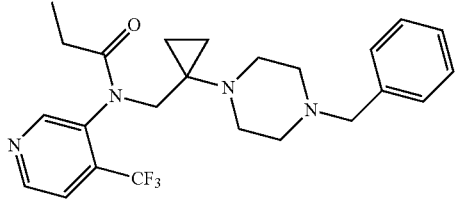 [SMILES: CCC(=O)N(CC1(N2CCN(Cc3ccccc3)CC2)CC1)c1cnccc1C(F)(F)F] | N-((1-(4-benzylpiperazin-1-yl)cyclopropyl)methyl)-N-(4-(trifluoromethyl)pyridin-3-yl)propionamide | A | 2.17 | 447 |
| 79 | 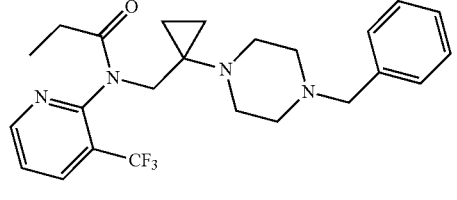 [SMILES: CCC(=O)N(CC1(N2CCN(Cc3ccccc3)CC2)CC1)c1ncccc1C#N] | N-((1-(4-benzylpiperazin-1-yl)cyclopropyl)methyl)-N-(3-(trifluoromethyl)pyridin-2-yl)propionamide | A | 2.26 | 447 |
| 80 | 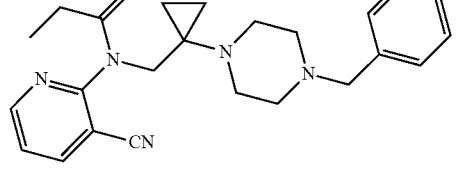 | N-((1-(4-benzylpiperazin-1-yl)cyclopropyl)methyl)-N-(3-cyanopyridin-2-yl)propionamide | A | 1.94 | 404 |

-continued

| EX | Structure | Chemical name | Method | Ret (min) | MS (M + H) |
|---|---|---|---|---|---|
| 81 | 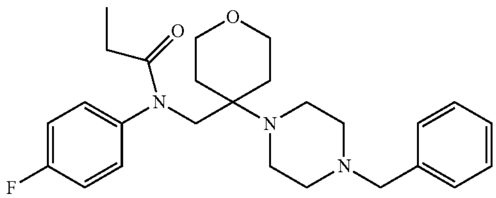 [SMILES: CCC(=O)N(CC1(N2CCN(Cc3ccccc3)CC2)CCOCC1)c1ccc(F)cc1] | N-((4-(4-benzylpiperazin-1-yl)tetrahydro-2H-pyran-4-yl)methyl)-N-(4-fluorophenyl) propionamide | A | 2.14 | 440 |
| 82 | 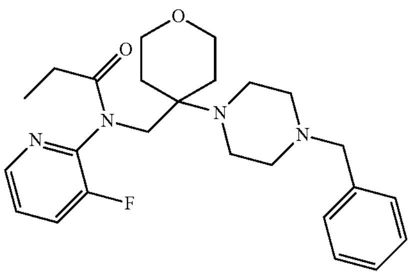 [SMILES: CCC(=O)N(CC1(N2CCN(Cc3ccccc3)CC2)CCOCC1)c1ncccc1F] | N-((4-(4-benzylpiperazin-1-yl)tetrahydro-2H-pyran-4-yl)methyl)-N-(3-fluoropyridin-2-yl)propionamide | A | 1.90 | 441 |
| 83 | 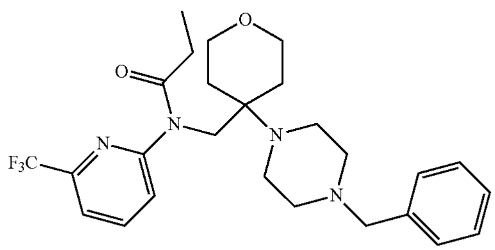 [SMILES: CCC(=O)N(CC1(N2CCN(Cc3ccccc3)CC2)CCOCC1)c1cccc(C(F)(F)F)n1] | N-((4-(4-benzylpiperazin-1-yl)tetrahydro-2H-pyran-4-yl)methyl)-N-(6-(trifluoromethyl)pyridin-2-yl)propionamide | A | 2.17 | 491 |
| 84 | 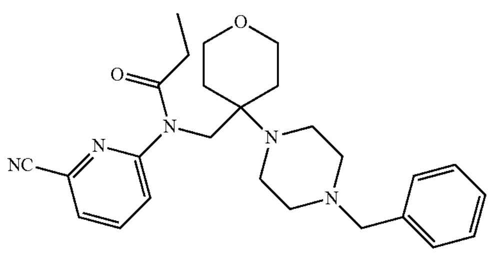 [SMILES: CCC(=O)N(CC1(N2CCN(Cc3ccccc3)CC2)CCOCC1)c1cccc(C#N)n1] | N-((4-(4-benzylpiperazin-1-yl)tetrahydro-2H-pyran-4-yl)methyl)-N-(6-cyanopyridin-2-yl)propionamide | A | 1.90 | 448 |
| 85 | 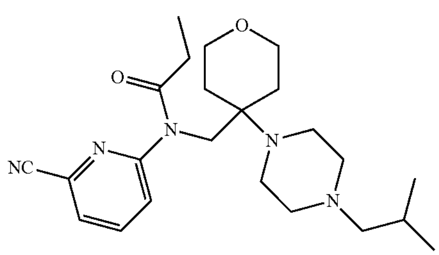 [SMILES: CCC(=O)N(CC1(N2CCN(CC(C)C)CC2)CCOCC1)c1cccc(C#N)n1] | N-(6-cyanopyridin-2-yl)-N-((4-(4-isobutylpiperazin-1-yl)tetrahydro-2H-pyran-4-yl)methyl)propionamide | A | 1.79 | 414 |
| 86 | 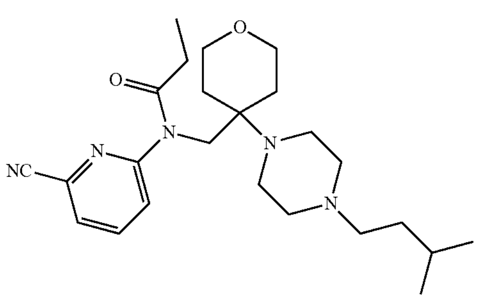 [SMILES: CCC(=O)N(CC1(N2CCN(CCC(C)C)CC2)CCOCC1)c1cccc(C#N)n1] | N-(6-cyanopyridin-2-yl)-N-((4-(4-isopentylpiperazin-1-yl)tetrahydro-2H-pyran-4-yl)methyl)propionamide | A | 1.79 | 428 |

-continued

| EX | Structure | Chemical name | Method | Ret (min) | MS (M + H) |
|---|---|---|---|---|---|
| 87 | 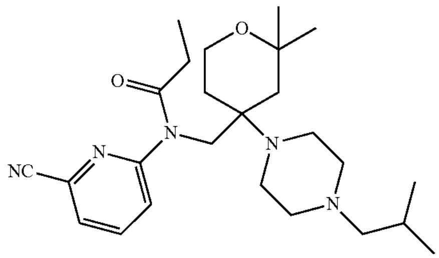 [SMILES: CCC(=O)N(CC1(N2CCN(CC(C)C)CC2)CCOC(C)(C)C1)c1cccc(C#N)n1] | N-(6-cyanopyridin-2-yl)-N-((4-(4-isobutylpiperazin-1-yl)-2,2-dimethyltetrahydro-2H-pyran-4-yl)methyl)propionamide | A | 2.09 | 442 |
| 88 | 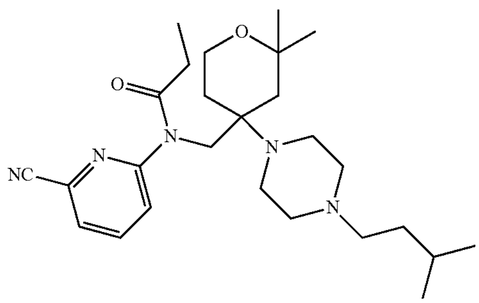 [SMILES: CCC(=O)N(CC1(N2CCN(CCC(C)C)CC2)CCOC(C)(C)C1)c1cccc(C#N)n1] | N-(6-cyanopyridin-2-yl)-N-((4-(4-isopentylpiperazin-1-yl)-2,2-dimethyltetrahydro-2H-pyran-4-yl)methyl)propionamide | A | 2.05 | 456 |
| 89 | 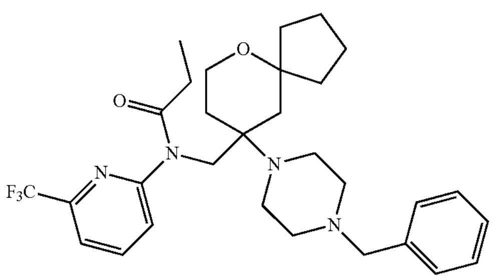 [SMILES: CCC(=O)N(CC1(N2CCN(Cc3ccccc3)CC2)CCOC2(CCCC2)C1)c1cccc(C(F)(F)F)n1] | N-((9-(4-benzylpiperazin-1-yl)-6-oxaspiro[4.5]decan-9-yl)methyl)-N-(6-(trifluoromethyl)pyridin-2-yl)propionamide | A | 2.61 | 545 |
| 90 | 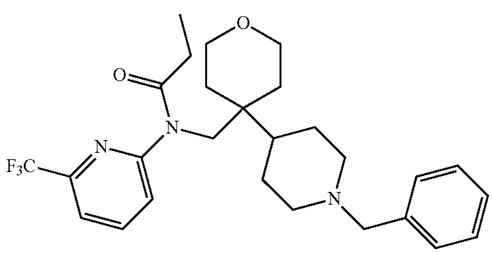 [SMILES: CCC(=O)N(CC1(C2CCN(Cc3ccccc3)CC2)CCOCC1)c1cccc(C(F)(F)F)n1] | N-((4-(1-benzylpiperidin-4-yl)tetrahydro-2H-pyran-4-yl)methyl)-N-(6-(trifluoromethyl)pyridin-2-yl)propionamide | C | 4.76 | 490.2 |
| 91 | 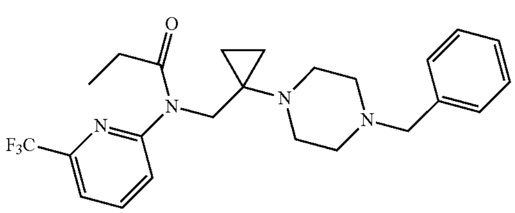 [SMILES: CCC(=O)N(CC1(N2CCN(Cc3ccccc3)CC2)CC1)c1cccc(C(F)(F)F)n1] | N-((1-(4-benzylpiperazin-1-yl)cyclopropyl)methyl)-N-(6-(trifluoromethyl)pyridin-2-yl)propionamide | A | 2.37 | 447 |
| 92 | 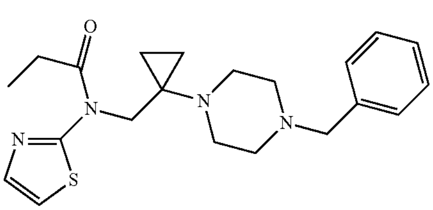 [SMILES: CCC(=O)N(CC1(N2CCN(Cc3ccccc3)CC2)CC1)c1nccs1] | N-((1-(4-benzylpiperazin-1-yl)cyclopropyl)methyl)-N-(thiazol-2-yl)propionamide | A | 2.29 | 385 |

-continued

| EX | Structure | Chemical name | Method | Ret (min) | MS (M + H) |
|---|---|---|---|---|---|
| 93 | 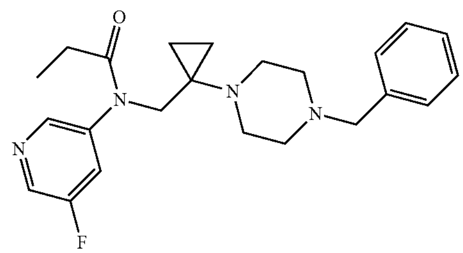 [SMILES: CCC(=O)N(CC1(N2CCN(Cc3ccccc3)CC2)CC1)c1cncc(F)c1] | N-((1-(4-benzylpiperazin-1-yl)cyclopropyl)methyl)-N-(5-fluoropyridin-3-yl)propionamide | A | 1.96 | 397 |
| 94 | 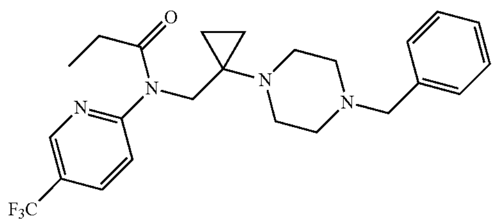 [SMILES: CCC(=O)N(CC1(N2CCN(Cc3ccccc3)CC2)CC1)c1ccc(C(F)(F)F)cn1] | N-((1-(4-benzylpiperazin-1-yl)cyclopropyl)methyl)-N-(5-(trifluoromethyl)pyridin-2-yl)propionamide | A | 2.98 | 447 |
| 95 | 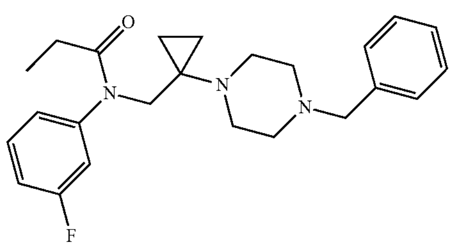 [SMILES: CCC(=O)N(CC1(N2CCN(Cc3ccccc3)CC2)CC1)c1cccc(F)c1] | N-((1-(4-benzylpiperazin-1-yl)cyclopropyl)methyl)-N-(3-fluorophenyl)propionamide | A | 2.33 | 396 |
| 96 | 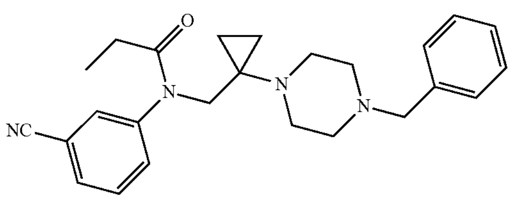 [SMILES: CCC(=O)N(CC1(N2CCN(Cc3ccccc3)CC2)CC1)c1cccc(C#N)c1] | N-((1-(4-benzylpiperazin-1-yl)cyclopropyl)methyl)-N-(3-cyanophenyl)propionamide | A | 2.13 | 403 |
| 97 | 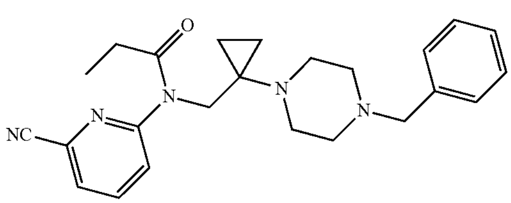 [SMILES: CCC(=O)N(CC1(N2CCN(Cc3ccccc3)CC2)CC1)c1cccc(C#N)n1] | N-((1-(4-benzylpiperazin-1-yl)cyclopropyl)methyl)-N-(6-cyanopyridin-2-yl)propionamide | A | 2.08 | 404 |
| 98 | 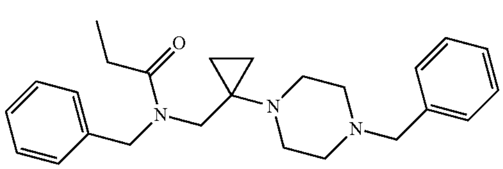 [SMILES: CCC(=O)N(Cc1ccccc1)CC1(N2CCN(Cc3ccccc3)CC2)CC1] | N-benzyl-N-((1-(4-benzylpiperazin-1-yl)cyclopropyl)methyl)propionamide | A | 2.29 | 392 |

Example 99. N-((4-(4-Benzylpiperazin-1-yl)tetrahydro-2H-pyran-4-yl)methyl)-N-ethylpropionamide

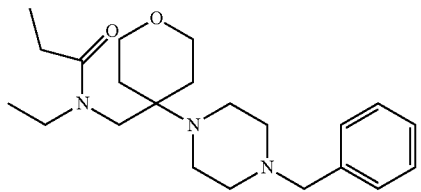 [SMILES: CCC(=O)N(CC)CC1(N2CCN(Cc3ccccc3)CC2)CCOCC1]

A solution of N-((4-(4-benzylpiperazin-1-yl)tetrahydro-2H-pyran-4-yl)methyl)propionamide (INT 4A, 90 mg, 0.261 mmol) and NaH (246 mg, 1.78 mmol) in THF anhydrous (5 mL) was stirred 30 min at rt. After that, bromoethane (194 μL, 2.6 mmol) was added and it was stirred at 70° C. overnight.

Additional bromoethane (194 μL, 2.6 mmol) and NaH (246 mg, 1.78 mmol) was added and the reaction mixture was stirred at 70° C. until 25% conversion was achieved (several days, checked by HPLC analysis). It was cooled down and the reaction mixture was washed with water. AcOEt was added and the organic layer was separated, dried over $Na_2SO_4$, filtered and concentrated. The crude residue was purified by flash chromatography on neutral alumina, gradient CH/AcOEt from (100:0) to (80:20) to give the title compound (33 mg, yield 35%).

HPLC-MS (Method A): Ret, 1.8 min; $ESI^+$-MS m/z, 374.2 (M+1).

Example 100. N-((4-(4-(3-Fluorobenzyl)piperazin-1-yl)tetrahydro-2H-pyran-4-yl)methyl)-N phenylpropionamide

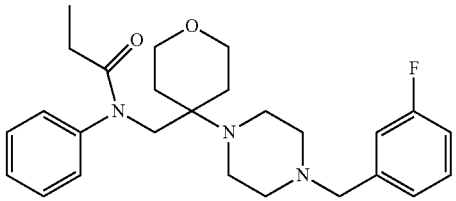 [SMILES: CCC(=O)N(CC1(N2CCN(Cc3cccc(F)c3)CC2)CCOCC1)c1ccccc1]

N-Phenyl-N-((4-(piperazin-1-yl)tetrahydro-2H-pyran-4-yl)methyl)propionamide (INT 19A, 50 mg, 0.15 mmol) was dissolved, under argon atmosphere, in MeOH (4 mL) in a process vial. 3-fluorobenzaldehyde (56 mg, 0.45 mmol) and sodium triacetoxyborohydride (40 mg, 0.60 mmol) were added, and the vial was sealed with a septum. The suspension was subjected to microwave irradiating conditions for 30 min at 120° C. and then cooled. The crude product was evaporated to dryness and then suspended in aqueous $NaHCO_3$. The mixture was extracted with DCM and washed with sat aqueous $NaHCO_3$ solution. The organic layer was dried with $Na_2SO_4$, filtered and concentrated. The residue was purified by flash chromatography on silica gel, gradient DCM to DCM:MeOH (0:5) to afford the title compound (40 mg, yield 60%).

HPLC-MS (Method A): Ret, 2.19 min; $ESI^+$-MS m/z, 440 (M+1).

A similar method was used for the preparation of examples 101-124 using the corresponding intermediates 19 as starting material and suitable aldehydes or ketones:

| EX | Structure | Chemical name | Method | Ret (min) | MS (M + H) |
|---|---|---|---|---|---|
| 101 | 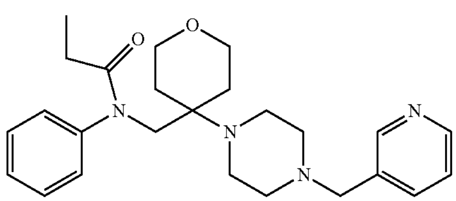 [SMILES: CCC(=O)N(CC1(N2CCN(Cc3cccnc3)CC2)CCOCC1)c1ccccc1] | N-phenyl-N-((4-(4-(pyridin-3-ylmethyl)piperazin-1-yl)tetrahydro-2H-pyran-4-yl)methyl)propionamide | A | 1.61 | 423 |
| 102 | 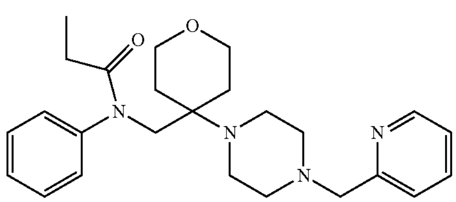 [SMILES: CCC(=O)N(CC1(N2CCN(Cc3ccccn3)CC2)CCOCC1)c1ccccc1] | N-phenyl-N-((4-(4-(pyridin-2-ylmethyl)piperazin-1-yl)tetrahydro-2H-pyran-4-yl)methyl)propionamide | A | 1.66 | 423 |
| 1053 | 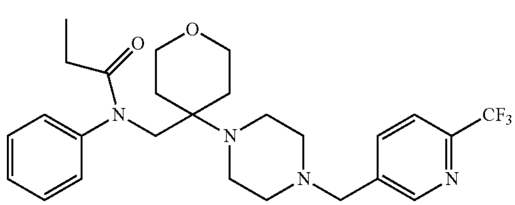 [SMILES: CCC(=O)N(CC1(N2CCN(Cc3ccc(C(F)(F)F)nc3)CC2)CCOCC1)c1ccccc1] | N-phenyl-N-((4-(4-((6-(trifluoromethyl)pyridin-3-yl)methyl)piperazin-1-yl)tetrahydro-2H-pyran-4-yl)methyl)propionamide | A | 2.07 | 491 |

| EX | Structure | Chemical name | Method | Ret (min) | MS (M + H) |
|---|---|---|---|---|---|
| 104 | 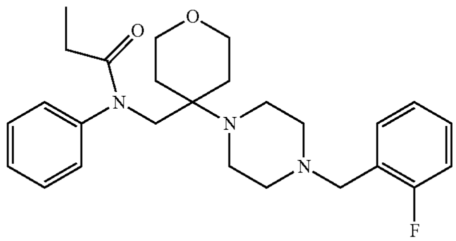 [SMILES: CCC(=O)N(CC1(N2CCN(Cc3ccccc3F)CC2)CCOCC1)c1ccccc1] | N-((4-(4-(2-fluorobenzyl)piperazin-1-yl)tetrahydro-2H-pyran-4-yl)methyl)-N-phenylpropionamide | A | 2.12 | 440 |
| 105 | 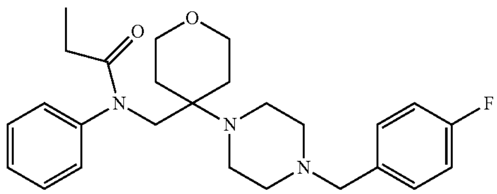 [SMILES: CCC(=O)N(CC1(N2CCN(Cc3ccc(F)cc3)CC2)CCOCC1)c1ccccc1] | N-((4-(4-(4-fluorobenzyl)piperazin-1-yl)tetrahydro-2H-pyran-4-yl)methyl)-N-phenylpropionamide | A | 2.13 | 440 |
| 106 | 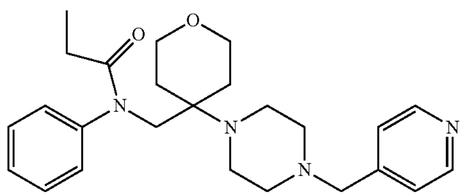 [SMILES: CCC(=O)N(CC1(N2CCN(Cc3ccncc3)CC2)CCOCC1)c1ccccc1] | N-phenyl-N-((4-(4-(pyridin-4-ylmethyl)piperazin-1-yl)tetrahydro-2H-pyran-4-yl)methyl)propionamide | A | 1.64 | 423 |
| 107 | 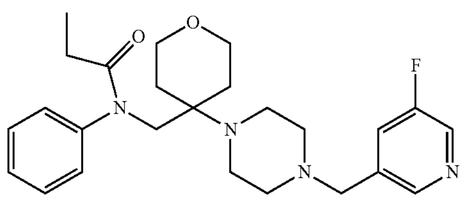 [SMILES: CCC(=O)N(CC1(N2CCN(Cc3cncc(F)c3)CC2)CCOCC1)c1ccccc1] | N-((4-(4-((5-fluoropyridin-3-yl)methyl)piperazin-1-yl)tetrahydro-2H-pyran-4-yl)methyl)-N-phenylpropionamide | A | | 441 |
| 108 | 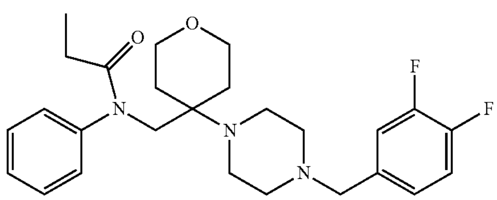 [SMILES: CCC(=O)N(CC1(N2CCN(Cc3ccc(F)c(F)c3)CC2)CCOCC1)c1ccccc1] | N-((4-(4-(3,4-difluorobenzyl)piperazin-1-yl)tetrahydro-2H-pyran-4-yl)methyl)-N-phenylpropionamide | A | 1.25 | 458 |
| 109 | 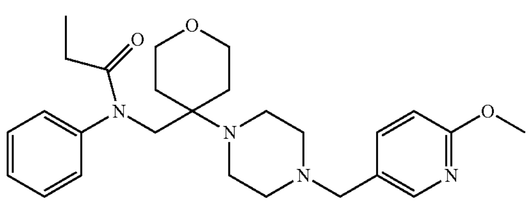 [SMILES: CCC(=O)N(CC1(N2CCN(Cc3ccc(OC)nc3)CC2)CCOCC1)c1ccccc1] | N-((4-(4-((6-methoxypyridin-3-yl)methyl)piperazin-1-yl)tetrahydro-2H-pyran-4-yl)methyl)-N-phenylpropionamide | A | 1.86 | 453 |
| 110 | 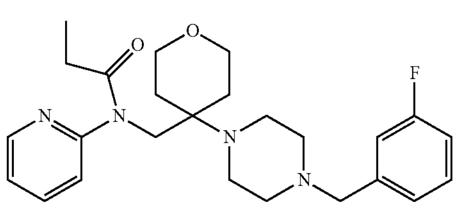 [SMILES: CCC(=O)N(CC1(N2CCN(Cc3cccc(F)c3)CC2)CCOCC1)c1ccccn1] | N-((4-(4-(3-fluorobenzyl)piperazin-1-yl)tetrahydro-2H-pyran-4-yl)methyl)-N-(pyridin-2-yl)propionamide | A | 1.87 | 441 |

-continued

| EX | Structure | Chemical name | Method | Ret (min) | MS (M + H) |
|---|---|---|---|---|---|
| 111 | 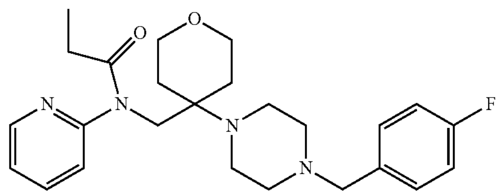 [SMILES: CCC(=O)N(CC1(N2CCN(Cc3ccc(F)cc3)CC2)CCOCC1)c1ccccn1] | N-((4-(4-(4-fluorobenzyl)piperazin-1-yl)tetrahydro-2H-pyran-4-yl)methyl)-N-(pyridin-2-yl)propionamide | A | 1.83 | 441 |
| 112 | 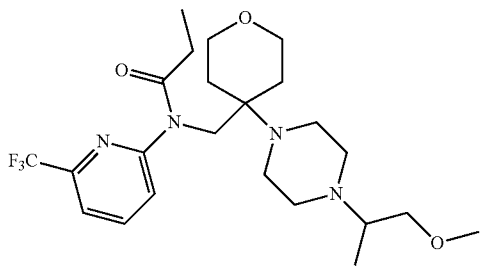 [SMILES: CCC(=O)N(CC1(N2CCN(C(C)COC)CC2)CCOCC1)c1cccc(C(F)(F)F)n1] | N-((4-(4-(1-methoxypropan-2-yl)piperazin-1-yl)tetrahydro-2H-pyran-4-yl)methyl)-N-(6-(trifluoromethyl)pyridin-2-yl)propionamide | A | 1.79 | 473 |
| 113 | 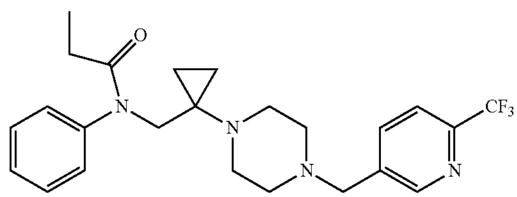 [SMILES: CCC(=O)N(CC1(N2CCN(Cc3ccc(C(F)(F)F)nc3)CC2)CC1)c1ccccc1] | N-phenyl-N-((1-(4-((6-(trifluoromethyl)pyridin-3-yl)methyl)piperazin-1-yl)cyclopropyl)methyl)propionamide | A | 2.20 | 447 |
| 114 | 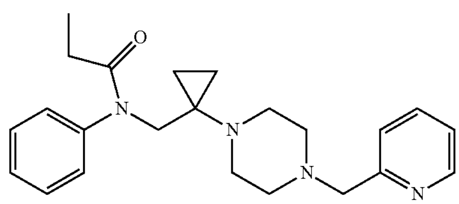 [SMILES: CCC(=O)N(CC1(N2CCN(Cc3ccccn3)CC2)CC1)c1ccccc1] | N-phenyl-N-((1-(4-(pyridin-2-ylmethyl)piperazin-1-yl)cyclopropyl)methyl)propionamide | A | 1.76 | 379 |
| 115 | 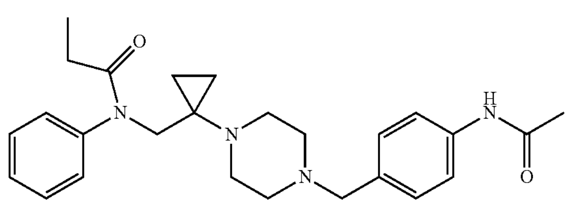 [SMILES: CCC(=O)N(CC1(N2CCN(Cc3ccc(NC(C)=O)cc3)CC2)CC1)c1ccccc1] | N-((1-(4-(4-acetamidobenzyl)piperazin-1-yl)cyclopropyl)methyl)-N-phenylpropionamide | A | 1.79 | 435 |
| 116 | 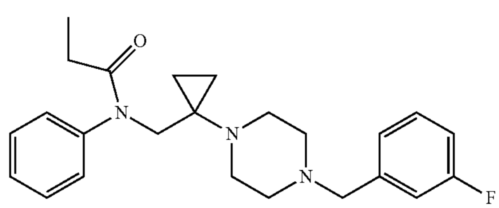 [SMILES: CCC(=O)N(CC1(N2CCN(Cc3cccc(F)c3)CC2)CC1)c1ccccc1] | N-((1-(4-(3-fluorobenzyl)piperazin-1-yl)cyclopropyl)methyl)-N-phenylpropionamide | A | 2.33 | 396 |
| 117 | 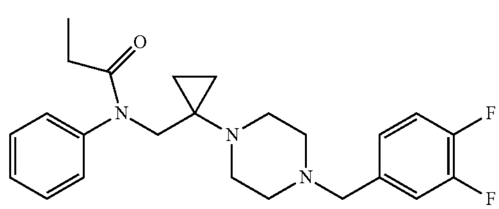 [SMILES: CCC(=O)N(CC1(N2CCN(Cc3ccc(F)c(F)c3)CC2)CC1)c1ccccc1] | N-((1-(4-(3,4-difluorobenzyl)piperazin-1-yl)cyclopropyl)methyl)-N-phenylpropionamide | A | 2.37 | 414 |

-continued

| EX | Structure | Chemical name | Method | Ret (min) | MS (M + H) |
|---|---|---|---|---|---|
| 118 | 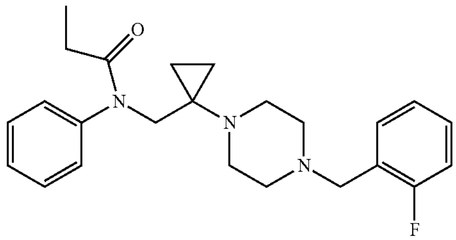 [SMILES: CCC(=O)N(CC1(N2CCN(Cc3ccccc3F)CC2)CC1)c1ccccc1] | N-((1-(4-(2-fluorobenzyl)piperazin-1-yl)cyclopropyl)methyl)-N-phenylpropionamide | A | 2.31 | 396 |
| 119 | 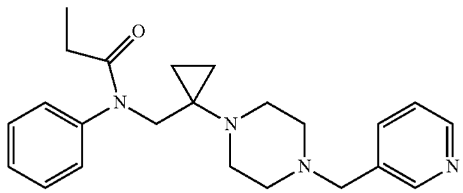 [SMILES: CCC(=O)N(CC1(N2CCN(Cc3cccnc3)CC2)CC1)c1ccccc1] | N-phenyl-N-((1-(4-(pyridin-3-ylmethyl)piperazin-1-yl)cyclopropyl)methyl)propionamide | A | 1.75 | 379 |
| 120 | 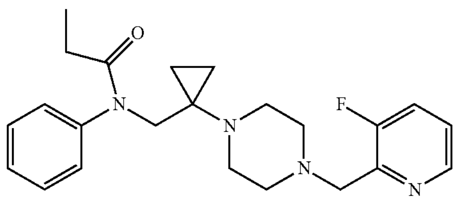 [SMILES: CCC(=O)N(CC1(N2CCN(Cc3ncccc3F)CC2)CC1)c1ccccc1] | N-((1-(4-((3-fluoropyridin-2-yl)methyl)piperazin-1-yl)cyclopropyl)methyl)-N-phenylpropionamide | A | 1.86 | 397 |
| 121 | 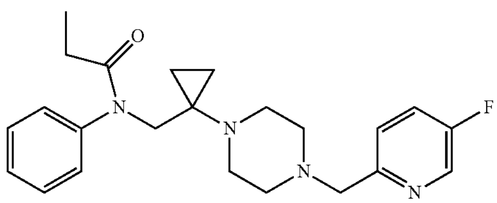 [SMILES: CCC(=O)N(CC1(N2CCN(Cc3ccc(F)cn3)CC2)CC1)c1ccccc1] | N-((1-(4-((5-fluoropyridin-2-yl)methyl)piperazin-1-yl)cyclopropyl)methyl)-N-phenylpropionamide | A | 1.91 | 397 |
| 122 | 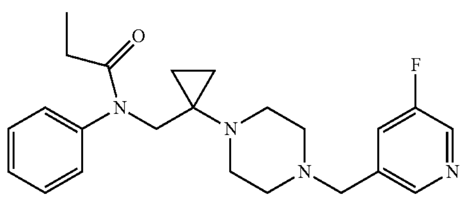 [SMILES: CCC(=O)N(CC1(N2CCN(Cc3cncc(F)c3)CC2)CC1)c1ccccc1] | N-((1-(4-((5-fluoropyridin-3-yl)methyl)piperazin-1-yl)cyclopropyl)methyl)-N-phenylpropionamide | A | 1.92 | 397 |
| 123 | 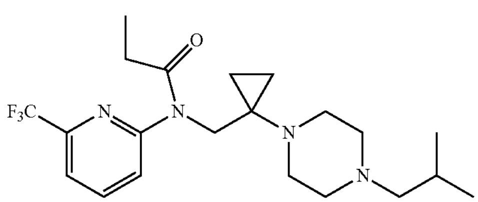 [SMILES: CCC(=O)N(CC1(N2CCN(CC(C)C)CC2)CC1)c1cccc(C(F)(F)F)n1] | N-((1-(4-isobutylpiperazin-1-yl)cyclopropyl)methyl)-N-(6-(trifluoromethyl)pyridin-2-yl)propionamide | A | 2.41 | 413 |
| 124 | 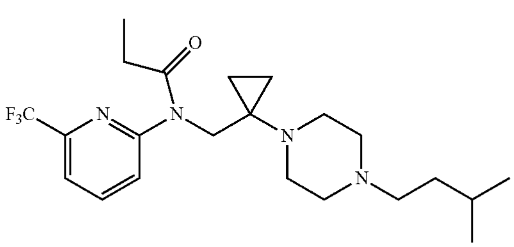 [SMILES: CCC(=O)N(CC1(N2CCN(CCC(C)C)CC2)CC1)c1cccc(C(F)(F)F)n1] | N-((1-(4-isopentylpiperazin-1-yl)cyclopropyl)methyl)-N-(6-(trifluoromethyl)pyridin-2-yl)propionamide | A | 2.33 | 427 |

Example 125. N-Methyl-4-((4-(4-((N-phenylpropionamido)methyl)tetrahydro-2H-pyran-4-yl)piperazin-1-yl)methyl)benzamide

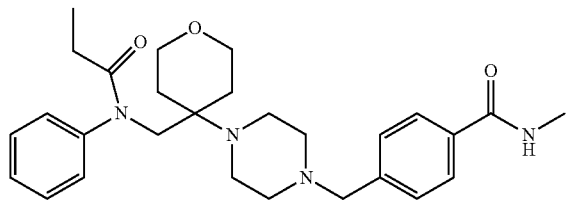 [SMILES: CCC(=O)N(CC1(N2CCN(Cc3ccc(C(=O)NC)cc3)CC2)CCOCC1)c1ccccc1]

A microwave vial was charged with N-phenyl-N-((4-(piperazin-1-yl)tetrahydro-2H-pyran-4-yl)methyl)propionamide (INT 19A, 50 mg, 0.15 mmol), EtOH (3 mL) and $K_2CO_3$ (62.5 mg, 0.45 mmol). Then 4-(chloromethyl)-N-methylbenzamide (55.4 mg, 0.30 mmol) was added and the vial was sealed and subjected to microwave irradiation for 15 min at 120° C. and then cooled. The solvents were concentrated in vacuo and the residue was partitioned between DCM and sat solution of $NaHCO_3$. The organic layer was dried over $Na_2SO_4$, filtered and concentrated. The crude residue was purified by flash chromatography on silica gel, gradient DCM:MeOH from (100:0) to (80:20) to give the title compound (41 mg, yield 56%).

HPLC-MS (Method A): Ret, 1.61 min; $ESI^+$-MS m/z, 479 (M+1).

This method was used for the preparation of examples 126-132 using the corresponding alkylating agents and intermediates 19 as starting materials.

| EX | Structure | Chemical name | Method | Ret (min) | MS (M + H) |
|---|---|---|---|---|---|
| *126 | 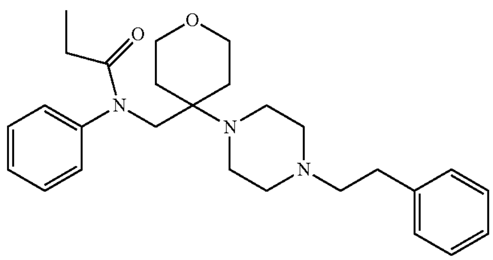 [SMILES: CCC(=O)N(CC1(N2CCN(CCc3ccccc3)CC2)CCOCC1)c1ccccc1] | N-((4-(4-phenethylpiperazin-1-yl)tetrahydro-2H-pyran-4-yl)methyl)-N-phenylpropionamide | A | 2.19 | 440 |
| 127 | 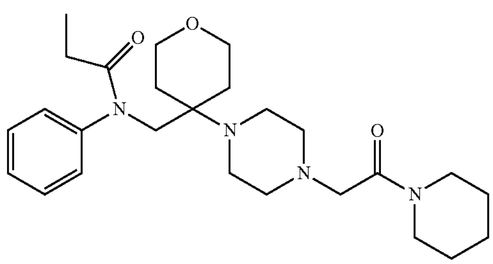 [SMILES: CCC(=O)N(CC1(N2CCN(CC(=O)N3CCCCC3)CC2)CCOCC1)c1ccccc1] | N-((4-(4-(2-oxo-2-(piperidin-1-yl)ethyl)piperazin-1-yl)tetrahydro-2H-pyran-4-yl)methyl)-N-phenylpropionamide | A | 1.79 | 457 |
| 128 | 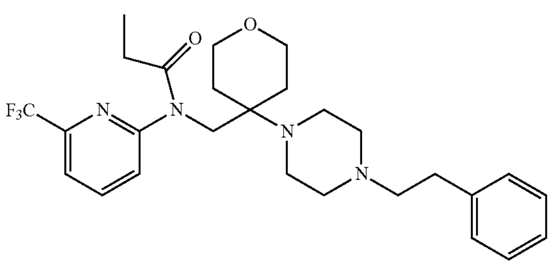 [SMILES: CCC(=O)N(CC1(N2CCN(CCc3ccccc3)CC2)CCOCC1)c1cccc(C(F)(F)F)n1] | N-((4-(4-phenethylpiperazin-1-yl)tetrahydro-2H-pyran-4-yl)methyl)-N-(6-(trifluoromethyl)pyridin-2-yl)propionamide | A | 2.20 | 505 |
| 129 | 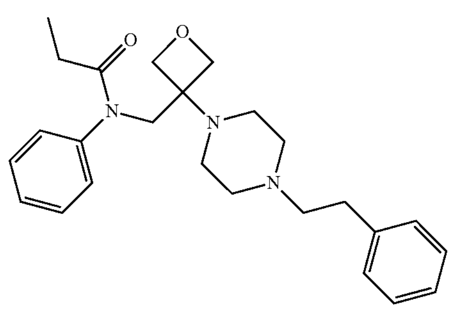 [SMILES: CCC(=O)N(CC1(N2CCN(CCc3ccccc3)CC2)COC1)c1ccccc1] | N-((3-(4-phenethylpiperazin-1-yl)oxetan-3-yl)methyl)-N-phenylpropionamide | A | 1.96 | 408 |

| EX | Structure | Chemical name | Method | Ret (min) | MS (M + H) |
|---|---|---|---|---|---|
| *130 | 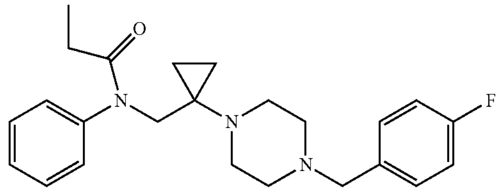 [SMILES: CCC(=O)N(CC1(N2CCN(Cc3ccc(F)cc3)CC2)CC1)c1ccccc1] | N-((1-(4-(4-fluorobenzyl)piperazin-1-yl)cyclopropyl)methyl)-N-phenylpropionamide | A | 2.31 | 396 |
| 131 | 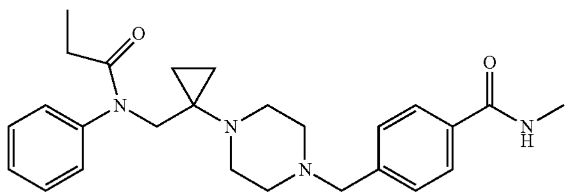 [SMILES: CCC(=O)N(CC1(N2CCN(Cc3ccc(C(=O)NC)cc3)CC2)CC1)c1ccccc1] | N-methyl-4-((4-(1-((N-phenylpropionamido)methyl)cyclopropyl)piperazin-1-yl)methyl)benzamide | A | 1.75 | 435 |
| 132 | 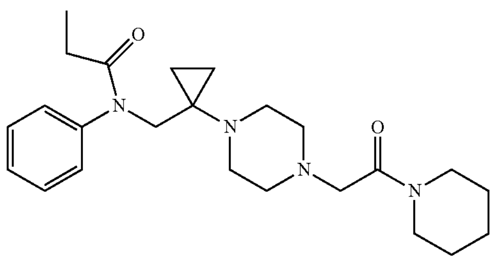 [SMILES: CCC(=O)N(CC1(N2CCN(CC(=O)N3CCCCC3)CC2)CC1)c1ccccc1] | N-((1-(4-(2-oxo-2-(piperidin-1-yl)ethyl)piperazin-1-yl)cyclopropyl)methyl)-N-phenylpropionamide | A | 1.88 | 413 |

*TEA was used as base instead of $K_2CO_3$.

Example 133. N-((4-(4-(1-Phenylethyl)piperazin-1-yl)tetrahydro-2H-pyran-4-yl)methyl)-N-(6-(trifluoromethyl)pyridin-2-yl)proplonamide

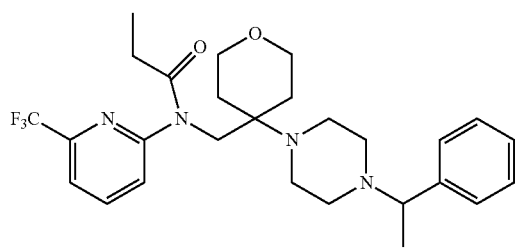 [SMILES: CCC(=O)N(CC1(N2CCN(C(C)c3ccccc3)CC2)CCOCC1)c1cccc(C(F)(F)F)n1]

(1-Bromoethyl)benzene (36.8 µL, 0.27 mmol) was added to a solution of N-((4-(piperazin-1-yl)tetrahydro-2H-pyran-4-yl)methyl)-N-(6-(trifluoromethyl)pyridin-2-yl) propionamide (INT 19D, 60 mg, 0.15 mmol) and $K_2CO_3$ (62 mg, 0.45 mmol) in ACN (4 mL). The reaction mixture was stirred at 50° C. overnight and then was cooled down to rt. AcOEt (10 mL) and sat aqueous $NaHCO_3$ solution (10 mL) was added and the phases were separated. The organic layer was dried over $Na_2SO_4$, filtered and concentrated. The crude residue was purified by flash chromatography on silica gel, eluents DCM:MeOH (982) to give the title compound as an oil (64 mg, yield 84%).

HPLC-MS (Method A): Ret, 2.26 min; ESI+-MS m/z, 505 (M+1).

This method was used for the preparation of examples 134-180 using the adequate alkylating agents and the corresponding intermediates 19 as starting materials.

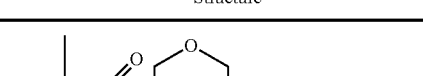

| EX | Structure | Chemical name | Metod | Ret (min) | MS (M + H) |
|---|---|---|---|---|---|
| 134 | 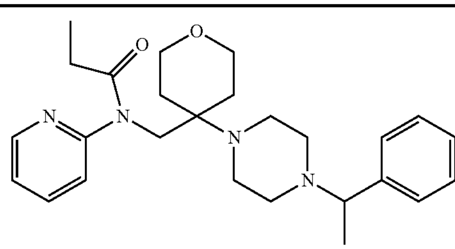 | N-((4-(4-(1-phenylethyl)piperazin-1-yl)tetrahydro-2H-pyran-4-yl)methyl)-N-(pyridin-2-yl)propionamide | A | 1.84 | 437 |

| EX | Structure | Chemical name | Metod | Ret (min) | MS (M + H) |
|---|---|---|---|---|---|
| 135 | 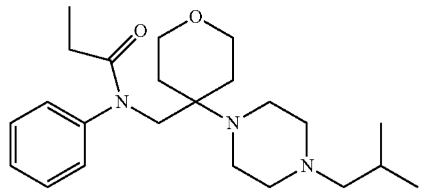 [SMILES: CCC(=O)N(CC1(N2CCN(CC(C)C)CC2)CCOCC1)c1ccccc1] | N-((4-(4-isobutylpiperazin-1-yl)tetrahydro-2H-pyran-4-yl)methyl)-N-phenylpropionamide | A | 2.00 | 388 |
| 136 | 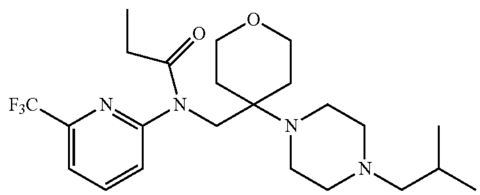 [SMILES: CCC(=O)N(CC1(N2CCN(CC(C)C)CC2)CCOCC1)c1cccc(C(F)(F)F)n1] | N-((4-(4-isobutylpiperazin-1-yl)tetrahydro-2H-pyran-4-yl)methyl)-N-(6-(trifluoromethyl)pyridin-2-yl)propionamide | A | 2.22 | 457 |
| 137 | 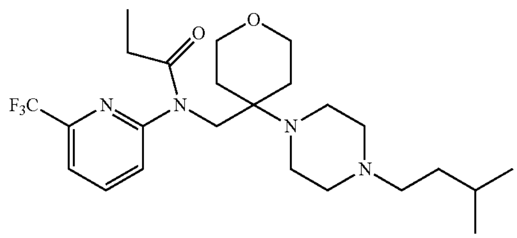 [SMILES: CCC(=O)N(CC1(N2CCN(CCC(C)C)CC2)CCOCC1)c1cccc(C(F)(F)F)n1] | N-((4-(4-isopentylpiperazin-1-yl)tetrahydro-2H-pyran-4-yl)methyl)-N-(6-(trifluoromethyl)pyridin-2-yl)propionamide | A | 2.19 | 471 |
| 138 | 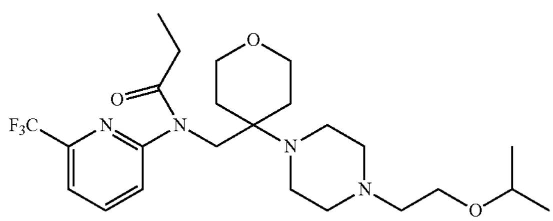 [SMILES: CCC(=O)N(CC1(N2CCN(CCOC(C)C)CC2)CCOCC1)c1cccc(C(F)(F)F)n1] | N-((4-(4-(2-isopropoxyethyl)piperazin-1-yl)tetrahydro-2H-pyran-4-yl)methyl)-N-(6-(trifluoromethyl)pyridin-2-yl)propionamide | A | 1.96 | 487 |
| 139 | 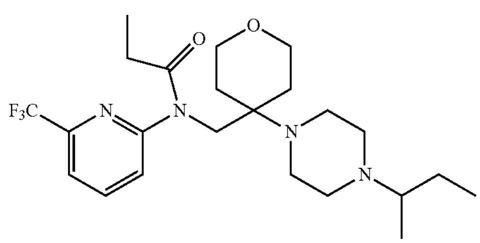 [SMILES: CCC(=O)N(CC1(N2CCN(C(C)CC)CC2)CCOCC1)c1cccc(C(F)(F)F)n1] | N-((4-(4-sec-butylpiperazin-1-yl)tetrahydro-2H-pyran-4-yl)methyl)-N-(6-(trifluoromethyl)pyridin-2-yl)propionamide | A | 1.86 | 457 |
| 140 | 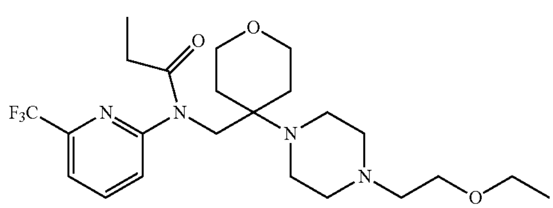 [SMILES: CCOCCN1CCN(C2(CN(C(=O)CC)c3cccc(C(F)(F)F)n3)CCOCC2)CC1] | N-((4-(4-(2-ethoxyethyl)piperazin-1-yl)tetrahydro-2H-pyran-4-yl)methyl)-N-(6-(trifluoromethyl)pyridin-2-yl)propionamide | A | 1.81 | 473 |
| 141 | 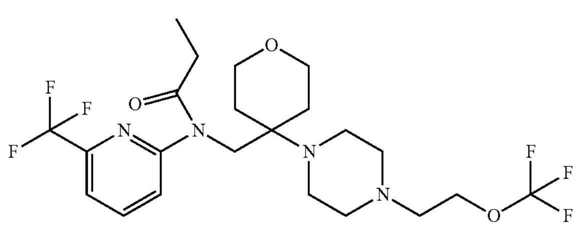 [SMILES: CCC(=O)N(CC1(N2CCN(CCOC(F)(F)F)CC2)CCOCC1)c1cccc(C(F)(F)F)n1] | N-((4-(4-(2-(trifluoromethoxy)ethyl)piperazin-1-yl)tetrahydro-2H-pyran-4-yl)methyl)-N-(trifluoromethyl)pyridin-2-yl)propionamide | A | 2.13 | 513 |

| EX | Structure | Chemical name | Metod | Ret (min) | MS (M + H) |
|---|---|---|---|---|---|
| 142 | 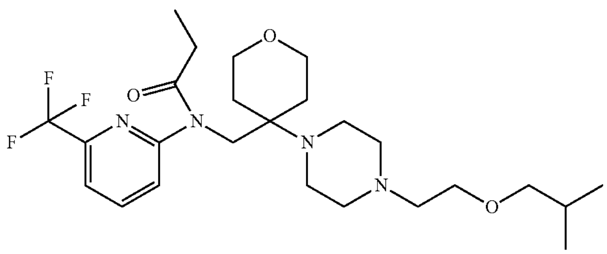 [SMILES: CCC(=O)N(CC1(N2CCN(CCOCC(C)C)CC2)CCOCC1)c1cccc(C(F)(F)F)n1] | N-((4-(4-(2-isobutoxyethyl)piperazin-1-yl)tetrahydro-2H-pyran-4-yl)methyl)-N-(6-(trifluoromethyl)pyridin-2-yl)propionamide | A | 2.17 | 501 |
| 143 | 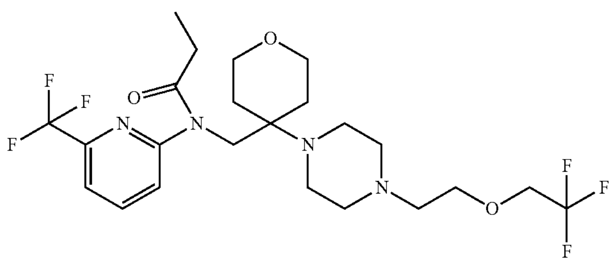 [SMILES: CCC(=O)N(CC1(N2CCN(CCOCC(F)(F)F)CC2)CCOCC1)c1cccc(C(F)(F)F)n1] | N-((4-(4-(2-(2,2,2-trifluoroethoxy)ethyl)piperazin-1-yl)tetrahydro-2H-pyran-4-yl)methyl)-N-(6-(trifluoromethyl)pyridin-2-yl)propionamide | A | 2.01 | 527 |
| 144 | 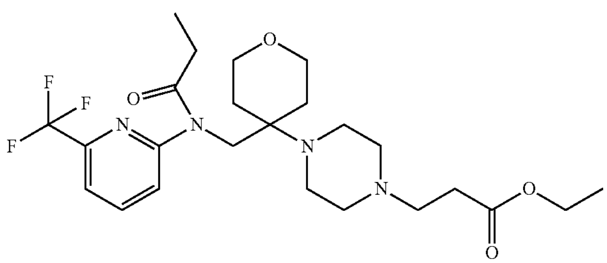 [SMILES: CCOC(=O)CCN1CCN(C2(CN(C(=O)CC)c3cccc(C(F)(F)F)n3)CCOCC2)CC1] | ethyl 3-(4-(4-((N-(6-(trifluoromethyl)pyridin-2-yl)propionamido)methyl)tetrahydro-2H-pyran-4-yl)piperazin-1-yl)propanoate | A | 1.90 | 501 |
| 145 | 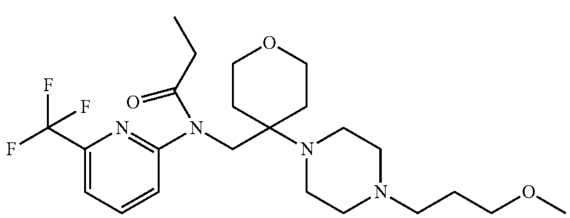 [SMILES: CCC(=O)N(CC1(N2CCN(CCCOC)CC2)CCOCC1)c1cccc(C(F)(F)F)n1] | N-((4-(4-(3-methoxypropyl)piperazin-1-yl)tetrahydro-2H-pyran-4-yl)methyl)-N-(6-(trifluoromethyl)pyridin-2-yl)propionamide | A | 1.70 | 473 |
| 146 | 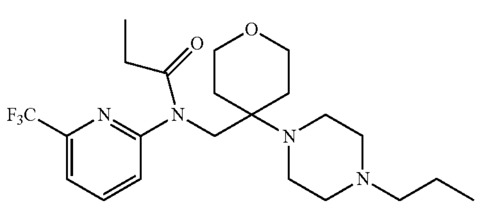 [SMILES: CCCN1CCN(C2(CN(C(=O)CC)c3cccc(C(F)(F)F)n3)CCOCC2)CC1] | N-((4-(4-propylpiperazin-1-yl)tetrahydro-2H-pyran-4-yl)methyl)-N-(6-(trifluoromethyl)pyridin-2-yl)propionamide | A | 1.83 | 443 |
| 147 | 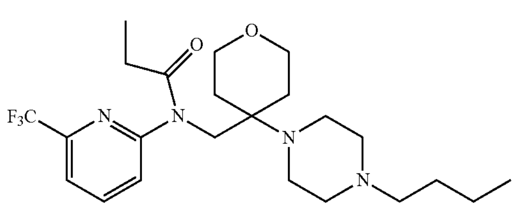 [SMILES: CCCCN1CCN(C2(CN(C(=O)CC)c3cccc(C(F)(F)F)n3)CCOCC2)CC1] | N-((4-(4-butylpiperazin-1-yl)tetrahydro-2H-pyran-4-yl)methyl)-N-(6-(trifluoromethyl)pyridin-2-yl)propionamide | A | 2.01 | 457 |

| EX | Structure | Chemical name | Metod | Ret (min) | MS (M + H) |
|---|---|---|---|---|---|
| 148 | 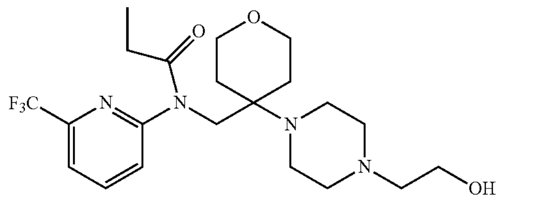 [SMILES: CCC(=O)N(CC1(N2CCN(CCO)CC2)CCOCC1)c1cccc(C(F)(F)F)n1] | N-((4-(4-(2-hydroxyethyl)piperazin-1-yl)tetrahydro-2H-pyran-4-yl)methyl)-N-(6-(trifluoromethyl)pyridin-2-yl)propionamide | A | 1.46 | 445 |
| 149 | 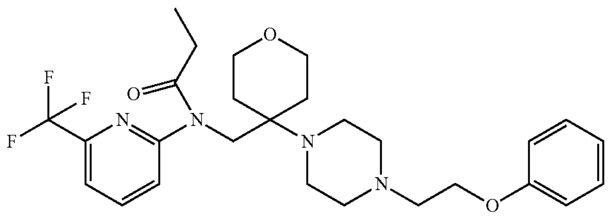 [SMILES: CCC(=O)N(CC1(N2CCN(CCOc3ccccc3)CC2)CCOCC1)c1cccc(C(F)(F)F)n1] | N-((4-(4-(2-phenoxyethyl)piperazin-1-yl)tetrahydro-2H-pyran-4-yl)methyl)-N-(6-(trifluoromethyl)pyridin-2-yl)propionamide | A | 2.18 | 521 |
| 150 | 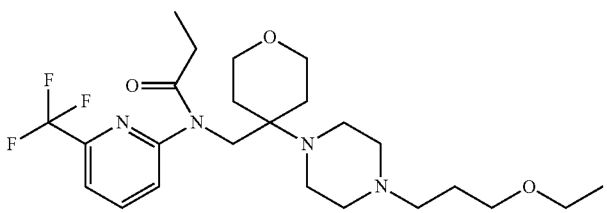 [SMILES: CCOCCCN1CCN(C2(CN(C(=O)CC)c3cccc(C(F)(F)F)n3)CCOCC2)CC1] | N-((4-(4-(3-ethoxypropyl)piperazin-1-yl)tetrahydro-2H-pyran-4-yl)methyl)-N-(6-(trifluoromethyl)pyridin-2-yl)propionamide | A | 1.83 | 487 |
| 151 | 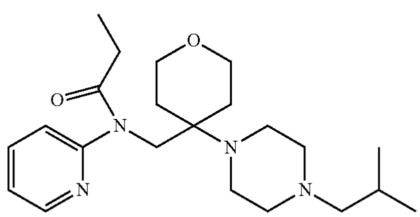 [SMILES: CCC(=O)N(CC1(N2CCN(CC(C)C)CC2)CCOCC1)c1ccccn1] | N-((4-(4-isobutylpiperazin-1-yl)tetrahydro-2H-pyran-4-yl)methyl)-N-(pyridin-2-yl)propionamide | A | 1.62 | 389 |
| 152 | 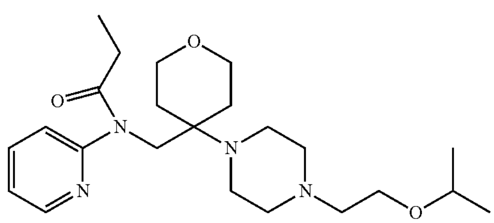 [SMILES: CCC(=O)N(CC1(N2CCN(CCOC(C)C)CC2)CCOCC1)c1ccccn1] | N-((4-(4-(2-isopropoxyethyl)piperazin-1-yl)tetrahydro-2H-pyran-4-yl)methyl)-N-(pyridin-2-yl)propionamide | A | 1.50 | 419 |
| 153 | 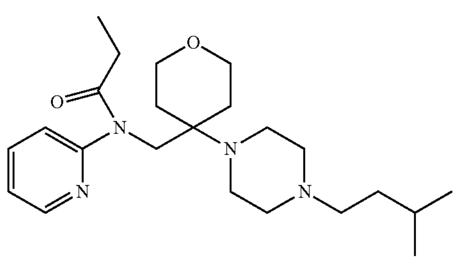 [SMILES: CCC(=O)N(CC1(N2CCN(CCC(C)C)CC2)CCOCC1)c1ccccn1] | N-((4-(4-isopentylpiperazin-1-yl)tetrahydro-2H-pyran-4-yl)methyl)-N-(pyridin-2-yl)propionamide | A | 1.65 | 403 |

| EX | Structure | Chemical name | Metod | Ret (min) | MS (M + H) |
|---|---|---|---|---|---|
| 154 | 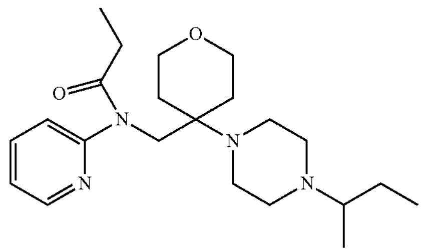 [SMILES: CCC(=O)N(CC1(N2CCN(C(C)CC)CC2)CCOCC1)c1ccccn1] | N-((4-(4-sec-butylpiperazin-1-yl)tetrahydro-2H-pyran-4-yl)methyl)-N-(pyridin-2-yl)propionamide | A | 1.32 | 389 |
| 155 | 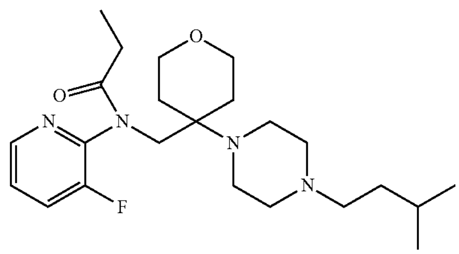 [SMILES: CCC(=O)N(CC1(N2CCN(CCC(C)C)CC2)CCOCC1)c1ncccc1F] | N-(3-fluoropyridin-2-yl)-N-((4-(4-isopentylpiperazin-1-yl)tetrahydro-2H-pyran-4-yl)methyl)propionamide | A | 1.83 | 421 |
| 156 | 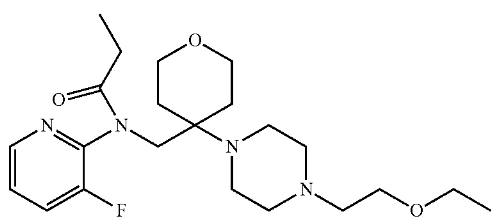 [SMILES: CCOCCN1CCN(C2(CN(C(=O)CC)c3ncccc3F)CCOCC2)CC1] | N-((4-(4-(2-ethoxyethyl)piperazin-1-yl)tetrahydro-2H-pyran-4-yl)methyl)-N-(3-fluoropyridin-2-yl)propionamide | A | 1.52 | 423 |
| 157 | 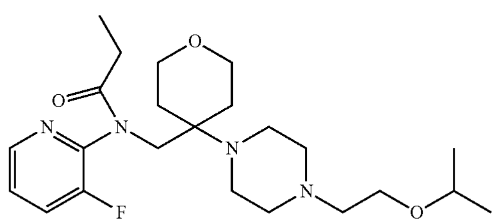 [SMILES: CCC(=O)N(CC1(N2CCN(CCOC(C)C)CC2)CCOCC1)c1ncccc1F] | N-(3-fluoropyridin-2-yl)-N-((4-(4-(2-isopropoxyethyl)piperazin-1-yl)tetrahydro-2H-pyran-4-yl)methyl)propionamide | A | 1.65 | 437 |
| 158 | 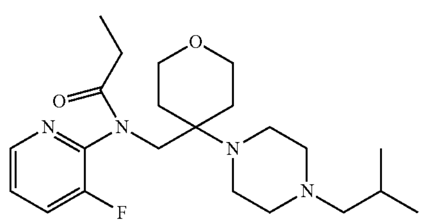 [SMILES: CCC(=O)N(CC1(N2CCN(CC(C)C)CC2)CCOCC1)c1ncccc1F] | N-(3-fluoropyridin-2-yl)-N-((4-(4-isobutylpiperazin-1-yl)tetrahydro-2H-pyran-4-yl)methyl)propionamide | A | 1.86 | 407 |
| 159 | 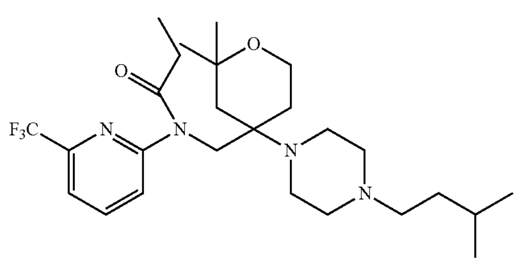 [SMILES: CCC(=O)N(CC1(N2CCN(CCC(C)C)CC2)CCOC(C)(C)C1)c1cccc(C(F)(F)F)n1] | N-((4-(4-isopentylpiperazin-1-yl)-2,2-dimethyltetrahydro-2H-pyran-4-yl)methyl)-N-(6-(trifluoromethyl)pyridin-2-yl)propionamide | A | 2.37 | 499 |

| EX | Structure | Chemical name | Metod | Ret (min) | MS (M + H) |
|---|---|---|---|---|---|
| 160 | 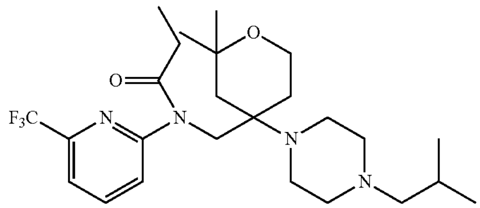 [SMILES: CCC(=O)N(CC1(N2CCN(CC(C)C)CC2)CCOC(C)(C)C1)c1cccc(C(F)(F)F)n1] | N-((4-(4-isobutylpiperazin-1-yl)-2,2-dimethyltetrahydro-2H-pyran-4-yl)methyl)-N-(6-(trifluoromethyl)pyridin-2-yl)propionamide | A | 2.45 | 485 |
| 161 | 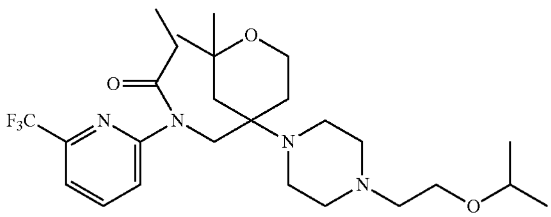 [SMILES: CCC(=O)N(CC1(N2CCN(CCOC(C)C)CC2)CCOC(C)(C)C1)c1cccc(C(F)(F)F)n1] | N-((4-(4-(2-isopropoxyethyl)piperazin-1-yl)-2,2-dimethyltetrahydro-2H-pyran-4-yl)methyl)-N-(6-(trifluoromethyl)pyridin-2-yl)propionamide | A | 2.13 | 515 |
| 162 | 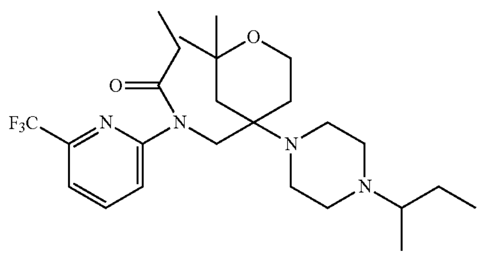 [SMILES: CCC(=O)N(CC1(N2CCN(C(C)CC)CC2)CCOC(C)(C)C1)c1cccc(C(F)(F)F)n1] | N-((4-(4-sec-butylpiperazin-1-yl)-2,2-dimethyltetrahydro-2H-pyran-4-yl)methyl)-N-(6-(trifluoromethyl)pyridin-2-yl)propionamide | A | 2.13 | 485 |
| 163 | 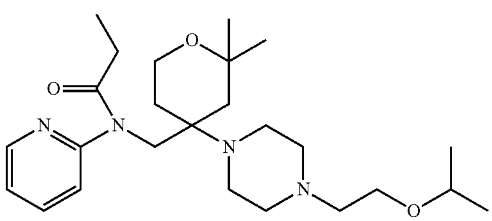 [SMILES: CCC(=O)N(CC1(N2CCN(CCOC(C)C)CC2)CCOC(C)(C)C1)c1ccccn1] | N-((4-(4-(2-isopropoxyethyl)piperazin-1-yl)-2,2-dimethyltetrahydro-2H-pyran-4-yl)methyl)-N-(pyridin-2-yl)propionamide | A | 1.74 | 447 |
| 164 | 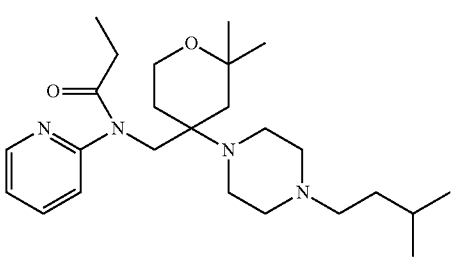 [SMILES: CCC(=O)N(CC1(N2CCN(CCC(C)C)CC2)CCOC(C)(C)C1)c1ccccn1] | N-((4-(4-isopentylpiperazin-1-yl)-2,2-dimethyltetrahydro-2H-pyran-4-yl)methyl)-N-(pyridin-2-yl)propionamide | A | 1.94 | 431 |
| 165 | 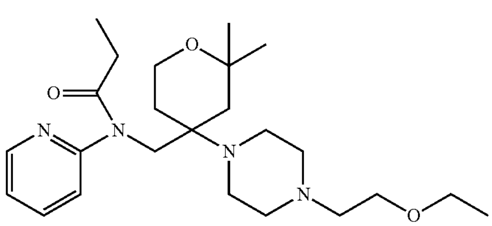 [SMILES: CCOCCN1CCN(C2(CN(C(=O)CC)c3ccccn3)CCOC(C)(C)C2)CC1] | N-((4-(4-(2-ethoxyethyl)piperazin-1-yl)-2,2-dimethyltetrahydro-2H-pyran-4-yl)methyl)-N-(pyridin-2-yl)propionamide | A | 1.62 | 433 |

| EX | Structure | Chemical name | Metod | Ret (min) | MS (M + H) |
|---|---|---|---|---|---|
| 166 | 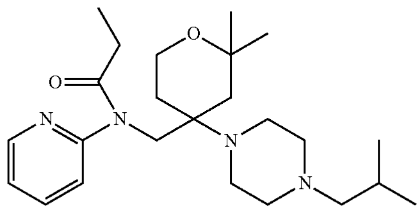 [SMILES: CCC(=O)N(CC1(N2CCN(CC(C)C)CC2)CCOC(C)(C)C1)c1ccccn1] | N-((4-(4-isobutylpiperazin-1-yl)-2,2-dimethyltetrahydro-2H-pyran-4-yl)methyl)-N-(pyridin-2-yl)propionamide | A | 1.98 | 417 |
| 167 | 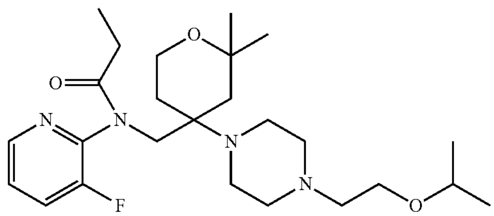 [SMILES: CCC(=O)N(CC1(N2CCN(CCOC(C)C)CC2)CCOC(C)(C)C1)c1ncccc1F] | N-(3-fluoropyridin-2-yl)-N-((4-(4-(2-isopropoxyethyl)piperazin-1-yl)-2,2-dimethyltetrahydro-2H-pyran-4-yl)methyl)propionamide | A | 1.81 | 465 |
| 168 | 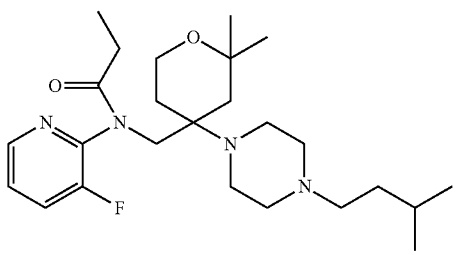 [SMILES: CCC(=O)N(CC1(N2CCN(CCC(C)C)CC2)CCOC(C)(C)C1)c1ncccc1F] | N-(3-fluoropyridin-2-yl)-N-((4-(4-isopentylpiperazin-1-yl)-2,2-dimethyltetrahydro-2H-pyran-4-yl)methyl)propionamide | A | 2.03 | 449 |
| 169 | 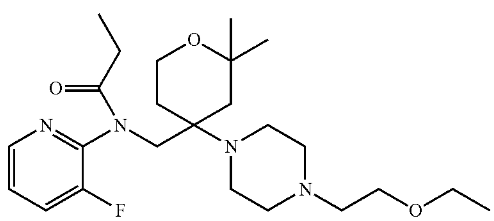 [SMILES: CCOCCN1CCN(C2(CN(C(=O)CC)c3ncccc3F)CCOC(C)(C)C2)CC1] | N-((4-(4-(2-ethoxyethyl)piperazin-1-yl)-2,2-dimethyltetrahydro-2H-pyran-4-yl)methyl)-N-(3-fluoropyridin-2-yl)propionamide | B | 1.68 | 451 |
| 170 | 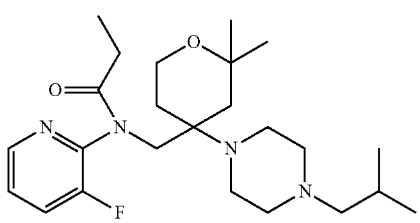 [SMILES: CCC(=O)N(CC1(N2CCN(CC(C)C)CC2)CCOC(C)(C)C1)c1ncccc1F] | N-(3-fluoropyridin-2-yl)-N-((4-(4-isobutylpiperazin-1-yl)-2,2-dimethyltetrahydro-2H-pyran-4-yl)methyl)propionamide | A | 2.06 | 435 |
| 171 | 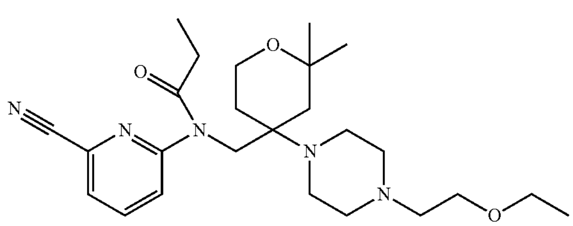 [SMILES: CCOCCN1CCN(C2(CN(C(=O)CC)c3cccc(C#N)n3)CCOC(C)(C)C2)CC1] | N-(6-cyanopyridin-2-yl)-N-((4-(4-(2-ethoxyethyl)piperazin-1-yl)-2,2-dimethyltetrahydro-2H-pyran-4-yl)methyl)propionamide | A | 1.70 | 458 |
| 172 | 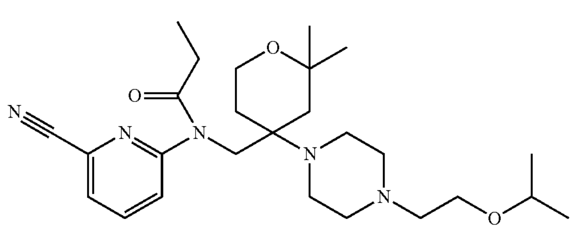 [SMILES: CCC(=O)N(CC1(N2CCN(CCOC(C)C)CC2)CCOC(C)(C)C1)c1cccc(C#N)n1] | N-(6-cyanopyridin-2-yl)-N-((4-(4-(2-isopropoxyethyl)piperazin-1-yl)-2,2-dimethyltetrahydro-2H-pyran-4-yl)methyl)propionamide | A | 1.83 | 472 |

| EX | Structure | Chemical name | Metod | Ret (min) | MS (M + H) |
|---|---|---|---|---|---|
| 173 | 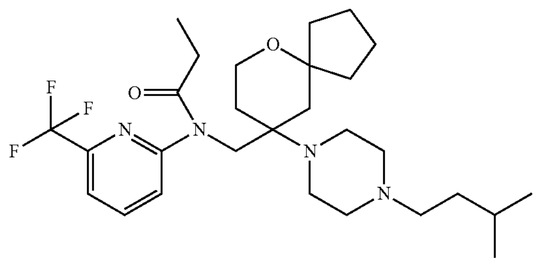 [SMILES: CCC(=O)N(CC1(N2CCN(CCC(C)C)CC2)CCOC2(CCCC2)C1)c1cccc(C(F)(F)F)n1] | N-((9-(4-isopentylpiperazin-1-yl)-6-oxaspiro[4.5]decan-9-yl)methyl)-N-(6-(trifluoromethyl)pyridin-2-yl)propionamide | A | 2.59 | 525 |
| 174 | 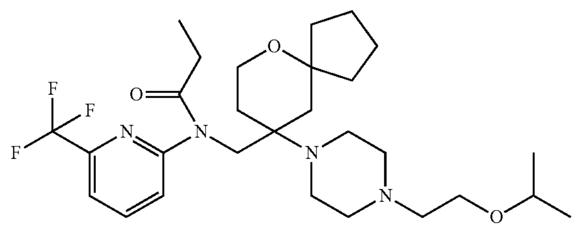 [SMILES: CCC(=O)N(CC1(N2CCN(CCOC(C)C)CC2)CCOC2(CCCC2)C1)c1cccc(C(F)(F)F)n1] | N-((9-(4-(2-isopropoxyethyl)piperazin-1-yl)-6-oxaspiro[4.5]decan-9-yl)methyl)-N-(6-(trifluoromethyl)pyridin-2-yl)propionamide | A | 2.35 | 541 |
| 175 | 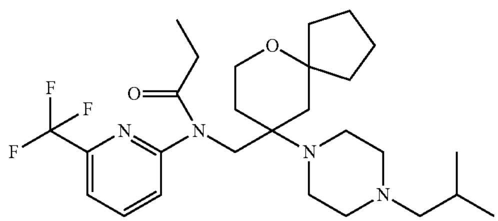 [SMILES: CCC(=O)N(CC1(N2CCN(CC(C)C)CC2)CCOC2(CCCC2)C1)c1cccc(C(F)(F)F)n1] | N-((9-(4-isobutylpiperazin-1-yl)-6-oxaspiro[4.5]decan-9-yl)methyl)-N-(6-(trifluoromethyl)pyridin-2-yl)propionamide | A | 2.69 | 511 |
| 176 | 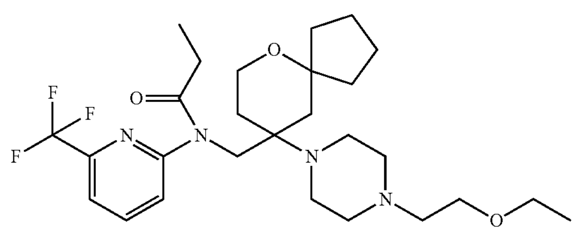 [SMILES: CCOCCN1CCN(C2(CN(C(=O)CC)c3cccc(C(F)(F)F)n3)CCOC3(CCCC3)C2)CC1] | N-((9-(4-(2-ethoxyethyl)piperazin-1-yl)-6-oxaspiro[4.5]decan-9-yl)methyl)-N-(6-(trifluoromethyl)pyridin-2-yl)propionamide | A | 2.23 | 527 |
| 177 | 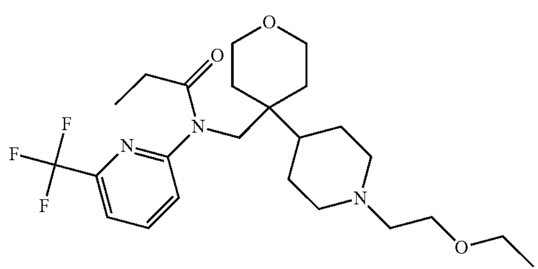 [SMILES: CCOCCN1CCC(C2(CN(C(=O)CC)c3cccc(C(F)(F)F)n3)CCOCC2)CC1] | N-((4-(1-(2-ethoxyethyl)piperidin-4-yl)tetrahydro-2H-pyran-4-yl)methyl)-N-(6-(trifluoromethyl)pyridin-2-yl)propionamide | C | 3.96 | 472 |
| 178 | 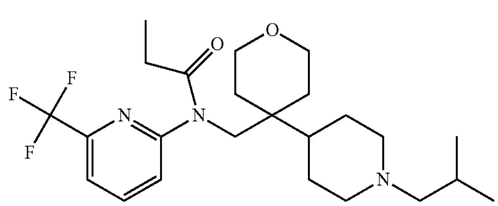 [SMILES: CCC(=O)N(CC1(C2CCN(CC(C)C)CC2)CCOCC1)c1cccc(C(F)(F)F)n1] | N-((4-(1-isobutylpiperidin-4-yl)tetrahydro-2H-pyran-4-yl)methyl)-N-(6-(trifluoromethyl)pyridin-2-yl)propionamide | C | 3.76 | 456 |

| EX | Structure | Chemical name | Metod | Ret (min) | MS (M + H) |
|---|---|---|---|---|---|
| 179 | 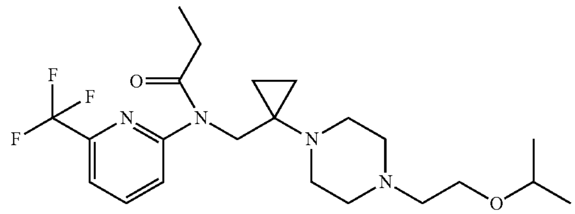 [SMILES: CCC(=O)N(CC1(N2CCN(CCOC(C)C)CC2)CC1)c1cccc(C(F)(F)F)n1] | N-((1-(4-(2-isopropoxyethyl)piperazin-1-yl)cyclopropyl)methyl)-N-(6-(trifluoromethyl)pyridin-2-yl)propionamide | A | 2.12 | 443 |
| *180 | 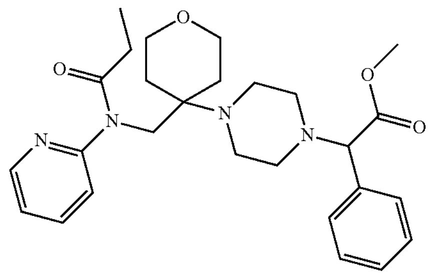 [SMILES: CCC(=O)N(CC1(N2CCN(C(C(=O)OC)c3ccccc3)CC2)CCOCC1)c1ccccn1] | Methyl 2-phenyl-2-(4-(4-((N-(pyridin-2-yl)propionamido)methyl)tetrahydro-2H-pyran-4-yl)piperazin-1-yl)acetate | A | 1.83 | 481 |

*DMF at rt overnight was used in the alkylation reaction to obtain compound example 183.

Example 181. N-((4-(4-(2-Hydroxy-1-phenylethyl)piperazin-1-yl)tetrahydro-2H-pyran-4-yl)methyl)-N-(pyridin-2-yl)proplonamide

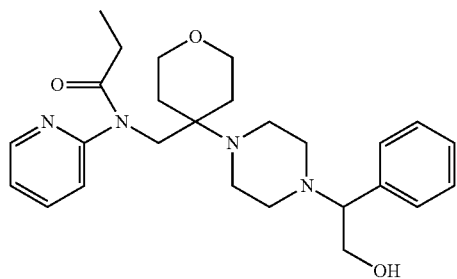 [SMILES: CCC(=O)N(CC1(N2CCN(C(CO)c3ccccc3)CC2)CCOCC1)c1ccccn1]

a) 2-Phenyl-2-(4-(4-((pyridin-2-ylamino)methyl)tetrahydro-2H-pyran-4-yl)piperazin-1-yl)ethanol LiAlH$_4$ solution (1M in THF, 153 µL, 0.15 mmol) was added at 0° C. to a solution of methyl 2-phenyl-2-(4-(4-((N-(pyridin-2-yl)propionamido)methyl)tetrahydro-2H-pyran-4-yl)piperazin-1-yl)acetate (Example 182, 0.08 g, 0.15 mmol) in THF (2 mL). The mixture was stirred 1 h at 0° C. After that, the excess of LiAlH$_4$ was quenched with ethyl acetate and sat aqueous potassium sodium tartrate solution and stirred for 10 min. The slurry was filtered and the filtrate partitioned between ethyl acetate and water. The organic layer was dried over sodium sulphate, filtered, and the solvent removed to give the title compound (0.068 mg, 100% yield).

HPLC-MS (Method A): Ret, 1.50 min; ESI+-MS m/z, 453 (M+1).

b) 2-Phenyl-2-(4-(4-((N-(pyridin-2-yl)propionamido)methyl)tetrahydro-2H-pyran-4-yl)piperazin-1-yl)ethyl propionate Propionyl chloride (43 µL, 0.492 mmol) was added to a solution of the compound obtained in step a (65 mg, 0.164 mmol) and dry TEA (50 µL, 0.361 mmol) in DCM (10 mL) under nitrogen atmosphere. The reaction mixture was stirred at rt overnight. Then, the mixture was washed twice with water and the organic layer was dried with Na$_2$SO$_4$, filtered and concentrated to dryness to give the title compound as colourless oil (80 mg, yield 94%).

HPLC-MS (Method A): Ret, 2.02 min; ESI$^+$-MS m/z, 509 (M+1).

c) Title Compound.

In a radley tube, the compound obtained in step b (80 mg, 0.155 mmol) was dissolved in MeOH (5 mL) and H$_2$O (1 mL). Potassium carbonate was then added and the reaction mixture was stirred at room temperature under nitrogen atmosphere until full conversion (TLC). The volatile components were removed and the residue was partitioned between AcOEt and H$_2$O. The organic layer was dried over sodium sulphate, filtered, and the solvent removed to give the title compound as colourless oil (53 mg, 75% yield).

HPLC-MS (Method A): Ret, 1.54 min; ESI+-MS m/z, 453 (M+1).

Example 182. N-((4-(4-(1-(4-Fluorophenyl)ethyl)piperazin-1-yl)tetrahydro-2H pyran-4-yl)methyl)-N-(6-(trifluoromethyl)pyridin-2-yl)proplonamide

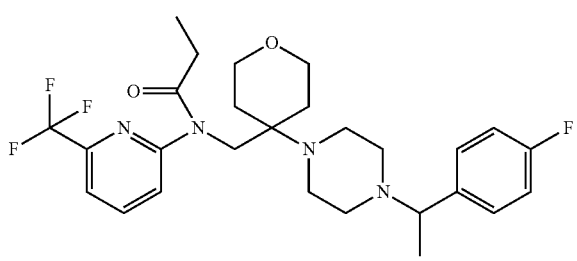 [SMILES: CCC(=O)N(CC1(N2CCN(C(C)c3ccc(F)cc3)CC2)CCOCC1)c1cccc(C(F)(F)F)n1]

DIPEA (52.2 µL, 0.3 mmol), KI (16.5 mg, 0.10 mmol) and 1-(1-chloroethyl)-4-fluorobenzene (48 mg, 0.3 mmol) were added to a solution of N-((4-(piperazin-1-yl)tetrahydro-2H-pyran-4-yl)methyl)-N-(6-(trifluoromethyl)pyridin-2-yl)propionamide (INT 19D, 40 mg, 0.10 mmol) in ACN (5 mL). The reaction mixture was subjected to microwave irradiation for 1 h at 80° C. and then cooled. The solvent was concentrated in vacuo and the residue was partitioned between DCM and sat aqueous solution of NaHCO₃. The organic layer was dried over Na₂SO₄, filtered and concentrated. The crude residue was purified by flash chromatography on neutral alumine, gradient CH:AcOEt from (100:0) to (80:20) to give the title compound as a colorless oil (17 mg, yield 32%).

HPLC-MS (Method A): Ret, 2.27 min; ESI+-MS m/z, 523 (M+1).

This method was used for the preparation of examples 183-187 using intermediate 19D and suitable alkyl halides as starting materials.

| EX | Structure | Chemical name | Method | Ret (min) | MS (M + H) |
|---|---|---|---|---|---|
| 183 | 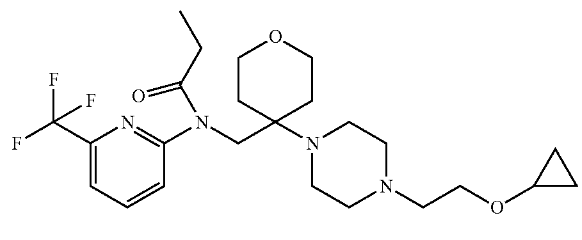 [SMILES: CCC(=O)N(CC1(N2CCN(CCOC3CC3)CC2)CCOCC1)c1cccc(C(F)(F)F)n1] | N-((4-(4-(2-cyclopropoxyethyl)piperazin-1-yl)tetrahydro-2H-pyran-4-yl)methyl)-N-(6-(trifluoromethyl)pyridin-2-yl)propionamide | A | 1.94 | 485 |
| 184 | 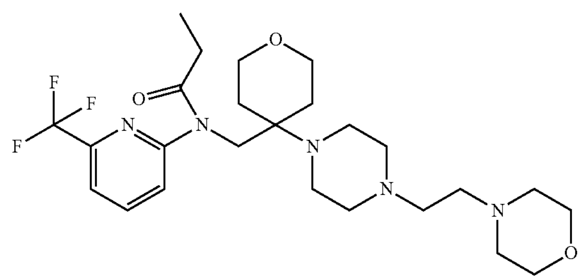 [SMILES: CCC(=O)N(CC1(N2CCN(CCN3CCOCC3)CC2)CCOCC1)c1cccc(C(F)(F)F)n1] | N-((4-(4-(2-morpholinoethyl)piperazin-1-yl)tetrahydro-2H-pyran-4-yl)methyl)-N-(6-(trifluoromethyl)pyridin-2-yl)propionamide | A | 1.61 | 514 |
| 185 | 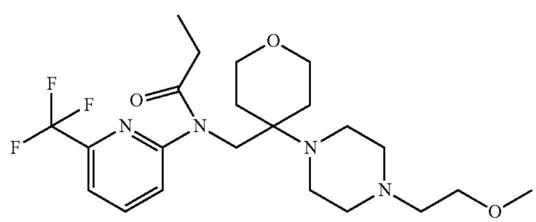 [SMILES: CCC(=O)N(CC1(N2CCN(CCOC)CC2)CCOCC1)c1cccc(C(F)(F)F)n1] | N-((4-(4-(2-methoxyethyl)piperazin-1-yl)tetrahydro-2H-pyran-4-yl)methyl)-N-(6-(trifluoromethyl)pyridin-2-yl)propionamide | A | 1.68 | 459 |
| 186 | 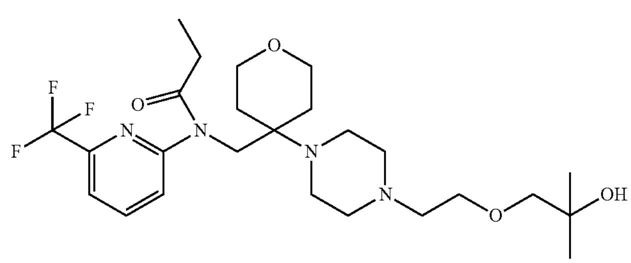 [SMILES: CCC(=O)N(CC1(N2CCN(CCOCC(C)(C)O)CC2)CCOCC1)c1cccc(C(F)(F)F)n1] | N-((4-(4-(2-(2-hydroxy-2-methylpropoxy)ethyl)piperazin-1-yl)tetrahydro-2H-pyran-4-yl)methyl)-N-(6-(trifluoromethyl)pyridin-2-yl)propionamide | A | 1.71 | 517 |
| 187 | 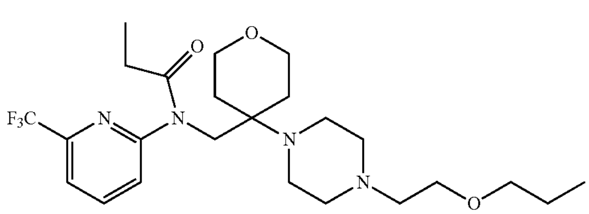 [SMILES: CCCOCCN1CCN(C2(CN(C(=O)CC)c3cccc(C(F)(F)F)n3)CCOCC2)CC1] | N-((4-(4-(2-propoxyethyl)piperazin-1-yl)tetrahydro-2H-pyran-4-yl)methyl)-N-(6-(trifluoromethyl)pyridin-2-yl)propionamide | B | 2.40 | 487 |

Example 188. N-((4-(4-(2-Hydroxy-2-methylpropyl)piperazin-1-yl)tetrahydro-2H-pyran-4-yl)methyl)-N-(6-(trifluoromethyl)pyridin-2-yl)proplonamide

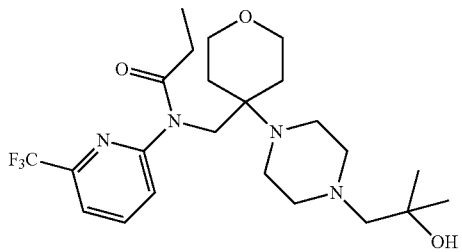 [SMILES: CCC(=O)N(CC1(N2CCN(CC(C)(C)O)CC2)CCOCC1)c1cccc(C(F)(F)F)n1]

A solution of N-((4-(piperazin-1-yl)tetrahydro-2H-pyran-4-yl)methyl)-N-(6-(trifluoromethyl)pyridin-2-yl)propionamide (INT 19D, 500 mg, 1.25 mmol), 2,2-dimethyloxirane (243 mg, 3.37 mmol) and TEA (379 mg, 3.74 mmol) in MeOH (20 mL) was stirred at 75° C. for 3 h. The solvent was concentrated in vacuo and the residue was partitioned between DCM and water. Mixture was made alkaline with 20% NaOH and the organic layer was separated, dried over Na$_2$SO$_4$, filtered and concentrated. The crude residue was purified by flash chromatography on neutral alumine, gradient CH:AcOEt from (100:0) to (50:50) to give the title compound (200 mg, yield 34%).

HPLC-MS (Method A): Ret, 1.81 min; ESI+-MS m/z, 473 (M+1).

Example 189. N-((4-(4-(2-(2-Fluoro-2-methylpropoxy)ethyl)piperazin-1-yl)tetrahydro-2H-pyran-4-yl)methyl)-N-(6-(trifluoromethyl)pyridin-2-yl)proplonamide

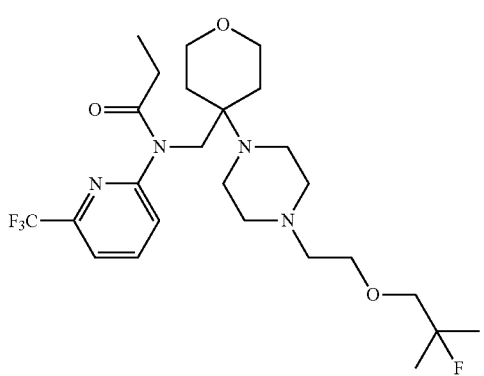 [SMILES: CCC(=O)N(CC1(N2CCN(CCOCC(C)(C)F)CC2)CCOCC1)c1cccc(C(F)(F)F)n1]

Deoxo-Fluor (Bis(2-methoxyethyl)aminosulfur trifluoride 50% in toluene, 50 µL) was added dropwise at 0° C. to a solution of N-((4-(4-(2-(2-hydroxy-2-methylpropoxy)ethyl)piperazin-1-yl)tetrahydro-2H-pyran-4-yl)methyl)-N-(6-(trifluoromethyl)pyridin-2-yl)propionamide (Example 186, 50 mg, 0.097 mmol) in toluene (2 mL). It was stirred for 1 h at 0° C. and 1 h at rt. Then, the solvent was concentrated in vacuo and the residue was partitioned between DCM and water at alkaline pH. The organic layer was separated, dried over Na$_2$SO$_4$, filtered and concentrated. The crude residue was purified by preparative HPLC (column X-Bridge C18, ACN: NH$_4$HCO$_3$ 10 mM from (2:98 to 95-5), flow 20 ml/min, rt) to give the title compound (10 mg, yield 20%).

HPLC-MS (Method A): Ret, 1.99 min; ESI+-MS m/z, 519 (M+1).

This method was used for the preparation of example 190 using example 188 as starting material.

| EX | Structure | Chemical name | Metod | Ret (min) | MS (M + H) |
|---|---|---|---|---|---|
| 190 | 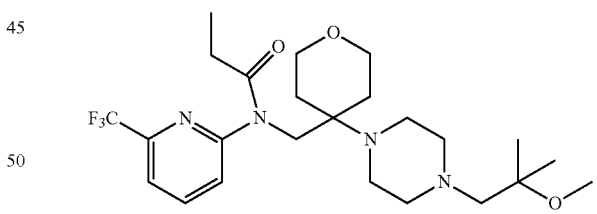 | N-((4-(4-(2-fluoro-2-methylpropyl)piperazin-1-yl)tetrahydro-2H-pyran-4-yl)methyl)-N-(6-(trifluoromethyl)pyridin-2-yl)propionamide | A | 2.24 | 475 |

Example 191. N-((4-(4-(2-Methoxy-2-methylpropyl)piperazin-1-yl)tetrahydro-2H-pyran-4-yl)methyl)-N-(6-(trifluoromethyl)pyridin-2-yl)proplonamide Dimethyl sulfate (50 µL, 0.529 mmol) and pyridine (42 µL, 0.529 mmol) was added to a solution of N-((4-(4-(2-hydroxy-2-methylpropyl)piperazin-1-yl)tetrahydro-2H-pyran-4-yl)methyl)-N-(6-(trifluoromethyl)pyridin-2-yl)propionamide (Example 190, 50 µL, 0.11 mmol) in DCM (5 mL) at rt. Additional dimethyl sulfate and pyridine was added and the reaction mixture was stirred until a good conversion was achieved (1 week, checked by HPLC analysis). Solvent was removed to dryness and the crude residue was purified by preparative HPLC (Column X-Bridge C18, ACN: NH$_4$HCO$_3$ 10 mM from (2:98 to 95-5), flow 20 ml/min, rt) to give the title compound (5 mg, yield 10%).

HPLC-MS (Method A): Ret, 1.39 min; ESI$^+$-MS m/z, 487 (M+1).

Example 192. N-((4-(4-(2-(3-Fluoropyridin-2-yl)ethyl)piperazin-1-yl)tetrahydro-2H-pyran-4-yl)methyl)-N-(6-(trifluoromethyl)pyridin-2-yl)proplonamide

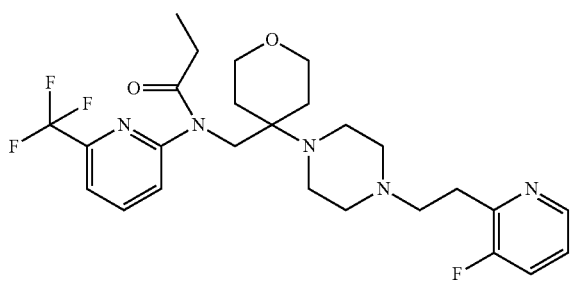 [SMILES: CCC(=O)N(CC1(N2CCN(CCc3ncccc3F)CC2)CCOCC1)c1cccc(C(F)(F)F)n1]

3-Fluoro-2-vinylpyridine hydrochloride (30 mg, 0.19 mmol) was added to a solution of N-((4-(piperazin-1-yl)tetrahydro-2H-pyran-4-yl)methyl)-N-(6-(trifluoromethyl)pyridin-2-yl)propionamide (INT 19D, 50 mg, 0.12 mmol) and DIPEA (32 µL, 0.19 mmol) in EtOH (3 mL). The reaction mixture was subjected to microwave irradiation for 1 h at 90° C. The crude product was concentrated to dryness and the residue was partitioned between AcOEt and water at pH alkaline. The crude residue was purified by preparative HPLC (Column X-Bridge C18, ACN: NH4HCO3 10 mM from (2:98 to 95-5), flow 20 ml/min, rt) to give the title compound (8 mg, yield 12%).

HPLC-MS (Method F): Ret, 1.86 min; ESI+-MS m/z, 524 (M+1).

Examples 193. N-((4-(4-(2-Hydroxy-2-phenylethyl)piperazin-1-yl)tetrahydro-2H-pyran-4-yl)methyl)-N-(6-(trifluoromethyl)pyridin-2-yl)propionamide and 194, N-((4-(4-(2-hydroxy-1-phenylethyl)piperazin-1-yl)tetrahydro-2H-pyran-4-yl)methyl)-N-(6-(trifluoromethyl)pyridin-2-yl)propionamide

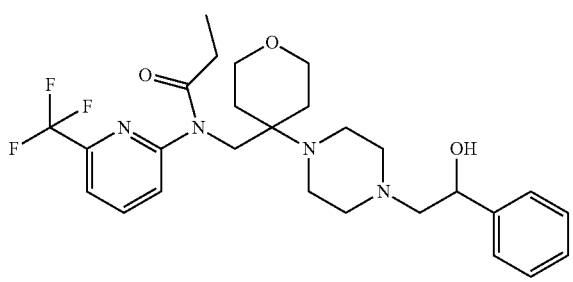

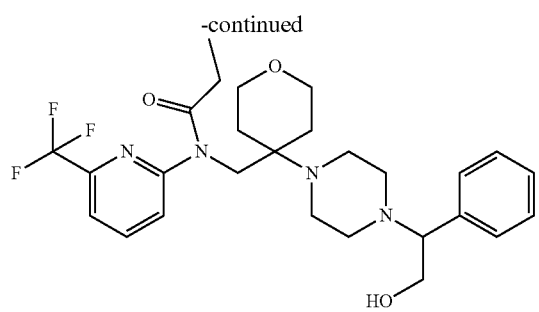

A solution of N-((4-(piperazin-1-yl)tetrahydro-2H-pyran-4-yl)methyl)-N-(6-(trifluoromethyl)pyridin-2-yl)propionamide (INT 19D, 80 mg, 0.2 mmol) and 2-phenyloxirane (211 mg, 1.75 mmol) in EtOH (5 mL) was heated at 70° C. in a sealed tube overnight. The reaction mixture was cooled to rt and the solvent was evaporated. The residue was purified by preparative HPLC (Column X-Bridge C18, ACN: NH4HCO3 10 mM from (2:98 to 95-5), flow 20 ml/min, rt) to give the title compounds (Example 196, 13 mg, 13% yield) and (Example 197, 6 mg, 6% Yield).

Example 193: HPLC-MS (Method B): Ret, 2.03 min; ESI+-MS m/z, 521 (M+1).

Example 194: HPLC-MS (Method B): Ret, 1.91 min; ESI+-MS m/z, 521 (M+1).

Example 195. N-((4-(4-Benzylpiperazin-1-yl)piperidin-4-yl)methyl)-N-phenylpropionamide

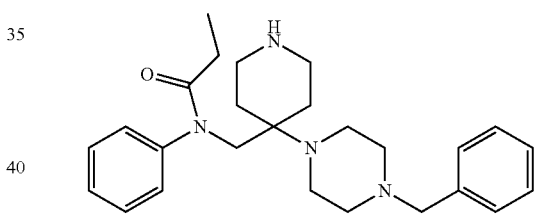

Boc deprotection was done following the procedure described in INT 7 and using tert-butyl 4-(4-benzylpiperazin-1-yl)-4-((N-phenylpropionamido)methyl)piperidine-1-carboxylate (INT 18C) as starting material.

HPLC-MS (Method A): Ret, 1.39 min; ESI+-MS m/z, 421 (M+1).

Examples 196-198 were prepared according to the procedure described in example 1, using the corresponding intermediates 3 as starting materials and propionyl chloride

| EX | Structure | Chemical name | Metod | Ret (min) | MS (M + H) |
|---|---|---|---|---|---|
| 196 | 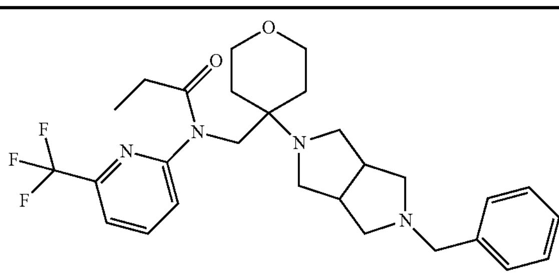 | N-((4-(5-benzylhexahydropyrrolo[3,4-c]pyrrol-2(1H)-yl)tetrahydro-2H-pyran-4-yl)methyl)-N-(6-(trifluoromethyl)pyridin-2-yl)propionamide | A | 2.31 | 517 |

| EX | Structure | Chemical name | Metod | Ret (min) | MS (M + H) |
|---|---|---|---|---|---|
| 197 | 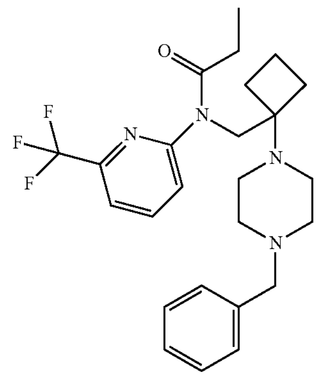 [SMILES: CCC(=O)N(CC1(N2CCN(Cc3ccccc3)CC2)CCC1)c1cccc(C(F)(F)F)n1] | N-((1-(4-benzylpiperazin-1-yl)cyclobutyl)methyl)-N-(6-(trifluoromethyl)pyridin-2-yl)propionamide | A | 2.45 | 461 |
| 198 | 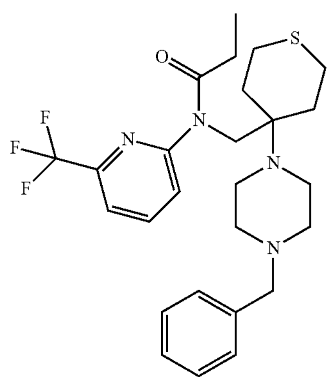 [SMILES: CCC(=O)N(CC1(N2CCN(Cc3ccccc3)CC2)CCSCC1)c1cccc(C(F)(F)F)n1] | N-((4-(4-benzylpiperazin-1-yl)tetrahydro-2H-thiopyran-4-yl)methyl)-N-(6-(trifluoromethyl)pyridin-2-yl)propionamide | A | 1.87 | 507 |

Examples 199-205 were prepared according to the procedure described in example 133, using the adequate alkylating agents and the corresponding intermediates 19 as starting materials

| EX | Structure | Chemical name | Metod | Ret (min) | MS (M + H) |
|---|---|---|---|---|---|
| 199 | 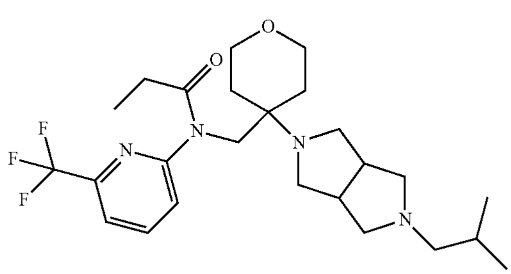 [SMILES: CCC(=O)N(CC1(N2CC3CN(CC(C)C)CC3C2)CCOCC1)c1cccc(C(F)(F)F)n1] | N-((4-(5-isobutylhexahydropyrrolo[3,4-c]pyrrol-2(1H)-yl)tetrahydro-2H-pyran-4-yl)methyl)-N-(6-(trifluoromethyl)pyridin-2-yl)propionamide | A | 2.08 | 483 |

| EX | Structure | Chemical name | Metod | Ret (min) | MS (M + H) |
|---|---|---|---|---|---|
| 200 | 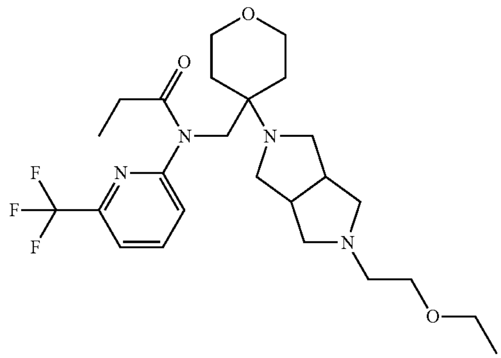 [SMILES: CCOCCN1CC2CN(C3(CN(C(=O)CC)c4cccc(C(F)(F)F)n4)CCOCC3)CC2C1] | N-((4-(5-(2-ethoxyethyl)hexahydropyrrolo[3,4-c]pyrrol-2(1H)-yl)tetrahydro-2H-pyran-4-yl)methyl)-N-(6-(trifluoromethyl)pyridin-2-yl)propionamide | A | 1.86 | 499 |
| 201 | 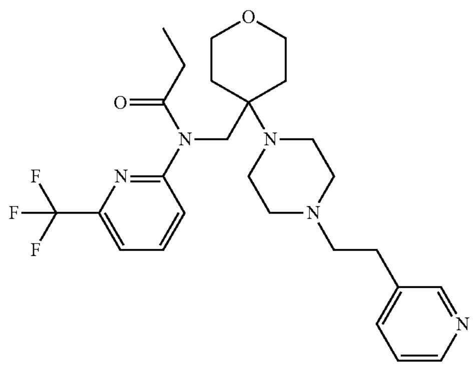 [SMILES: CCC(=O)N(CC1(N2CCN(CCc3cccnc3)CC2)CCOCC1)c1cccc(C(F)(F)F)n1] | N-((4-(4-(2-(pyridin-3-yl)ethyl)piperazin-1-yl)tetrahydro-2H-pyran-4-yl)methyl)-N-(6-(trifluoromethyl)pyridin-2-yl)propionamide | A | 1.76 | 506 |
| 202 | 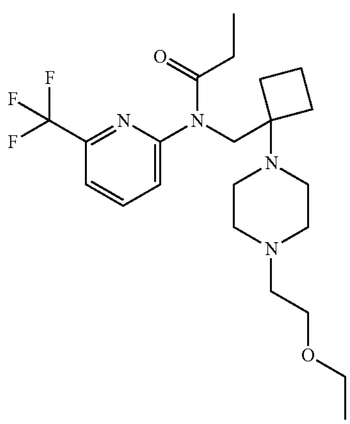 [SMILES: CCOCCN1CCN(C2(CN(C(=O)CC)c3cccc(C(F)(F)F)n3)CCC2)CC1] | N-((1-(4-(2-ethoxyethyl)piperazin-1-yl)cyclobutyl)methyl)-N-(6-(trifluoromethyl)pyridin-2-yl)propionamide | A | 2.05 | 443 |
| 203 | 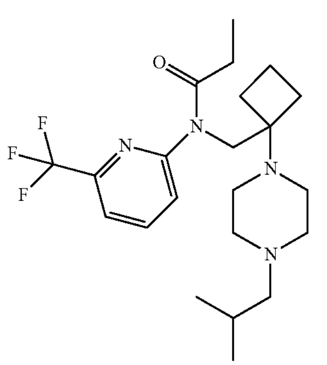 [SMILES: CCC(=O)N(CC1(N2CCN(CC(C)C)CC2)CCC1)c1cccc(C(F)(F)F)n1] | N-((1-(4-isobutylpiperazin-1-yl)cyclobutyl)methyl)-N-(6-(trifluoromethyl)pyridin-2-yl)propionamide | A | 2.53 | 427 |

| EX | Structure | Chemical name | Metod | Ret (min) | MS (M + H) |
|---|---|---|---|---|---|
| 204 | 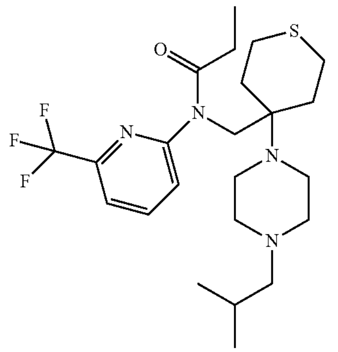 [SMILES: CCC(=O)N(CC1(N2CCN(CC(C)C)CC2)CCSCC1)c1cccc(C(F)(F)F)n1] | N-((4-(4-isobutylpiperazin-1-yl)tetrahydro-2H-thiopyran-4-yl)methyl)-N-(6-(trifluoromethyl)pyridin-2-yl)propionamide | A | 2.61 | 473 |
| 205 | 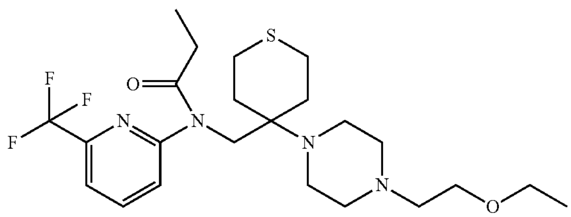 [SMILES: CCOCCN1CCN(C2(CN(C(=O)CC)c3cccc(C(F)(F)F)n3)CCSCC2)CC1] | N-((4-(4-(2-ethoxyethyl)piperazin-1-yl)tetrahydro-2H-thiopyran-4-yl)methyl)-N-(6-(trifluoromethyl)pyridin-2-yl)propionamide | A | 2.17 | 489 |

Example 206. N-((4-(4-(2-(pyridin-4-ethyl)ethyl)piperazin-1-yl)tetrahydro-2H-pyran-4-yl)methyl)-N-(6-(trifluoromethyl)pyridin-2-yl)propionamide

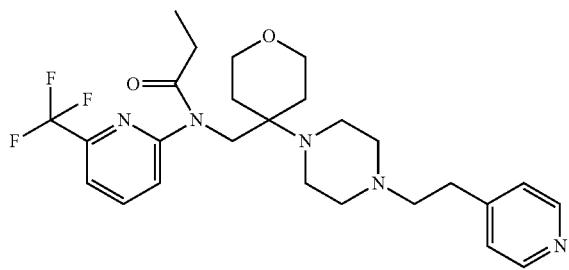 [SMILES: CCC(=O)N(CC1(N2CCN(CCc3ccncc3)CC2)CCOCC1)c1cccc(C(F)(F)F)n1]

Example 206 was prepared according to the procedure described in example 192, using 4-vinylpyridine as reagent.

HPLC-MS (Method A): Ret, 1.87 min: ESI+-MS m/z, 506 (M+1).

Table of Examples with Binding to the μ-Opioid Receptor and The☐ σ$_1$-Receptor:
Biological Activity
Pharmacological Study
Human σ$_1$ receptor radioligand Assay To investigate binding properties of test compounds to human σ$_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human μ-opioid receptor radioligand assay To investigate binding properties of test compounds to human μ-opioid receptor, transfected CHO-K1 cell membranes and [$^3$H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the σ$_1$ receptor and the μ-opioid receptor it is a very preferred embodiment in which the compounds are selected which act as dual ligands of the σ$_1$ receptor and the μ-opioid receptor and especially compounds which have a binding expressed as K$_i$ which is preferably <1000 nM for both receptors, more preferably <500 nM, even more preferably <100 nM.

The following scale as been adopted for representing the binding to the the σ$_1$ receptor and the μ-opioid receptor expressed as K$_i$:

+ Both K$_i$-μ and K$_i$-σ$_1$ >=500 nM
++ One K$_i$<500 nM while the other K$_i$ is >=500 nM
+++ Both K$_i$-μ and K$_i$-σ$_1$ <500 nM
++++ Both K$_i$-μ and K$_i$-σ$_1$ <100 nM All compounds prepared in the present application exhibit binding to the σ$_1$ receptor and the μ-opioid receptor, in particular the following binding results are shown:

| EX | μ and σ₁ dual |
|---|---|
| 1 | ++++ |
| 2 | ++++ |
| 3 | ++++ |
| 4 | ++++ |
| 5 | ++++ |
| 6 | +++ |
| 7 | ++ |
| 8 | +++ |
| 9 | ++ |
| 10 | +++ |
| 11 | ++ |
| 12 | + |
| 13 | ++++ |
| 14 | ++ |
| 15 | ++ |
| 16 | +++ |
| 17 | +++ |
| 18 | +++ |
| 19 | ++++ |
| 20 | ++++ |
| 21 | +++ |
| 22 | ++ |
| 23 | ++ |
| 24 | + |
| 25 | ++++ |
| 26 | +++ |
| 27 | +++ |
| 28 | ++++ |
| 29 | ++++ |
| 30 | ++++ |
| 31 | ++ |
| 32 | ++++ |
| 33 | +++ |
| 34 | ++++ |
| 35 | ++++ |
| 36 | +++ |
| 37 | +++ |
| 38 | ++ |
| 39 | ++ |
| 40 | ++ |
| 41 | + |
| 42 | ++ |
| 43 | ++ |
| 44 | ++++ |
| 45 | + |
| 46 | ++++ |
| 47 | ++ |
| 48 | ++ |
| 49 | ++ |
| 50 | +++ |
| 51 | +++ |
| 52 | +++ |
| 53 | +++ |
| 54 | +++ |
| 55 | +++ |
| 56 | +++ |
| 57 | ++ |
| 58 | ++ |
| 59 | +++ |
| 60 | +++ |
| 61 | +++ |
| 62 | ++ |
| 63 | ++ |
| 64 | +++ |
| 65 | +++ |
| 66 | ++++ |
| 67 | +++ |
| 68 | ++ |
| 69 | ++ |
| 70 | ++ |
| 71 | ++ |
| 72 | ++ |
| 73 | ++ |
| 74 | ++ |
| 75 | +++ |
| 76 | +++ |
| 77 | ++++ |
| 78 | +++ |
| 79 | +++ |
| 80 | +++ |
| 81 | +++ |
| 82 | ++++ |
| 83 | ++++ |
| 84 | +++ |
| 85 | + |
| 86 | +++ |
| 87 | + |
| 88 | ++ |
| 89 | ++++ |
| 90 | ++++ |
| 91 | ++++ |
| 92 | +++ |
| 93 | +++ |
| 94 | ++ |
| 95 | ++++ |
| 96 | +++ |
| 97 | +++ |
| 98 | +++ |
| 99 | ++ |
| 100 | ++++ |
| 101 | +++ |
| 102 | + |
| 103 | + |
| 104 | +++ |
| 105 | ++++ |
| 106 | ++ |
| 107 | +++ |
| 108 | +++ |
| 109 | +++ |
| 110 | +++ |
| 111 | +++ |
| 112 | ++ |
| 113 | ++ |
| 114 | +++ |
| 115 | ++ |
| 116 | ++++ |
| 117 | ++++ |
| 118 | ++++ |
| 119 | +++ |
| 120 | + |
| 121 | + |
| 122 | +++ |
| 123 | ++++ |
| 124 | ++++ |
| 125 | ++ |
| 126 | ++++ |
| 127 | + |
| 128 | ++++ |
| 129 | +++ |
| 130 | ++++ |
| 131 | ++ |
| 132 | ++ |
| 133 | ++++ |
| 134 | ++ |
| 135 | +++ |
| 136 | +++ |
| 137 | ++++ |
| 138 | ++++ |
| 139 | ++ |
| 140 | +++ |
| 141 | +++ |
| 142 | ++++ |
| 143 | +++ |
| 144 | +++ |
| 145 | +++ |
| 146 | +++ |
| 147 | +++ |
| 148 | + |
| 149 | ++++ |
| 150 | +++ |
| 151 | + |
| 152 | + |
| 153 | ++ |
| 154 | + |
| 155 | +++ |
| 156 | ++ |

-continued

| EX | µ and σ₁ dual |
|---|---|
| 157 | +++ |
| 158 | ++ |
| 159 | ++++ |
| 160 | +++ |
| 161 | +++ |
| 162 | + |
| 163 | + |
| 164 | ++ |
| 165 | + |
| 166 | + |
| 167 | +++ |
| 168 | ++ |
| 169 | + |
| 170 | ++ |
| 171 | + |
| 172 | + |
| 173 | +++ |
| 174 | +++ |
| 175 | +++ |
| 176 | +++ |
| 177 | +++ |
| 178 | ++ |
| 179 | +++ |
| 180 | + |
| 181 | + |
| 182 | +++ |
| 183 | +++ |
| 184 | + |
| 185 | ++ |
| 186 | ++ |
| 187 | +++ |
| 188 | ++ |
| 189 | ++++ |
| 190 | +++ |
| 191 | + |
| 192 | ++ |
| 193 | +++ |
| 194 | ++ |
| 195 | ++ |
| 196 | ++ |
| 197 | ++++ |
| 198 | ++++ |
| 199 | + |
| 200 | + |
| 201 | ++ |
| 202 | +++ |
| 203 | +++ |
| 204 | +++ |
| 205 | +++ |
| 206 | +++ |

The invention claimed is:
1. A compound of general Formula (I):

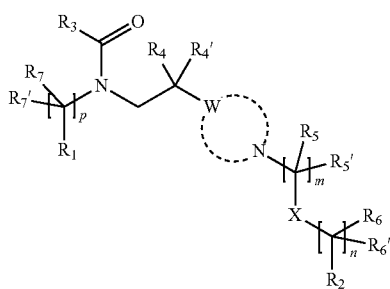

wherein
m is 1 or 2;
n is 0, 1 or 2;
p is 0, 1 or 2;
W is nitrogen or carbon;

X is a bond, —C(R$_x$R$_{x'}$)—, C═O, —C(O)O— or —O—;
  wherein R$_x$ is selected from the group consisting of halogen, —OR$_{15}$, substituted or unsubstituted C$_{1-6}$ alkyl, substituted or unsubstituted C$_{2-6}$ alkenyl and substituted or unsubstituted C$_{2-6}$ alkynyl;
R$_{x'}$ is selected from the group consisting of hydrogen, halogen, substituted or unsubstituted C$_{1-6}$ alkyl, substituted or unsubstituted C$_{2-6}$ alkenyl and substituted or unsubstituted C$_{2-6}$ alkynyl;
R$_{15}$ is selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl;
R$_1$ is selected from the group consisting of substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
  wherein the cycloalkyl, aryl or heterocyclyl in R$_1$ if substituted, is substituted with one or more substituent/s selected from the group consisting of halogen, —R$_{11}$, —OR$_{11}$, —NO$_2$, —NR$_{11}$R$_{11'''}$, NR$_{11}$C(O)R$_{11'}$, —NR$_{11}$S(O)$_2$R$_{11'}$, —S(O)$_2$NR$_{11}$R$_{11'}$, —NR$_{11}$C(O)NR$_{11'}$R$_{11''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, —NR$_{11}$S(O)$_2$NR$_{11'}$R$_{11''}$ and C(CH$_3$)$_2$OR$_{11}$;
  and wherein the cycloalkyl or non-aromatic heterocyclyl in R$_1$, if substituted, may also be substituted with

or ═O;
  wherein the alkyl, alkenyl or alkynyl in R$_1$, if substituted, is substituted with one or more substituent/s selected from the group consisting of —OR$_{11}$, halogen, —CN, haloalkyl, haloalkoxy, —SR$_{11}$, —S(O)R$_{11}$, and —S(O)$_2$R$_{11}$;
  wherein R$_{11}$, R$_{11'}$ and R$_{11''}$ are independently selected from the group consisting of hydrogen, unsubstituted C$_{1-6}$ alkyl, unsubstituted C$_{2-6}$ alkenyl and unsubstituted C$_{2-6}$ alkynyl;
  and wherein R$_{11'''}$ is selected from the group consisting of hydrogen, unsubstituted C$_{1-6}$ alkyl, unsubstituted C$_{2-6}$ alkenyl, unsubstituted C$_{2-6}$ alkynyl and -Boc;
R$_2$ is selected from the group consisting of hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
  wherein the cycloalkyl, aryl or heterocyclyl in R$_2$, if substituted, is substituted with one or more substituent/s selected from the group consisting of halogen, —R$_{12}$, —OR$_{12}$, —NO$_2$, —NR$_{12}$R$_{12'''}$, NR$_{12}$C(O)R$_{12'}$, —NR$_{12}$S(O)$_2$R$_{12'}$, —S(O)$_2$NR$_{12}$R$_{12'}$, —NR$_{12}$C(O)NR$_{12'}$R$_{12''}$, —SR$_{12}$, —S(O)R$_{12}$, S(O)$_2$R$_{12}$, —CN, haloalkyl, haloalkoxy, —C(O)OR$_{12}$, —C(O)NR$_{12}$R$_{12'}$, —NR$_{12}$S(O)$_2$NR$_{12'}$R$_{12''}$ and C(CH$_3$)$_2$OR$_{12}$;
  and wherein the cycloalkyl or non-aromatic heterocyclyl in R$_2$, if substituted, may also be substituted with

or =O;
wherein the alkyl, alkenyl or alkynyl in $R_2$, if substituted, is substituted with one or more substituent/s selected from the group consisting of —$OR_{12}$, halogen, —CN, haloalkyl, haloalkoxy, —$SR_{12}$, —$S(O)R_{12}$, and —$S(O)_2R_{12}$;
wherein $R_{12}$, $R_{12'}$ and $R_{12''}$ are independently selected from the group consisting of hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;
$R_3$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_9R_{9'}$ and —$CH_2OR_9$;
wherein $R_9$ and $R_{9'}$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_4$ and $R_{4'}$ are independently selected from the group consisting of substituted or unsubstituted $C_{1-6}$ alkyl, substituted or unsubstituted $C_{2-6}$ alkenyl and substituted or unsubstituted $C_{2-6}$ alkynyl,
or $R_4$ and $R_{4'}$ together with the carbon atom to which they are attached, form a cycle of Formula (A) (with "●" marking the carbon atom to which $R_4$ and $R_{4'}$ are attached):

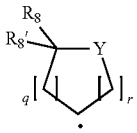

(A)

wherein
q is 0 or 1;
r is 0, 1 or 2;
Y is —$CH_2$—, —$N(R_y)$—, —S— or —O—;
$R_8$ and $R_{8'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
or $R_8$ and $R_{8'}$ together with the carbon atom to which they are attached, form a $C_{3-6}$ cycloalkyl;
$R_y$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_5$ and $R_{5'}$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, —$CH_2OR_{10}$ and —$C(O)OR_{10}$;

wherein $R_{10}$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_6$ and $R_{6'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_7$ and $R_{7'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
and wherein

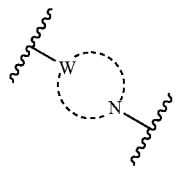

is selected from

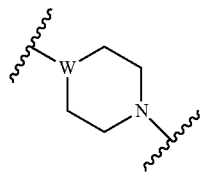 , 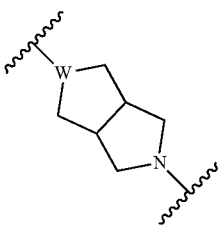 and

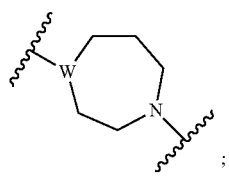 ;

wherein
the alkyl, alkenyl or alkynyl, other than those defined in $R_1$ or $R_2$, if substituted, is substituted with one or more substituent/s selected from the group consisting of —$OR_{13}$, halogen, —CN, haloalkyl, haloalkoxy, —$SR_{13}$, —$S(O)R_{13}$, and —$S(O)_2R_{13}$;
wherein $R_{13}$ is selected from hydrogen, unsubstituted $C_{1-6}$ alkyl, unsubstituted $C_{2-6}$ alkenyl, and unsubstituted $C_{2-6}$ alkynyl;
the aryl, heterocyclyl or cycloalkyl other than those defined in $R_1$ or $R_2$, if substituted, is substituted with one or more substituent/s selected from the group consisting of halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$NR_{14}S(O)_2NR_{14'}R_{14''}$ and $C(CH_3)_2OR_{14}$;
and wherein the cycloalkyl or non-aromatic heterocyclyl, other than those defined in $R_1$ or $R_2$, if substituted, may also be substituted with

or =O;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally as a stereoisomer, a racemate or a mixture of at least two stereoisomers, in any mixing ratio, or a corresponding salt thereof, or a corresponding solvate thereof;

with the provisos that:
—[$CR_5R_{5'}]_m$—X—($CR_6R_{6'})_n$—$R_2$ is not unsubstituted methyl;
or
$R_1$ is neither an unsubstituted nor an N-alkyl-substituted compound of the following formula:

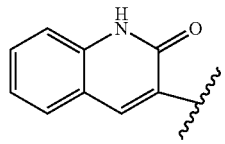

2. The compound according to claim 1, wherein

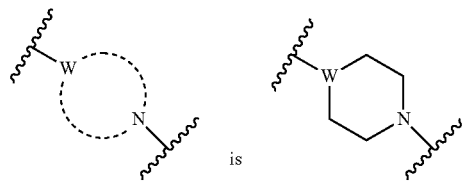

and W is nitrogen or carbon.

3. The compound according to claim 2, wherein W is nitrogen.

4. The compound according to claim 1, wherein the compound is a compound of general formula (I$^{4'}$)

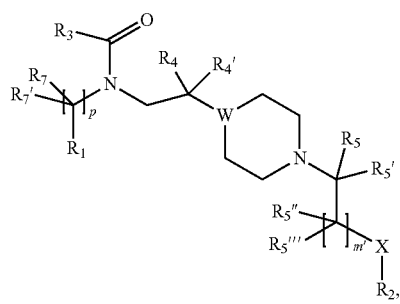

wherein
m' is 0 or 1;
p is 0, 1 or 2;

W is nitrogen or carbon;

X is a bond, —C($R_xR_{x'}$)—, C=O, —C(O)O— or —O—;
wherein $R_x$ is selected from the group consisting of halogen, —$OR_{15}$, substituted or unsubstituted $C_{1-6}$ alkyl, substituted or unsubstituted $C_{2-6}$ alkenyl and substituted or unsubstituted $C_{2-6}$ alkynyl;

$R_{x'}$ is selected from the group consisting of hydrogen, halogen, substituted or unsubstituted $C_{1-6}$ alkyl, substituted or unsubstituted $C_{2-6}$ alkenyl and substituted or unsubstituted $C_{2-6}$ alkynyl;

$R_{15}$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted monocyclic heterocyclyl and unsubstituted polycyclic heterocyclyl;

wherein the cycloalkyl, aryl or heterocyclyl in $R_1$ if substituted, is substituted with one or more substituent/s selected from the group consisting of halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$NR_{11}S(O)_2NR_{11'}R_{11''}$ and $C(CH_3)_2OR_{11}$;

and wherein the cycloalkyl or non-aromatic heterocyclyl in $R_1$, if substituted, may also be substituted with

or =O;

wherein the alkyl, alkenyl or alkynyl in $R_1$, if substituted, is substituted with one or more substituent/s selected from the group consisting of —$OR_{11}$, halogen, —CN, haloalkyl, haloalkoxy, —$SR_{11}$, —$S(O)R_{11}$, and —$S(O)_2R_{11}$;

wherein $R_{11}$, $R_{11'}$ and $R_{11''}$ are independently selected from the group consisting of hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

$R_2$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, wherein the cycloalkyl, aryl or heterocyclyl in $R_2$, if substituted, is substituted with one or more substituent/s selected from the group consisting of halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$NR_{12}S(O)_2NR_{12'}R_{12''}$ and $C(CH_3)_2OR_{12}$;

and wherein the cycloalkyl or non-aromatic heterocyclyl in $R_2$, if substituted, may also be substituted with

or =O;
wherein the alkyl, alkenyl or alkynyl in $R_2$, if substituted, is substituted with one or more substituent/s selected from the group consisting of —$OR_{12}$, halogen, —CN, haloalkyl, haloalkoxy, —$SR_{12}$, —$S(O)R_{12}$, and —$S(O)_2R_{12}$;
wherein $R_{12}$, $R_{12'}$ and $R_{12''}$ are independently selected from the group consisting of hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;
$R_3$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, —$NR_9R_{9'}$ and —$CH_2OR_9$;
wherein $R_9$ and $R_9'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_4$ and $R_{4'}$ are independently selected from the group consisting of substituted or unsubstituted $C_{1-6}$ alkyl, substituted or unsubstituted $C_{2-6}$ alkenyl and substituted or unsubstituted $C_{2-6}$ alkynyl,
or $R_4$ and $R_{4'}$, together with the carbon atom to which they are attached, form a cycle of Formula (A), with "●" marking the carbon atom to which $R_4$ and $R_{4'}$ are attached:

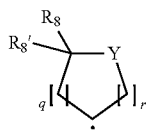

(A)

wherein
q is 0 or 1
r is 0, 1 or 2
Y is —$CH_2$—, —$N(R_y)$—, —S— or —O—;
$R_8$ and $R_{8'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
or $R_8$ and $R_{8'}$, together with the carbon atom to which they are attached, form a $C_{3-6}$ cycloalkyl;
$R_y$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_5$ and $R_{5'}$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, —$CH_2OR_{10}$ and —$C(O)OR_{10}$;
wherein $R_{10}$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_{5''}$ and $R_{5'''}$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, —$CH_2OR_{10'}$ and —$C(O)OR_{10'}$;
wherein $R_{10'}$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_7$ and $R_{7'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
wherein
the alkyl, alkenyl or alkynyl, other than those defined in $R_1$ or $R_2$, if substituted, is substituted with one or more substituent/s selected from the group consisting of —$OR_{13}$, halogen, —CN, haloalkyl, haloalkoxy, —$SR_{13}$, —$S(O)R_{13}$, and —$S(O)_2R_{13}$;
wherein $R_{13}$ is selected from the group consisting of hydrogen, unsubstituted $C_{1-6}$ alkyl, unsubstituted $C_{2-6}$ alkenyl, and unsubstituted $C_{2-6}$ alkynyl;
the aryl, heterocyclyl or cycloalkyl other than those defined in $R_1$ or $R_2$, if substituted, is substituted with one or more substituent/s selected from the group consisting of halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$NR_{14}S(O)_2NR_{14'}R_{14''}$ and $C(CH_3)_2OR_{14}$;
and wherein the cycloalkyl or non-aromatic heterocyclyl, other than those defined in $R_1$ or $R_2$, if substituted, may also be substituted with

or =O;
wherein $R_{14}$, $R_{14'}$ and $R_{14''}$ are independently selected from the group consisting of hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;
and wherein $R_{14'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;
optionally as a stereoisomer, a racemate or a mixture of at least two stereoisomers, in any mixing ratio, or a corresponding salt thereof, or a corresponding solvate thereof.

5. The compound according to claim 1, wherein X is a bond, C=O, —C(O)O— or —O—.

6. The compound according to claim 5, wherein X is a bond or —O—.

7. The compound according to claim 1, wherein $R_1$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted monocyclic heterocyclyl.

8. The compound according to claim 7, wherein $R_1$ is substituted or unsubstituted ethyl, substituted or unsubstituted isobutyl, substituted or unsubstituted phenyl, substituted or unsubstituted pyridine and substituted or unsubstituted thiazole.

9. The compound according to claim 1, wherein $R_2$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl.

10. The compound according to claim 9, wherein $R_2$ is selected from the group consisting of substituted or unsubstituted methyl, substituted or unsubstituted ethyl, substituted or unsubstituted isopropyl, substituted or unsubstituted isobutyl, —$CF_3$, —$CH_2CF_3$, substituted or unsubstituted phenyl, substituted or unsubstituted pyridine, substituted or unsubstituted piperidine, substituted or unsubstituted morpholine and substituted or unsubstituted cyclopropyl.

11. The compound according to claim 1, wherein $R_3$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted heterocyclyl, —$NR_9R_9{'}$ and —$CH_2OR_9$;
wherein $R_9$ and $R_9{'}$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl.

12. The compound according to claim 11, wherein $R_3$ is substituted or unsubstituted ethyl.

13. The compound according to claim 11, wherein $R_9$ and $R_9{'}$ are independently selected from the group consisting of hydrogen, substituted or unsubstituted methyl, and substituted or unsubstituted ethyl.

14. The compound according to claim 1, wherein $R_4$ and $R_{4'}$ are independently selected from the group consisting of substituted or unsubstituted $C_{1-6}$ alkyl, substituted or unsubstituted $C_{2-6}$ alkenyl and substituted or unsubstituted $C_{2-6}$ alkynyl.

15. The compound according to claim 14, wherein $R_4$ and $R_{4'}$ are both substituted or unsubstituted methyl.

16. The compound according to claim 1, wherein $R_4$ and $R_{4'}$, together with the carbon atom to which they are attached, form a cycle of Formula (A).

17. The compound according to claim 16, wherein the cycle of Formula (A) is selected from the group consisting of substituted or unsubstituted tetrahydropyran, substituted or unsubstituted tetrahydrothiopyran, substituted or unsubstituted cyclopropyl, substituted or unsubstituted cyclobutyl, substituted or unsubstituted oxetane, substituted or unsubstituted cyclohexyl and substituted or unsubstituted piperidine.

18. The compound according to claim 1, wherein the compound is selected from the group consisting of:
N-((4-(4-benzylpiperazin-1-yl)tetrahydro-2H-pyran-4-yl)methyl)-N-phenylpropionamide
N-((4-(4-benzylpiperazin-1-yl)tetrahydro-2H-pyran-4-yl)methyl)-N-(2-chlorophenyl)propionamide
N-((4-(4-benzylpiperazin-1-yl)tetrahydro-2H-pyran-4-yl)methyl)-N-(2-methoxyphenyl)propionamide
N-((4-(4-benzylpiperazin-1-yl)tetrahydro-2H-pyran-4-yl)methyl)-N-(2-fluorophenyl)propionamide
N-((4-(4-benzylpiperazin-1-yl)tetrahydro-2H-pyran-4-yl)methyl)-N-(3-fluorophenyl)propionamide
N-((4-(4-benzylpiperazin-1-yl)tetrahydro-2H-pyran-4-yl)methyl)-N-(5-fluoropyridin-2-yl)propionamide
N-((4-(4-benzylpiperazin-1-yl)tetrahydro-2H-pyran-4-yl)methyl)-N-(5-(trifluoromethyl)pyridin-2-yl)propionamide
N-((4-(4-benzylpiperazin-1-yl)tetrahydro-2H-pyran-4-yl)methyl)-N-(4-(trifluoromethyl)pyridin-2-yl)propionamide
N-((4-(4-benzylpiperazin-1-yl)tetrahydro-2H-pyran-4-yl)methyl)-N-(5-(trifluoromethyl)pyridin-3-yl)propionamide
N-((4-(4-benzylpiperazin-1-yl)tetrahydro-2H-pyran-4-yl)methyl)-N-(5-fluoropyridin-3-yl)propionamide
N-((4-(4-benzylpiperazin-1-yl)tetrahydro-2H-pyran-4-yl)methyl)-N-(6-(trifluoromethyl)pyridin-3-yl)propionamide
N-((4-(4-benzylpiperazin-1-yl)tetrahydro-2H-pyran-4-yl)methyl)-N-(pyridin-4-yl)propionamide
N-((4-(4-benzylpiperazin-1-yl)tetrahydro-2H-pyran-4-yl)methyl)-N-(1-phenylethyl)propionamide
N-benzyl-N-((4-(4-benzylpiperazin-1-yl)tetrahydro-2H-pyran-4-yl)methyl)propionamide
N-((4-(4-benzylpiperazin-1-yl)tetrahydro-2H-pyran-4-yl)methyl)-N-isobutylpropionamide
N-((4-(4-benzylpiperazin-1-yl)-2,2-dimethyltetrahydro-2H-pyran-4-yl)methyl)-N-(pyridin-2-yl)propionamide
N-((9-(4-benzylpiperazin-1-yl)-6-oxaspiro[4.5]decan-9-yl)methyl)-N-(pyridin-2-yl)propionamide
N-((3-(4-benzylpiperazin-1-yl)oxetan-3-yl)methyl)-N-phenylpropionamide
N-((1-(4-benzylpiperazin-1-yl)cyclohexyl)methyl)-N-phenylpropionamide
N-((1-(4-phenethylpiperazin-1-yl)cyclohexyl)methyl)-N-phenylpropionamide
N-((1-(4-phenethylpiperazin-1-yl)cyclohexyl)methyl)-N-(pyridin-2-yl)propionamide
N-((4-(4-benzylpiperazin-1-yl)-1-methylpiperidin-4-yl)methyl)-N-phenylpropionamide
N-((1-methyl-4-(4-phenethylpiperazin-1-yl)piperidin-4-yl)methyl)-N-phenylpropionamide
N-((4-(4-benzylpiperazin-1-yl)-1-methylpiperidin-4-yl)methyl)-N-(4-ethoxyphenyl)propionamide
N-(2-(4-benzylpiperazin-1-yl)-2-methylpropyl)-N-phenylpropionamide
N-(2-methyl-2-(4-phenethylpiperazin-1-yl)propyl)-N-phenylpropionamide
N-(2-methyl-2-(4-phenethylpiperazin-1-yl)propyl)-N-(pyridin-2-yl)propionamide
N-((1-(4-benzylpiperazin-1-yl)cyclopropyl)methyl)-N-phenylpropionamide
N-((1-(4-phenethylpiperazin-1-yl)cyclopropyl)methyl)-N-phenylpropionamide
N-((1-(4-benzylpiperazin-1-yl)cyclopropyl)methyl)-N-(pyridin-2-yl)propionamide
N-((1-(4-benzylpiperazin-1-yl)cyclopropyl)methyl)-N-(pyridin-4-yl)propionamide
N-((1-(4-benzylpiperazin-1-yl)cyclopropyl)methyl)-N-(2-methoxyphenyl)propionamide
N-((1-(4-benzylpiperazin-1-yl)cyclopropyl)methyl)-N-(5-fluoropyridin-2-yl)propionamide
N-((1-(4-benzylpiperazin-1-yl)cyclopropyl)methyl)-N-(2-chlorophenyl)propionamide N-((1-(4-benzylpiperazin-1-yl)cyclopropyl)methyl)-N-(2-fluorophenyl)propionamide
N-((1-(4-benzylpiperazin-1-yl)cyclopropyl)methyl)-N-(pyridin-3-yl)propionamide
N-((4-(4-benzylpiperazin-1-yl)tetrahydro-2H-pyran-4-yl)methyl)-2-methoxy-N-phenylacetamide
N-((4-(4-benzylpiperazin-1-yl)tetrahydro-2H-pyran-4-yl)methyl)-N-(pyridin-2-yl)thiophene-2-carboxamide
N-((4-(4-isobutylpiperazin-1-yl)tetrahydro-2H-pyran-4-yl)methyl)-2-methoxy-N-(6-(trifluoromethyl)pyridin-2-yl)acetamide
N-((4-(4-isobutylpiperazin-1-yl)tetrahydro-2H-pyran-4-yl)methyl)-N-(6-(trifluoromethyl)pyridin-2-yl)acetamide
N-((4-(4-benzylpiperazin-1-yl)-1-methylpiperidin-4-yl)methyl)-N-phenylthiazole-2-carboxamide
N-((4-(4-benzylpiperazin-1-yl)-1-methylpiperidin-4-yl)methyl)-N-phenylthiophene-2-carboxamide
N-(2-(4-benzylpiperazin-1-yl)-2-methylpropyl)-2-methoxy-N-phenylacetamide
N-(2-methyl-2-(4-phenethylpiperazin-1-yl)propyl)-N-phenylfuran-2-carboxamide
3-ethyl-1-(2-methyl-2-(4-phenethylpiperazin-1-yl)propyl)-1-phenylurea
N-((1-(4-benzylpiperazin-1-yl)cyclopropyl)methyl)-2-methoxy-N-phenylacetamide
N-((1-(4-benzylpiperazin-1-yl)cyclopropyl)methyl)-N-(pyridin-2-yl)thiophene-2-carboxamide
1-(2-(4-benzylpiperazin-1-yl)-2-methylpropyl)-3-ethyl-1-phenylurea
1((4-(4-benzylpiperazin-1-yl)tetrahydro-2H-pyran-4-yl)methyl)-3-ethyl-1-(pyridin-2-yl)urea
3-ethyl-1-((1-(4-phenethylpiperazin-1-yl)cyclohexyl)methyl)-1-phenylurea
2-methoxy-N-(2-methyl-2-(4-phenethylpiperazin-1-yl)propyl)-N-phenylacetamide
1((1-(4-benzylpiperazin-1-yl)cyclopropyl)methyl)-3-ethyl-1-phenylurea
3-ethyl-1((1-(4-phenethylpiperazin-1-yl)cyclopropyl)methyl)-1-phenylurea
N-((4-(4-benzylpiperazin-1-yl)tetrahydro-2H-pyran-4-yl)methyl)-N-(2-hydroxyphenyl)propionamide
N-((1-(4-benzylpiperazin-1-yl)cyclopropyl)methyl)-N-(2-hydroxyphenyl)propionamide
N-((4-(4-benzylpiperazin-1-yl)tetrahydro-2H-pyran-4-yl)methyl)-N-(pyridin-2-yl)propionamide
N-((4-(4-benzylpiperazin-1-yl)tetrahydro-2H-pyran-4-yl)methyl)-N-(3-cyanophenyl)propionamide
N-((4-(4-benzylpiperazin-1-yl)tetranydro-2H-pyran-4-yl)methyl)-N-(3-cyanopyridin-2-yl)propionamide
N-((4-(4-benzylpiperazin-1-yl)tetrahydro-2H-pyran-4-yl)methyl)-N-(3 (thfluoromethyl)pyridin-2-yl)propionamide
N-((4-(4-benzylpiperazin-1-yl)tetrahydro-2H-pyran-4-yl)methyl)-N-(3-cyano-6-(trifluoromethyl)pyridin-2-yl)propionamide
N-((4-(4-benzylpiperazin-1-yl)tetrahydro-2H-pyran-4-yl)methyl)-N-(6-cyano-5-fluoropyridin-2-yl)propionamide
N-(3-cyanopyridin-2-yl)-N-((4-(4-isobutylpiperazin-1-yl)tetrahydro-2H-pyran-4-yl)methyl)propionamide
N-((4-(4-isobutylpiperazin-1-yl)tetrahydro-2H-pyran-4-yl)methyl)-N-(3-(trifluoromethyl)pyridin-2-yl)propionamide
N-((4-(4-benzylpiperazin-1-yl)-2,2-dimethyltetrahydro-2H-pyran-4-yl)methyl)-N-(3-fluoropyridin-2-yl)propionamide
N-((4-(4-benzylpiperazin-1-yl)-2,2-dimethyltetrahydro-2H-pyran-4-yl)methyl)-N-(6-cyanopyridin-2-yl)propionamide
N-((4-(4-benzylpiperazin-1-yl)-2,2-dimethyltetrahydro-2H-pyran-4-yl)methyl-N-(6-(trifluoromethyl)pyridin-2-yl)propionamide
N-((4-(4-benzylpiperazin-1-yl)-2,2-dimethyltetrahydro-2H-pyran-4-yl)methyl)-N-(3-(trifluoromethyl)pyridin-2-yl)propionamide
N-((4-(4-benzylpiperazin-1-yl)-2,2-dimethyltetrahydro-2H-pyran-4-yl)methyl)-N-(3-cyanopyridin-2-yl)propionamide
N-(2-(4-(2-fluorophenethyl)piperazin-1-yl)-2-methylpropyl)-N-(3-fluoropyridin-2-yl)propionamide
N-(2-(4-(2-(3-fluoropyridin-2-yl)ethyl)piperazin-1-yl)-2-methylpropyl)-N-(pyridin-2-yl)propionamide
N-(2-fluorophenyl)-N-(2-(4-(2-(3-fluoropyridin-2-yl)ethyl)piperazin-1-yl)-2-methylpropyl)propionamide
N-(2-(4-(2-(3-fluoropyridin-2-yl)ethyl)piperazin-1-yl)-2-methylpropyl)-N-phenylpropionamide
N-(3-fluoropyridin-2-yl)-N-(2-(4-(2-isopropoxyethyl)piperazin-1-yl)-2-methylpropyl)propionamide
N-(3-fluoropyridin-2-yl)-N-(2-(4-isobutylpiperazin-1-yl)-2-methylpropyl)propionamide
N-(3-fluoropyridin-2-yl)-N-(2-(4-isopentylpiperazin-1-yl)-2-methylpropyl)propionamide
N-((1-(4-benzylpiperazin-1-yl)cyclopropyl)methyl)-N-(2-(trifluoromethyl)pyridin-3-yl)propionamide
N-((1-(4-benzylpiperazin-1-yl)cyclopropyl)methyl)-N-(3-fluoropyridin-2-yl)propionamide
N-((1-(4-benzylpiperazin-1-yl)cyclopropyl)methyl)-N-(4-(trifluoromethyl)pyridin-3-yl)propienarnide
N-((1-(4-benzylpiperazin-1-yl)cyclopropyl)methyl)-N-(3-(trifluoromethyl)pyridin-2-yl)propionamide
N-((1-(4-benzylpiperazin-1-yl)cyclopropyl)methyl)-N-(3-cyanopyridin-2-yl)propionamide
N-((4-4-benzylpiperazin-1-yl)tetrahydro-2H-pyran-4-yl)methyl)-N-(4-fluorophenyl)propionamide
N-((4-(4-benzylpiperazin-1-yl)tetrahydro-2H-pyran-4-yl)methyl)-N-(3-fluoropyridin-2-yl)propionamide
N-((4-(4-benzylpiperazin-1-yl)tetrahydro-2H-pyran-4-yl)methyl)-N-(6-(trifluoromethyl)pyridin-2-yl)propionamide
N-((4-(4-benzylpiperazin-1-yl)tetrahydro-2H-pyran-4-yl)methyl)-N-(6-cyanopyridin-2-yl)propionamide
N-(6-cyanopyridin-2-yl)-N-((4-(4-isobutylpiperazin-1-yl)tetrahydro-2H-pyran-4-yl)methyl)propionamide
N-(6-cyanopyridin-2-yl)-N-(4-(4-isopentylpiperazin-1-yl)tetrahydro-2H-pyran-4-yl)methyl)propionamide
N-(6-cyanopyridin-2-yl)-N-((4-(4-isobutylpiperazin-1-yl)-2.2-dimethyltetrahydro-2H-pyran-4-yl)methyl)propionamide
N-(6-cyanopyridin-2-yl)-N-(4-(4-isopentylpiperazin-1-yl)-2,2-dimethyltetrahydro-2H-pyran-4-yl)methyl)propionamide
N-((9-(4-benzylpiperazin-1-yl)-6-oxaspiro[4.5]decan-9-yl)methyl)-N-(6-(trifluoromethyl)pyridin-2-yl)propionamide
N-((4-(1-benzylpipendin-4-yl)tetrahydro-2H-pyran-4-yl)methyl)-N-(6-(trifluoromethyl)pyridin-2-yl)propionamide
N-((1-(4-benzylpiperazin-1-yl)cyclopropyl)methyl)-N-(6-(trifluoromethyl)pyridin-2-yl)propionamide
N-((1-(4-benzylpiperazin-1-yl)cyclopropyl)methyl)-N-(thiazol-2yl)propionamide
N-((1-(4-benzylpiperazin-1-yl)cyclopropyl)methyl)-N-(5-fluoropyridin-3-yl)propionamide N-((1-(4-benzylpiperazin-1-yl)cyclopropyl)methyl)-N-(5-(trifluoromethyl)pyridin-2-yl)propionamide
N-((1-(4-benzylpiperazin-1-yl)cyclopropyl)methyl)-N-(3-fluorophenyl)propionamide
N-((1-(4-benzylpiperazin-1-yl)cyclopropyl)methyl)-N-(3-cyanophenyl)propionannide
N-((1-(4-benzylpiperazin-1-yl)cyclopropyl)methyl)-N-(6-cyanopyridin-2-yl)propionamide
N-benzyl-N-((1-(4-benzylpiperazin-1-yl)cyclopropyl)methyl)propionamide
N-((4-(4-benzylpiperazin-1-yl)tetrahydro-2H-pyran-4-yl)methyl)-N-ethylpropionamide
N-((4-(4-(3-fluorobenzylpiperazin-1-yl)tetranydro-2H-pyran-4-yl)methyl)-N-phenylpropionamide
N-phenyl-N-((4-(4-(pyridin-3-ylmethyl)piperazin-1-yl)tetrahydro-2H-pyran-4-yl)methyl)propionamide
N-phenyl-N-((4-(4-(pyridin-2-ylmethyl)piperazin-1-yl)tetrahydro-2H-pyran-4-yl)methyl)propionamide
N-phenyl-N-((4-(4((6-(trifluoromethyl)pyridin-3-yl)methyl)piperazin-1-yl)tetrahydro-2H-pyran-4-yl)methyl)propionamide
N-((4-(4-(2-fluorobenzyl)piperazin-1-yl)tetrahydro-2H-pyran-4-yl)methyl)-N-phenylpropionamide
N-((4(4-4-fluorobenzyl)piperazin-1-yl)tetrahydro-2H-pyran-4-yl)methyl)-N-phenylpropionamide
N-phenyl-N-((4-(4-(pyridin-4-ylmethyl)piperazin-1-yl)tetrahydro-2H-pyran-4-yl)methyl)propionamide
N-((4-(4-((5-fluoropyridin-3-yl)methyl)piperazin-1-yl)tetrahydro-2H-pyran-4-yl)methyl)-N-phenylpropionamide
N-((4-(4-(3,4-difluorobenzyl)piperazin-1-yl)tetrahydro-2H-pyran-4-yl)methyl)-N-phenylpropionamide
N-((4-(4-((6-methoxypyridin-3-yl)methyl)piperazin-1-yl)tetrahydro-2H-pyran-4-yl)methyl)-N-phenylpropionamide
N-((4-(4-(3-fluorobenzyl)piperazin-1-yl)tetrahydro-2H-pyran-4-yl)methyl)-N-(pyridin-2-yl)propionamide
N-((4-(4-(4-fluorobenzyl)piperazin-1-yl)tetrahydro-2H-pyran-4-yl)methyl)-N-(pyridin-2-yl)propionamide
N-((4-(4-(1-methoxypropan-2-yl)piperazin-1-yl)tetrahydro-2H-pyran-4-yl)methyl)-N-(6-(trifluoromethyl)pyridin-2-yl)propionamide
N-phenyl-N-((1-(4((6-(trifluoromethyl)pyridin-3-yl)methyl)piperazin-1-yl)cyclopropyl)methyl)propionamide
N-phenyl-N-((1-(4-(pyridin-2-ylmethyl)piperazin-1-yl)cyclopropyl)methyl)propionamide
N-((1-(4-(4-acetamidobenzyl)piperazin-1-yl)cyclopropyl)methyl)-N-phenylpropionamide
N-((1-(4-(3-fluorobenzyl)piperazin-1-yl)cyclopropyl)methyl)-N-phenylpropionamide
N-((1-(4-(3,4-difluorobenzyl)piperazin-1-yl)cyclopropyl)methyl)-N-phenylpropionamide
N-((1-(4-(2-fluorobenzyl)piperazin-1-yl)cyclopropyl)methyl)-N-phenylpropionamide
N-phenyl-N-((1-(4-(pyridin-3-ylmethyl)piperazin-1-yl)cyclopropyl)methyl)propionamide
N-((1-(4-(3-fluoropyridin-2-yl)methyl)piperazin-1-yl)cyclopropyl)methyl)-N-phenylpropionamide
N-((1-(4-((5-fluoropyridin-2-yl)methyl)piperazin-1-yl)cyclopropyl)methyl)-N-phenylpropionamide
N-((1-(4-((5-fluoropyridin-3-yl)methyl)piperazin-1-yl)cyclopropyl)methyl)-N-phenylpropionamide
N-((1-(4-isobutylpiperazin-1-yl)cyclopropyl)methyl)-N-(6-(trifluoromethyl)pyridin-2-yl)propionamide
N-((1-(4-isopentylpiperazin-1-yl)cyclopropyl)methyl)-N-(6-(trifluoromethyl)pyridin-2-yl)propionamide
N-methyl-4-((4-(4-((N-phenylpropionamido)methyl)tetrahydro-2H-pyran-4-yl)piperazin-1-yl)methyl)benzamide
N-((4-(4-phenethylpiperazin-1-yl)tetrahydro-2H-pyran-4-yl)methyl)-N-phenylpropionamide
N-((4-(4-(2-oxo-2-(piperidin-1-yl)ethyl)piperazin-1-yl)tetrahydro-2H-pyran-4-yl)methyl)-N-phenylpropionamide
N-((4-(4-phenethylpiperazin-1-yl)tetrahydro-2H-pyran-4-yl)methyl)-N-(6-(trifluoromethyl)pyridin-2-yl)propionamide
N-((3-(4-phenethylpiperazin-1-yl)oxetan-3-yl)methyl)-N-phenylpropionamide
N-((1-(4-(4-fluorobenzyl)piperazin-1-yl)cyclopropyl)methyl)-N-phenylpropionamide
N-methyl-4-(4-1-((N-phenylpropionamido)methyl)cyclopropyl)piperazin-1-yl)methyl)benzamide
N-((1-(4-(2-oxo-2-(piperidin-1-yl)ethyl)piperazin-1-yl)cyclopropyl)methyl)-N-phenylpropionamide
N-((4-(4-(1-phenylethyl)piperazin-1-yl)tetrahydro-2H-pyran-4-yl)methyl)-N-(6-(trifluoromethyl)pyridin-2-yl)propionamide
N-((4-(4-(1-phenylethyl)piperazin-1-yl)tetrahydro-2H-pyran-4-yl)methyl)-N-(pyridin-2-yl)propionamide
N-((4-(4-isobutylpiperazin-1-yl)tetrahydro-2H-pyran-4-yl)methyl)-N-phenylpropionamide
N-((4-(4-isobutylpiperazin-1-yl)tetrahydro-2H-pyran-4-yl)methyl)-N-(6-(trifluoromethyl)pyridin-2-yl)propionamide
N-((4-(4-isopentylpiperazin-1-yl)tetrahydro-2H-pyran-4-yl)methyl)-N-(6-(trifluoromethyl)pyridin-2-yl)propionamide
N-((4-(4-(2-isopropoxyethyl)piperazin-1-yl)tetrahydro-2H-pyran-4-yl)methyl)-N-(6-(trifluoromethyl)pyridin-2-yl)propionamide
N-((4-(4-sec-butylpiperazin-1-yl)tetrahydro-2H-pyran-4-yl)methyl)-N-(6-(trifluoromethyl)pyridin-2-yl)propionamide
N-((4-(4-(2-ethoxyethyl)piperazin-1-yl)tetrahydro-2H-pyran-4-yl)methyl)-N-(6-(trifluoromethyl)pyridin-2-yl)propionamide
N-((4-(4-(2-(trifluoromethoxy)ethyl)piperazin-1-yl)tetrahydro-2H-pyran-4-yl)methyl)-N-(6-(trifluoromethyl)pyridin-2-yl)propionamide
N-((4-(4-(2-isobutoxyethyl)piperazin-1-yl)tetrahydro-2H-pyran-4-yl)methyl)-N-(6-(trifluoromethyl)pyridin-2-yl)propionamide
N-((4-(4-(2-(2,2,2-trifluoroethoxy)ethyl)piperazin-1-yl)tetrahydro-2H-pyran-4-yl)methyl)-N-(6-(trifluoromethyl)pyridin-2-yl)propionamide
ethyl 3-(4-(4((N-(6-(trifluoromethyl)pyridin-2-yl)propionamido)methyl)tetrahydro-2H-pyran-4-yl)piperazin-1-yl)propanoate
N-((4-(4-(3-methoxypropyl)piperazin-1-yl)tetrahydro-2H-pyran-4-yl)methyl)-N-(6-(trifluoromethyl)pyridin-2-yl)propionamide
N-((4-4-propylpiperazin-1-yl)tetrahydro-2H-pyran-4-yl)methyl)-N-(6-(trifluoromethyl)pyridin-2-yl)propionamide
N-((4-(4-butylpiperazin-1-yl)tetrahydro-2H-pyran-4-yl)methyl)-N-(6-(trifluoromethyl)pyridin-2-yl)propionamide
N-((4-(4-(2-hydroxyethyl)piperazin-1-yl)tetrahydro-2H-pyran-4-yl)methyl)-N-(6-(trifluoromethyl)pyridin-2-yl)propionamide N-((4-(4-(2-phenoxyethyl)piperazin-1-yl)tetrahydro-2H-pyran-4-yl)methyl)-N-(6-(trifluoromethyl)pyridin-2-yl)propionamide N-((4-(4-(3-ethoxypropyl)piperazin-1-yl)tetrahydro-2H-pyran-4-yl)methyl)-N-(6-(trifluoromethyl)pyridin-2-yl)propionamide N-((4-(4-isobutylpiperazin-1-yl)tetrahydro-2H-pyran-4-yl)methyl)-N-(pyridin-2-yl)propionamide N-((4-(4-(2-isopropoxyethyl)piperazin-1-yl)tetrahydro-2H-pyran-4-yl)methyl)-N-(pyridin-2-yl)propionamide N-((4-(4-isopentylpiperazin-1-yl)tetrahydro-2H-pyran-4-yl)methyl)-N-(pyridin-2-yl)propionamide N-((4-(4-sec-butylpiperazin-1-yl)tetrahydro-2H-pyran-4-yl)methyl)-N-(pyridin-2-yl)propionamide N-(3-fluoropyridin-2-yl)-N-((4-(4-isopentylpiperazin-1-yl)tetrahydro-2H-pyran-4-yl)methyl)propionamide N-((4-(4-(2-ethoxyethyl)piperazin-1-yl)tetrahydro-2H-pyran-4-yl)methyl)-N-(3-fluoropyridin-2-yl)propionamide N-(3-fluoropyridin-2-yl)-N-((4-(4-(2-isopropoxyethyl)piperazin-1-yl)tetrahydro-2H-pyran-4-yl)methyl)propionamide N-(3-fluoropyridin-2-yl)-N-((4-(4-isobutylpiperazin-1-yl)tetrahydro-2H-pyran-4-yl)methyl)propionamide N-((4-(4-isopentylpiperazin-1-yl)-2,2-dimethyltetrahydro-2H-pyran-4-yl)methyl)-N-(6-(trifluoromethyl)pyridin-2-yl)propionamide N-((4(4-isobutylpiperazin-1-yl)-2,2-dimethyltetrahydro-2H-pyran-4-yl)methyl)-N-(6-(trifluoromethyl)pyridin-2-yl)propionamide N-((4-(4-(2-isopropoxyethyl)piperazin-1-yl)-2,2-dimethyltetrahydro-2H-pyran-4-yl)methyl)-N-(6-(trifluoromethyl)pyridin-2-yl)propionamide N-((4-(4-sec-butylpiperazin-1-yl)-2,2-dimethyltetrahydro-2H-pyran-4-yl)methyl)-N-(6-(trifluoromethyl)pyridin-2-yl)propionamide N-((4-(4-(2-isopropoxyethyl)piperazin-1-yl)-2,2-dimethyltetrahydro-2H-pyran-4-yl)methyl)-N-(pyridin-2-yl)propionamide N-((4-(4-isopentylpiperazin-1-yl)-2,2-dimethyltetrahydro-2H-pyran-4-yl)methyl)-N-(pyridin-2-yl)propionamide N-((4-(4-(2-ethoxyethyl)piperazin-1-yl)-2,2-dimethyltetrahydro-2H-pyran-4-yl)methyl)-N-(pyridin-2-yl)propionamide N-((4-(4-isobutylpiperazin-1-yl)-2,2-dimethyltetrahydro-2H-pyran-4-yl)methyl)-N-(pyridin-2-yl)propionamide N-(3-fluoropyridin-2-yl)-N-((4-(4-(2-isopropoxyethyl)piperazin-1-yl)-2,2-dimethyltetrahydro-2H-pyran-4-yl)methyl)propionamide N-(3-fluoropyridin-2-yl)-N-((4-(4-isopentylpiperazin-1-yl)-2,2-dmethyltetrahydro-2H-pyran-4-yl)methyl)propionamide N-((4-(4-(2-ethoxyethyl)piperazin-1-yl)-2,2-dimethyltetrahydro-2H-pyran-4-yl)methyl)-N-(3-fluoropyridin-2-yl)propionamide N-(3-fluoropyridin-2-yl)-N-((4-(4-isobutylpiperazin-1-yl)-2,2-dimethyltetranydro-2H-pyran-4-yl)methyl)propionamide N-(6-cyanopyridin-2-yl)-N-((4-(4-(2-ethoxyethyl)piperazin-1-yl)-2,2-dimethyltetrahydro-2H-pyran-4-yl)methyl)propionamide N-(6-cyanopyridin-2-yl)-N-((4-(4-(2-isopropoxyethyl)piperazin-1-yl)-2,2-dimethyltetrahydro-2H-pyran-4-yl)methyl)propionamide N-((9-(4-isopentylpiperazin-1-yl)-6-oxaspiro[4.5]decan-9-yl)methyl)-N-(6-(trifluoromethyl)pyridin-2-yl)propionamide N-((9-(4-(2-isopropoxyethyl)piperazin-1-yl)-6-oxaspiro[4.5]decan-9-yl)methyl)-N-(6-(trifluoromethyl)pyridin-2-yl)propionamide N-((9-(4-isobutylpiperazin-1-yl)-6-oxaspiro[4.5]decan-9-yl)methyl)-N-(6-(trifluoromethyl)pyridin-2-yl)propionamide N-((9-(4-(2-ethoxyethyl)piperazin-1-yl)-6-oxaspiro[4.5]decan-9-yl)methyl)-N-(6-(trifluoromethyl)pyridin-2-yl)propionamide N-((4-(1-(2-ethoxyethyl)piperidin-4-yl)tetrahydro-2H-pyran-4-yl)methyl)-N-(6-(trifluoromethyl)pyridin-2-yl)propionamide N-((4-(1-isobutylpiperidin-4-yl)tetrahydro-2H-pyran-4-yl)methyl)-N-(6-(trifluoremethyl)pyridin-2-yl)propionamide N-((1-(4-(2-isopropoxyethyl)piperazin-1-yl)cyclopropyl)methyl)-N-(6-(trifluoromethyl)pyridin-2-yl)propionamide methyl 2-phenyl-2-(4-(4((N-(pyridin-2-yl)propionamido)methyl)tetrahydro-2H-pyran-4-yl)piperazin-1-yl)acetate N-((4-(4-(2-hydroxy-1-phenylethyl)piperazin-1-yl)tetrahydro-2H-pyran-4-yl)methyl)-N-(pyridin-2-yl)propionamide N-((4-(4-(1-(4-fluorophenyl)ethyl)piperazin-1-yl)tetrahydro-2H-pyran-4-yl)methyl)-N-(6-(trifluoromethyl)pyridin-2-yl)propionamide N-((4-(4-(2-cyclopropoxyethyl)piperazin-1-yl)tetrahydro-2H-pyran-4-yl)methyl)-N-(6-(trifluoromethyl)pyridin-2-yl)propionamide N-((4-(4-(2-morpholinoethyl)piperazin-1-yl)tetrahydro-2H-pyran-4-yl)methyl)-N-(6-(trifluoromethyl)pyridin-2-yl)propionamide N-((4-(4-(2-methoxyethyl)piperazin-1-yl)tetrahydro-2H-pyran-4-yl)methyl)-N-(6-(trifluoromethyl)pyridin-2-yl)propionamide N-((4-(4-(2-(2-hydroxy-2-methylpropoxy)ethyl)piperazin-1-yl)tetrahydro-2H-pyran-4-yl)methyl)-N-(6-(trifluoromethyl)pyridin-2-yl)propionamide N-((4-(4-(2-propoxyethyl)piperazin-1-yl)tetrahydro-2H-pyran-4-yl)methy)-N-(6-(trifluoromethyl)pyridin-2-yl)propionamide N-((4-(4-(2-hydroxy-2-methylpropyl)piperazin-1-yl)tetrahydro-2H-pyran-4-yl)methyl)-N-(6-(trifluoromethyl)pyridin-2-yl)propionamide N-((4-(4-(2-(2-fluoro-2-methylpropoxy)ethyl)piperazin-1-yl)tetrahydro-2H-pyran-4-yl)methyl)-N-(6-(trifluoromethyl)pyridin-2-yl)propionamide N-((4-(4-(2-fluoro-2-methylpropyl)piperazin-1-yl)tetrahydro-2H-pyran-4-yl)methyl)-N-(6-(trifluoromethyl)pyridin-2-yl)propionamide N-((4-(4-(2-Methoxy-2-methylpropyl)piperazin-1-yl)tetrahydro-2H-pyran-4-yl)methyl)-N-(6-(trifluoromethyl)pyridin-2-yl)propionamide N-((4-(4-(2-(3-Fluoropyridin-2-yl)ethyl)piperazin-1-yl)tetrahydro-2H-pyran-4-yl)methyl)-N-(6-(trifluoromethyl)pyridin-2-yl)propionamide N-((4-(4-(2-hydroxy-2-phenylethyl)piperazin-1-yl)tetrahydro-2H-pyran-4-yl)methyl)-N-(6-(trifluoromethyl)pyridin-2-yl)propionamide N-((4-(4-(2-hydroxy-1-phenylethyl)piperazin-1-yl)tetrahydro-2H-pyran-4-yl)methyl)-N-(6-(trifluoromethyl)pyridin-2-yl)propionamide N-((4-(4-benzylpiperazin-1-yl)piperidin-4-yl)methyl)-N-phenylpropionamide
optionally as a stereoisomer, a racemate or a mixture of at least two stereoisomers, in any mixing ratio, or a corresponding salt thereof, or a corresponding solvate thereof.

19. The compound according to claim 1, wherein the compound is selected from the group consisting of:
N-((4-(5-benzylhexehydropyrrolo[3,4-c]pyrrol-2(1H)-yl)tetrahydro-2H-pyran-4-yl)methyl)-N-(6-(trifluoremethyl)pyridin-2-yl)propionamide
N-((1(4-benzylpiperazin-1-yl)cyclobutyl)methyl)-N-(6-trifluoromethyl)pyridin-2-yl)propionamide
N-((4-(4-benzylpiperazin-1-yl)tetrahydro-2H-thiopyran-4yl)methyl)-N-(6-(trifluoromethyl)pyridin-2-yl)propionamide
N-((4-(5-isobutylhexahydropyrrolo[3,4-c]pyrrol-2(1H)-yl)tetrahydro-2H-pyran-4-yl)methyl)-N-(6-(trifluoromethyl)pyridin-2-yl)propionamide
N-((4-(5-(2-ethoxyethyl)hexahydropyrrolo[3,4-c]pyrrol-2(1H)-yl)tetrahydro-2H-pyran-4-yl)methyl)-N-(6-(trifluoromethyl)pyridin-2-yl)propionamide
N-((4-(4-(2-(pyridin-3-yl)ethyl)piperazin-1-yl)tetrahydro-2H-pyran-4-yl)methyl)-N-(6-(trifluoromethyl)pyridin-2-yl)propionamide
N-((1-(4-(2-ethoxyethyl)piperazin-1-yl)cyclobutyl)methyl)-N-(6-(trifluoromethyl)pyridin-2-yl)propionamide
N-((1-(4-isobutylpiperazin-1-yl)cyclobutyl)methyl)-N-(6-(trifluoremethyl)pyridin-2-yl)propionamide
N-((4-(4-isobutylpiperazin-1-yl)tetrahydro-2H-thiopyran-4-yl)methyl-N-(6-(trifluoromethyl)pyridin-2-yl)propionamide
N-((4-(4-(2-ethoxyethyl)piperazin-1-yl)tetrahydro-2-H-thiopyran-4-yl)methyl)-N-(6-(trifluoromethyl)pyridin-2-yl)propionamide
N-((4-(4-(2-(pyridin-4-yl)ethyl)piperazin-1-yl)tetrahydro-2H-pyran-4-yl)methyl)-N-(6-(trifluoromethyl)pyridin-2-yl)propionamide
optionally as a stereoisomer, a racemate or in form of a mixture of at least two stereoisomers, in any mixing ratio, or a corresponding salt thereof, or a corresponding solvate thereof.

20. A process for the preparation of the compound of Formula (I) as defined in claim 1, wherein the process comprises reacting a compound of Formula (VIII)

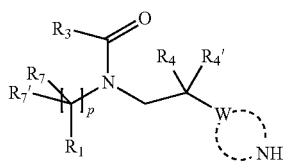

VIII with a compound of formula (Xa) through an alkylation reaction or (Xb) through a reductive amination reaction

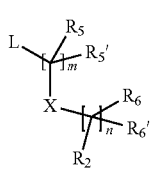

IXa

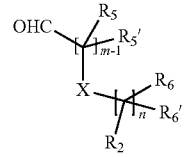

IXb or wherein the process comprises an acylation reaction of a compound of formula Vb

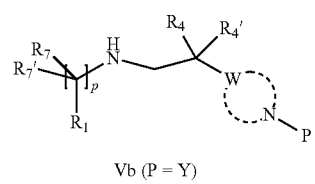

Vb (P = Y)

with an acyl halide of formula VIa or with an anhydride of formula VIb,

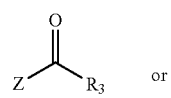

VIa or

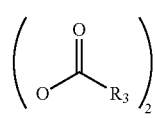

VIb or wherein the process comprises treating compounds of formula Xb

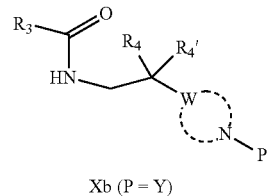

Xb (P = Y)

with a reagent of formula Xb with a reagent of formula IVa

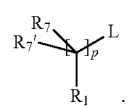

IVa

21. A process for the preparation of the compound of Formula (I) according to claim 1, employlng a compound of Formula IIa, IIb, IIIa, IIIb, IVa, IVb, Va, Vb, VIa, VIb, VIc, VII, VIII, IXa, IXb, Xa, Xb, XI, XII, XIIIa, XIIIb, XIVa, XIVb, XV, XVIa or XVIb:

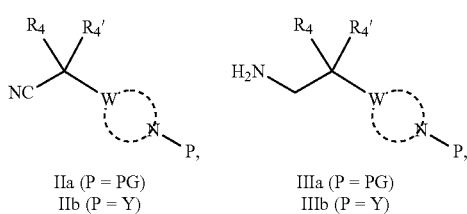

22. A pharmaceutical composition which comprises the compound according to claim 1, or a pharmaceutically acceptable salt thereof, and a pharmaceutically acceptable carrier, adjuvant or vehicle.

23. A method of treating pain in a subject in need thereof, comprising administration of an effective amount of the compound according to claim 1.

24. The method according to claim 23, wherein the pain is selected from the group consisting of medium to severe pain, visceral pain, chronic pain, cancer pain, migraine, inflammatory pain, acute pain, neuropathic pain, allodynia, and hyperalgesia.

25. The compound according to claim 1, wherein the compound is in the form of an enantiomer or a diastereomer or in the form of a mixture of enantiomers and/or diastereomers, in any mixing ratio.

26. The compound according to claim 4, wherein the compound is in the form of an enantiomer or a diastereomer or in the form of a mixture of enantiomers and/or diastereomers, in any mixing ratio.

27. The compound according to claim 18, wherein the compound is in the form of an enantiomer or a diastereomer or in the form of a mixture of enantiomers and/or diastereomers, in any mixing ratio.

28. The compound according to claim 19, wherein the compound is in the form of an enantiomer or a diastereomer or in the form of a mixture of enantiomers and/or diastereomers, in any mixing ratio.

* * * * *

UNITED STATES PATENT AND TRADEMARK OFFICE
CERTIFICATE OF CORRECTION

Page 1 of 2

PATENT NO. : 10,428,051 B2
APPLICATION NO. : 15/746877
DATED : October 1, 2019
INVENTOR(S) : Monica Garcia-Lopez et al.

It is certified that error appears in the above-identified patent and that said Letters Patent is hereby corrected as shown below:

In the Claims

<u>In Claim 18</u>:

Column 247, Line 49: "tetranydro-" should read -- tetrahydro- --

Column 247, Line 52: "-N-(3 (thfluoromethyl)" should read -- -N-(3-(trifluoromethyl) --

Column 248, Line 32: "propienarnide" should read -- propionamide --

Column 248, Line 37: "N-((4-4-" should read -- "N-((4-(4- --

Column 248, Line 48: "-N-(4-(4-" should read -- -N-((4-(4- --

Column 248, Line 51: "-2.2-" should read -- -2,2- --

Column 248, Line 53: "-N-(4-(4-" should read -- -N-((4-(4- --

Column 248, Line 59: "-benzylpipendin-" should read -- -benzylpiperidin- --

Column 248, Line 65: "-2yl)" should read -- -2-yl) --

Column 249, Line 13: "-fluorobenzylpiperazin-1-yl)tetranydro-" should read
-- -fluorobenzyl)piperazin-1-yl)tetrahydro- --

Column 249, Line 19: "-N-((4((6-" should read -- -N-((4-((6- --

Column 249, Line 58: "-(4-(3-" should read -- -(4-((3- --

Column 250, Line 17: "-4-(4-1-" should read -- -4-((4-(1- --

Signed and Sealed this
Fourth Day of February, 2020

Andrei Iancu
*Director of the United States Patent and Trademark Office*

CERTIFICATE OF CORRECTION (continued)
U.S. Pat. No. 10,428,051 B2

Column 250, Line 59: "N-((4-4-" should read -- N-((4-(4- --

Column 251, Line 54: "-2,2-dmethyltetrahydro-" should read -- -2,2-dimethyltetra-hydro- --

Column 251, Line 60: "-2,2-dimethyltetranydro-" should read -- -2,2-dimethyltetra-hydro- --

Column 252, Line 18: "–(trifluoremethyl)pyridin-" should read -- –(trifluoromethyl)pyridin- --

In Claim 19:

Column 253, Line 09: "-benzylhexehydropyrrolo[" should read -- -benzylhexahydropyrrolo[ --

Column 253, Lines 10 and 11: "-(trifluoremethyl)" should read -- -(trifluoromethyl) --

Column 253, Line 13: "trifluoromethyl)" should read -- (trifluoromethyl) --

Column 253, Line 14: "4yl)" should read -- 4-yl) --

Column 253, Line 29: "-(trifluoremethyl)" should read -- (trifluoromethyl) --

Column 253, Line 31: ")methyl-N-" should read -- )methyl)-N- --

Column 253, Line 33: "-2-H-" should read -- -2H- --

In Claim 21:

Column 255, the formula IVa, Line 12: the "$R^7$" below the first "$R^7$" should read -- $R^{7'}$ --

Column 255, the formula IVb, Line 15: the "$R^7$" below the first "$R^7$" should read -- $R^{7'}$ --

Column 255, the formula Va Vb, Line 20: the "$R^7$" below the first "$R^7$" should read -- $R^{7'}$ --

Column 255, the formula VII, Line 41: the "$R^7$" below the first "$R^7$" should read -- $R^{7'}$ --

Column 255, the formula VIII, Line 49: the "$R^7$" below the first "$R^7$" should read -- $R^{7'}$ --

Column 256, the formula XII, Line 19: the "$R^7$" below the first "$R^7$" should read -- $R^{7'}$ --

Column 256, the formula XIVa XIVb, Line 24: the "$R^7$" below the first "$R^7$" should read -- $R^{7'}$ --

Column 256, the formula XV, Line 32: the "$R^7$" below the first "$R^7$" should read -- $R^{7'}$ --